United States Patent
Cuny et al.

(10) Patent No.: US 7,129,228 B2
(45) Date of Patent: *Oct. 31, 2006

(54) HETEROCYCLIC ANALGESIC COMPOUNDS AND METHODS OF USE THEREOF

(75) Inventors: Gregory D. Cuny, Hudson, MA (US); Liming Shao, Lincoln, MA (US); James R. Hauske, Concord, MA (US); Michele L. R. Heffernan, Framingham, MA (US); Brian M. Aquila, Marlborough, MA (US); Xinhe Wu, Shrewsbury, MA (US); Fengjiang Wang, Northborough, MA (US); Thomas D. Bannister, Northborough, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/754,101

(22) Filed: Jan. 7, 2004

(65) Prior Publication Data

US 2004/0209846 A1    Oct. 21, 2004

Related U.S. Application Data

(62) Division of application No. 09/579,398, filed on May 25, 2000, now Pat. No. 6,677,332.

(60) Provisional application No. 60/195,809, filed on Apr. 11, 2000, provisional application No. 60/168,979, filed on Dec. 3, 1999, provisional application No. 60/135,721, filed on May 25, 1999.

(51) Int. Cl.
*A61P 25/00* (2006.01)
*A61K 31/445* (2006.01)
*A61K 31/675* (2006.01)
*C07F 9/28* (2006.01)
*C07D 211/00* (2006.01)

(52) U.S. Cl. .................. 514/89; 514/315; 514/327; 514/331; 546/22; 546/24; 546/217; 546/233; 546/234; 546/242; 546/247

(58) Field of Classification Search ............... 514/89, 514/315, 327, 331; 546/22, 24, 217, 233, 546/234, 242, 247
See application file for complete search history.

(56) References Cited

U.S. PATENT DOCUMENTS

| | | | |
|---|---|---|---|
| 3,164,600 A | 1/1965 | Janssen et al. | 260/293.4 |
| 3,655,675 A | 4/1972 | Carabateas | 260/293.74 |
| 3,998,834 A | 12/1976 | Janssen et al. | 260/293.68 |
| 4,138,492 A | 2/1979 | Noverola et al. | 424/267 |
| 4,167,574 A | 9/1979 | Janssens | 424/267 |
| 4,584,303 A | 4/1986 | Huang et al. | 514/326 |
| 4,791,120 A | 12/1988 | Lin et al. | 514/326 |
| 4,791,121 A | 12/1988 | Kudzma et al. | 514/326 |
| 4,831,192 A | 5/1989 | Lin et al. | 546/210 |
| 4,859,685 A | 8/1989 | Jerussi et al. | 514/329 |
| 4,863,918 A | 9/1989 | Gala et al. | 514/213 |
| 4,871,749 A | 10/1989 | Lin et al. | 514/326 |
| 4,900,738 A | 2/1990 | Bagley et al. | 514/322 |
| 4,912,109 A | 3/1990 | Bagley et al. | 514/252 |
| 4,916,142 A | 4/1990 | Bagley et al. | 514/318 |
| 4,921,864 A | 5/1990 | Kudzma et al. | 514/326 |
| 4,939,161 A | 7/1990 | Lalinde et al. | 514/326 |
| 4,954,506 A | 9/1990 | Bagley et al. | 514/272 |
| 4,957,929 A | 9/1990 | Kudzma et al. | 514/326 |
| 4,994,471 A | 2/1991 | Lalinde et al. | 514/326 |
| 5,013,742 A | 5/1991 | Kudzma et al. | 514/329 |
| 5,015,781 A | 5/1991 | Robin et al. | 568/683 |
| 5,198,449 A | 3/1993 | Shanklin, Jr. | 514/317 |
| 5,290,796 A | 3/1994 | DeHaven-Hudkins et al. | 514/326 |
| 5,817,678 A | 10/1998 | Kim et al. | 514/326 |
| 6,451,842 B1 | 9/2002 | Shiota et al. | 514/422 |
| 6,635,661 B1 * | 10/2003 | Cuny et al. | 514/331 |
| 6,645,980 B1 * | 11/2003 | Cuny et al. | 514/312 |
| 6,677,332 B1 * | 1/2004 | Cuny et al. | 514/212.02 |
| 2003/0069418 A1 * | 4/2003 | Aquila et al. | 544/59 |

FOREIGN PATENT DOCUMENTS

| | | |
|---|---|---|
| DE | 2 340 874 | 2/1974 |
| EP | 0 160 422 A1 | 11/1985 |
| EP | 0 256 798 | 2/1988 |
| EP | 0 261 842 A1 | 3/1988 |
| EP | 0 277 794 A2 | 8/1988 |
| EP | 0 333 427 A1 | 9/1989 |
| EP | 0 343 900 A2 | 11/1989 |
| EP | 394 039 | 10/1990 |
| EP | 0 396 282 | 11/1990 |
| EP | 0 466 585 A1 | 1/1992 |
| FR | 2 338 043 | 8/1977 |
| FR | 2 729 142 A1 | 7/1996 |
| GB | 1 382 526 | 2/1975 |

(Continued)

OTHER PUBLICATIONS

Stefan Van Den Branden et al. "Mimicking of Ergot Alkaloids and Synthetic Piperidine Druge 2.5-Substituted Piperidines Derived from Cis and Trans Ethyl 1-Benzyl-6-Cyano-3-Piperidinecarboxylate", Tetrahedron 48 (44): 9753-9766 (1992).

(Continued)

*Primary Examiner*—Brenda Coleman
(74) *Attorney, Agent, or Firm*—Dana M. Gordon; Foley Hoag LLP

(57) ABSTRACT

One aspect of the present invention relates to novel heterocyclic compounds. A second aspect of the present invention relates to the use of the novel heterocyclic compounds as ligands for various cellular receptors, including opiate receptors, other G-protein-coupled receptors, and ion channels. An additional aspect of the present invention relates to the use of the novel heterocyclic compounds as analgesics.

28 Claims, 3 Drawing Sheets

FOREIGN PATENT DOCUMENTS

| | | |
|---|---|---|
| GB | 1 382 965 | 2/1975 |
| JP | 02-138170 | 5/1990 |
| JP | 031 482 23 | 6/1991 |
| JP | 110 355 55 | 2/1999 |
| WO | WO89/04300 | 5/1989 |
| WO | WO 97/08155 | 3/1997 |
| WO | WO 97/18813 | 5/1997 |
| WO | WO 98/28275 | 7/1998 |
| WO | WO 99/24423 | 5/1999 |
| WO | WO 99/33806 | 7/1999 |
| WO | WO 00/06545 | 2/2000 |
| WO | WO 00/09491 | 2/2000 |
| WO | WO 00/023438 | 4/2000 |
| WO | WO 00/26186 | 5/2000 |
| WO | WO 00/27815 | 5/2000 |
| WO | WO 00/53596 | 9/2000 |
| WO | WO 00/71518 A2 | 11/2000 |

OTHER PUBLICATIONS

Sternfeld et al.; "Synthesis and Serotonergic Activity of 3-[2-(Pyrrolidin-1-yl)ethyl] Indoles: Potent Agonist for the h5-HT$_{1D}$ Receptor with High Selectivity Over the h5-HT$_{1B}$ Receptor", J. Med. Chem. 42: 677-690, (1999).

International Search Report made on PCT/US 00/ 14579, mailed on Nov. 29, 2000.

Harada et al.; "Development of Potent Seratonin-3 (5-HT$_3$) Receptor Antagonists. I. Structure-Activity Relationships of 2-Alkoxy-4-amino-5-chlorobenzamide Derivatives", Chem. Pharm. Bull.43 (8): 1364-1378 (1995).

Muro et al.; "115499q Preparation of (pyridycarbomoyl) Piperidine Derivatives as Cardiovascular Agents and Antihypertensives", Chemical Abstracts, 107(13): 6001, (Sep. 28, 1987).

Welstead et al., Aminoalkylindoles With Central Nervous System Activity, P. D., 10: 1015-1021, (Nov. 1967).

Zheng et al.; "Design and Synthesis of Antiplatelet Nipecotamides with a Dual Mechanism of Action", Medicinal Chemistry Research 7(4): 219-227, (1997).

International Search Report Completed on Jul. 12, 2002 and Mailed on Aug. 20, 2002.

Golovin et al.; "Synthesis of Substituted cis-3-aminoethyl-4-Hydroxypiperidines and Their acyl Derivatives", Khim, Geterotsiki. Soedin, 10: 1363-8,(1978) CAS print out.

Carelli et al.; "Substituted N-(Pyridylmethyl) Anilides with Local Anesthetic Action", Farmaco Ed. Sci. 16: 375-386, (1961); Chemical Abstracts Accession No. 1962: 31337, Document No. 56: 31337.

Kakefuda et al., An Efficient Synthesis of (+)-6,7-dimethyoxy-1-oxo-2-(3-piperidyl)-1,2,3,4-tetrahydroisoqunioline, Synthetic Communications, vol. 31, No. 3, pp. 401-408, 2001.

CAPLUS printout of COSTAKIS et al., Synthesis and Preliminary Pharmacological Study of some .alpha.-phenylalkylamines, Annales Pharmaceutiques Francaise, vol. 36, No. 7-8, pp. 349-360, 1978.

CAPLUS printout of PITRE et al., 1-Amino-1,3-diphenylethane Derivatives, Farmaco Edizione Scientifica, vol. 17, pp. 130-140, 1962.

* cited by examiner

Figure 2

| | $ED_{50}$ (i.v., µg/kg) | | |
|---|---|---|---|
| | Mice (Tail Flick) | Rat (Tail Flick) | Rat (Hot plate) |
| 6 | <500 | | <500 |
| 30 | <1000 | <500 | <1000 |
| 32 | <1000 | <500 | <500 |
| Racemic 71 | | <500 | <2500 |
| 71 | | <1000 | >2500 |
| 73 | | <500 | <500 |
| 57 | | <500 | >2500 |
| 152 | | <500 | <2500 |
| 151 | | <500 | <2500 |
| 69 | <2500 | | |
| 82 | | <500 | <2500 |
| 83 | | <500 | <1000 |
| 84 | | <500 | <2500 |
| 163 | | <2500 | >2500 |
| 195 | | <500 | <2500 |
| 196 | | >2500 | |
| 197 | | <500 | <500 |
| 198 | | <500 | <500 |
| Morphine | <2500 | <2500 | >2500 |
| Fentanyl | | <500 | <500 |

Figure 3

|  | Dose = 3 x ED$_{50}$ | | Dose = 10 x ED$_{50}$ | |
|---|---|---|---|---|
| Compound | % Change pCO$_2$ | % Change pO$_2$ | % Change pCO$_2$ | % Change pO$_2$ |
| 6 | Negative | Negative | Positive | Negative |
| 30 | Negative | Positive | Negative | Negative |
| 32 | Positive | Negative | Positive | Negative |
| 57 | Positive | Negative | Positive | Negative |
| 82 | Negative | Negative | Positive | Negative |
| 71 | Negative | Positive | Negative | Positive |
| 73 | Positive | Negative | Positive | Negative |
| 83 | Negative | Negative | Positive | Negative |
| 84 | Negative | Negative | Negative | Negative |
| 152 | Negative | Negative | Positive | Negative |
| 151 | Positive | Negative | Positive | Negative |
| 44 | Negative | Negative | Positive | Negative |
| 197 | Positive | Negative | Positive | Negative |
| 198 | Positive | Negative | Positive | Negative |
| Fentanyl | 31 +/- 6 | -32 +/- 5 | 52 +/- 6 | -45 +/- 5 |
| Morphine | 38 +/- 8 | -36 +/- 2 | 75 +/- 10 | -57 +/- 3 |

HETEROCYCLIC ANALGESIC COMPOUNDS AND METHODS OF USE THEREOF

RELATED APPLICATIONS

This application is a divisional of U.S. patent application Ser. No. 09/579,398, filed May 25, 2000 now U.S. Pat. No. 6,677,332; which claims the benefit of priority to: U.S. Provisional Patent Application Ser. No. 60/195,809, filed Apr. 11, 2000; U.S. Provisional Patent Application Ser. No. 60/168,979, filed Dec. 3, 1999; and U.S. Provisional Patent Application Ser. No. 60/135,721, filed May 25, 1999.

BACKGROUND OF THE INVENTION

Pain is an unpleasant sensation varying in severity in a local part of the body or several parts of the body resulting from injury, disease, or emotional disorder. Pain can be classified according to its duration. Acute pain, which lasts less than one month, usually has a readily identifiable cause and signals tissue damage. In addition, acute pain syndromes can be episodic, for example recurrent discomfort from arthritis. Chronic pain can be defined as pain that persists more than one month beyond the usual course of an acute illness or injury, or pain that recurs at intervals over months or years, or pain that is associated with a chronic pathologic process. In contrast to acute pain, chronic pain loses its adaptive biologic function. Depression is common, and abnormal illness behavior often compounds the patient's impairment.

Millions of people suffer from chronic or intractable pain. Persistent pain varies in etiology and presentation. In some cases, symptoms and signs may be evident within a few weeks to a few months after the occurrence of an injury or the onset of disease, e.g. cancer or AIDS. Like many illnesses that at one time were not well understood, pain and its many manifestations may be poorly treated and seriously underestimated. Inappropriately treated pain seriously compromises the patient's quality of life, causing emotional suffering and increasing the risk of lost livelihood and disrupted social integration. Severe chronic pain affects both the pediatric and adult population, and often leads to mood disorders, including depression and, in rare cases, suicide.

In the last several years, health policy-makers, health professionals, regulators, and the public have become increasingly interested in the provision of better pain therapies. This interest is evidenced, in part, by the U.S. Department of Health and Human Services' dissemination of Clinical Practice Guidelines for the management of acute pain and cancer pain. There is currently no nationally accepted consensus for the treatment of chronic pain not due to cancer, yet the economic and social costs of chronic pain are substantial, with estimates ranging in the tens of billions of dollars annually.

Three general classes of drugs are currently available for pain management, nonsteriodal anti-inflammatories, opioids, and adjuvant analgesics. The nonsteriodal anti-inflammatories class includes drugs such as aspirin, ibuprofen, diclofenac, acetaminophen, celecoxib, and rofecoxib. The opioid class includes morphine, oxycodone, fentanyl, and pentazocine. Adjuvant analgesics include various antidepressants, anticonvulsants, neuroleptics, and corticosteroids.

Opioids are the major class of analgesics used in the management of moderate to severe pain because of their effectiveness, ease of titration, and favorable risk-to-benefit ratio. Opioids produce analgesia by binding to specific receptors both within and outside the CNS. Opioid analgesics are classified as full agonists, partial agonists, or mixed agonist-antagonists, depending on the receptors to which they bind and their intrinsic activities at each receptor.

Three subclasses of opioid receptor have been identified in humans, namely the $\delta$-, $\kappa$-, and $\mu$-opioid receptors. Analgesia is thought to involve activation of $\mu$ and/or $\kappa$ receptors. Notwithstanding their low selectivity for $\mu$ over $\kappa$ receptors, it is likely that morphine and morphine-like opioid agonists produce analgesia primarily through interaction with $\mu$ receptors; selective agonists of $\kappa$ receptors in humans produce analgesia, because rather than the euphoria associated with morphine and congeners, these compounds often produce dysphoria and psychotomimetic effects. The consequences of activating $\delta$ receptors in humans remain unclear.

Although opioids can be very effective in pain management, they do cause several side effects, such as respiratory depression, constipation, physical dependence, tolerance, withdraw. These unwanted effects can severely limit their use.

Opioids are known to produce respiratory depression that is proportional to their analgesia. This respiratory depression can be life threatening. This results in a narrow range between the effective dose and a dose that produces respiratory depression. Because of this narrow therapeutic index, patients receiving opioid therapy must be closely monitored for signs of respiratory failure.

Opioids can also cause constipation in individuals receiving them. This side effect can be severe and may require prolonged hospitalization, or even surgical intervention.

Commonly used full agonists include morphine, hydromorphone, meperidine, methadone, levorphanol, and fentanyl. These opioids are classified as full agonists because there is not a ceiling to their analgesic efficacy, nor will they reverse or antagonize the effects of other opioids within this class when given simultaneously. Side effects include respiratory depression, constipation, nausea, urinary retention, confusion, and sedation. Morphine is the most commonly used opioid for moderate to severe pain because of its availability in a wide variety of dosage forms, its well-characterized pharmacokinetics and pharmacodynamics, and its relatively low cost. Meperidine may be useful for brief courses (e.g., a few days) to treat acute pain and to manage rigors (shivering) induced by medication, but it generally should be avoided in patients with cancer because of its short duration of action (2.5 to 3.5 hours) and its toxic metabolite, normeperidine. This metabolite accumulates, particularly when renal function is impaired, and causes CNS stimulation, which may lead to dysphoria, agitation, and seizures; meperidine, therefore, should not be used if continued opioid use is anticipated.

The development of physical dependence with repeated use is a characteristic feature of the opioid drugs, and the possibility of developing drug dependence is one of the major limitations of their clinical use. Almost all opioid users rapidly develop drug dependency which can lead to apathy, weight loss, loss of sex drive, anxiety, insomnia, and drug cravings. Although physical dependence is common, addiction and abuse are not common in pain patients who are treated appropriately with opioid drugs.

Historically, the development of analgesic tolerance was believed to limit the ability to use opioids efficaciously on a long-term basis for pain management. Tolerance, or decreasing pain relief with the same dosage over time, has not proven to be a prevalent limitation to long-term opioid use. Experience with treating cancer pain has shown that what initially appears to be tolerance is usually progression of the disease. Furthermore, for most opioids, there does not appear to be an arbitrary upper dosage limit, as was once thought.

Cessation of opioid administration may result in a withdrawal syndrome. Symptoms of withdrawal are often the opposite of the effects achieved by the drug; withdrawal from morphine, however, results in complex symptoms that may seem unrelated to its effects. Misunderstanding of addiction and mislabeling of patients as addicts result in unnecessary withholding of opioid medications. Addiction is a compulsive disorder in which an individual becomes preoccupied with obtaining and using a substance, the continued use of which results in a decreased quality of life. Studies indicate that the de novo development of addiction is low when opioids are used for the relief of pain. Furthermore, even opioid addicts can benefit from the carefully supervised, judicious use of opioids for the treatment of pain due to cancer, surgery, or recurrent painful illnesses such as sickle cell disease.

The known opioids have been very effective in pain management. However, they have restricted use because of several potentially severe side effects. Therefore, there is a current need for pharmaceutical agents that retain the analgesic properties of the known opioid, but that have reduced side effect profiles.

SUMMARY OF THE INVENTION

One aspect of the present invention relates to novel heterocyclic compounds. A second aspect of the present invention relates to the use of the novel heterocyclic compounds as ligands for various cellular receptors, including opiate receptors, other G-protein-coupled receptors, and ion channels. An additional aspect of the present invention relates to the use of the novel heterocyclic compounds as analgesics.

BRIEF DESCRIPTION OF THE FIGURES

FIG. 2 presents the $ED_{50}s$ for certain compounds of the present invention, morphine and fentanyl when administered i.v. to mice and rats (See Example 79).

FIG. 3 depicts the changes in $pO_2$ and $pCO_2$ levels in rats caused by the i.v. administration of certain compounds of the present invention, morphine and fentanyl. Changes in these blood gases can be used as an indication of respiratory depression in the rats.

DETAILED DESCRIPTION OF THE INVENTION

Figure 1:
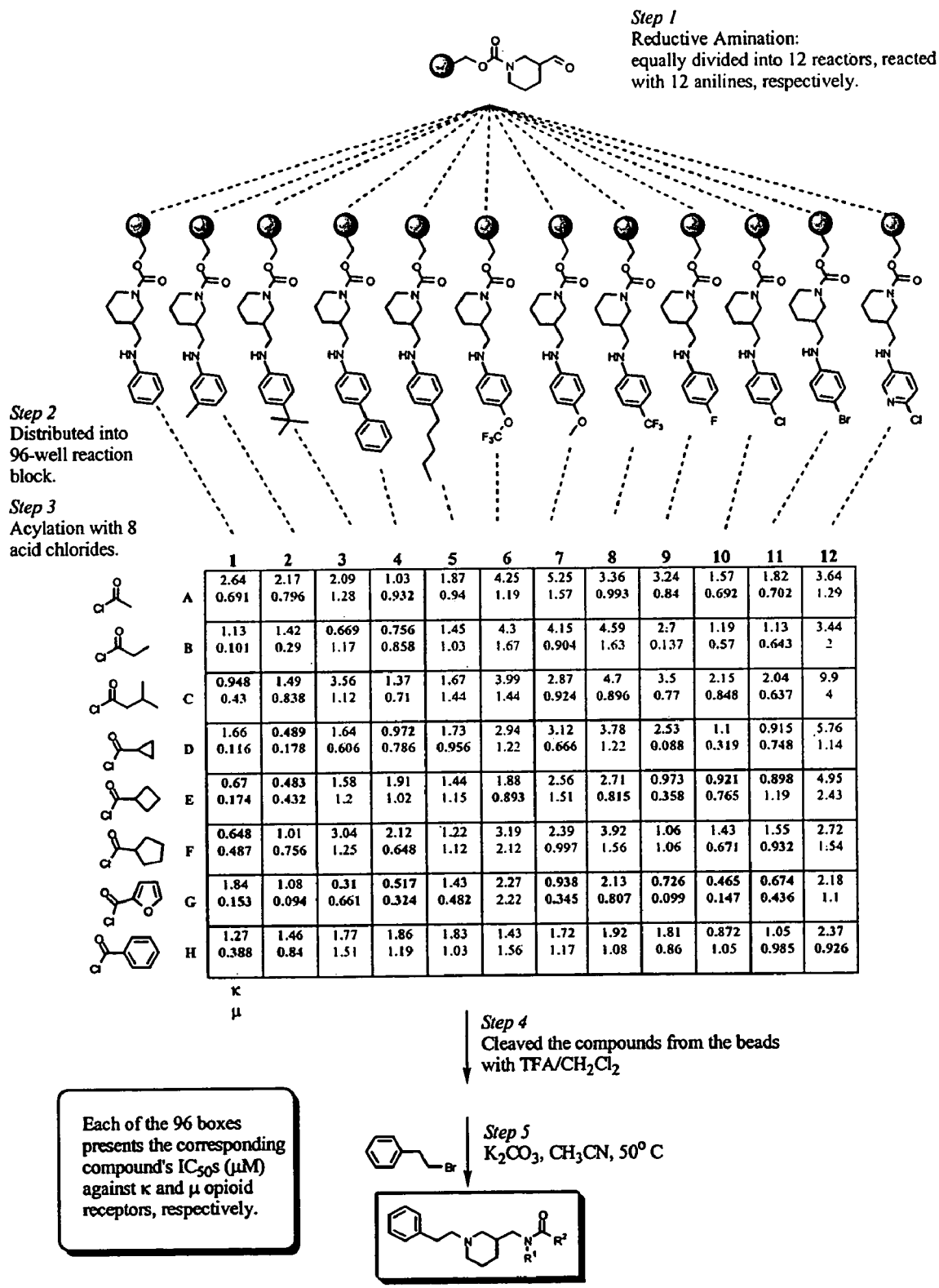
FIG. 1 depicts schematically the combinatorial library described in Example 77, and the reactants, reagents and conditions used to prepare it.

Pain is an unpleasant sensation varying in severity in a local part of the body or several parts of the body resulting from injury, disease, or emotional disorder. Pain can be classified according to its duration. Acute pain, which lasts less than one month, usually has a readily identifiable cause (e.g., hip fracture) and signals tissue damage. The associated effect is often anxiety, and the concomitant physiologic findings are those of sympathetic stimulation (e.g., tachycardia, tachypnea, diaphoresis). In addition, acute pain syndromes can be episodic, for example recurrent discomfort from arthritis.

Chronic pain can be defined as pain that persists more than one month beyond the usual course of an acute illness or injury, or pain that recurs at intervals over months or years, or pain that is associated with a chronic pathologic process. In contrast to acute pain, chronic pain loses its adaptive biologic function. Depression is common, and abnormal illness behavior often compounds the patient's impairment. Chronic pain can be divided broadly into that which is inferred to be predominantly somatogenic and that which is inferred to be predominantly psychogenic. A similar classification based on inferred pathophysiology designates chronic pain as nociceptive (commensurate with ongoing activation of pain-sensitive nerve fibers), neuropathic (due to aberrant somatosensory processing in afferent neural pathways), or psychogenic.

Nociceptive pain can be somatic or visceral. Most chronic pain in the elderly is nociceptive and somatic; arthritis, cancer pain, and myofascial pain are most common. Relief is likely with removal of the peripheral cause (e.g., reducing periarticular inflammation), and analgesic drugs are often effective.

A common subtype of neuropathic pain, known collectively as peripheral neuropathic pain, is presumably sustained by mechanisms that involve disturbances in the peripheral nerve or nerve root; neuroma formation after axonal injury and nerve compression are the two major processes. Another subtype of neuropathic pain is related to the reorganization of nociceptive information processing by the CNS; it persists without ongoing activation of pain-sensitive fibers. This type of pain, known collectively as the deafferentation syndromes, includes postherpetic neuralgia, central pain (which can result from a lesion at any level of the CNS), phantom limb pain, and others. A third subtype of neuropathic pain, often called sympathetically maintained pain, can be ameliorated by interruption of sympathetic nerves to the painful area; the prototypic disorder is reflex sympathetic dystrophy. The precise mechanisms involved in these disorders are conjectural, but all can produce an unfamiliar pain, often described as burning and stabbing. Currently, this type of pain responds poorly to analgesics.

Some patients have persistent pain without either nociceptive foci or evidence of a neuropathic mechanism for the pain. Many others have nociceptive lesions that do not sufficiently explain the degree of pain and disability. Psychopathologic processes account for these complaints in some patients. If no evidence for a psychological cause is found, the pain is referred to as idiopathic. Many patients have an idiopathic pain syndrome that is best described by the generic diagnosis chronic nonmalignant pain syndrome, a term denoting pain and disability disproportionate to an identifiable somatic cause and usually related to a more pervasive set of abnormal illness behaviors. Some of these patients may be labeled by the more formal psychiatric diagnosis of somatoform pain disorder. Others have complaints that constitute a specific pain diagnosis, most commonly the failed low back syndrome or atypical facial pain. Still others have significant organic lesions (e.g., lumbar arachnoiditis) but also have a clear psychological contribution associated with excessive disability. Diagnosis may be difficult, but the relative contributions of both organic and psychological components of the pain can be defined.

Another clinically useful classification of chronic pain is broadly syndromic. For example, chronic pain may be part of a medical illness (e.g., cancer or arthritis). A mixture of pathophysiologic mechanisms may be involved; e.g., tumor invasion of nerve and bone may cause neuropathic and somatic nociceptive pains, respectively, and psychological factors may be prominent.

Three general classes of drugs are currently available for pain management, nonsteriodal anti-inflammatories, opioids, and adjuvant analgesics. The nonsteriodal anti-inflammatories class includes drugs such as aspirin, ibuprofen, diclofenac, acetaminophen, and rofecoxib. The opioid class includes morphine, oxycodone, fentanyl, and pentazocine. Adjuvant analgesics include various antidepressants, anticonvulsants, neuroleptics, and corticosteroids.

Of the three classes of pharmaceutical agents used for pain management, opioid are usually most efficacious for treating moderate to severe pain. Although opioids can be very effective in pain management, they do cause several side effects, such as respiratory depression, constipation, physical dependence, tolerance, withdraw. These unwanted effects can severely limit their use. Therefore, there is a current need for pharmaceutical agents that retain the analgesic properties of the known opioid, but have reduced side effect profiles for the treatment of pain.

Opioids, specifically ligands for the μ-opioid receptor, are the major class of analgesics used in the management of moderate to severe pain because of their effectiveness, ease of titration, and favorable risk-to-benefit ratio. Unfortunately, the opioids currently available have several unwanted side-effects, such as respiratory depression and constipation. In addition, these agents may lead to tolerance and dependence. Research into the development of new, selective ligands for opioid receptors holds the promise of yielding potent analgesics that lack the side effects of morphine and its congeners. Applicants herein disclose novel analgesics, including selective ligands for opioid receptors. Individual compounds described herein promise to have agonistic, antagonistic, and hybrid effects on opioid and other cellular receptors. Additionally, new compounds reported herein may possess analgesic properties free from respiratory depression and the potential for physical dependence associated with ti-opioid receptor ligands, such as morphine and fentanyl. Moreover, new compounds reported herein may possess properties for the treatment of physical or psychological additions, psychiatric disorders, and neurological pathologies, such as tinnitus.

The μ-opioid receptor is a member of a family of cell surface proteins that permit intracellular transduction of extracellular signals. Cell surface proteins provide eukaryotic and prokaryotic cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as growth hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. For example, neuron gene expression is modulated by numerous extracellular signals, including neurotransmitters and membrane electrical activity. Transsynaptic signals cause rapid responses in neurons that occur over a period of time ranging from milleseconds, such as the opening of ligandgated channels, to seconds and minutes, such as second messenger-mediated events. Genes in neural cells that are responsive to transsynaptic stimulation and membrane electrical activity, include genes, called immediate early genes, whose transcription is activated rapidly, within minutes, and transiently (see, e.g., Sheng et al. (1990) Neuron 4: 477–485), and genes whose expression requires protein synthesis and whose expression is induced or altered over the course of hours.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as neurotransmitters, growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

The G protein transmembrane signaling pathways consist of three proteins: receptors, G proteins and effectors. G proteins, which are the intermediaries in transmembrane signaling pathways, are heterodimers and consist of alpha, beta and gamma subunits. Among the members of a family of G proteins the alpha subunits differ. Functions of G proteins are regulated by the cyclic association of GTP with the alpha subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors, which are glycoproteins, are known to share certain structural similarities and homologies (see, e-g., Gilman, A. G., Ann. Rev. Biochem. 56: 615–649 (1987), Strader, C. D. et al. The FASEB Journal 3: 1825–1832 (1989), Kobilka, B. K., et al. Nature 329:75–79 (1985) and Young et al. Cell 45: 711–719 (1986)). Among the G protein-coupled receptors that have been identified and cloned are the substance P receptor, the angiotensin receptor, the alpha- and beta-adrenergic receptors and the serotonin receptors. G protein-coupled receptors share a conserved structural motif. The general and common structural features of the G protein-coupled receptors are the existence of seven hydrophobic stretches of about 20–25 amino acids each surrounded by eight hydrophilic regions of variable length. It has been postulated that each of the seven hydrophobic regions forms a transmembrane alpha helix and the intervening hydrophilic regions form alternately intracellularly and extracellularly exposed loops. The third cytosolic loop between transmembrane domains five and six is the intracellular domain responsible for the interaction with G proteins.

G protein-coupled receptors are known to be inducible. This inducibility was originally described in lower eukaryotes. For example, the cAMP receptor of the cellular slime mold, Dictyostelium, is induced during differentiation (Klein et al., Science 241: 1467–1472 (1988). During the Dictyostelium discoideum differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R. A., et al. Cell 58: 235–239 (1989) and Devreotes, P., Science 245: 1054–1058 (1989)).

Definitions

For convenience, certain terms employed in the specification, examples, and appended claims are collected here.

The abbreviation "CNS" refers to the central nervous system of an organism.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The terms "inverse agonist" and "negative antagonist" refer to compounds that are selective ligands for an inactive form of a cellular receptor which exists as an equilibrating mixture of active and inactive forms.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhiydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran., isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

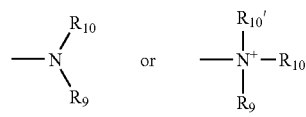

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

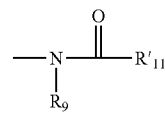

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

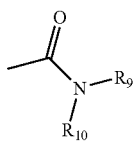

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

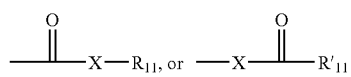

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

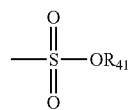

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

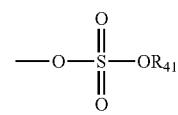

in which $R_{41}$ is as defined above.

The term "sulfonamido" is art recognized and includes a moiety that can be represented by the general formula:

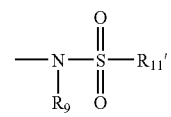

in which $R_9$ and $R'_{11}$ are as defined above.

The term "sulfamoyl" is art-recognized and includes a moiety that can be represented by the general formula:

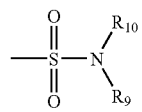

in which $R_9$ and $R_{10}$ are as defined above.

The term "sulfonyl", as used herein, refers to a moiety that can be represented by the general formula:

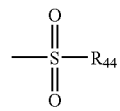

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

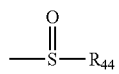

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

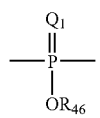

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

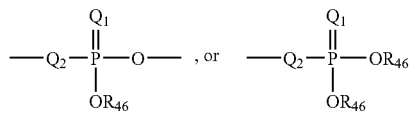

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds of the Invention.

In certain embodiments, the compounds of the present invention are represented by A:

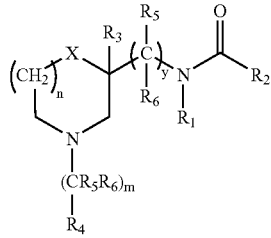

wherein
 m is 1, 2, 3 or 4;
 n is 1 or 2;
 y is 1, or 2;
 $R_1$ represents alkyl, aryl, heteroaryl, or cycloalkyl;
 $R_2$ represents independently for each occurrence H, alkyl, fluoroalkyl, aryl, heteroaryl, or cycloalkyl;
 $R_1$ and $R_2$ may be connected through a covalent bond;
 $R_3$ represents independently for each occurrence H, alkyl, aryl, $OR_2$, $OC(O)R_2$, $CH_2OR_2$, or $CO_2R_2$; wherein any two instances of $R_3$ may be connected by a covalent tether whose backbone consists of 1, 2, 3, or 4 carbon atoms;
 $R_4$ represents independently for each occurrence H, alkyl, aryl, heteroaryl, alkenyl, or cycloalkyl;
 $R_5$ represents independently for each occurrence H, alkyl, $CH_2Y$, aryl, heteroaryl, F, $OR_2$, or $OC(O)R_2$;
 $R_6$ represents independently for each occurrence H, alkyl, $CH_2Y$, aryl, heteroaryl, F, $OR_2$, or $OC(O)R_2$;
 Y represents independently for each occurrence $OR_2$, $N(R_2)_2$, $SR_2$, $S(O)R_2$, $S(O)_2R_2$, or $P(O)(OR_2)_2$;
 a covalent bond may connect $R_4$ and an instance of $R_5$ or $R_6$ that is attached to the carbon chain between $R_4$ and the ring nitrogen explicitly shown in A;
 any two geminal or vicinal instances of $R_5$ and $R_6$ may be connected through a covalent bond;
 X represents $C(R_3)_2$, O, S, SO, $SO_2$, $NR_2$, $NC(O)OR_2$, or C=O; and
 the stereochemical configuration at any stereocenter of a compound represented by A is R, S, or a mixture of these configurations.

In certain embodiments, the compounds of the present invention are represented by A and the attendant definitions, wherein X is $C(R_3)_2$, O, $NR_2$, or C=O.

In certain embodiments, the compounds of the present invention are represented by A and the attendant definitions, wherein X is $C(R_3)_2$, O, or $NR_2$.

In certain embodiments, the compounds of the present invention are represented by A and the attendant definitions, wherein X is $C(R_3)_2$.

In certain embodiments, the compounds of the present invention are represented by A and the attendant definitions, wherein m is 2 or 3.

In certain embodiments, the compounds of the present invention are represented by A and the attendant definitions, wherein n is 1.

In certain embodiments, the compounds of the present invention are represented by A and the attendant definitions, wherein y is 1.

In certain embodiments, the compounds of the present invention are represented by A and the attendant definitions, wherein $R_1$ represents aryl or heteroaryl.

In certain embodiments, the compounds of the present invention are represented by A and the attendant definitions, wherein $R_2$ represents independently for each occurrence alkyl.

In certain embodiments, the compounds of the present invention are represented by A and the attendant definitions, wherein $R_3$ represents independently for each occurrence H or alkyl.

In certain embodiments, the compounds of the present invention are represented by A and the attendant definitions, wherein $R_4$ represents cycloalkyl, aryl, or heteroaryl.

In certain embodiments, the compounds of the present invention are represented by A and the attendant definitions, wherein $R_5$ represents independently for each occurrence H, alkyl, aryl, heteroaryl, or F.

In certain embodiments, the compounds of the present invention are represented by A and the attendant definitions, wherein $R_6$ represents independently for each occurrence H, alkyl, aryl, heteroaryl, or F.

In certain embodiments, the compounds of the present invention are represented by A and the attendant definitions, wherein X is $C(R_3)_2$, O, $NR_2$, or C=O; and n is 1.

In certain embodiments, the compounds of the present invention are represented by A and the attendant definitions, wherein X is $C(R_3)_2$, O, or $NR_2$; and n is 1.

In certain embodiments, the compounds of the present invention are represented by A and the attendant definitions, wherein X is $C(R_3)_2$; and n is 1.

In certain embodiments, the compounds of the present invention are represented by A and the attendant definitions, wherein X is $C(R_3)_2$, O, $NR_2$, or C=O; and y is 1.

In certain embodiments, the compounds of the present invention are represented by A and the attendant definitions, wherein X is $C(R_3)_2$, O, or $NR_2$; and y is 1.

In certain embodiments, the compounds of the present invention are represented by A and the attendant definitions, wherein X is $C(R_3)_2$; and y is 1.

In certain embodiments, the compounds of the present invention are represented by A and the attendant definitions, wherein X is $C(R_3)_2$, O, $NR_2$, or C=O; and $R_1$ represents aryl or heteroaryl.

In certain embodiments, the compounds of the present invention are represented by A and the attendant definitions, wherein X is $C(R_3)_2$, O, or $NR_2$; and $R_1$ represents aryl or heteroaryl.

In certain embodiments, the compounds of the present invention are represented by A and the attendant definitions, wherein X is $C(R_3)_2$; and $R_1$ represents aryl or heteroaryl.

In certain embodiments, the compounds of the present invention are represented by A and the attendant definitions, wherein X is $C(R_3)_2$, O, $NR_2$, or C=O; and $R_2$ represents independently for each occurrence alkyl.

In certain embodiments, the compounds of the present invention are represented by A and the attendant definitions, wherein X is $C(R_3)_2$, O, or $NR_2$; and $R_2$ represents independently for each occurrence alkyl.

In certain embodiments, the compounds of the present invention are represented by A and the attendant definitions, wherein X is $C(R_3)_2$; and $R_2$ represents independently for each occurrence alkyl.

In certain embodiments, the compounds of the present invention are represented by A and the attendant definitions, wherein X is $C(R_3)_2$, O, $NR_2$, or C=O; n is 1; and $R_1$ represents aryl or heteroaryl.

In certain embodiments, the compounds of the present invention are represented by A and the attendant definitions, wherein X is $C(R_3)_2$, O, or $NR_2$; n is 1; and $R_1$ represents aryl or heteroaryl.

In certain embodiments, the compounds of the present invention are represented by A and the attendant definitions, wherein X is $C(R_3)_2$; n is 1; and $R_1$ represents aryl or heteroaryl.

In certain embodiments, the compounds of the present invention are represented by A and the attendant definitions, wherein X is $C(R_3)_2$, O, $NR_2$, or C=O; n is 1; $R_1$ represents aryl or heteroaryl; and $R_2$ represents independently for each occurrence alkyl.

In certain embodiments, the compounds of the present invention are represented by A and the attendant definitions, wherein X is $C(R_3)_2$, O, or $NR_2$; n is 1; $R_1$ represents aryl or heteroaryl; and $R_2$ represents independently for each occurrence alkyl.

In certain embodiments, the compounds of the present invention are represented by A and the attendant definitions, wherein X is $C(R_3)_2$; n is 1; $R_1$ represents aryl or heteroaryl; and $R_2$ represents independently for each occurrence alkyl.

In certain embodiments, the compounds of the present invention are represented by A and the attendant definitions, wherein X is $C(R_3)_2$, O, $NR_2$, or C=O; n is 1; $R_1$ represents aryl or heteroaryl; $R_2$ represents independently for each occurrence alkyl; and $R_3$ represents independently for each occurrence H or alkyl.

In certain embodiments, the compounds of the present invention are represented by A and the attendant definitions, wherein X is $C(R_3)_2$, O, or $NR_2$; n is 1; $R_1$ represents aryl or heteroaryl; $R_2$ represents independently for each occurrence alkyl; and $R_3$ represents independently for each occurrence H or alkyl.

In certain embodiments, the compounds of the present invention are represented by A and the attendant definitions, wherein X is $C(R_3)_2$; n is 1; $R_1$ represents aryl or heteroaryl; $R_2$ represents independently for each occurrence alkyl; and $R_3$ represents independently for each occurrence H or alkyl.

In certain embodiments, the compounds of the present invention are represented by A and the attendant definitions, wherein X is $C(R_3)_2$, O, $NR_2$, or C=O; n is 1; $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by A and the attendant definitions, wherein X is $C(R_3)_2$, O, or $NR_2$; n is 1; $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by A and the attendant definitions, wherein X is $C(R_3)_2$; n is 1; $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by A and the attendant definitions, wherein X is $C(R_3)_2$, O, $NR_2$, or C=O; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and $R_5$ represents independently for each occurrence H, alkyl, aryl, heteroaryl, or F.

In certain embodiments, the compounds of the present invention are represented by A and the attendant definitions, wherein X is $C(R_3)_2$, O, or $NR_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and R represents independently for each occurrence H, alkyl, aryl, heteroaryl, or F.

In certain embodiments, the compounds of the present invention are represented by A and the attendant definitions, wherein X is $C(R_3)_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and $R_5$ represents independently for each occurrence H, alkyl, aryl, heteroaryl, or F.

In certain embodiments, the compounds of the present invention are represented by A and the attendant definitions, wherein X is $C(R_3)_2$, O, $NR_2$, or C=O; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In certain embodiments, the compounds of the present invention are represented by A and the attendant definitions, wherein X is $C(R_3)_2$, O, or $NR_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In certain embodiments, the compounds of the present invention are represented by A and the attendant definitions, wherein X is $C(R_3)_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In certain embodiments, the compounds of the present invention are represented by A and the attendant definitions, wherein X is $C(R_3)_2$; m is 2; n is 1; $R_1$ represents aryl; $R_2$ represents independently for each occurrence alkyl; $R_3$ represents independently for each occurrence H; $R_4$ represents aryl; $R_5$ represents independently for each occurrence H or alkyl; and $R_6$ represents independently for each occurrence H or alkyl.

In assays based on opioid receptors from mammalian brain, certain compounds according to general structure A have $IC_{50}$ values less than 10 μM against at least one subclass of opioid receptor, more preferably less than 5 μM, and most preferably less than 1 μM.

In certain embodiments, the compounds of the present invention are represented by B:

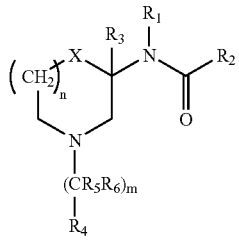

wherein
m is 1, 2, 3 or 4;
n is 1 or 2;
$R_1$ represents H, alkyl, aryl, heteroaryl, or cycloalkyl;
$R_2$ represents independently for each occurrence H, alkyl, fluoroalkyl, aryl, heteroaryl, or cycloalkyl;
$R_1$ and $R_2$ may be connected through a covalent bond;
$R_3$ represents independently for each occurrence H, alkyl, aryl, $OR_2$, $OC(O)R_2$, $CH_2OR_2$, or $CO_2R_2$; wherein any two instances of $R_3$ may be connected by a covalent tether whose backbone consists of 1, 2, 3, or 4 carbon atoms;
$R_4$ represents independently for each occurrence H, alkyl, aryl, heteroaryl, alkenyl, or cycloalkyl;
$R_5$ represents independently for each occurrence H, alkyl, $CH_2Y$, aryl, heteroaryl, F, $OR_2$, or $OC(O)R_2$;
$R_6$ represents independently for each occurrence H, alkyl, $CH_2Y$, aryl, heteroaryl, F, $OR_2$, or $OC(O)R_2$;
Y represents independently for each occurrence $OR_2$, $N(R_2)_2$, $SR_2$, $S(O)R_2$, $S(O)_2R_2$, or $P(O)(OR_2)_2$;
a covalent bond may connect $R_4$ and an instance of $R_5$ or $R_6$ that is attached to the carbon chain between $R_4$ and the ring nitrogen explicitly shown in B;
any two geminal or vicinal instances of $R_5$ and $R_6$ may be connected through a covalent bond;
X represents $C(R_3)_2$, O, S, SO, $SO_2$, $NR_2$, $NC(O)OR_2$, or C=O; and
the stereochemical configuration at any stereocenter of a compound represented by B is R or S.

In certain embodiments, the compounds of the present invention are represented by B and the attendant definitions, wherein X is $C(R_3)_2$, O, $NR_2$, or C=O.

In certain embodiments, the compounds of the present invention are represented by B and the attendant definitions, wherein X is $C(R_3)_2$, O, or $NR_2$.

In certain embodiments, the compounds of the present invention are represented by B and the attendant definitions, wherein X is $C(R_3)_2$.

In certain embodiments, the compounds of the present invention are represented by B and the attendant definitions, wherein m is 2 or 3.

In certain embodiments, the compounds of the present invention are represented by B and the attendant definitions, wherein n is 1.

In certain embodiments, the compounds of the present invention are represented by B and the attendant definitions, wherein $R_1$ represents aryl or heteroaryl.

In certain embodiments, the compounds of the present invention are represented by B and the attendant definitions, wherein $R_2$ represents independently for each occurrence alkyl.

In certain embodiments, the compounds of the present invention are represented by B and the attendant definitions, wherein $R_3$ represents independently for each occurrence H or alkyl.

In certain embodiments, the compounds of the present invention are represented by B and the attendant definitions, wherein $R_4$ represents cycloalkyl, aryl, or heteroaryl.

In certain embodiments, the compounds of the present invention are represented by B and the attendant definitions, wherein $R_5$ represents independently for each occurrence H, alkyl, aryl, heteroaryl, or F.

In certain embodiments, the compounds of the present invention are represented by B and the attendant definitions, wherein $R_6$ represents independently for each occurrence H, alkyl, aryl, heteroaryl, or F.

In certain embodiments, the compounds of the present invention are represented by B and the attendant definitions, wherein X is $C(R_3)_2$, O, $NR_2$, or C=O; and n is 1.

In certain embodiments, the compounds of the present invention are represented by B and the attendant definitions, wherein X is $C(R_3)_2$, O, or $NR_2$; and n is 1.

In certain embodiments, the compounds of the present invention are represented by B and the attendant definitions, wherein X is $C(R_3)_2$; and n is 1.

In certain embodiments, the compounds of the present invention are represented by B and the attendant definitions, wherein X is $C(R_3)_2$, O, $NR_2$, or C=O; and $R_1$ represents aryl or heteroaryl.

In certain embodiments, the compounds of the present invention are represented by B and the attendant definitions, wherein X is $C(R_3)_2$, O, or $NR_2$; and $R_1$ represents aryl or heteroaryl.

In certain embodiments, the compounds of the present invention are represented by B and the attendant definitions, wherein X is $C(R_3)_2$; and $R_1$ represents aryl or heteroaryl.

In certain embodiments, the compounds of the present invention are represented by B and the attendant definitions, wherein X is $C(R_3)_2$, O, $NR_2$, or C=O; and $R_2$ represents independently for each occurrence alkyl.

In certain embodiments, the compounds of the present invention are represented by B and the attendant definitions, wherein X is $C(R_3)_2$, O, or $NR_2$; and $R_2$ represents independently for each occurrence alkyl.

In certain embodiments, the compounds of the present invention are represented by B and the attendant definitions, wherein X is $C(R_3)_2$; and $R_2$ represents independently for each occurrence alkyl.

In certain embodiments, the compounds of the present invention are represented by B and the attendant definitions, wherein X is $C(R_3)_2$, O, $NR_2$, or C=O; n is 1; and $R_1$ represents aryl or heteroaryl.

In certain embodiments, the compounds of the present invention are represented by B and the attendant definitions, wherein X is $C(R_3)_2$, O, or $NR_2$; n is 1; and $R_1$ represents aryl or heteroaryl.

In certain embodiments, the compounds of the present invention are represented by B and the attendant definitions, wherein X is $C(R_3)_2$; n is 1; and $R_1$ represents aryl or heteroaryl.

In certain embodiments, the compounds of the present invention are represented by B and the attendant definitions, wherein X is $C(R_3)_2$, O, $NR_2$, or C=O; n is 1; $R_1$ represents aryl or heteroaryl; and $R_2$ represents independently for each occurrence alkyl.

In certain embodiments, the compounds of the present invention are represented by B and the attendant definitions, wherein X is C(R$_3$)$_2$, O, or NR$_2$; n is 1; R$_1$ represents aryl or heteroaryl; and R$_2$ represents independently for each occurrence alkyl.

In certain embodiments, the compounds of the present invention are represented by B and the attendant definitions, wherein X is C(R$_3$)$_2$; n is 1; R$_1$ represents aryl or heteroaryl; and R$_2$ represents independently for each occurrence alkyl.

In certain embodiments, the compounds of the present invention are represented by B and the attendant definitions, wherein X is C(R$_3$)$_2$, O, NR$_2$, or C=O; n is 1; R$_1$ represents aryl or heteroaryl; R$_2$ represents independently for each occurrence alkyl; and R$_3$ represents independently for each occurrence H or alkyl.

In certain embodiments, the compounds of the present invention are represented by B and the attendant definitions, wherein X is C(R$_3$)$_2$, O, or NR$_2$; n is 1; R$_1$ represents aryl or heteroaryl; R$_2$ represents independently for each occurrence alkyl; and R$_3$ represents independently for each occurrence H or alkyl.

In certain embodiments, the compounds of the present invention are represented by B and the attendant definitions, wherein X is C(R$_3$)$_2$; n is 1; R$_1$ represents aryl or heteroaryl; R$_2$ represents independently for each occurrence alkyl; and R$_3$ represents independently for each occurrence H or alkyl.

In certain embodiments, the compounds of the present invention are represented by B and the attendant definitions, wherein X is C(R$_3$)$_2$, O, NR$_2$, or C=O; n is 1; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

In certain embodiments, the compounds of the present invention are represented by B and the attendant definitions, wherein X is C(R$_3$)$_2$, O, or NR$_2$; n is 1; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

In certain embodiments, the compounds of the present invention are represented by B and the attendant definitions, wherein X is C(R$_3$)$_2$; n is 1; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

In certain embodiments, the compounds of the present invention are represented by B and the attendant definitions, wherein X is C(R$_3$)$_2$, O, NR$_2$, or C=O; n is 1; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_5$ represents independently for each occurrence H, alkyl, aryl, heteroaryl, or F.

In certain embodiments, the compounds of the present invention are represented by B and the attendant definitions, wherein X is C(R$_3$)$_2$, O, or NR$_2$; n is 1; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_2$ represents independently for each occurrence H, alkyl, aryl, heteroaryl, or F.

In certain embodiments, the compounds of the present invention are represented by B and the attendant definitions, wherein X is C(R$_3$)$_2$; n is 1; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_5$ represents independently for each occurrence H, alkyl, aryl, heteroaryl, or F.

In certain embodiments, the compounds of the present invention are represented by B and the attendant definitions, wherein X is C(R$_3$)$_2$, O, NR$_2$, or C=O; n is 1; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; R$_5$ represents independently for each occurrence H, alkyl, aryl, heteroaryl, or F; and R$_6$ represents independently for each occurrence H, alkyl, aryl, heteroaryl, or F.

In certain embodiments, the compounds of the present invention are represented by B and the attendant definitions, wherein X is C(R$_3$)$_2$, O, or NR$_2$; n is 1; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; R$_5$ represents independently for each occurrence H, alkyl, aryl, heteroaryl, or F; and R$_6$ represents independently for each occurrence H, alkyl, aryl, heteroaryl, or F.

In certain embodiments, the compounds of the present invention are represented by B and the attendant definitions, wherein X is C(R$_3$)$_2$; n is 1; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; R$_5$ represents independently for each occurrence H, alkyl, aryl, heteroaryl, or F; and R$_6$ represents independently for each occurrence H, alkyl, aryl, heteroaryl, or F.

In assays based on opioid receptors from mammalian brain, certain compounds according to general structure B have IC$_{50}$ values less than 10 μM against at least one subclass of opioid receptor, more preferably less than 5 μM, and most preferably less than 1 μM.

In certain embodiments, the compounds of the present invention are represented by C:

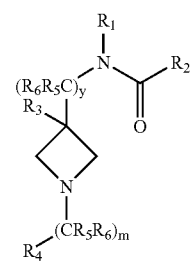

wherein
  m is 1, 2, 3 or 4;
  y is 0, 1 or 2;
  R$_1$ represents H, alkyl, aryl, heteroaryl, or cycloalkyl;
  R$_2$ represents independently for each occurrence H, alkyl, fluoroalkyl, aryl, heteroaryl, or cycloalkyl;
  R$_1$ and R$_2$ may be connected through a covalent bond;
  R$_3$ represents independently for each occurrence H, alkyl, aryl, OR$_2$, OC(O)R$_2$, CH$_2$OR$_2$, or CO$_2$R$_2$;
  R$_4$ represents H, alkyl, aryl, heteroaryl, alkenyl, or cycloalkyl;
  R$_5$ represents independently for each occurrence H, alkyl, CH$_2$Y, aryl, heteroaryl, F, OR$_2$, or OC(O)R$_2$;
  R$_6$ represents independently for each occurrence H, alkyl, CH$_2$Y, aryl, heteroaryl, F, OR$_2$, or OC(O)R$_2$;
  Y represents independently for each occurrence OR$_2$, N(R$_2$)$_2$, SR$_2$, S(O)R$_2$, S(O)$_2$R$_2$, or P(O)(OR$_2$)$_2$;

a covalent bond may connect $R_4$ and an instance of $R_5$ or $R_6$ that is attached to the carbon chain between $R_4$ and the ring nitrogen explicitly shown in C;

any two geminal or vicinal instances of $R_5$ and $R_6$ may be connected through a covalent bond; and the stereochemical configuration at any stereocenter of a compound represented by C is R, S, or a mixture of these configurations.

In certain embodiments, the compounds of the present invention are represented by C and the attendant definitions, wherein m is 2 or 3.

In certain embodiments, the compounds of the present invention are represented by C and the attendant definitions, wherein y is 1.

In certain embodiments, the compounds of the present invention are represented by C and the attendant definitions, wherein $R_1$ represents aryl or heteroaryl.

In certain embodiments, the compounds of the present invention are represented by C and the attendant definitions, wherein $R_2$ represents independently for each occurrence alkyl.

In certain embodiments, the compounds of the present invention are represented by C and the attendant definitions, wherein $R_3$ represents independently for each occurrence H or alkyl.

In certain embodiments, the compounds of the present invention are represented by C and the attendant definitions, wherein $R_4$ represents cycloalkyl, aryl, or heteroaryl.

In certain embodiments, the compounds of the present invention are represented by C and the attendant definitions, wherein R, represents independently for each occurrence H, alkyl, aryl, heteroaryl, or F.

In certain embodiments, the compounds of the present invention are represented by C and the attendant definitions, wherein R, represents independently for each occurrence H, alkyl, aryl, heteroaryl, or F.

In certain embodiments, the compounds of the present invention are represented by C and the attendant definitions, wherein $R_4$ represents aryl or heteroaryl; and $R_2$ represents independently for each occurrence alkyl.

In certain embodiments, the compounds of the present invention are represented by C and the attendant definitions, wherein $R_1$ represents aryl or heteroaryl; $R_2$ represents independently for each occurrence alkyl; and $R_3$ represents independently for each occurrence H or alkyl.

In certain embodiments, the compounds of the present invention are represented by C and the attendant definitions, wherein R, represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by C and the attendant definitions, wherein $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and $R_5$ represents independently for each occurrence H, alkyl, aryl, heteroaryl, or F.

In certain embodiments, the compounds of the present invention are represented by C and the attendant definitions, wherein $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In assays based on opioid receptors from mammalian brain, certain compounds according to general structure C have $IC_{50}$ values less than 10 μM against at least one subclass of opioid receptor, more preferably less than 5 μM, and most preferably less than 1 μM.

In certain embodiments, the compounds of the present invention are represented by D:

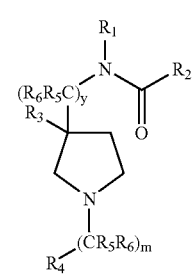

wherein
m is 1, 2, 3 or 4;
y is 0, 1 or 2;
$R_1$ represents H, alkyl, aryl, heteroaryl, or cycloalkyl;
$R_2$ represents independently for each occurrence H, alkyl, fluoroalkyl, aryl, heteroaryl, or cycloalkyl;
$R_1$ and $R_2$ may be connected through a covalent bond;
$R_3$ represents independently for each occurrence H, alkyl, aryl, $OR_2$, $OC(O)R_2$, $CH_2OR_2$, or $CO_2R_2$;
$R_4$ represents H, alkyl, aryl, heteroaryl, alkenyl, or cycloalkyl;
$R_5$ represents independently for each occurrence H, alkyl, $CH_2Y$, aryl, heteroaryl, F, $OR_2$, or $OC(O)R_2$;
$R_6$ represents independently for each occurrence H, alkyl, $CH_2Y$, aryl, heteroaryl, F, $OR_2$, or $OC(O)R_2$;
Y represents independently for each occurrence $OR_2$, $N(R_2)_2$, $SR_2$, $S(O)R_2$, $S(O)_2R_2$, or $P(O)(OR_2)_2$;
a covalent bond may connect $R_4$ and an instance of $R_5$ or $R_6$ that is attached to the carbon chain between $R_4$ and the ring nitrogen explicitly shown in D;
any two geminal or vicinal instances of $R_5$ and $R_6$ may be connected through a covalent bond; and
the stereochemical configuration at any stereocenter of a compound represented by D is R or S.

In certain embodiments, the compounds of the present invention are represented by D and the attendant definitions, wherein m is 2 or 3.

In certain embodiments, the compounds of the present invention are represented by D and the attendant definitions, wherein y is 1.

In certain embodiments, the compounds of the present invention are represented by D and the attendant definitions, wherein $R_1$ represents aryl or heteroaryl.

In certain embodiments, the compounds of the present invention are represented by D and the attendant definitions, wherein $R_2$ represents independently for each occurrence alkyl.

In certain embodiments, the compounds of the present invention are represented by D and the attendant definitions, wherein $R_3$ represents independently for each occurrence H or alkyl.

In certain embodiments, the compounds of the present invention are represented by D and the attendant definitions, wherein $R_4$ represents cycloalkyl, aryl, or heteroaryl.

In certain embodiments, the compounds of the present invention are represented by D and the attendant definitions, wherein $R_5$ represents independently for each occurrence H, alkyl, aryl, heteroaryl, or F.

In certain embodiments, the compounds of the present invention are represented by D and the attendant definitions, wherein $R_6$ represents independently for each occurrence H, alkyl, aryl, heteroaryl, or F.

In certain embodiments, the compounds of the present invention are represented by D and the attendant definitions, wherein $R_1$ represents aryl or heteroaryl; and $R_2$ represents independently for each occurrence alkyl.

In certain embodiments, the compounds of the present invention are represented by D and the attendant definitions, wherein $R_1$ represents aryl or heteroaryl; $R_2$ represents independently for each occurrence alkyl; and $R_3$ represents independently for each occurrence H or alkyl.

In certain embodiments, the compounds of the present invention are represented by D and the attendant definitions, wherein $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by D and the attendant definitions, wherein $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and $R_5$ represents independently for each occurrence H, alkyl, aryl, heteroaryl, or F.

In certain embodiments, the compounds of the present invention are represented by D and the attendant definitions, wherein $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In assays based on opioid receptors from mammalian brain, certain compounds according to general structure D have $IC_{50}$ values less than 10 μM against at least one subclass of opioid receptor, more preferably less than 5 μM, and most preferably less than 1 μM.

In certain embodiments, the compounds of the present invention are represented by E:

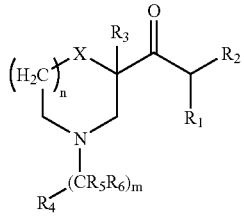

wherein
m is 1, 2, 3 or 4;
n is 1 or 2;
$R_1$ represents H, alkyl, aryl, heteroaryl, or cycloalkyl;
$R_2$ represents independently for each occurrence H, alkyl, fluoroalkyl, aryl, heteroaryl, or cycloalkyl;
$R_1$ and $R_2$ may be connected through a covalent bond;

$R_3$ represents independently for each occurrence H, alkyl, aryl, $OR_2$, $OC(O)R_2$, $CH_2OR_2$, or $CO_2R_2$; wherein any two instances of $R_3$ may be connected by a covalent tether whose backbone consists of 1, 2, 3, or 4 carbon atoms;

$R_4$ represents H, alkyl, aryl, heteroaryl, alkenyl, or cycloalkyl;

$R_5$ represents independently for each occurrence H, alkyl, $CH_2Y$, aryl, heteroaryl, F, $OR_2$, or $OC(O)R_2$;

$R_6$ represents independently for each occurrence H, alkyl, $CH_2Y$, aryl, heteroaryl, F, $OR_2$, or $OC(O)R_2$;

Y represents independently for each occurrence $OR_2$, $N(R_2)_2$, $SR_2$, $S(O)R_2$, $S(O)_2R_2$, or $P(O)(OR_2)_2$;

a covalent bond may connect $R_4$ and an instance of $R_5$ or $R_6$ that is attached to the carbon chain between $R_4$ and the ring nitrogen explicitly shown in E;

any two geminal or vicinal instances of $R_5$ and $R_6$ may be connected through a covalent bond;

X represents $C(R_3)_2$, O, S, SO, $SO_2$, $NR_2$, $NC(O)OR_2$, or C=O; and the stereochemical configuration at any stereocenter of a compound represented by E is R, S, or a mixture of these configurations.

In certain embodiments, the compounds of the present invention are represented by E and the attendant definitions, wherein X is $C(R_3)_2$, O, $NR_2$, or C=O.

In certain embodiments, the compounds of the present invention are represented by E and the attendant definitions, wherein X is $C(R_3)_2$, O, or $NR_2$.

In certain embodiments, the compounds of the present invention are represented by E and the attendant definitions, wherein X is $C(R_3)_2$.

In certain embodiments, the compounds of the present invention are represented by E and the attendant definitions, wherein m is 2 or 3.

In certain embodiments, the compounds of the present invention are represented by E and the attendant definitions, wherein n is 1.

In certain embodiments, the compounds of the present invention are represented by E and the attendant definitions, wherein $R_1$ represents aryl or heteroaryl.

In certain embodiments, the compounds of the present invention are represented by E and the attendant definitions, wherein $R_2$ represents independently for each occurrence alkyl.

In certain embodiments, the compounds of the present invention are represented by E and the attendant definitions, wherein $R_3$ represents independently for each occurrence H or alkyl.

In certain embodiments, the compounds of the present invention are represented by E and the attendant definitions, wherein $R_4$ represents cycloalkyl, aryl, or heteroaryl.

In certain embodiments, the compounds of the present invention are represented by E and the attendant definitions, wherein $R_5$ represents independently for each occurrence H, alkyl, aryl, heteroaryl, or F.

In certain embodiments, the compounds of the present invention are represented by E and the attendant definitions, wherein R represents independently for each occurrence H, alkyl, aryl, heteroaryl, or F.

In certain embodiments, the compounds of the present invention are represented by E and the attendant definitions, wherein X is $C(R_3)_2$, O, $NR_2$, or C=O; and n is 1.

In certain embodiments, the compounds of the present invention are represented by E and the attendant definitions, wherein X is $C(R_3)_2$, O, or $NR_2$; and n is 1.

In certain embodiments, the compounds of the present invention are represented by E and the attendant definitions, wherein X is $C(R_3)_2$; and n is 1.

In certain embodiments, the compounds of the present invention are represented by E and the attendant definitions, wherein X is $C(R_3)_2$, O, $NR_2$, or C=O; and $R_1$ represents aryl or heteroaryl.

In certain embodiments, the compounds of the present invention are represented by E and the attendant definitions, wherein X is $C(R_3)_2$, O, or $NR_2$; and $R_1$ represents aryl or heteroaryl.

In certain embodiments, the compounds of the present invention are represented by E and the attendant definitions, wherein X is $C(R_3)_2$; and $R_1$ represents aryl or heteroaryl.

In certain embodiments, the compounds of the present invention are represented by E and the attendant definitions, wherein X is $C(R_3)_2$, O, $NR_2$, or C=O; and $R_2$ represents independently for each occurrence alkyl.

In certain embodiments, the compounds of the present invention are represented by E and the attendant definitions, wherein X is $C(R_3)_2$, O, or $NR_2$; and $R_2$ represents independently for each occurrence alkyl.

In certain embodiments, the compounds of the present invention are represented by E and the attendant definitions, wherein X is $C(R_3)_2$; and $R_2$ represents independently for each occurrence alkyl.

In certain embodiments, the compounds of the present invention are represented by E and the attendant definitions, wherein X is $C(R_3)_2$, O, $NR_2$, or C=O; n is 1; and $R_1$ represents aryl or heteroaryl.

In certain embodiments, the compounds of the present invention are represented by E and the attendant definitions, wherein X is $C(R_3)_2$, O, or $NR_2$; n is 1; and $R_1$ represents aryl or heteroaryl.

In certain embodiments, the compounds of the present invention are represented by E and the attendant definitions, wherein X is $C(R_3)_2$; n is 1; and $R_1$ represents aryl or heteroaryl.

In certain embodiments, the compounds of the present invention are represented by E and the attendant definitions, wherein X is $C(R_3)_2$, O, $NR_2$, or C=O; n is 1; $R_1$ represents aryl or heteroaryl; and $R_2$ represents independently for each occurrence alkyl.

In certain embodiments, the compounds of the present invention are represented by E and the attendant definitions, wherein X is $C(R_3)_2$, O, or $NR_2$; n is 1; $R_1$ represents aryl or heteroaryl; and $R_2$ represents independently for each occurrence alkyl.

In certain embodiments, the compounds of the present invention are represented by E and the attendant definitions, wherein X is $C(R_3)_2$; n is 1; $R_1$ represents aryl or heteroaryl; and $R_2$ represents independently for each occurrence alkyl.

In certain embodiments, the compounds of the present invention are represented by E and the attendant definitions, wherein X is $C(R_3)_2$, O, $NR_2$, or C=O; n is 1; $R_1$ represents aryl or heteroaryl; $R_2$ represents independently for each occurrence alkyl; and $R_3$ represents independently for each occurrence H or alkyl.

In certain embodiments, the compounds of the present invention are represented by E and the attendant definitions, wherein X is $C(R_3)_2$, O, or $NR_2$; n is 1; $R_1$ represents aryl or heteroaryl; $R_2$ represents independently for each occurrence alkyl; and $R_3$ represents independently for each occurrence H or alkyl.

In certain embodiments, the compounds of the present invention are represented by E and the attendant definitions, wherein X is $C(R_3)_2$; n is 1; $R_1$ represents aryl or heteroaryl; $R_2$ represents independently for each occurrence alkyl; and $R_3$ represents independently for each occurrence H or alkyl.

In certain embodiments, the compounds of the present invention are represented by E and the attendant definitions, wherein X is $C(R_3)_2$, O, $NR_2$, or C=O; n is 1; $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by E and the attendant definitions, wherein X is $C(R_3)_2$, O, or $NR_2$; n is 1; $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by E and the attendant definitions, wherein X is $C(R_3)_2$; n is 1; $R_1$ represents aryl or heteroaryl; $R_2$ represents independently for each occurrence alkyl; $R_3$ represents independently for each occurrence H or alkyl; and $R_4$ represents cycloalkyl, aryl, or heteroaryl.

In certain embodiments, the compounds of the present invention are represented by E and the attendant definitions, wherein X is $C(R_3)_2$, O, $NR_2$, or C=O; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and R represents independently for each occurrence H, alkyl, aryl, heteroaryl, or F.

In certain embodiments, the compounds of the present invention are represented by E and the attendant definitions, wherein X is $C(R_3)_2$, O, or $NR_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and $R_5$ represents independently for each occurrence H, alkyl, aryl, heteroaryl, or F.

In certain embodiments, the compounds of the present invention are represented by E and the attendant definitions, wherein X is $C(R_3)_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; and $R_5$ represents independently for each occurrence H, alkyl, aryl, heteroaryl, or F.

In certain embodiments, the compounds of the present invention are represented by E and the attendant definitions, wherein X is $C(R_3)_2$, O, $NR_2$, or C=O; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In certain embodiments, the compounds of the present invention are represented by E and the attendant definitions, wherein X is $C(R_3)_2$, O, or $NR_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In certain embodiments, the compounds of the present invention are represented by E and the attendant definitions, wherein X is $C(R_3)_2$; n is 1; $R_1$ represents aryl or heteroaryl; $R_2$ represents independently for each occurrence alkyl; $R_3$ represents independently for each occurrence H or alkyl; $R_4$ represents cycloalkyl, aryl, or heteroaryl; $R_5$ represents independently for each occurrence H, alkyl, aryl, heteroaryl, or F; and $R_6$ represents independently for each occurrence H, alkyl, aryl, heteroaryl, or F.

In assays based on opioid receptors from mammalian brain, certain compounds according to general structure E have $IC_{50}$ values less than 10 µM against at least one subclass of opioid receptor, more preferably less than 5 µM, and most preferably less than 1 µM.

In certain embodiments, the compounds of the present invention are represented by F:

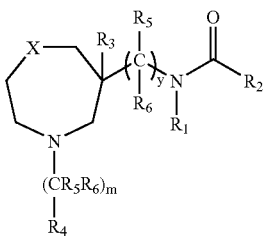

wherein m is 1, 2, 3 or 4;

y is 0, 1, or 2;

$R_1$ represents H, alkyl, aryl, heteroaryl, or cycloalkyl;

$R_2$ represents independently for each occurrence H, alkyl, fluoroalkyl, aryl, heteroaryl, or cycloalkyl;

$R_1$ and $R_2$ may be connected through a covalent bond;

$R_3$ represents independently for each occurrence H, alkyl, aryl, $OR_2$, $OC(O)R_2$, $CH_2OR_2$, or $CO_2R_2$;

$R_4$ represents independently for each occurrence H, alkyl, aryl, heteroaryl, alkenyl, or cycloalkyl;

$R_5$ represents independently for each occurrence H, alkyl, $CH_2Y$, aryl, heteroaryl, F, $OR_2$, or $OC(O)R_2$;

$R_6$ represents independently for each occurrence H, alkyl, $CH_2Y$, aryl, heteroaryl, F, $OR_2$, or $OC(O)R_2$;

Y represents independently for each occurrence $OR_2$, $N(R_2)_2$, $SR_2$, $S(O)R_2$, $S(O)_2R_2$, or $P(O)(OR_2)_2$;

a covalent bond may connect $R_4$ and an instance of $R_5$ or $R_6$ that is attached to the carbon chain between $R_4$ and the ring nitrogen explicitly shown in F;

any two geminal or vicinal instances of $R_5$ and $R_6$ may be connected through a covalent bond;

X represents O, S, SO, $SO_2$, $NR_2$, $NC(O)OR_2$, or C=O; and the stereochemical configuration at any stereocenter of a compound represented by F is R, S, or a mixture of these configurations.

In certain embodiments, the compounds of the present invention are represented by F and the attendant definitions, wherein X is O, $NR_2$, or C=O.

In certain embodiments, the compounds of the present invention are represented by F and the attendant definitions, wherein X is O or $NR_2$.

In certain embodiments, the compounds of the present invention are represented by F and the attendant definitions, wherein X is $NR_2$.

In certain embodiments, the compounds of the present invention are represented by F and the attendant definitions, wherein m is 2 or 3.

In certain embodiments, the compounds of the present invention are represented by F and the attendant definitions, wherein y is 1.

In certain embodiments, the compounds of the present invention are represented by F and the attendant definitions, wherein $R_1$ represents aryl or heteroaryl.

In certain embodiments, the compounds of the present invention are represented by F and the attendant definitions, wherein $R_2$ represents independently for each occurrence alkyl.

In certain embodiments, the compounds of the present invention are represented by F and the attendant definitions, wherein $R_3$ represents independently for each occurrence H or alkyl.

In certain embodiments, the compounds of the present invention are represented by F and the attendant definitions, wherein $R_4$ represents cycloalkyl, aryl, or heteroaryl.

In certain embodiments, the compounds of the present invention are represented by F and the attendant definitions, wherein $R_5$ represents independently for each occurrence H, alkyl, aryl, heteroaryl, or F.

In certain embodiments, the compounds of the present invention are represented by F and the attendant definitions, wherein $R_6$ represents independently for each occurrence H, alkyl, aryl, heteroaryl, or F.

In certain embodiments, the compounds of the present invention are represented by F and the attendant definitions, wherein X is O, $NR_2$, or C=O; and y is 1.

In certain embodiments, the compounds of the present invention are represented by F and the attendant definitions, wherein X is O or $NR_2$; and y is 1.

In certain embodiments, the compounds of the present invention are represented by F and the attendant definitions, wherein X is $NR_2$; and y is 1.

In certain embodiments, the compounds of the present invention are represented by F and the attendant definitions, wherein X is O, $NR_2$, or C=O; and $R_1$ represents aryl or heteroaryl.

In certain embodiments, the compounds of the present invention are represented by F and the attendant definitions, wherein X is O or $NR_2$; and $R_1$ represents aryl or heteroaryl.

In certain embodiments, the compounds of the present invention are represented by F and the attendant definitions, wherein X is $NR_2$; and $R_1$ represents aryl or heteroaryl.

In certain embodiments, the compounds of the present invention are represented by F and the attendant definitions, wherein X is O, $NR_2$, or C=O; and $R_2$ represents independently for each occurrence alkyl.

In certain embodiments, the compounds of the present invention are represented by F and the attendant definitions, wherein X is O or $NR_2$; and $R_2$ represents independently for each occurrence alkyl.

In certain embodiments, the compounds of the present invention are represented by F and the attendant definitions, wherein X is $NR_2$; and $R_2$ represents independently for each occurrence alkyl.

In certain embodiments, the compounds of the present invention are represented by F and the attendant definitions, wherein X is O, $NR_2$, or C=O; $R_1$ represents aryl or heteroaryl; and $R_2$ represents independently for each occurrence alkyl.

In certain embodiments, the compounds of the present invention are represented by F and the attendant definitions, wherein X is O or $NR_2$; $R_1$ represents aryl or heteroaryl; and $R_2$ represents independently for each occurrence alkyl.

In certain embodiments, the compounds of the present invention are represented by F and the attendant definitions, wherein X is NR$_2$; R$_1$ represents aryl or heteroaryl; and R$_2$ represents independently for each occurrence alkyl.

In certain embodiments, the compounds of the present invention are represented by F and the attendant definitions, wherein X is O, NR$_2$, or C=O; R$_1$ represents aryl or heteroaryl; R$_2$ represents independently for each occurrence alkyl; and R$_3$ represents independently for each occurrence H or alkyl.

In certain embodiments, the compounds of the present invention are represented by F and the attendant definitions, wherein X is O or NR$_2$; R$_1$ represents aryl or heteroaryl; R$_2$ represents independently for each occurrence alkyl; and R$_3$ represents independently for each occurrence H or alkyl.

In certain embodiments, the compounds of the present invention are represented by F and the attendant definitions, wherein X is NR$_2$; R$_1$ represents aryl or heteroaryl; R$_2$ represents independently for each occurrence alkyl; and R$_3$ represents independently for each occurrence H or alkyl.

In certain embodiments, the compounds of the present invention are represented by F and the attendant definitions, wherein X is O, NR$_2$, or C=O; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

In certain embodiments, the compounds of the present invention are represented by F and the attendant definitions, wherein X is O or NR$_2$; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

In certain embodiments, the compounds of the present invention are represented by F and the attendant definitions, wherein X is NR$_2$; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

In certain embodiments, the compounds of the present invention are represented by F and the attendant definitions, wherein X is O, NR$_2$, or C=O; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_5$ represents independently for each occurrence H, alkyl, aryl, heteroaryl, or F.

In certain embodiments, the compounds of the present invention are represented by F and the attendant definitions, wherein X is O or NR$_2$; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_5$ represents independently for each occurrence H, alkyl, aryl, heteroaryl, or F.

In certain embodiments, the compounds of the present invention are represented by F and the attendant definitions, wherein X is NR$_2$; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_5$ represents independently for each occurrence H, alkyl, aryl, heteroaryl, or F.

In certain embodiments, the compounds of the present invention are represented by F and the attendant definitions, wherein X is O, NR$_2$, or C=O; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; R$_5$ represents independently for each occurrence H, alkyl, aryl, heteroaryl, or F; and R$_6$ represents independently for each occurrence H, alkyl, aryl, heteroaryl, or F.

In certain embodiments, the compounds of the present invention are represented by F and the attendant definitions, wherein X is O or NR$_2$; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; R$_5$ represents independently for each occurrence H, alkyl, aryl, heteroaryl, or F; and R$_6$ represents independently for each occurrence H, alkyl, aryl, heteroaryl, or F.

In certain embodiments, the compounds of the present invention are represented by F and the attendant definitions, wherein X is NR$_2$; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; R$_5$ represents independently for each occurrence H, alkyl, aryl, heteroaryl, or F; and R$_6$ represents independently for each occurrence H, alkyl, aryl, heteroaryl or F.

In assays based on opioid receptors from mammalian brain, certain compounds according to general structure F have IC$_{50}$ values less than 10 µM against at least one subclass of opioid receptor, more preferably less than 5 µM, and most preferably less than 1 µM.

In certain embodiments, the present invention relates to a compound represented by A, C, E, or F and the corresponding attendant defintions, wherein said compound is a single stereoisomer.

In certain embodiments, the present invention relates to a formulation, comprising a compound represented by A, B, C, D, E, or F and the corresponding attendant defintions; and a pharmaceutically acceptable excipient.

In certain embodiments, the present invention relates to a method of treating pain, drug addiction, or tinnitus in a mammal, comprising the step of administering to a mammal with pain, drug addiction, or tinnitus an effective amount of a formulation comprising a compound represented by A, B, C, D, E, or F and the corresponding attendant defintions; and a pharmaceutically acceptable excipient. In certain embodiments of this method, said mammal is a primate, equine, canine or feline. In certain embodiments of this method, said mammal is a human. In certain embodiments of this method, said formulation is administered orally. In certain embodiments of this method, said formulation is administered intravenously. In certain embodiments of this method, said formulation is administered sublingually. In certain embodiments of this method, said formulation is administered ocularly.

In certain embodiments, the present invention relates to ligands for G-protein-coupled or opioid receptors, wherein the ligands are represented by any of generalized structures A, B, C, D, E and F, and any of the sets of definitions associated with one of those structures. Preferably the ligands of the present invention are antagonists, agonists, partial agonists or inverse agonists of one or more G-protein-coupled or opioid receptor. In any event, the ligands of the present invention preferably exert their effect on the receptors at a concentration less than about 10 micromolar, more preferably at a concentration less than about 1 micromolar, and most preferably at a concentration less than 100 nanomolar. In other embodiments, the ligands of the present invention bind to multiple families of G-protein-coupled receptors. In certain embodiments, the ligands of the present invention bind selectively to a single family of G-protein-coupled or opioid receptors. In other embodiments, the ligands of the present invention bind selectively to a subtype of receptor within a family of G-protein-coupled or opioid receptors.

In certain embodiments, the selectivity of a ligand for a specific family or subtype of receptor renders that ligand an effective therapeutic agent for an acute or chronic ailment, disease or malady. In certain embodiments, the selectivity of a ligand for a specific family or subtype of receptor consists of a binding affinity for that family or subtype of receptor at least a factor of ten greater than its binding affinity for other families or subtypes of G-protein-coupled or opioid receptors. In certain embodiments, the selectivity of a ligand for a specific family or subtype of receptor consists of a binding affinity for that family or subtype of receptor at least a factor of one hundred greater than its binding affinity for other families or subtypes of G-protein-coupled or opioid receptors. In certain embodiments, the selectivity of a ligand for a specific family or subtype of receptor consists of a binding affinity for that family or subtype of receptor at least a factor of one thousand greater than its binding affinity for other families or subtypes of G-protein-coupled or opioid receptors.

The present invention contemplates pharmaceutical formulations (see below) of the ligands of the present invention. In certain embodiments, the pharmaceutical formulations will comprise ligands of the present invention that effect only a specific family or subtype of G-protein-coupled or opioid receptor, and thereby have a therapeutic effect on an acute or chronic ailment, disease or malady that is at least in part due to biochemical or physiological processes associated with the receptor(s). In certain embodiments, the pharmaceutical formulations will comprise ligands of the present invention that effect only a subtype of receptor, and thereby have a therapeutic effect on an acute or chronic ailment, disease or malady that is at least in part due to biochemical or physiological processes associated with the specific subtype of receptor. The Background of the Invention (see above) teaches examples of acute or chronic ailments, diseases or maladies that are caused or exacerbated by biochemical or physiological processes associated with specific G-protein-coupled or opioid receptors. One of ordinary skill in the art will be able to accumulate, by reference to the scientific literature, a more comprehensive list of acute or chronic ailments, diseases or maladies that are caused or exacerbated by biochemical or physiological processes associated with specific G-protein-coupled or opioid receptors. The present invention contemplates pharmaceutical formulations of ligands of the present invention that will be of medicinal value against the aforementioned acute or chronic ailments, diseases or maladies.

Biochemical Activity at Cellular Receptors, and Assays to Detect that Activity

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radioligand to a targeted receptor through the delineation of its total and nonspecific binding components. Total binding is defined as the amount of radioligand that remains following the rapid separation of the radioligand bound in a receptor preparation (cell homogenates or recombinate receptors) from that which is unbound. The nonspecific binding component is defined as the amount of radioligand that remains following separation of the reaction mixture consisting of receptor, radioligand and an excess of unlabeled ligand. Under this condition, the only radioligand that remains represents that which is bound to components other that receptor. The specific radioligand bound is determined by subtracting the nonspecific from total radioactivity bound. For a specific example of radioligand binding assay for µ-opioid receptor, see Wang, J. B. et al. *FEBS Letters* 1994, 338, 217.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315–21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and olfactory neuron channels [see, Altenhofen, W. et al. (1991) Proc. Natl. Acad. Sci U.S.A. 88:9868–9872 and Dhallan et al. (1990) Nature 347:184–187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes $Ca^{2+}$ as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<–>cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<–>and COS-7 cell lines, which express the Type I human muscarinic (HM1) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may used in the assay. The cell surface protein may endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403–410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330–334); the rat alpha 3 subunit (Boulter et al. (1986), Nature 319:368–374); the rat alpha 4 subunit (Goldman et al. (1987) cell 48:965–973); the rat alpha 5 subunit (Boulter et al. (1990) J. Biol. Chem. 265:4472–4482); the rat beta 2 subunit (Deneris et al. (1988) Neuron 1:45–54); the rat beta 3 subunit (Deneris et al. (1989) J. Biol. Chem. 264: 6268–6272); the rat beta 4 subunit (Duvoisin et al. (1989) Neuron 3:487–496); combinations of the rat alpha subunits, beta subunits and alpha and beta subunits; GABA receptors (e.g., the bovine alpha 1 and beta 1 subunits (Schofield et al. (1987) Nature 328:221–227); the bovine alpha 2 and alpha 3 subunits (Levitan et al. (1988) Nature 335:76–79); the gamma-subunit (Pritchett et al. (1989) Nature 338:582–585); the beta 2 and beta 3 subunits (Ymer et alo (1989) EMBO J. 8:1665–1670); the delta subunit (Shivers, B. D. (1989) Neuron 3:327–337); and the like); glutamate receptors (e.g., receptor isolated from rat brain (Hollmann et al. (1989) Nature 342:643–648); and the like); adrenergic receptors (e.g., human beta 1 (Frielle et al. (1987) Proc. Natl.

Acad. Sci. 84.:7920–7924); human alpha 2 (Kobilka et al. (1987) Science 238:650–656); hamster beta 2 (Dixon et al. (1986) Nature 321:75–79); and the like); dopamine receptors (e.g., human D2 (Stormann et al. (1990) Molec. Pharm.37:1–6); rat (Bunzow et al. (1988) Nature 336: 783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Reporter gene constructs are prepared by operatively linking a reporter gene with at least one transcriptional regulatory element. If only one transcriptional regulatory element is included it must be a regulatable promoter, At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements include, but are not limited to, promoters, enhancers, and repressor and activator binding sites, Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In Vivo Activity Assays

Various experimental procedures, well known in the art, are useful in the present invention to assess the analgesic effect of compounds, such as the "Wail flick" and "hot plate" tests. The "tail flick" test can be performed by applying a noxious thermal stimulus to the rat's tail and determining the time until the nociceptive tail flick occurs. Analgesia is demonstrated by an increase in time to occurrence of a tail flick response. The "hot plate" test is similarly performed, except that the noxious thermal stimulus is applied to the rat's paws.

An experimental procedure, well known in the art, useful in the present invention to assess the ability of compounds to cause respiratory depression is to monitor blood gases. This method employees measuring the partial pressures of oxygen and carbon dioxide in blood samples taken from animals following compound administration. A decrease in the partial pressures of oxygen and an increase in the partial pressure of carbon dioxide may be indicative of respiratory depression.

An experimental procedure, well known in the art, useful in the present invention to assess the ability of compounds to cause inhibition of gastrointestinal motility is the "charcoal meal test". This method measures the propulsion of intestinal contents following administration of test compounds. A decrease in the propulsion of intestinal contents may be indicative of inhibition of gastrointestinal motility.

Various experimental procedures, well known in the art, are useful in the present invention to assess the ability of compounds to cause tolerance. Tolerance can be defined as a condition characterized by unresponsiveness or decreased responsiveness following prolonged or multiple exposure to a compound compared to the responsiveness demonstrated upon initial exposure.

Various experimental procedures, well known in the art, are useful in the present invention to assess the ability of compounds to cause physical dependence. In the present invention, the ability of test compounds to cause physical dependence was accessed by giving animals escalating doses of test compounds for five days. After the final dose the animals were given naloxone, an opioid antagonist and observed for behavioral signs of dependence, such as vertical jumping.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3)

topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human. beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylnethyl cellulose in varying proportions to provide the desired release profile, other polymer matrices, liposomes and/or microspheres. They may be formulated for rapid release, e.g., freezedried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofliryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Properfluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ ($=823,543$) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

EXAMPLE 1

Synthesis of N-Boc-3-piperidinemethanol (2)

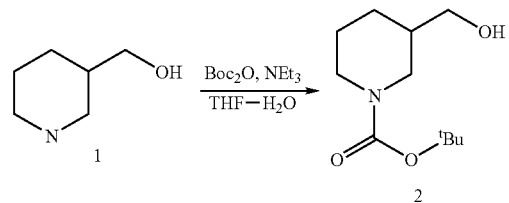

A solution of 3-piperidinemethanol (1) (15.20 g, 0.132 mol) in 30 mL of THF and 30 mL of H$_2$O was cooled in ice-water bath and NEt$_3$ (20 mL) was added with stirring. Stirring and cooling were continued while di-tert-butyl dicarbonate (34.56 g, 1.2 eq.) was introduced. The mixture was warmed to room temperature and stirred overnight. 100 mL of ethyl acetate and 20 mL of H$_2$O were added to mixture. The aqueous layer was extracted with ethyl acetate (2×100 mL). The extracts were combined and washed with aqueous potassium carbonate (sat., 2×50 mL), aqueous HCl (5%, 2×50 mL), brine (50 mL), and dried over anhydrous sodium sulfate, filtered and evaporated. Colorless oil 28.5 g (100%). TLC R$_f$=0.21 (ethyl acetate/hexane, 1:2).

EXAMPLE 2

Synthesis of N-Boc-piperidin-3-yl-formaldehyde (3)

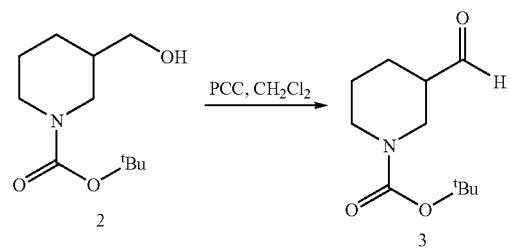

To a stirred suspension of pyridinium chlorochromate (98%, 34.0 g, 0.155 mol) and Celite (24 g) in 200 mL of dry CH$_2$Cl$_2$ was added N-Boc-3-piperidinemethanol (2) (22.15 g, 0.103 mol) in 30 mL of CH$_2$Cl$_2$ in one portion, and the mixture was stirred at room temperature overnight. The mixture was filtered by passing through a funnel filled with 20 g of Celite. After the solvent was removed, the remaining oily residue was purified by a flash column (silica gel; hexane:ethyl acetate, 4:1) to afford 3 as a colorless oil 17.5 g (80%).

EXAMPLE 3

Synthesis of N-(1-Boc-piperidin-3-ylmethyl)-aniline (4)

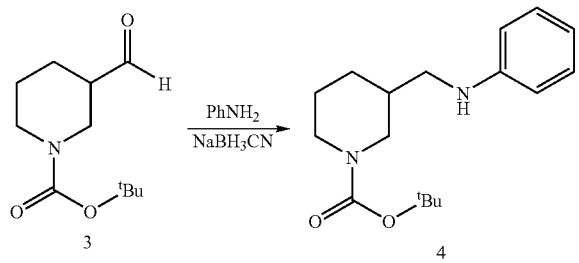

To a solution of N-Boc-piperidin-3-yl-formaldehyde 3 (5.20 g, 24.4 mmol) in 50 mL of dry methanol and 50 mL of trimethylorthoformate was added aniline (2.50 g, 1.1 eq.), and the mixture was stirred at room temperature for 30 minutes. NaBH$_3$CN (95%, 1.84 g, 1.1 eq.) was introduced in one portion, and the mixture was stirred at room temperature overnight. The mixture was quenched with 30 mL of aqueous potassium carbonate (sat.), then extracted with ethyl acetate (3×100 mL). The extracts were combined and washed with aqueous NaHCO$_3$ (sat., 2×50 mL), brine (50 mL), and dried over anhydrous sodium sulfate. After the solvent was removed, the remaining oily residue was purified by a flash column chromatography (silica gel, hexane: ethyl acetate (1:1) to afford N-(1-Boc-piperidin-3-ylmethyl)-aniline 4 as white solid (5.60 g, 79%). IR (film, cm$^{-1}$) 3520, 3263, 3004, 2976, 2932, 2854, 1688, 1589, 1521, 1482, 1422, 1365, 1267, 1243, 1175, 1150, 794, 709; $^1$H NMR (CDCl$_3$, ppm) 7.20 (t, 2H, J=7.8 Hz), 6.72 (t, 1H, J=6.8 Hz), 6.63 (d, 2H, J=8.3 Hz), 4.00–3.78 (m, 3H), 3.07–2.70 (m, 4H), 2.00–1.20 (m, 5H), 1.48 (s, overlap, 9H).

EXAMPLE 4

Synthesis of N-(1-Boc-piperidin-3-ylmethyl)-N-phenyl-propionamide (5)

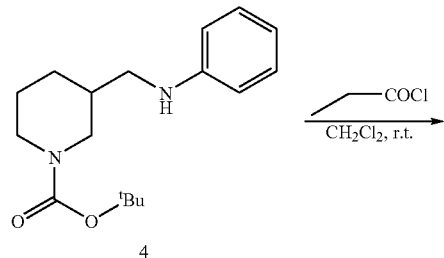

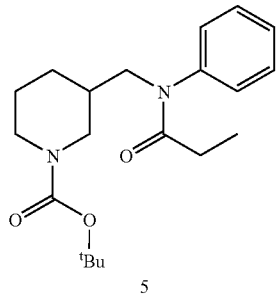

To a solution of N-(1-Boc-piperidin-3-ylmethyl)-aniline 4 (4.60 g, 15.8 mmol) and N,N-diisopropylethylamine (1.40 mL, 15.8 mmol) in 25 mL of dry methylene chloride was added propionyl chloride (1.40 mL, 15.8 mmol) dropwise at 0° C. After being stirred at room temperature overnight, the reaction mixture was quenched with 30 mL of H$_2$O and extracted with ethyl acetate (3×100 mL). The extracts were combined and washed with aqueous HCl (5%, 20 mL), NaHCO$_3$ (sat., 2×30 mL), brine (50 mL), and dried over anhydrous sodium sulfate. After the solvent was removed, the remaining oily residue was purified by a flash column chromatography (silica gel, hexane:ethyl acetate) to afford N-(1-Boc-piperidin-3-ylmethyl)-N-phenyl-propionamide 5 as a colorless oil (4.50 g, 82%). IR (film, cm$^{-1}$) 2975, 2934, 2854, 1690, 1663, 1591, 1496, 1422, 1402, 1365, 1265, 1242, 1176, 1149, 1038, 962,775, 702; $^1$H NMR (CDCl$_3$, ppm) 7.44–7.22 (m, 5H), 4.09–3.22 (m, 4H), 2.80–2.09 (m, 2H), 2.06 (q, 2H, J=7.5 Hz), 1.75–1.19 (m, 5H), 1.48(s, overlap, 9H), 1.06 (t, 3H, J=7.5 Hz).

EXAMPLE 5

Synthesis of N-(1-Phenethyl-piperidin-3-ylmethyl)-N-phenyl-propionamide (6)

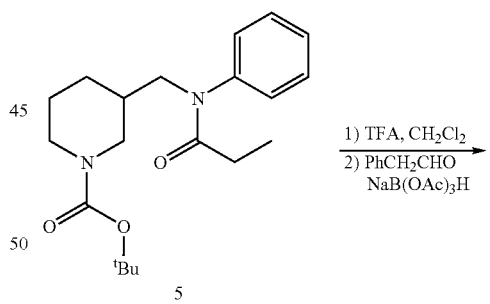

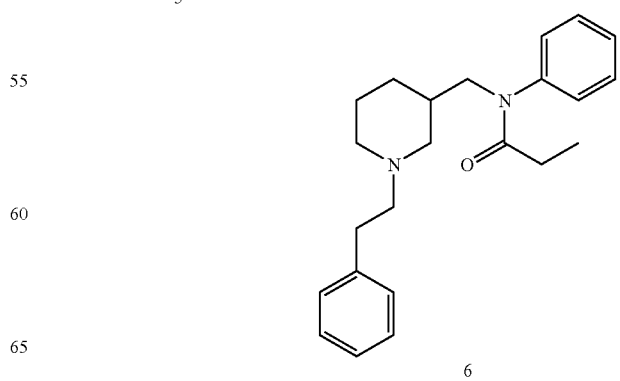

Trifluoroacetic acid (5 mL) was added dropwise to a solution of N-(1-Boc-piperidin-3-ylmethyl)-N-phenyl-propionamide 5 (1.21 g, 3.49 mmol) in 5 mL of dry $CH_2Cl_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (5.0 mL) and phenylacetaldehyde (5.3 mL, 2M/in DMF, 5.3 mmol) was added. The mixture was stirred at room temperature for 30 min. $NaB(OAc)_3H$ (95%, 1.18 g, 5.3 mmol.) was introduced in one portion, and the mixture was stirred at room temperature overnight. The mixture was quenched with 10 mL of aqueous potassium carbonate (sat.), then extracted with ethyl acetate (3×60 mL). The extracts were combined and washed with aqueous $NaHCO_3$ (sat., 2×10 mL), brine (30 mL), and dried over anhydrous sodium sulfate. After the solvent was removed, the remaining oily residue was purified by a flash column chromatography to give 6. IR (film, $cm^{-1}$) 3060, 3026, 2934, 2854, 2800, 2765, 1662, 1495, 1452, 1401, 1262, 1203, 1150, 1106, 966, 1033, 775, 749; LRMS 351.

EXAMPLE 6

Synthesis of N-(1-Benzyl-piperidin-3-ylmethyl)-N-phenyl-propionamide (7)

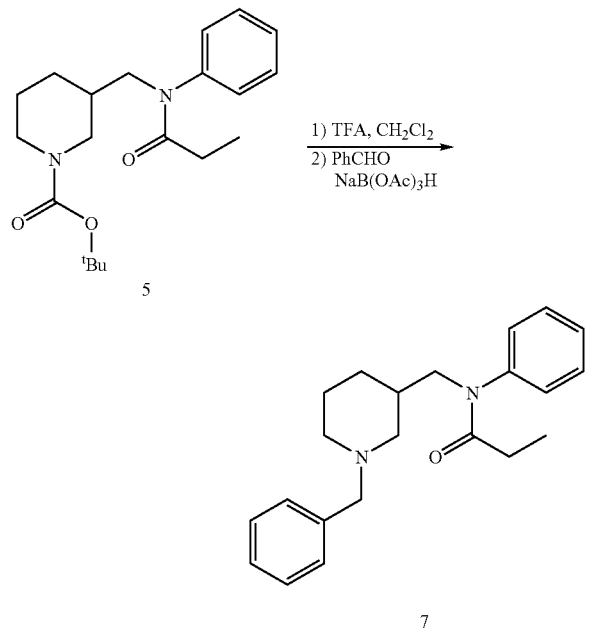

Trifluoroacetic acid (0.5 mL) was added dropwise to a solution of N-(1-Boc-piperidin-3-ylmethyl)-N-phenyl-propionamide 5 (31 mg, 0.090 mmol) in 0.5 mL of dry $CH_2Cl_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (0.5 mL) and benzaldehyde (13.6 µL, 1.5 eq.) was added. The mixture was stirred at room temperature for 30 min. $NaB(OAc)_3H$ (95%, 28.45 mg, 1.5 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous $NaHCO_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford N-(1-Benzyl-piperidin-3-ylmethyl)-N-phenyl-propionamide 7 as a colorless oil (26.6 mg, 88%). LRMS 337.

EXAMPLE 7

N-[1-(Thiophen-2-ylmethyl)-piperidin-3-ylmethyl]-N-phenyl-propionamide (8)

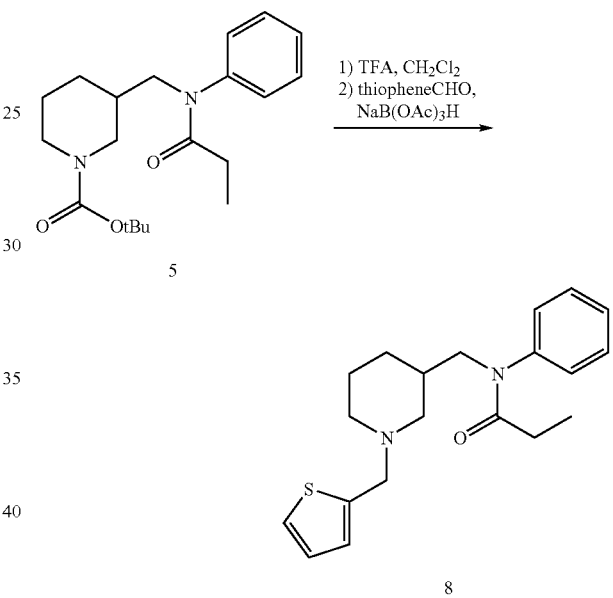

Trifluoroacetic acid (0.5 mL) was added dropwise to a solution of N-(1-Boc-piperidin-3-ylmethyl)-N-phenyl-propionamide 5 (31 mg, 0.090 mmol) in 0.5 mL of dry $CH_2Cl_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (0.5 mL) and 2-thiophene carboxaldehyde (12.5 µL, 1.5 eq.) was added. The mixture was stirred at room temperature for 30 min. $NaB(OAc)_3H$ (95%, 28.45 mg, 1.5 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous $NaHCO_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford N-[1-(Thiophen-2-ylmethyl)-piperidin-3-ylmethyl]-N-phenyl-propionamide 8 as a colorless oil (25.2 mg, 82%). LRMS 343.

EXAMPLE 8

Synthesis of (N-[1-(4-pyridinyl-N-oxidomethyl)-piperidin-3-ylmethyl]-N-phenyl-propionamide (9)

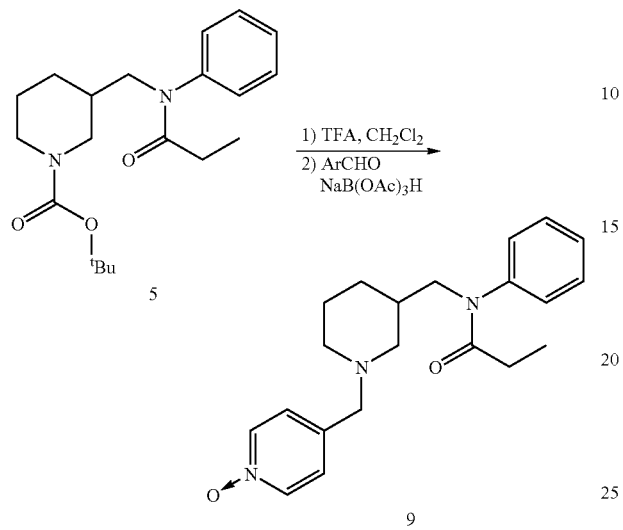

Trifluoroacetic acid (0.5 mL) was added dropwise to a solution of N-(1-Boc-piperidin-3-ylmethyl)-N-phenyl-propionamide 5 (31 mg, 0.090 mmol) in 0.5 mL of dry CH$_2$Cl$_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (0.5 mL) and 4-pyridinecarboxaldehyde N-oxide (17 mg, 1.5 eq.) was added. The mixture was stirred at room temperature for 30 min. NaB(OAc)$_3$H (95%, 28.45 mg, 1.5 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford 9 as a colorless oil (18.7 mg, 59%). LRMS 354.

EXAMPLE 9

Synthesis of (N-[1-(4-Methoxybenzyl)-piperidin-3-ylmethyl]-N-phenyl-propionamide (10)

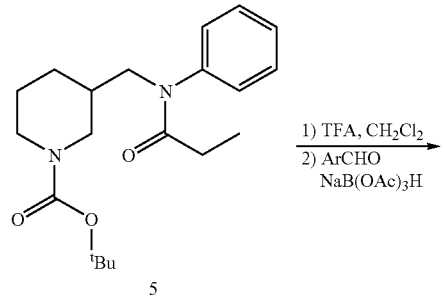

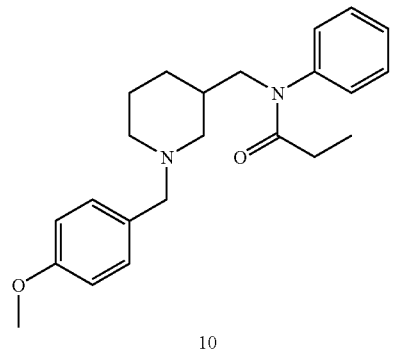

Trifluoroacetic acid (0.5 mL) was added dropwise to a solution of N-(1-Boc-piperidin-3-ylmethyl)-N-phenyl-propionamide 5 (31 mg, 0.090 mmol) in 0.5 mL of dry CH$_2$Cl$_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (0.5 mL) and 4-anisaldehyde (16.7 μL, 1.5 eq.) was added. The mixture was stirred at room temperature for 30 min. NaB(OAc)$_3$H (95%, 28.45 mg, 1.5 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford N-[1-(4-Methoxybenzyl)-piperidin-3-ylmethyl]-N-phenyl-propionamide 10 as a colorless oil (18.7 mg, 59%). LRMS 366.

EXAMPLE 10

Synthesis of (N-[1-(1H-Imidazol-2-ylmethyl)-piperidin-3-ylmethyl]-N-phenyl-propionamide (11)

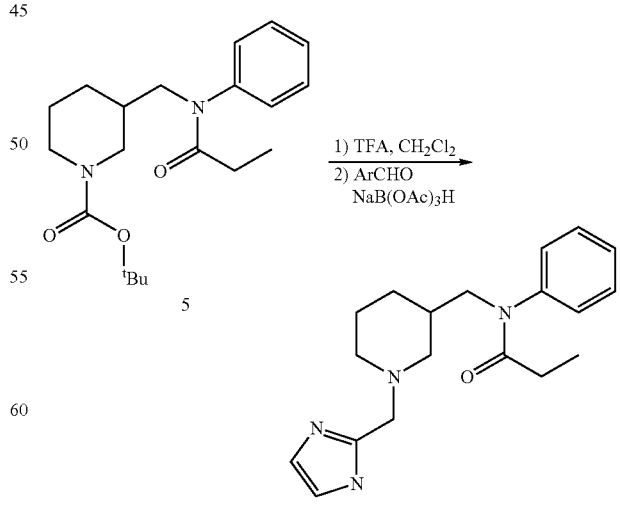

Trifluoroacetic acid (0.5 mL) was added dropwise to a solution of N-(1-Boc-piperidin-3-ylmethyl)-N-phenyl-propionamide 5 (21 mg, 0.061 mmol) in 0.5 mL of dry CH$_2$Cl$_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (0.5 mL) and 2-imidazole carboxaldehyde (8.7 mg, 1.5 eq.) was added. The mixture was stirred at room temperature for 30 min. NaB(OAc)$_3$H (95%, 20.3 mg, 1.5 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford N-[1-(1H-Imidazol-2-ylmethyl)-piperidin-3-ylmethyl]-N-phenyl-propionamide 11 as a colorless oil (10.7 mg, 54%). LRMS 327.

EXAMPLE 11

Synthesis of (N-[1-(Pyridin-3-ylmethyl)-piperidin-3-ylmethyl]-N-phenyl-propionamide (12)

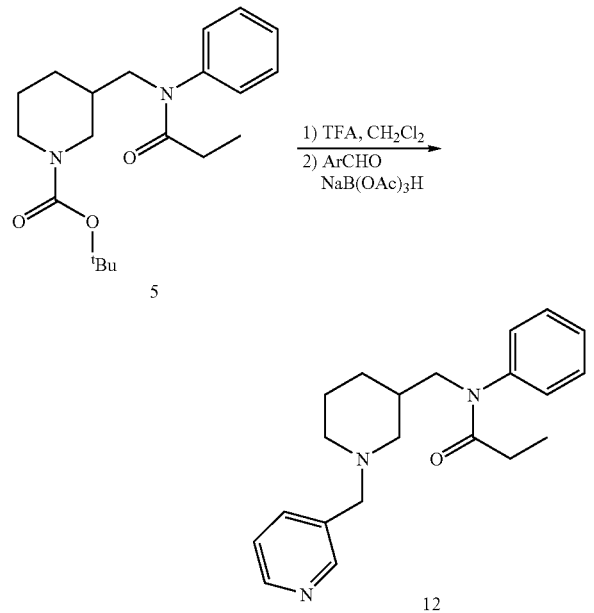

Trifluoroacetic acid (0.5 mL) was added dropwise to a solution of N-(1-Boc-piperidin-3-ylmethyl)-N-phenyl-propionamide 5 (21 mg, 0.061 mmol) in 0.5 mL of dry CH$_2$Cl$_2$ at 0° C. (ice-water). The reaction mixture was stirred at room temperature for 30 minutes. TLC showed the reaction was complete. After removal of the solvents, the residue was dried under vacuum for 3 hrs. The crude compound was dissolved in DMF (0.5 mL) and 3-pyridine carboxaldehyde (8.6 μL, 1.5 eq.) was added. The mixture was stirred at room temperature for 30 min. NaB(OAc)$_3$H (95%, 20.3 mg, 1.5 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 μL), brine (10 mL), and dried over anhydrous sodium sulfate. After the solvent was removed, the remaining oily residue was purified by preparative thin layer chromatography (EtOAc/MeOH, 9:1) to afford N-[1-(Pyridin-3-ylmethyl)-piperidin-3-ylmethyl]-N-phenyl-propionamide 12 as a colorless oil (15.6 mg, 76%). LRMS 338.

EXAMPLE 12

Synthesis of Furan-2-carboxylic acid N-(1-Boc-piperidin-3-ylmethyl)-N-phenyl amide (13)

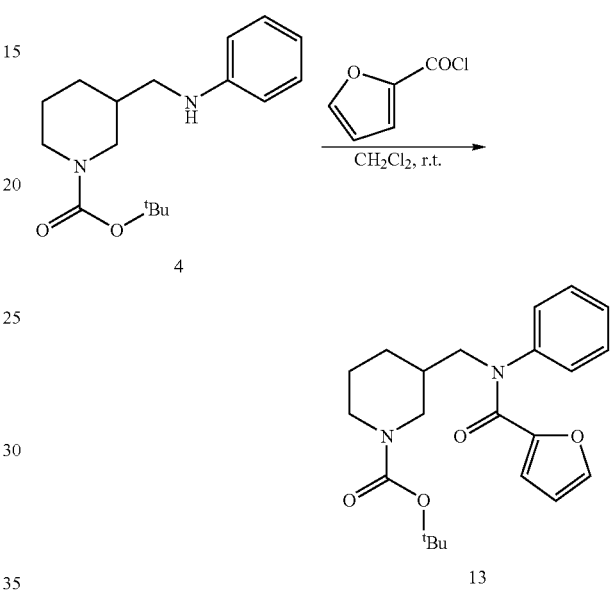

To a stirred suspension of N-(1-Boc-piperidin-3-ylmethyl)-aniline 4 (61.0 mg, 0.21 mmol) and piperidinomethyl polystyrene resin (60 mg) in 0.6 mL of dry CH$_2$Cl$_2$ was added 2-furoyl chloride (95%, 35.1 mg, 1.2 eq.) at room temperature. After being shaken at room temperature for 4 hours, the reaction mixture was passed through an aminopropyl NH2 cartridge and washed with CH$_2$Cl$_2$. Removal of CH$_2$Cl$_2$ afforded furan-2-carboxylic acid N-(1-Boc-piperidin-3-ylmethyl)-N-phenyl amide 13 (75 mg, 93%). LRMS 285 (M-100)$^+$.

EXAMPLE 13

Synthesis of Furan-2-carboxylic acid N-(1-phenethylpiperidin-3-ylmethyl)-N-phenyl amide (14)

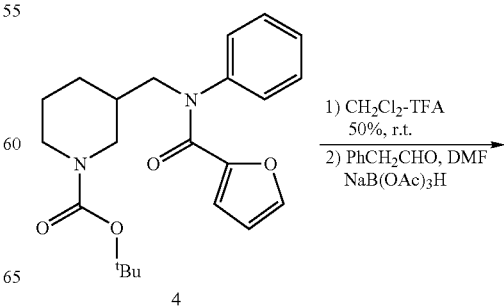

-continued

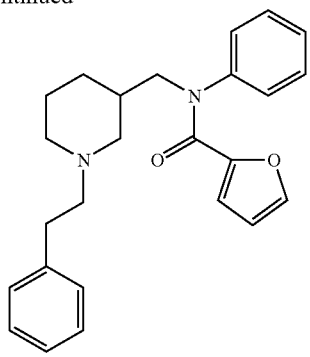

14

Trifluoroacetic acid (0.5 mL) was added dropwise to a solution of furan-2-carboxylic acid N-(1-Boc-piperidin-3-ylmethyl)-N-phenyl amide 13 (46 mg, 0.12 mmol) in 0.5 mL of dry $CH_2Cl_2$ at 0° C. (ice-water). The reaction mixture was stirred at room temperature for 30 minutes. TLC showed the reaction was complete. After removal of the solvents, the residue was dried under vacuum for 3 hrs (LRMS 285). The crude compound was dissolved in DMF (0.5 mL) and was added phenylacetaldehyde (150 μL, 2M/in DMF). The mixture was stirred at room temperature for 30 min. $NaB(OAc)_3H$ (95%, 55 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous $NaHCO_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford Furan-2-carboxylic acid N-(1-phenethylpiperidin-3-ylmethyl)-N-phenyl amide 14 as a colorless oil (20.3 mg, 44%). LRMS 389.

EXAMPLE 14

Synthesis of Thiophene-2-carboxylic acid N-(1-Boc-piperidin-3-ylmethyl)-N-phenyl amide (15)

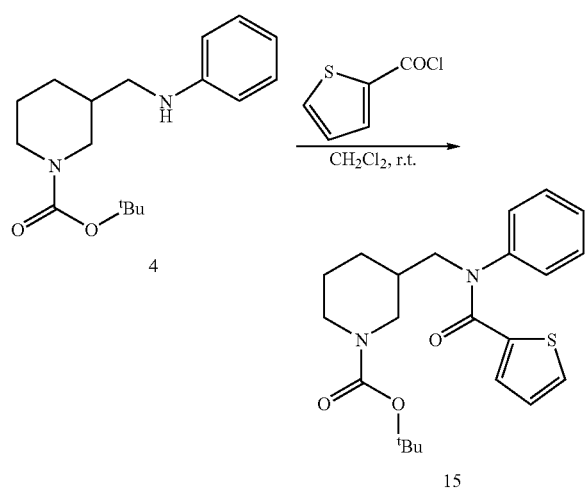

To a stirred suspension of N-(1-Boc-piperidin-3-ylmethyl)-aniline 4 (60.9 mg, 0.21 mmol) and piperidinomethyl polystyrene resin (60 mg) in 0.6 mL of dry $CH_2Cl_2$ was added 2-thiophenecarbonyl chloride (97%, 39.2 mg, 1.2 eq.) at room temperature. After being shaken at room temperature for 4 hours, the reaction mixture was passed through an aminopropyl $NH_2$ cartridge and washed with $CH_2Cl_2$. Removal of $CH_2Cl_2$ afforded thiophene-2-carboxylic acid N-(1-Boc-piperidin-3-ylmethyl)-N-phenyl amide 15 (82.1 mg, 98%). LRMS 300 (M-100)+.

EXAMPLE 15

Synthesis of Thiophene-2-carboxylic acid N-(1-phenethylpiperidin-3-ylmethyl)-N-phenyl amide (16)

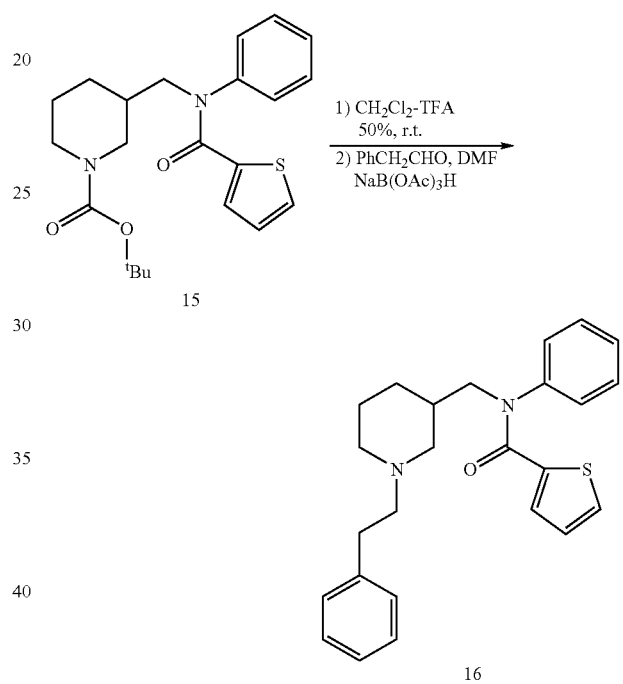

Trifluoroacetic acid (0.5 mL) was added dropwise to a solution of thiophene-2-carboxylic acid N-(1-Boc-piperidin-3-ylmethyl)-N-phenyl amide 15 (46.7 mg, 0.12 mmol) in 0.5 mL of dry $CH_2Cl_2$ at 0° C. (ice-water). The reaction mixture was stirred at room temperature for 30 minutes. TLC showed the reaction was complete. After removal of the solvents, the residue was dried under vacuum for 3 hrs (LRMS 301). The crude compound was dissolved in DMF (0.5 mL) and phenylacetaldehyde (150 μL, 2M/in DMF) was added. The mixture was stirred at room temperature for 30 min. $NaB(OAc)_3H$ (95%, 55 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous $NaHCO_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford thiophene-2-carboxylic acid N-(1-phenethylpiperidin-3-ylmethyl)-N-phenyl amide 16 as an oil (25.2 mg, 53%). LRMS 405.

EXAMPLE 16

Synthesis of N-(1-Boc-piperidin-3-ylmethyl)-N-(pyridin-3-yl)amine (17)

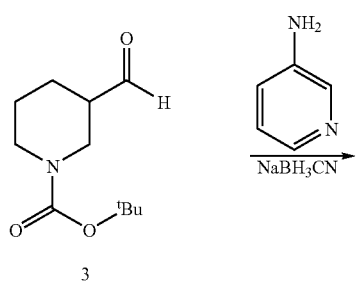

3

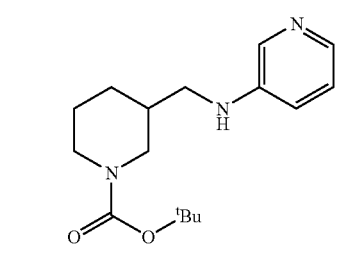

17

To a solution of N-Boc-piperidin-3-yl-formaldehyde 3 (0.89 g, 4.16 mmol) in 3 mL of dry methanol and 3 mL of trimethylorthoformate was added 3-aminopyridine (0.39 g, 1 eq.), and the mixture was stirred at room temperature for 1.5 hours. NaBH₃CN (95%, 0.29 g, 1.05 eq.) was introduced in one portion, and the mixture was stirred at room temperature overnight. The mixture was quenched with 10 mL of aqueous potassium carbonate (sat.), then extracted with ethyl acetate (3×30 ML). The extracts were combined and washed with aqueous NaHCO₃ (sat., 2×10 mL), brine (20 mL), and dried over anhydrous sodium sulfate. After the solvent was removed, the remaining oily residue was purified by flash column chromatography (silica gel, hexane/ethyl acetate) to afford N-(1-Boc-piperidin-3-ylmethyl)-N-(pyridin-3-yl) amine 17 as a white solid (0.91 g, 75%). LRMS 292.

EXAMPLE 17

Synthesis of N-(1-Boc-piperidin-3-ylmethyl)-N-(pyridin-3-yl)propionamide (18)

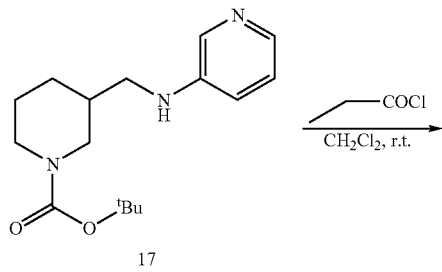

17

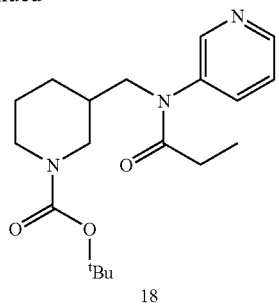

18

To a solution of N-(1-Boc-piperidin-3-ylmethyl)-N-(pyridin-3-yl) amine 17 (100 mg, 0.34 mmol) and piperidinomethyl polystyrene resin (100 mg) in 1 mL of dry CH₂Cl₂ was added propionyl chloride (30 μL, 1 eq.) at room temperature. After being shaken at room temperature overnight, the reaction mixture was passed through an aminopropyl NH₂ cartridge and washed with CH₂Cl₂. Removal of CH₂Cl₂ afforded N-(1-Boc-piperidin-3-ylmethyl)-N-(pyridin-3-yl) propionamide 18 (85 mg, 71%). LRMS 248 (M-100)⁺.

EXAMPLE 18

Synthesis of N-(1-Phenethyl-piperidin-3-ylmethyl)-N-(pyridin-3-yl)propionamide (19)

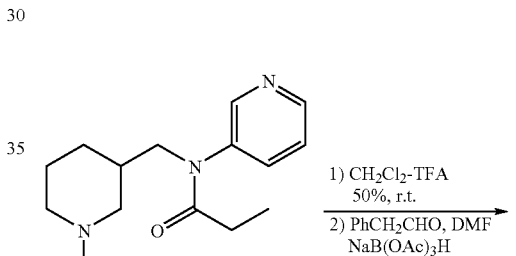

18

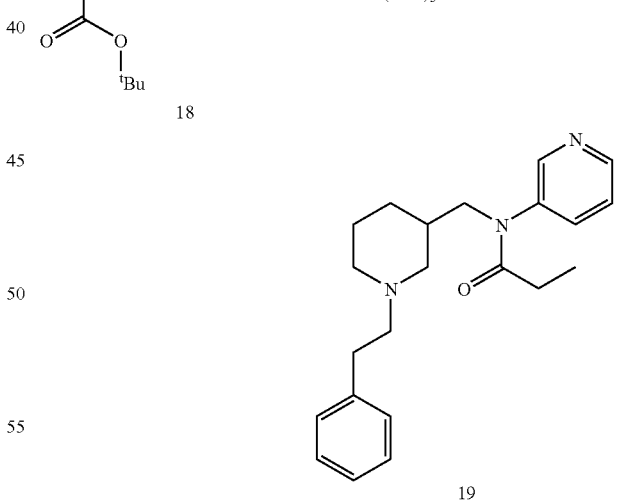

19

Trifluoroacetic acid (0.5 mL) was added dropwise to a solution of N-(1-Boc-piperidin-3-ylmethyl)-N-(pyridin-3-yl) propionamide 18 (42.5 mg, 0.12 mmol) in 0.5 mL of dry CH₂Cl₂ at 0° C. (ice-water). The reaction mixture was stirred at room temperature for 30 minutes. After removal of the solvents, the residue was dried under vacuum for 3 hrs (LRMS 248). The crude compound was dissolved in DMF (0.5 mL) and phenylacetaldehyde (122 μL, 2M/in DMF) was added. The mixture was stirred at room temperature for 30 min. NaB(OAc)₃H (95%, 58 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO₃ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford N-(1-Phenethyl-piperidin-3-ylmethyl)-N-(pyridin-3-yl)propionamide 19 as an oil (9.2 mg, 28%). IR (film, cm⁻¹) 3026, 2933, 2852, 2794, 2765, 1666, 1479, 1421, 1396, 1261, 1237, 1214, 1188, 1159, 1114, 1078, 1026, 749, 719. LRMS 352.

EXAMPLE 19

Synthesis of Furan-2-carboxylic acid N-(1-Boc-piperidin-3-ylmethyl)-N-(pyridin-3-yl)amide (20)

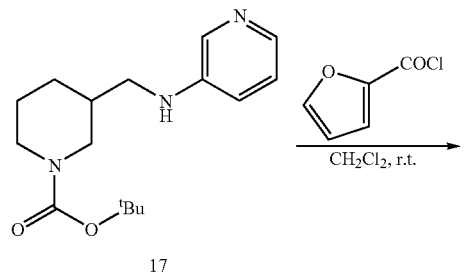

17

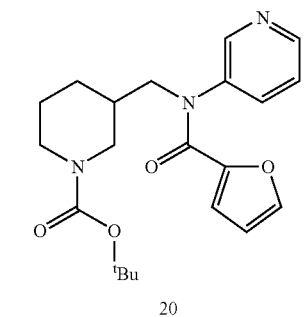

20

To a solution of N-(1-Boc-piperidin-3-ylmethyl)-N-(pyridin-3-yl) amine 17 (99 mg, 0.34 mmol) and piperidinomethyl polystyrene resin (100 mg) in 1 mL of dry CH₂Cl₂ was added 2-furoyl chloride (95%, 56.0 mg, 1.2 eq.) at room temperature. After being shaken at room temperature overnight, the reaction mixture was passed through an aminopropyl NH₂ cartridge and washed with CH₂Cl₂. Removal of CH₂Cl₂ afforded furan-2-carboxylic acid N-(1-Boc-piperidin-3-ylmethyl)-N-(pyridin-3-yl) amide 20 (80 mg, 61%). LRMS 286 (M-100)⁺.

EXAMPLE 20

Synthesis of Furan-2-carboxylic acid N-(1-phenethyl-piperidin-3-ylmethyl)-N-(pyridin-3-yl)amide (21)

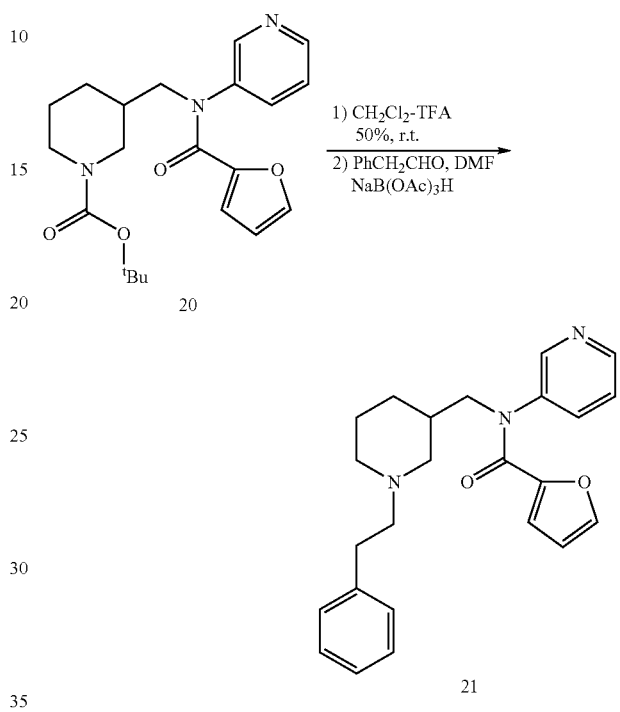

Trifluoroacetic acid (0.5 mL) was added dropwise to a solution of furan-2-carboxylic acid N-(1-Boc-piperidin-3-ylmethyl)-N-(pyridin-3-yl) amide 20 (37 mg, 0.096 mmol) in 0.5 mL of dry CH₂Cl₂ at 0° C. (ice-water). The reaction mixture was stirred at room temperature for 30 minutes. After removal of the solvents, the residue was dried under vacuum for 3 hrs (LRMS 286). The crude compound was dissolved in DMF (0.5 mL) and phenylacetaldehyde (95 μL, 2M/in DMF) was added. The mixture was stirred at room temperature for 30 min. NaB(OAc)₃H (95%, 45 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO₃ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford furan-2-carboxylic acid N-(1-phenethyl-piperidin-3-ylmethyl)-N-(pyridin-3-yl) amide 21 as an oil (21.8 mg, 58%). IR (film, cm⁻¹) 3024, 2932, 2854, 2801, 2767, 1647, 1574, 1478, 1424, 1397, 1306, 1226, 1186, 1113, 1027, 1011, 752, 715; ¹H NMR (CDCl₃, ppm) 8.61 (d, 1H), 8.51 (d, 1H), 7.58 (m, 1H), 7.36 (m, 1H), 7.29–7.18 (m, 6H), 6.26 (m, 2H), 3.85 (ddd, 2H, J=32.7, 13.7, 6.6 Hz), 2.96 (m, 2H), 2.81 (m, 2H), 2.62 (m, 2H), 2.04 (m, 3H), 1.76 (m, 2H), 1.60 (m, 1H), 1.19 (m, 1H). LRMS 390.

EXAMPLE 21

Synthesis of Cyclopropanecarboxylic acid N-(1-Boc-piperidin-3-ylmethyl)-N-(pyridin-3-yl)amide (22)

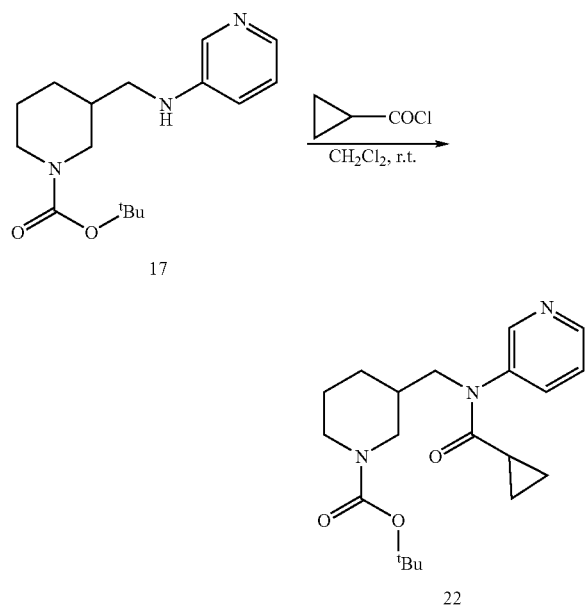

To a solution of N-(1-Boc-piperidin-3-ylmethyl)-N-(pyridin-3-yl) amine 17 (56 mg, 0.19 mmol) and piperidinomethyl polystyrene resin (3.5 mM/g, 60 mg) in 0.6 mL of dry CH₂Cl₂ was added cyclopropanecarbonyl chloride (98%, 21 µL, 1.2 eq.) at room temperature. After being shaken at room temperature overnight, the reaction mixture was passed through an aminopropyl NH₂ cartridge and washed with CH₂Cl₂. Removal of CH₂Cl₂ afforded Cyclopropanecarboxylic acid N-(1-Boc-piperidin-3-ylmethyl)-N-(pyridin-3-yl) amide 22 (50 mg, 73%). LRMS 260 (M-100)⁺.

EXAMPLE 22

Synthesis of Cyclopropanecarboxylic acid N-(1-phenethyl-piperidin-3-ylmethyl)-N-(pyridin-3-yl) amide (23)

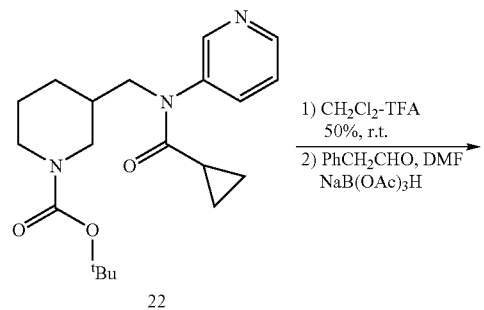

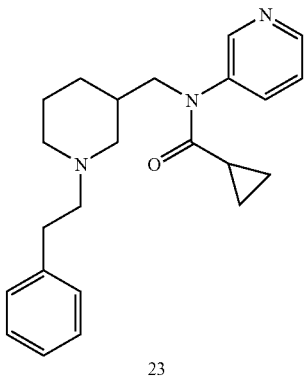

Trifluoroacetic acid (0.5 mL) was added dropwise to a solution of Cyclopropanecarboxylic acid N-(1-Boc-piperidin-3-ylmethyl)-N-(pyridin-3-yl) amide 22 (46 mg, 0.128 mmol) in 0.5 mL of dry CH₂Cl₂ at 0° C. (ice-water). The reaction mixture was stirred at room temperature for 30 minutes. After removal of the solvents, the residue was dried under vacuum for 3 hrs (LRMS 260). The crude compound was dissolved in DMF (0.5 mL) and phenylacetaldehyde (130 µL, 2M/in DMF) was added. The mixture was stirred at room temperature for 30 min. NaB(OAc)₃H (95%, 57 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO₃ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford cyclopropanecarboxylic acid N-(1-phenethyl-piperidin-3-ylmethyl)-N-(pyridin-3-yl) amide 23 as oil (23.5 mg, 51%). IR (film, cm⁻¹) 3026, 2931, 2854, 2800, 2765, 1657, 1582, 1573, 1479, 1445, 1408, 1263, 1202, 1188, 1118, 1025, 748, 735; ¹H NMR (CDCl₃, ppm) 8.62 (m, 2H), 7.65 (d, 1H, J=8.1 Hz), 7.41 (dd, 1H, J=12.7, 4.8 Hz), 7.33–7.19 (m, 5H), 3.72 (m, 2H), 2.90 (m, 2H), 2.80 (m, 2H), 2.58 (m, 2H), 2.03 (m, 1H), 1.87 (m, 2H), 1.70 (m, 2H), 1.56 (m, 1H), 1.26 (m, 2H), 1.09 (m, 3H), 0.69(m, 1H); LRMS 364.

EXAMPLE 23

Synthesis of N-Boc-(R)-nipecotic acid (25)

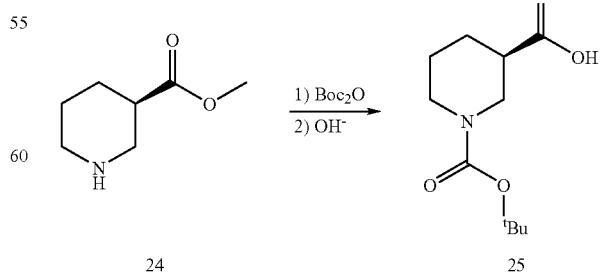

A solution of ethyl N-Boc-(R)-nipecotate-L-tartrate (24) (10.00 g, 32.5 mol) in 50 mL of dioxane and 50 mL of H₂O was cooled in ice-water bath and NEt₃ (9 mL) was added with stirring. Stirring and cooling were continued while di-tert-butyl dicarbonate (7.44 g, 1.05 eq.) was introduced. The mixture was warmed to room temperature and stirred for 4 h. 100 mL of Ethyl acetate and 20 mL of H₂O were added to mixture. The aqueous layer was extracted with ethyl acetate (2×100 mL). The extracts were combined and washed with aqueous potassium carbonate (sat., 2×50 mL), aqueous HCl (5%, 2×50 mL), brine (50 mL), and dried over anhydrous sodium sulfate, filtered and evaporated to give ethyl N-Boc-(R)-nipecotate as a colorless oil 8.37 g (100%).

To a solution of ethyl N-Boc-(R)-nipecotate (7.61 g, 29.6 mmol) in 25 mL of methanol was added LiOH (2.48 g, 2 eq.) in 25 mL of H₂O dropwise at 4° C. The reaction mixture was stirred overnight at 4° C. The pH of the mixture was adjusted to ca. 1 by adding aqueous HCl (10% w/w). The aqueous layer was extracted with ethyl acetate (3×100 mL). The extracts were combined and washed with aqueous NH₄Cl (sat., 2×50 mL), brine (50 mL), and dried over anhydrous Na₂SO₄, filtered and evaporated to give N-Boc-(R)-nipecotic acid 25 as a white solid 6.25 g (92%).

EXAMPLE 24

Synthesis of (R)-1-Boc-piperidine-3-carboxylic acid phenyl amide (26)

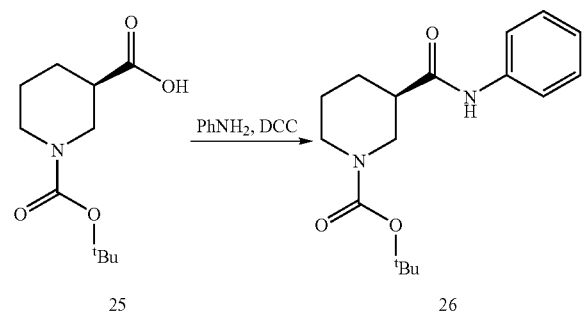

To a solution of N-Boc-(R)-nipecotic acid 25 (4.00 g, 17.5 mmol) and aniline (1.67 mL, 1.05 eq.) in 30 mL of dry CH₂Cl₂ was added DCC (4.88 g, 1.05 eq.) in one portion at 0° C. The mixture was stirred at room temperature for 4 hours. Filtration and removal of the solvent gave an oily crude product, which was purified by flash column chromatography (silica gel, hexane:ethyl acetate) to afford (R)-1-Boc-piperidine-3-carboxylic acid phenyl amide 26 as a colorless oil (5.26 g, 99%).

EXAMPLE 25

Synthesis of (R)-1-Phenethyl piperidine-3-carboxylic acid phenyl amide (27)

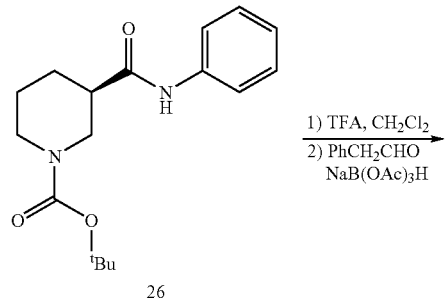

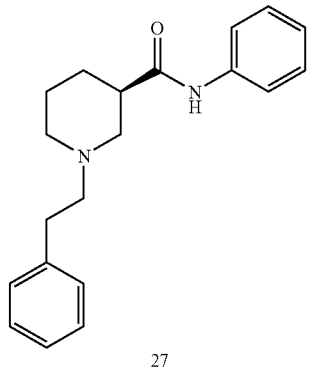

Trifluoroacetic acid (0.5 mL) was added dropwise to (R)-1-Boc-piperidine-3-carboxylic acid phenyl amide 26 (46.7 mg, 0.154 mmol) in 0.5 mL of dry CH₂Cl₂ at 0° C. (ice-water). The reaction mixture was stirred at room temperature for 30 minutes. After removal of the solvents, the residue was dried under vacuum for 3 hrs (LRMS 309). The crude compound was dissolved in DMF (0.5 mL) and phenylacetaldehyde (154 µL, 2M/in DMF) was added. The mixture was stirred at room temperature for 30 min. NaB(OAc)₃H (95%, 101 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO₃ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford (R)-1-Phenethyl piperidine-3-carboxylic acid phenyl amide 27 as an oil (8.2 mg, 17%). LRMS 309.

EXAMPLE 26

Synthesis of (R)—N-(1-Boc-piperidin-3-ylmethyl)-aniline (28)

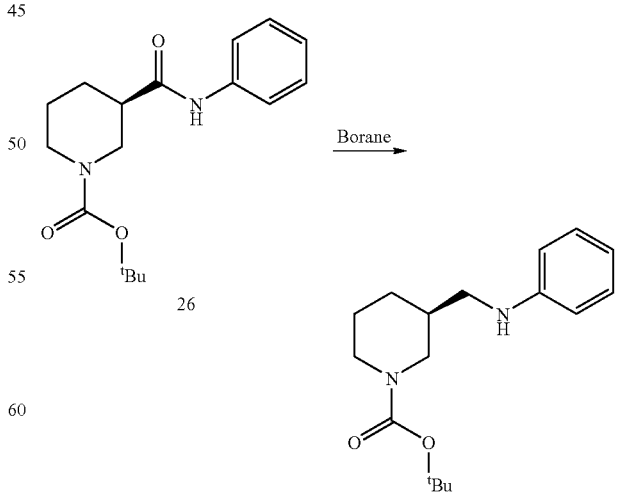

(R)-1-Boc-piperidine-3-carboxylic acid phenyl amide 26 (5.26 g, 17.28 mmol) in 20 mL of dry THF was added slowly to 34.5 mL of 1.0 M borane in THF while stirring in an ice bath. The mixture was refluxed for 2 hours, then cooled in an ice bath, and quenched with 20 mL of aqueous HCl (10%), then treated with NaOH (10%) to pH ~10. The mixture was extracted with ethyl acetate (3×100 mL). The extracts were combined and washed with brine (2×50 mL), and dried over anhydrous sodium sulfate. After the solvent was removed, the remaining oily residue was passed through a short column (silica gel, ethyl acetate) to afford (R)—N-(1-Boc-piperidin-3-ylmethyl)-aniline 28 as a colorless oil (4.59 g, 91%).

EXAMPLE 27

Synthesis of (R) N-(1-Phenethyl-piperidin-3-ylmethyl)-N-phenyl-propionamide (30)

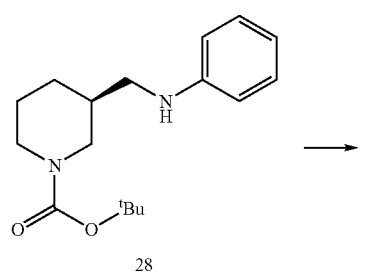

28

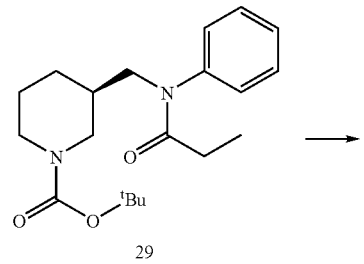

29

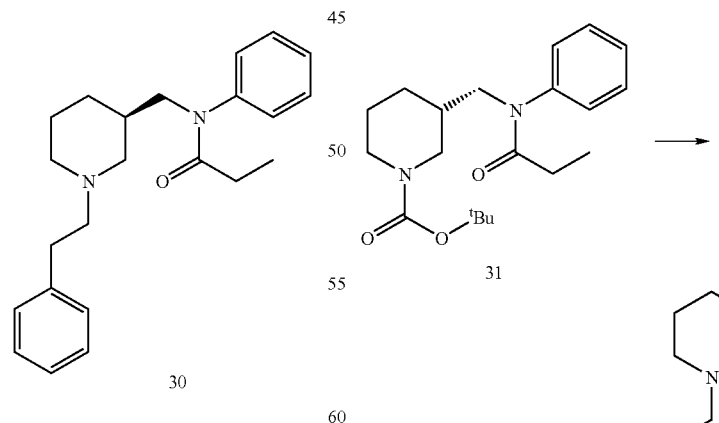

30

Following a procedure similar to that described in Examples 4 and 5, (R)—N-(1-Boc-piperidin-3-ylmethyl)-aniline 28 was converted first to (R)—N-(1-Boc-piperidin-3-ylmethyl)-N-phenyl-propionamide 29, and then to (R) N-(1-Phenethyl-piperidin-3-ylmethyl)-N-phenyl-propionamide 30 (LRMS 350).

EXAMPLE 28

Synthesis of (S)—N-(1-Boc-piperidin-3-ylmethyl)-N-phenyl-propionamide (31)

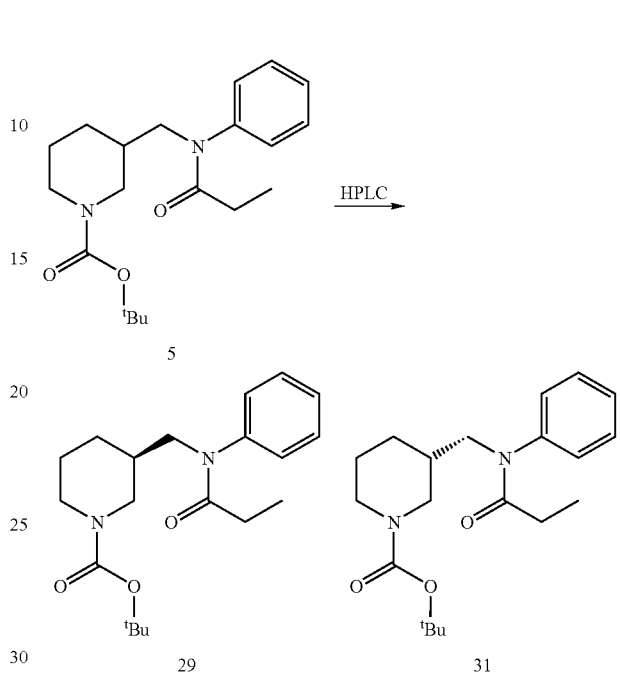

Resolution of (racemic)-5 was effected by HPLC on a Chiralpak AD semipreparative column (hexane/isopropyl alcohol, 95:5). The first compound to separate was (R)-29. The second was (S)—N-(1-Boc-piperidin-3-ylmethyl)-N-phenyl-propionamide 31.

EXAMPLE 29

Synthesis of (S) N-(1-Phenethyl-piperidin-3-ylmethyl)-N-phenyl-propionamide (32)

Following the procedures described in Example 5, (S)—N-(1-Boc-piperidin-3-ylmethyl)-N-phenyl-propionamide 31 was converted to (S) N-(1-Phenethyl-piperidin-3-ylmethyl)-N-phenyl-propionamide 32 (LRMS 350).

EXAMPLE 30

Lack of Acute in Vivo Toxicity of 6 in Mice

A 7 mg/mL solution of 6 in 50 mM aqueous sodium acetate was prepared. A dose of 1 mg/kg was administered to four male mice via tail vein injections. The mice showed no adverse effects from the compound. Furthermore, a dose of 10 mg/kg was administered to four male mice via intraperitoneal injections. Likewise, the mice showed no adverse effects from the compound at this concentration.

EXAMPLE 31

In Vivo Analgesia of 6 in Mice

A "tail-flick" analgesia model known in the art was utilized (D'Amour et al *J. Pharmacol. Exp. Ther.* 1941, 72, 74). Groups of four male mice weighing ~22 g were treated with 6. Compound 6 was dissolved in a vehicle of 50 mM aqueous sodium acetate for both intraperitoneal and intravenous administration. The control group received vehicle alone. Before treatment (0 minute), pre-selection was done by using a focused beam of radiant heat applied to the middle dorsal surface of the animal tail to elicit a tail flick response within 6–7.5 seconds. Compound 6 was administered for 30 minutes and 1 minute for ip and iv injection, respectively, before the stimulation by the focused beam of radiant heat used as pre-selection. The time required to elicit the tail-flick response was recorded for each animal and a maximum cut-off of 15 seconds was set. Prolongation by 50% or more of the time required to elicit a tail-flick response relative to pretreated animals indicated analgesic activity. The results of these experiments are recorded in Table 2. See also FIG. 2.

TABLE 2

| Compound | Route | $ED_{50}$ |
| --- | --- | --- |
| 6 | ip | 7 mg/kg |
| 6 | iv | 0.3 mg/kg |

EXAMPLE 32

Agonism of Opiate Receptors

This example demonstrates significant agonism of opiate $\mu$, $\kappa$, and $\delta$ receptors by (S)-32 and significant agonism of opiate $\mu$, $\kappa$ by (R)-30, utilizing procedures outlined by Maguire et al. (*Eur. J. Pharmacol.* 1992, 213, 219). The results are recorded in Table 3.

TABLE 3

| Compound | $\mu$ | $\kappa$ | $\delta$ |
| --- | --- | --- | --- |
| (R)-30 | 0.3 μM | 0.3 μM | — |
| (S)-32 | 0.1 μM | 0.1 μM | 0.1 μM |

EXAMPLE 33

1-Phenethylpiperidine-3-carboxylic acid phenylamide 35

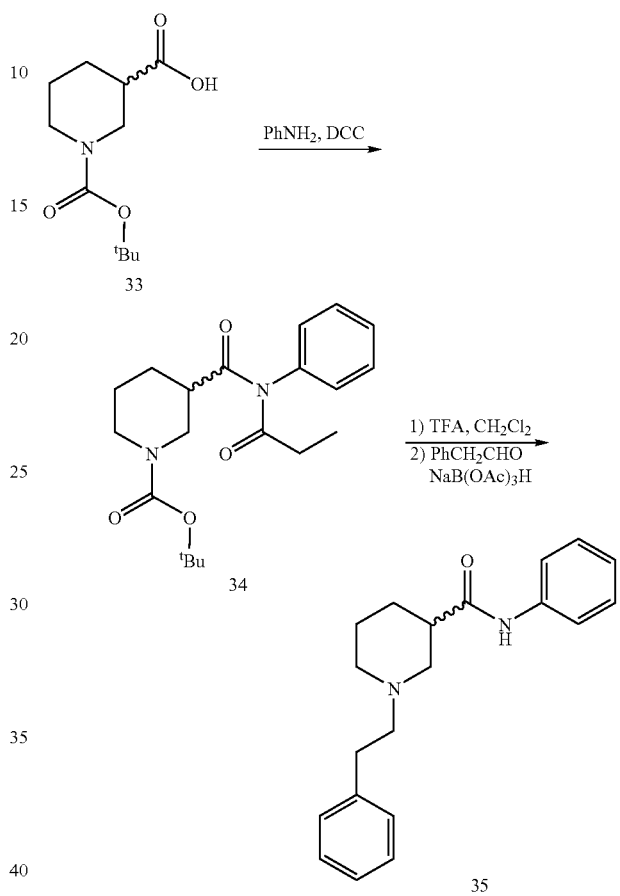

To a solution of N-Boc-nipecotic acid 33 (102 mg, 0.445 mmol) and aniline (41 μL, 1.0 eq.) in 2 mL of dry $CH_2Cl_2$ was added DCC-resin (430 mg). The reaction mixture was shaken at room temperature overnight. Filtration and removal of the solvent gave oily crude product, which was purified by flash column chromatography (silica gel, hexane: ethyl acetate) to afford 1-Boc-piperidine-3-carboxylic acid phenyl amide 34 as a colorless oil (120 mg, 89%).

Trifluoroacetic acid (0.5 mL) was added dropwise to 1-Boc-piperidine-3-carboxylic acid phenyl amide 34 (62 mg, 0.20 mmol) in 0.5 mL of dry $CH_2Cl_2$ at 0° C. (ice-water). The reaction mixture was stirred at room temperature for 30 minutes. After removal of the solvents, the residue was dried under vacuum for 3 hrs. The crude product was used in the next step without purification.

The crude compound from the previous step was dissolved in DMF (0.5 mL) and phenylacetaldehyde (400 μL, 2M/in DMF) was added. The mixture was stirred at room temperature for 30 min. $NaB(OAc)_3H$ (95%, 90 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous $NaHCO_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford 1-Phenethylpiperidine-3-carboxylic acid phenylamide 35. LRMS 309.

EXAMPLE 34

1-Phenethylpiperidine-3-carboxylic acid N-phenyl-N-ethylamide 37

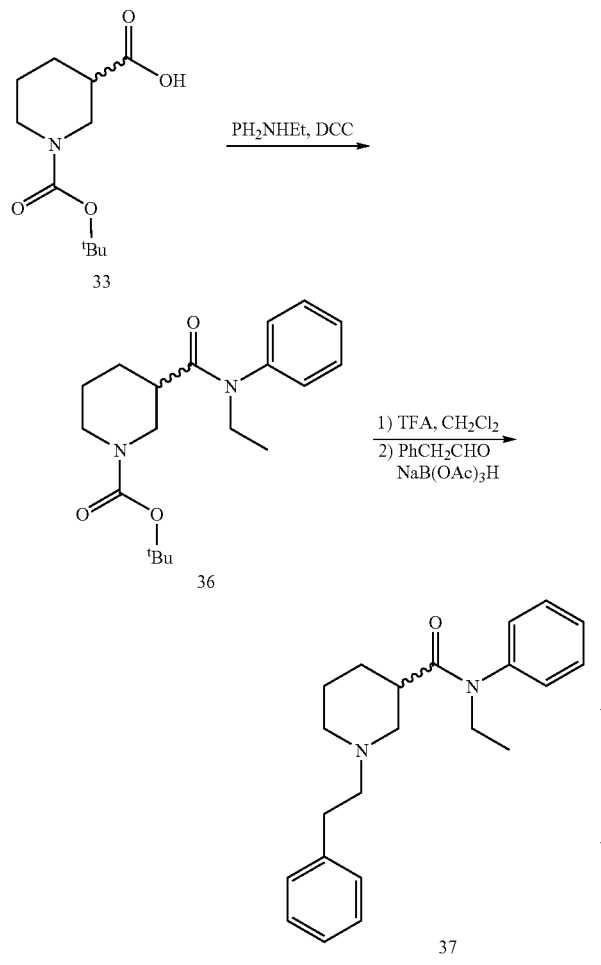

To a solution of N-Boc-nipecotic acid 33 (113 mg, 0.493 mmol) and ethylaniline (62 µL, 1.0 eq.) in 2 mL of dry CH$_2$Cl$_2$ was added DCC-resin (480 mg). The reaction mixture was shaken at room temperature overnight. Filtration and removal of the solvent gave an oily crude product, which was purified by flash column chromatography (silica gel, hexane:ethyl acetate) to afford 1-Boc-piperidine-3-carboxylic acid N-phenyl-N-ethhylamide 36 as a colorless oil (150 mg, 92%).

Trifluoroacetic acid (0.5 mL) was added dropwise to a 1-Boc-piperidine-3-carboxylic acid N-phenyl-N-ethhylamide 36 (56 mg, 0.168 mmol) in 0.5 mL of dry CH$_2$Cl$_2$ at 0° C. (ice-water). The reaction mixture was stirred at room temperature for 30 minutes. After removal of the solvents, the residue was dried under vacuum for 3 hrs. The crude product was used in the next step without purification.

The crude compound from the previous step was dissolved in DMF (0.5 mL) and phenylacetaldehyde (67 mg, 3 eq.) was added. The mixture was stirred at room temperature for 30 min. NaB(OAc)$_3$H (95%, 112 mg, 3 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford 1-Phenethylpiperidine-3-carboxylic acid N-phenyl-N-ethhylamide 37. LRMS 336.

EXAMPLE 35

Methoxyacetic acid N-(1-phenethylpiperidin-3-ylmethyl)-N-phenylamide 39

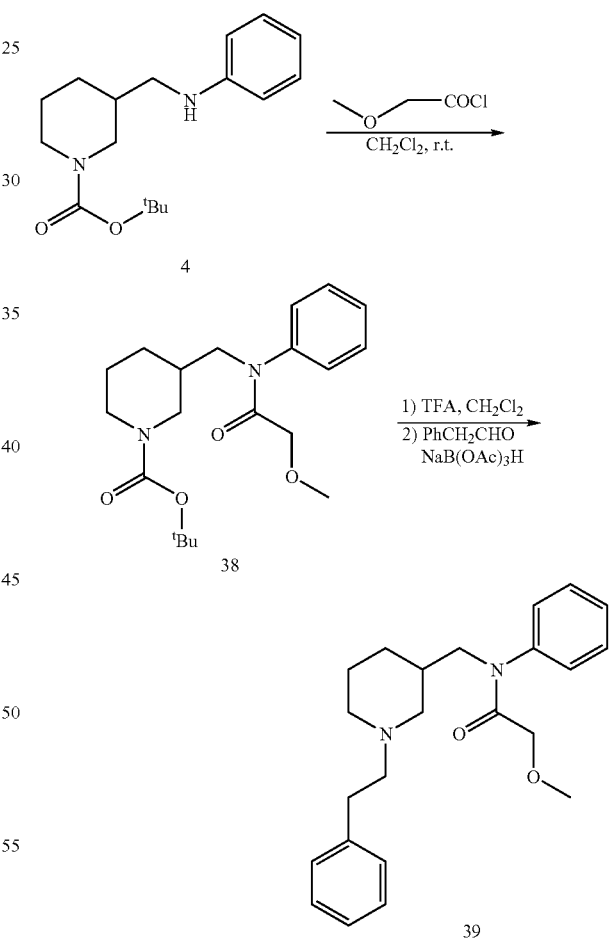

To a stirred suspension of N-(1-Boc-piperidin-3-ylmethyl)-aniline 4 (101 mg, 0.348 mmol) and piperidinomethyl polystyrene resin (110 mg) in 2 mL of dry CH$_2$Cl$_2$ was added methoxyacetyl chloride (97%, 34 µL, 1.05 eq.) at room temperature. After being shaken at room temperature for 4 hours, the reaction mixture was passed through an aminopropyl NH$_2$ cartridge and washed with CH$_2$Cl$_2$ Removal of CH$_2$Cl$_2$ afforded methoxyacetic acid N-(1-Boc-piperidin-3-ylmethyl)-N-phenylamide 38 (70 mg, 56%).

Trifluoroacetic acid (0.5 mL) was added dropwise to a solution of methoxyacetic acid N-(1-Boc-piperidin-3-ylmethyl)-N-phenyl amide 38 (61.8 mg, 0.17 mmol) in 0.5 mL of dry CH$_2$Cl$_2$ at 0° C. (ice-water). The reaction mixture was stirred at room temperature for 20 minute. TLC showed the reaction was complete. After removal of the solvents, the residue was dried under vacuum for 3 hrs. The crude product was used in the next step without purification.

The crude compound from the previous step was dissolved in DMF (1.0 mL) and phenylacetaldehyde (68.3 mg, 3 eq.) was added. The mixture was stirred at room temperature for 30 min. NaB(OAc)$_3$H (95%, 108 mg, 3 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford Methoxyacetic acid N-(1-phenethylpiperidin-3-ylmethyl)-N-phenylamide 39 as a colorless oil (31 mg, 49%). LRMS 363.

EXAMPLE 36

N-(1-(3'-Phenyl)propylpiperidin-3-ylmethyl)-N-phenylpropionamide 44

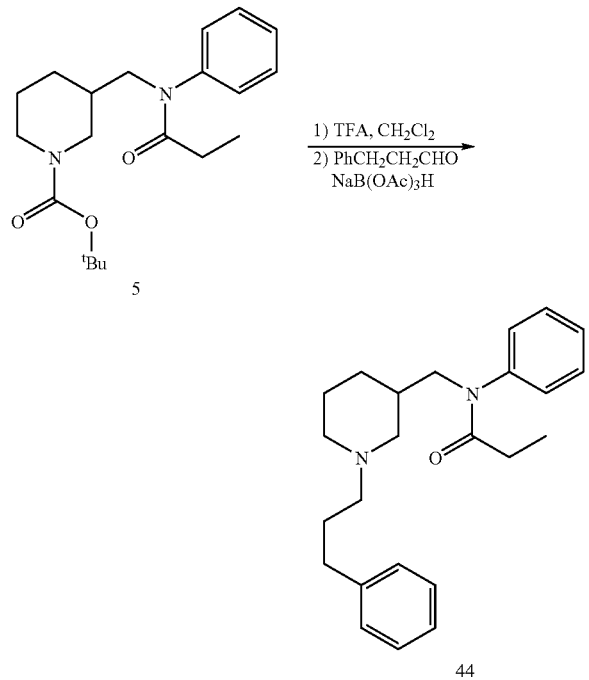

Trifluoroacetic acid (0.5 mL) was added dropwise to a solution of compound N-(1-Boc-piperidin-3-ylmethyl)-N-phenylpropionamide 5 (58 mg, 0.167 mmol) in 0.5 mL of dry CH$_2$Cl$_2$ at 0° C. (ice-water). The reaction mixture was stirred at room temperature for 30 minutes. TLC showed the reaction was complete. After removal of the solvents, the residue was dried under vacuum for 3 hrs. The crude product was used in the next step without purification.

The crude compound from the previous step was dissolved in DMF (0.5 mL) and benzaldehyde (46 μL, 2 eq.) was added. The mixture was stirred at room temperature for 30 min. NaB(OAc)$_3$H (95%, 75 mg, 2 eq.) was introduced in one portion, and the mixture was shaken at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 9:1) to afford N-(1-(3'-Phenyl)propylpiperidin-3-ylmethyl)-N-phenylpropionamide 44 as a colorless oil (49 mg, 80%). LRMS 364.

EXAMPLE 37

N-Boc-3-Azetidinecarboxylic acid 46

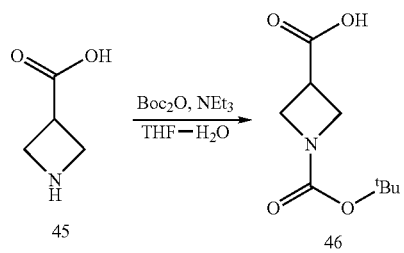

A solution of 3-Azetidinecarboxylic acid (45) (250 mg, 2.47 mmol) in 5 mL of THF and 5 mL of H$_2$O was cooled in an ice-water bath and NEt$_3$ (689 μL) was added with stirring. Stirring and cooling were continued while di-tert-butyl dicarbonate (570 mg, 1.05 eq.) was introduced. The mixture was warmed to room temperature and stirred overnight. 20 mL of Ethyl acetate and 10 mL of H$_2$O were added to mixture. The aqueous layer was extracted with ethyl acetate (2×20 mL). The extracts were combined and washed with aqueous potassium carbonate (sat., 2×10 mL), aqueous HCl (5%, 2×10 mL), brine (10 mL), and dried over anhydrous sodium sulfate, and filtered. Removal of solvents gave 46 as a white solid 0.50 g (100%)

EXAMPLE 38

N-(1-Boc-Azetidine-3-ylmethyl)aniline 48

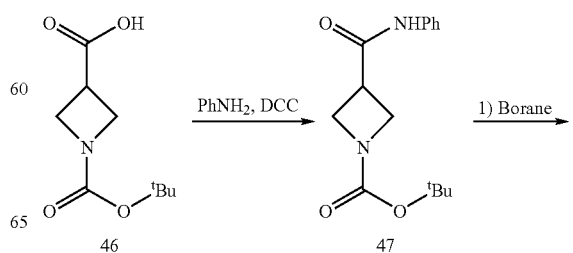

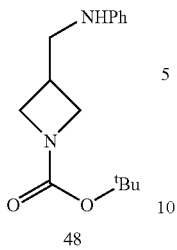

48

To a solution of N-Boc-3-Azetidinecarboxylic acid 46 (0.50 g, 2.48 mmol) and aniline (274 μL, 1.1 eq.) in 5 mL of dry CH$_2$Cl$_2$ was added DCC (730 mg, 1.1 eq.) in one portion at 0° C. The mixture was stirred at room temperature for 3 hours. Filtration and removal of the solvent gave an oily crude product, which was purified by flash column chromatography (silica gel, hexane:ethyl acetate) to afford 1-Boc-Azetidine-3-carboxylic acid phenylamide 47 as a colorless oil (660 mg, 96%).

1-Boc-Azetidine-3-carboxylic acid phenylamide 47 (650 mg, 2.35 mmol) in 5 mL of dry THF was added slowly to 5 mL of 1.0 M borane in THF while stirring in an ice bath. The mixture was refluxed for 3 hours, then cooled in ice bath and quenched with 5 mL of aqueous HCl (10%), then treated with NaOH (10%) to pH ~10. The mixture was extracted with ethyl acetate (3×20 mL). The extracts were combined and washed with brine (2×10 mL), and dried over anhydrous sodium sulfate. After the solvent was removed, the remaining oily residue was passed through a short column (silica gel, ethyl acetate) to afford N-(1-Boc-azetidine-3-ylmethyl)aniline 48 as a colorless oil (520 mg, 84%).

EXAMPLE 39

N-(1-phenethylazetidine-3-ylmethyl)-N-phenylpropionamide 50

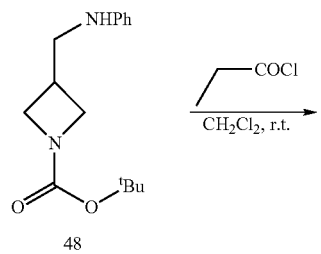

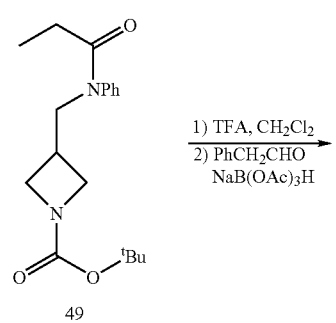

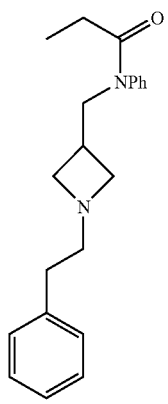

50

To a solution of N-(1-Boc-Azetidine-3-ylmethyl)aniline 48 (218.6 mg, 0.791 mmol) and piperidinomethyl polystyrene resin (250 mg) in 2 mL of dry CH$_2$Cl$_2$ was added propionyl chloride (77 μL, 1 eq.) at room temperature. After being shaken at room temperature overnight, the reaction mixture was passed through an aminopropyl NH$_2$ cartridge and washed with CH$_2$Cl$_2$ Removal of CH$_2$Cl$_2$ afforded N-(1-Boc-azetidine-3-ylmethyl)-N-phenylpropionamide 49 (241 mg, 96%).

Trifluoroacetic acid (2 mL) was added dropwise to a solution of N-(1-Boc-azetidine-3-ylmethyl)-N-phenylpropionamide 49 (241 mg, 0.757 mmol) in 2 mL of dry CH$_2$Cl$_2$ at 0° C. (ice-water). The reaction mixture was stirred at room temperature for 20 minute. After removal of the solvents, the residue was dried under vacuum for 2 hrs. The crude product 6 was used in the next step without purification.

The crude compound from the previous step was dissolved in DMF (3 mL) and phenylacetaldehyde (303 mg, 3 eq.) was added. The mixture was stirred at room temperature for 30 min. NaB(OAc)$_3$H (95%, 481 mg, 3 eq.) was introduced in one portion, and the mixture was stirred at room temperature overnight. The mixture was quenched with 5 mL of aqueous potassium carbonate (sat.), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by flash column chromatography. N-(1-phenethylazetidine-3-ylmethyl)-N-phenylpropionamide 50 (124 mg, 51%). LRMS 322.

EXAMPLE 40

Cyclopropanecarboxylic acid N-(1-phenethylpiperidin-3-ylmethyl)-N-phenamide 52

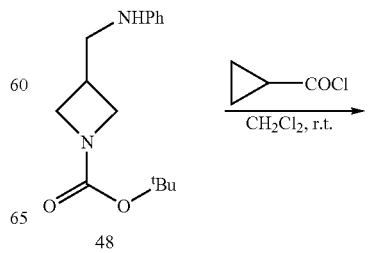

EXAMPLE 41

N-(1-Boc-morpholin-2-yl-methyl)aniline 55

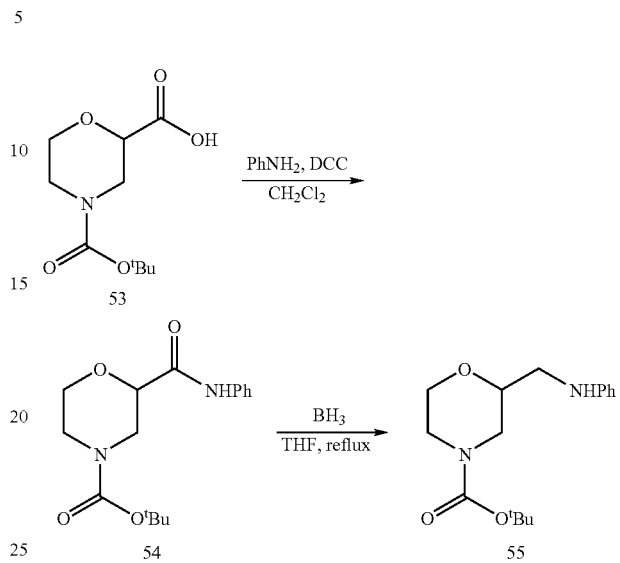

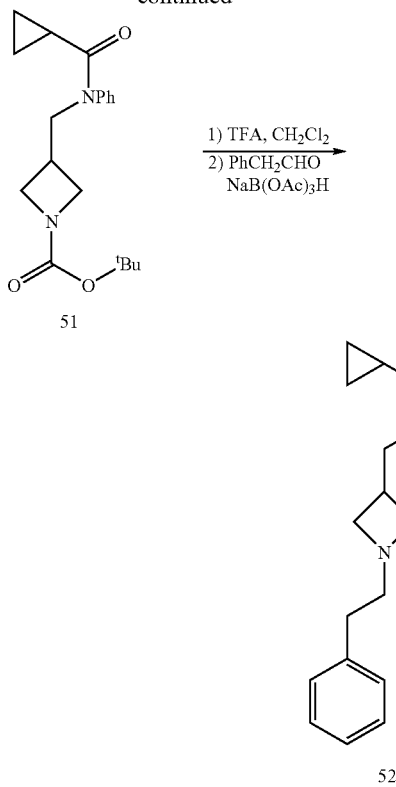

To a solution of N-(1-Boc-Azetidine-3-ylmethyl)-aniline 48 (108.7 mg, 0.393 mmol) and piperidinomethyl polystyrene resin (130 mg) in 2 mL of dry $CH_2Cl_2$ was added cyclopropanecarbonyl chloride (98%, 40 µL, 1.1 eq.) at room temperature. After being shaken at room temperature overnight, the reaction mixture was passed through an aminopropyl $NH_2$ cartridge and washed with $CH_2Cl_2$. Removal of $CH_2Cl_2$ afforded cyclopropanecarboxylic acid N-(1-Boc-piperidin-3-ylmethyl)-N-phenamide 51 (120 mg, 92%).

Trifluoroacetic acid (2 mL) was added dropwise to a solution of cyclopropane-carboxylic acid N-(1-Boc-piperidin-3-ylmethyl)-N-phenamide 51 (87.5 mg, 0.265 mmol) in 2 mL of dry $CH_2Cl_2$ at 0° C. (ice-water). The reaction mixture was stirred at room temperature for 20 minute. After removal of the solvents, the residue was dried under vacuum for 2 hrs. The crude product was used in the next step without purification.

The crude compound from the previous step was dissolved in DMF (3 mL) and phenylacetaldehyde (106 mg, 3 eq.) was added. The mixture was stirred at room temperature for 30 min. $NaB(OAc)_3H$ (95%, 168 mg, 3 eq.) was introduced in one portion, and the mixture was stirred at room temperature overnight. The mixture was quenched with 5 mL of aqueous potassium carbonate (sat.), then extracted with ethyl acetate (3×10 mL). The extracts were combined and washed with aqueous $NaHCO_3$ (sat., 2×5 mL), brine (10 mL), and dried over anhydrous sodium sulfate. After the solvent was removed, the remaining oily residue was purified by flash column chromatography to afford cyclopropanecarboxylic acid N-(1-phenethylpiperidin-3-ylmethyl)-N-phenamide 52 (46 mg, 50%). LRMS 344.

To a solution of N-Boc-2-carboxymorpholine 53 (20 g, 86.95 mmol), aniline (8.71 ml, 95.58 mmol) in $CH_2Cl_2$ (200 ml) at 0° C. was added DCC (21.19 g, 102.69 mmol) in several portions. The mixture was stirred at room temperature for 3 hrs. The white precipitate was removed by filtration. The filtrate was washed with 5% HCl, sat. $NaHCO_3$ and then dried over $Na_2SO_4$, filtered and evaporated. The residue was dried by azotropic evaporation with benzene to give 54 as a white solid. LRMS calculated for $C_{16}H_{22}N_2O_4$ 306, found 306.

To a solution of N-Boc-morpholine-2-carboxylic acid phenylamide 54 from the previous experiment in THF (100 ml) at 0° C. was added $BH_3$-THF solution (1.0 M, 180 ml) through an addition funnel. After addition, the mixture was refluxed for 7 hrs. The reaction was quenched by slow addition of aq. $NaHCO_3$. THF was removed by evaporation. The residue was extracted with EtOAc (3×50 ml). The combined organic solution was dried with $Na_2SO_4$, filtered and evaporated. The residue crystallized upon standing at room temperature to give 55 as a white solid (17.15 g). More solid (about 2 g) was obtained from the mother liquid (76%).

EXAMPLE 42

N-(2'-phenylethylmorpholin-2-yl-methyl)-N-phenyl-propionamide 57

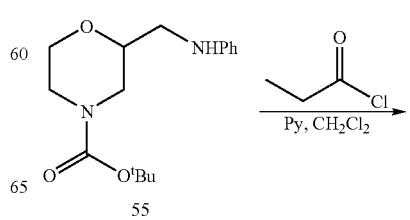

-continued

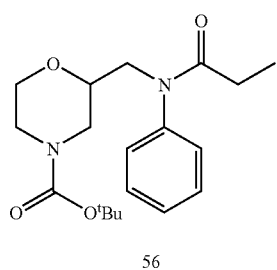

56

1) TFA, CH$_2$Cl$_2$
2) PhCH$_2$CH$_2$Br
K$_2$CO$_3$

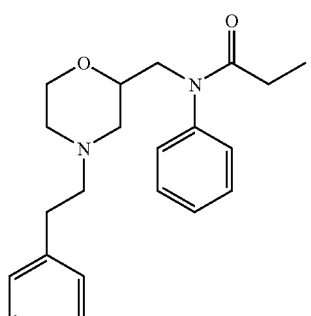

57

To a solution of N-(1-Boc-morpholin-2-yl-methyl)-aniline 55 (7.49 g, 25.65 mmol), pyridine (3.1 ml, 38.48 mmol) in CH$_2$Cl$_2$ (50 ml) at 0° C. was added propionyl chloride (2.45 ml, 28.20 mmol). After stirring for 30 min, the mixture was washed with sat. NaHCO$_3$, dried over Na$_2$SO$_4$, filtered and evaporated to give a colorless oil, which crystallized upon standing at room temperature to give a white solid 56 (5.49 g, 60%).

To a solution of N-(1-Boc-morpholin-2-yl-methyl)-N-phenyl-propionamide 56 (5.40 g, 15.50 mmol) in CH$_2$Cl$_2$ (10 ml) at 0° C. was added TFA (10 ml). After stirring for 2.5 hr, solvent and excess TFA was removed by evaporation. The residue was dissolved in 20 ml of CH$_2$Cl$_2$, neutralized with sat. NaHCO$_3$. Organic layer was separated, washed with sat. NaHCO$_3$, and dried with Na$_2$SO$_4$. After evaporation of the solvent, the light yellow oil was dissolved in CH$_3$CN (10 ml), to which H$_2$O (10 ml), K$_2$CO$_3$ (4.80 g) and (2-bromoethyl) benzene (2.2 ml) was added. The mixture was stirred at 70° C. for 6 hrs. After cool down to room temperature, the organic layer was separated. Aqueous layer was extracted with EtOAc (2×10 ml). The combined organic solution was dried with Na$_2$SO$_4$, filtered and evaporated. The crude product was purified by flash silica gel chromatography (4% MeOH in CH$_2$Cl$_2$) to give a colorless oil 57 (5.00, 92%). $^1$H-NMR (300 MHz, CDCl$_3$) δ 7.5–7.20 (m, 10H), 3.90–3.55 (m, 5H), 2.90–2.50 (m, 6H), 2.20 (m, 1H), 2.00 (m, 3H), 1.0 (m, 3H), LRMS calculated for C$_{22}$H$_{28}$N$_2$O$_2$ 352. found 352.

EXAMPLE 43

HPLC Separation of the Enantiomers of 57

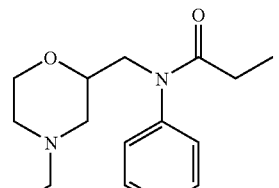

57

HPLC Separation

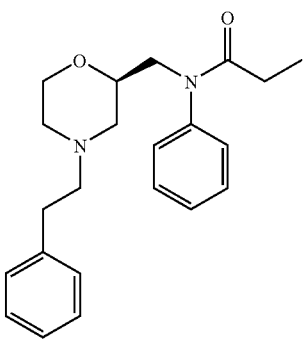

151

+

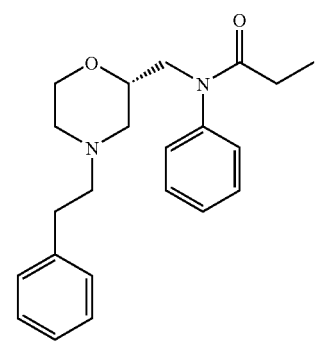

152

The enantiomers of 57 were separated using a preparative HPLC procedure. The conditions were as follows: ChiralPak AD column; 10% i-PrOH in hexane; μ=5 mL/min; and λ=254 nm. The absolute configuration of the chiral centers was not determined. The first peak (retention time=10.45 min) was arbitrarily assigned structure 152, and the second peak (retention time=11.99 min) was arbitrarily assigned structure 151.

EXAMPLE 44

Cyclopropanecarboxylic acid N-(2'-phenylethylmorpholin-2-yl-methyl)-N-phenyl amide 59

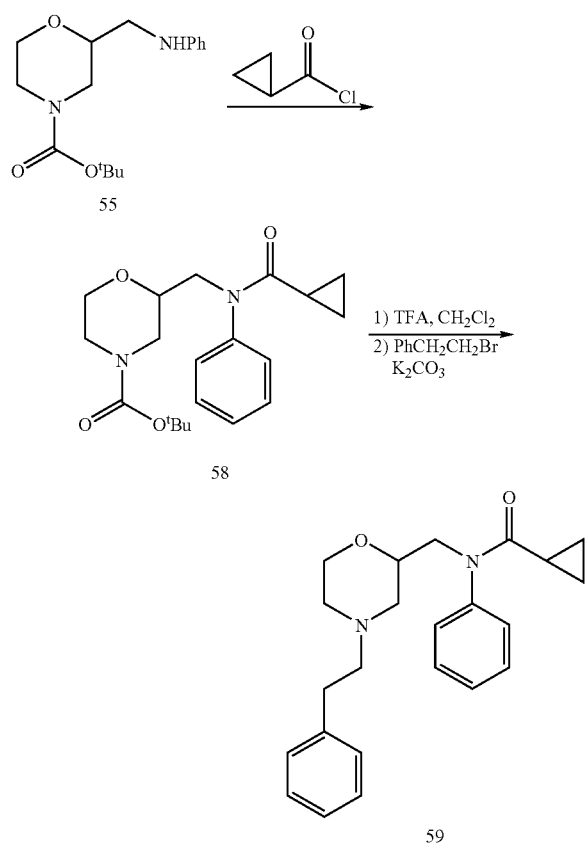

To a solution of N-(1-Boc-morpholin-2-yl-methyl)-aniline 55 (91.5 mg, 0.313 mmol), piperidinomethyl polystyrene resin (116 mg) in 1 mL of dry $CH_2Cl_2$ was added cyclopropanecarbonyl chloride (98%, 34 µL, 1.2 eq.) at room temperature. After being shaken at room temperature 1 h, the reaction mixture was passed through an aminopropyl $NH_2$ cartridge and washed with $CH_2Cl_2$. Removal of $CH_2Cl_2$ afforded Cyclopropanecarboxylic acid N-(2'-Boc-morpholin-2-yl-methyl)-N-phenyl amide 58 (91 mg, 81%).

Trifluoroacetic acid (0.5 mL) was added dropwise to a solution of Cyclopropane-carboxylic acid N-(2'-Boc-morpholin-2-yl-methyl)-N-phenyl amide 58 (63.2 mg, 0.175 mmol) in 0.5 mL of dry $CH_2Cl_2$ at 0° C. (ice-water). The reaction mixture was stirred at room temperature for 20 minute. After removal of the solvents, the residue was dried under vacuum for 2 hrs. The crude product was used in the next step without purification.

The crude product was dissolved in 2 ml of $CH_3CN$, to which $K_2CO_3$ (75 mg) and (2-bromoethyl) benzene (47 µL, 2 eq.) was added. The mixture was stirred at 50° C. for 4 hrs. After cool down to room temperature, 2 mL of $NaHCO_3$ (sat.) and 10 mL of EtOAc were added. The organic layer was separated. Aqueous layer was extracted with EtOAc (2×5 mL). The combined organic solution was dried over $Na_2SO_4$, filtered and evaporated. The crude product was purified by flash silica gel chromatography to give a colorless oil Cyclopropanecarboxylic acid N-(2'-phenylethylmorpholin-2-yl-methyl)-N-phenyl amide 59 (55 mg, 86%). LRMS 364.

EXAMPLE 45

N-(1-Boc-piperidin-3-(R)-ylcarboxy)-N-(pyridin-3-yl)amide 64

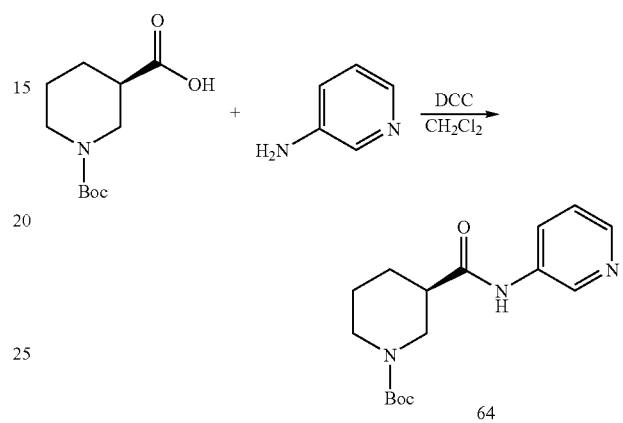

A solution of R-Boc-nipecotic acid (6.54 mmol, 1.50 g) and 3-aminopyridine (1.1 equiv, 7.20 mmol, 677 mg) in $CH_2Cl_2$ at 0° C. was treated with DCC (2.0 equiv, 13.08 mmol, 2.70 g) under Ar. The reaction mixture was allowed to warm to 25° C. and stirred for 12 h. The reaction mixture was then filtered to remove the urea and the solvents were removed in vacuo. Chromatography ($SiO_2$, 2.5 cm×30.5 cm, 3:1 hexane-EtOAc) gave 64 (1.26 g, 2.00 g theoretical, 63%) as a white solid: $R_f$ 0.33 ($SiO_2$, 3:1 hexane-EtOAc), LRMS m/z 305 ($M^+$, $C_{16}H_{23}N_3O_3$, requires 305).

EXAMPLE 46

N-(1-Phenethyl-piperidin-3-R-ylmethyl)-N-(pyridin-3-yl)cyclopropionamide 66

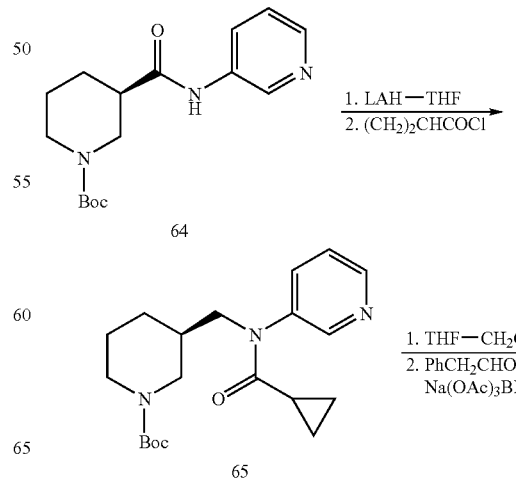

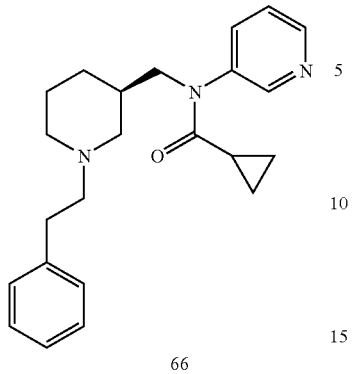

66

A solution of 64 (0.33 mmol, 100 mg) in THF at 0° C. was treated with 1M LAH in THF (2.0 equiv, 0.655 mmol, 655 µL) under Ar. The reaction mixture was allowed to warm to 25° C. and stirred for 1 h. The reaction mixture was then cooled to 0° C. and quenched with 10% aqueous HCl. The pH was then adjusted to 10 with 10% aqueous NaOH and the reaction mixture was extracted with 3×EtOAc (25 mL). The organics were dried with $NaCl_{(sat)}$ and $MgSO_{4(s)}$. The resulting amine was carried directly to the next step.

The above solution in $CH_2Cl_2$ at 0° C. was treated with cyclopropanecarbonyl chloride (1.1 equiv, 0.36 mmol, 33 µL) and diisopropylethylamine (2.0 equiv, 0.652 mmol, 114 µL) under Ar. The reaction mixture warmed to 25° C. and stirred for 12 h. After the reaction mixture was quenched with 10% aqueous $NaHCO_3$ and then extracted with 3×EtOAc (25 mL). Chromatography ($SiO_2$, 1.3 cm×30.5 cm, 3:1 EtOAc-Hexane) provided 65 (53 mg, 117 mg theoretical, 45%) as a golden oil: $R_f$ 0.32 ($SiO_2$, 3:1 EtOAc -Hexane); LRMS m/z 359 ($M^+$, $C_{20}H_{29}N_3O_3$, requires 359).

Compound 65 (0.15 mmol, 33 mg) was treated with 20% TFA-$CH_2Cl_2$ under Ar. The reaction mixture stirred for 1 h. The solvents were removed in vacuo and the resulting oil was dried for 3 h under vaccum. The resulting crude amine salt was used directly without purification.

The above compound and phenylacetaldehyde (2.0 equiv, 0.29 mmol, 34 µL) were dissolved in DMF (500 µL) under Ar. After stirring for 1 h at 25 ° C., the reaction mixture was treated with $Na(OAc)_3BH$ (2.0 equiv, 62 mg, 0.29 mmol) and stirred for 12 h at 25° C. The reaction mixture was quenched with 10% aqueous $NaHCO_3$.and then extracted with 3×EtOAc (25 mL). Chromatography (PTLC, $SiO_2$, 20 cm×20 cm, 1 mm, 9:1 EtOAc-$CH_3OH$) provided 66 (19 mg, 53 mg theoretical, 36%) as a golden oil: $R_f$ 0.26 ($SiO_2$, 3:1 EtOAc-Hexane),; LRMS m/z 363 ($M^+$, $C_{23}H_{29}N_3O$, requires 363).

EXAMPLE 47

N-(1-tert-Butyloxy-piperidin-3-S-ylcarboxy)-N-(pyridin-3-yl)amide 67

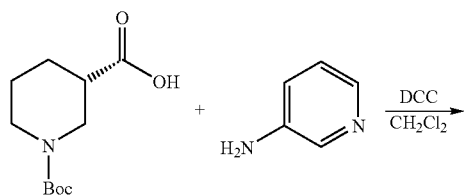

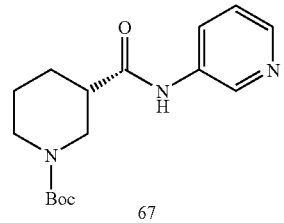

67

A solution of S-Boc-nipecotic acid (6.54 mmol, 1.50 g) and 3-aminopyridine (1.1 equiv, 7.20 mmol, 677 mg) in $CH_2Cl_2$ (25 mL) at 0° C. was treated with DCC (2.0 equiv, 13.08 mmol, 2.70 g) under Ar. The reaction mixture was allowed to warm to 25° C. and stirred for 12 h. The reaction mixture was then filtered to remove the urea and the solvents were removed in vacuo. Chromatography ($SiO_2$, 2.5 cm×30.5 cm, 3:1 hexane-EtOAc) gave 67 (1.08 g, 2.00 g theoretical, 54%) as a white solid: $R_f$ 0.33 ($SiO_2$, 3:1 hexane-EtOAc), LRMS m/z 305 ($M^+$, $C_{16}H_{23}N_3O_3$, requires 305).

EXAMPLE 48

N-(1-Phenethyl-piperidin-3-S-ylmethyl)-N-(pyridin-3-yl)cyclopropionamide 69

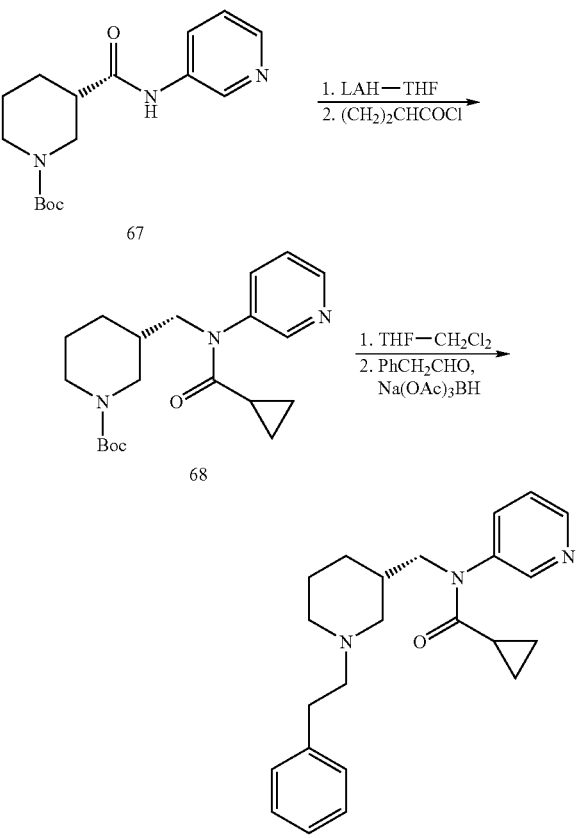

A solution of 67 (3.37 mmol, 1.03 g) in THF (5 mL) at 0° C. was treated with 1M LAH in THF (2.0 equiv, 6.74 mmol, 6.74 mL) under Ar. The reaction mixture was allowed to warm to 25° C. and stirred for 1 h. The reaction mixture was then cooled to 0° C. and quenched with 10% aqueous HCl. The pH was then adjusted to 10 with 10% aqueous NaOH and the reaction mixture was extracted with 3×EtOAc (25 mL). The organics were dried with NaCl$_{(sat)}$ and MgSO$_4$. The resulting amine was carried directly to the next step.

The above solution in CH$_2$Cl$_2$ at 0° C. was treated with cyclopropanecarbonyl chloride (1.5 equiv, 3.66 mmol, 332 μL) and diisopropylethylamine (1.1 equiv, 2.68 mmol, 467 μL) under Ar. The reaction mixture warmed to 25° C. and stirred for 12 h. After the reaction mixture was quenched with 10% aqueous NaHCO$_3$ and then extracted with 3×EtOAc (25 mL). Chromatography (SiO$_2$, 1.3 cm×30.5 cm, 3:1 EtOAc-Hexane) provided 68 (263 mg, 877 mg theoretical, 30%) as a golden oil: R$_f$ 0.32 (SiO$_2$, 3:1 EtOAc-Hexane); LRMS m/z 359 (M$^+$, C$_{20}$H$_{29}$N$_3$O$_3$, requires 359).

Compound 68 (3.37 mmol, 1.21 g) was treated with 20% TFA-CH$_2$Cl$_2$ under Ar. The reaction mixture stirred for 1 h. The solvents were removed in vacuo and the resulting oil was dried for 3 h under vacuum. The resulting crude amine salt was used directly without purification.

The above compound and phenylacetaldehyde (2.0 equiv, 6.74 mmol, 790 μL) were dissolved in DMF (10 mL) under Ar. After stirring for 1 h at 25 ° C., the reaction mixture was treated with Na(OAc)$_3$BH (2.0 equiv, 1.43 g, 6.74 mmol) and stirred for 12 h at 25° C. The reaction mixture was quenched with 10% aqueous NaHCO$_3$. and then extracted with 3×EtOAc (25 mL). Chromatography (PTLC, SiO$_2$, 20 cm×20 cm, 1 mm, 9:1 EtOAc-CH$_3$OH) provided 69 (0.200 g, 1.22 g theoretical, 16%) as a golden oil: R$_f$ 0.26 EtOAc-Hexane); LRMS m/z 363 (M$^+$, C$_{23}$H$_{29}$N$_3$O, requires 363).

EXAMPLE 49

(R)-Cyclopropanecarboxylic acid N-(1-phenethylpiperidin-3-ylmethyl)-N-phenamide 71

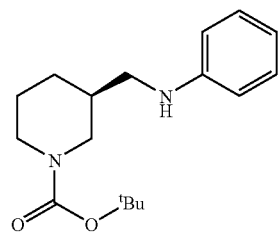

28

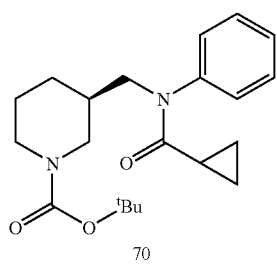

70

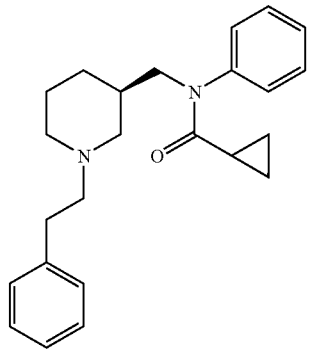

71

Following a procedure similar to that described in Example 48, compound 28 gave (R)-Cyclopropanecarboxylic acid N-(1-phenethylpiperidin-3-ylmethyl)-N-phenamide 71. LRMS 362.

EXAMPLE 50

(S)-Cyclopropanecarboxylic acid N-(1-phenethylpiperidin-3-ylmethyl)-N-phenamide 73

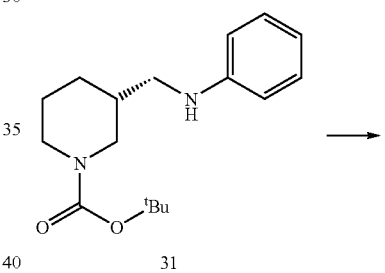

31

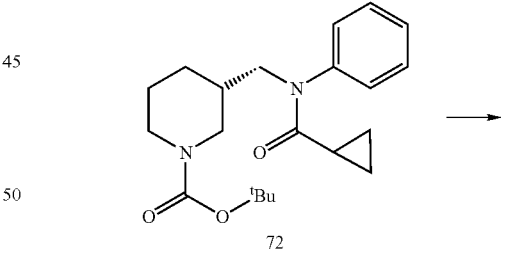

72

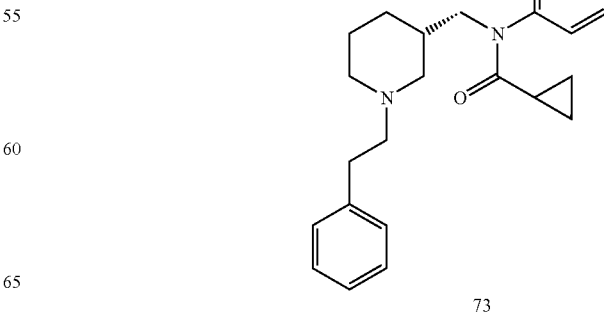

73

Following a procedure similar to that described in Example 48, compound 31 gave (S)-Cyclopropanecarboxylic acid N-(1-phenethylpiperidin-3-ylmethyl)-N-phenamide 73. LRMS 362.

EXAMPLE 51

Cyclopropanecarboxylic acid N-(1-Phenethylpiperidin-3-ylmethyl)-N-(pyridin-2-yl)amide 76

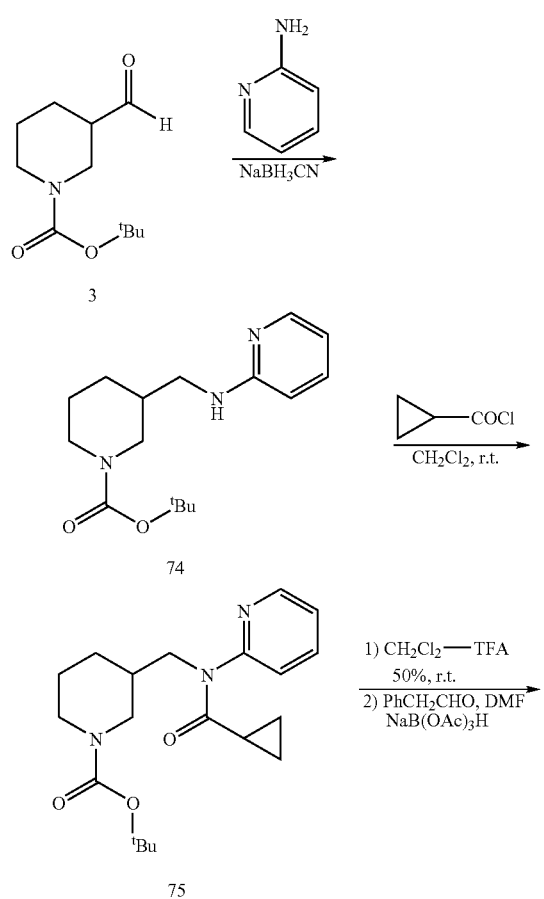

Following the procedures described in Examples 3–5, compound 3 gave Cyclopropanecarboxylic acid N-(1-Phenethylpiperidin-3-ylmethyl)-N-(pyridin-2-yl)amide 76. LRMS 359.

EXAMPLE 52

N-Benzylpropanolamine 77

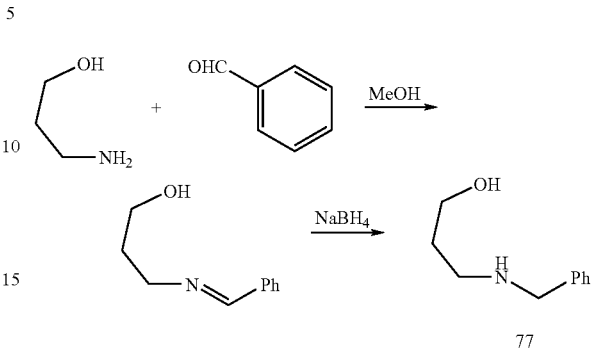

3-Amino-1-propanol (60.5 mL, 792 mmol) was added to a solution of benzaldehyde (76.6 mL, 754 mmol) in MeOH (1.51 L, 0.5 M), and the solution was stirred and heated to 75° C. After 25 minutes, the reaction was cooled to room temperature, and then to 0° C. in an ice bath. Solid NaBH$_4$ (28.52 g, 754 mmol) was added over 20 minutes, and the reaction was allowed to warm to room temperature, with stirring, overnight. Water was added, the solvent was removed in vacuo, and EtOAc was added. The organic layer was removed and treated with 5% aqueous HCl. The new aqueous layer was removed, EtOAc was added, and 10% aqueous NaOH was added dropwise to basify the solution. The aqueous layer was extracted with EtOAc (2×), and the combined organics were dried with Na$_2$SO$_4$, and concentrated in vacuo to obtain pure N-benzylpropanolamine (77). Crude product 77 was used without purification in the next step. $^1$H NMR (CD$_3$OD) 7.4–7.2 (5H, m), 4.95 (2H, broad s), 3.75 (2H, broad s), 3.64 (2H, t, J=6.2 Hz), 2.70 (2H, t, J=7.1 Hz), 1.77 (2H, q, J=6.7 Hz). $^{13}$C NMR (CD$_3$OD) 140.79, 129.61, 128.28, 61.78, 54.68, 47.56, 33.10 ppm. LRMS: 165.91.

EXAMPLE 53

4-Benzyl-2-chloromethyl-1,4-oxazepane 79

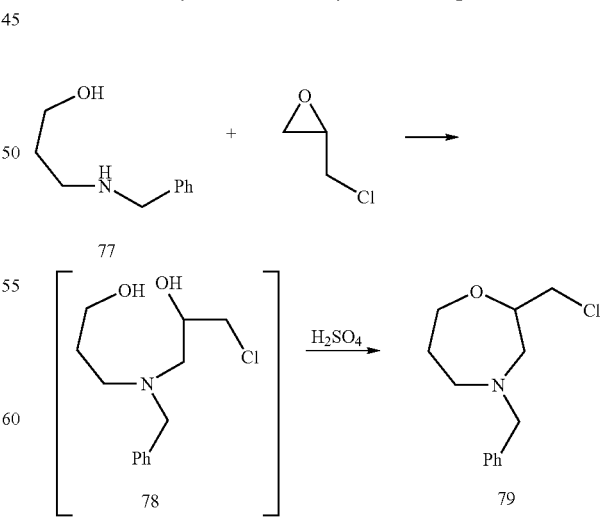

N-benzylpropanolamine (77) (5.00 g, 30.3 mmol) was dissolved in epichlorohydrin (23.7 mL, 303 mmol) and heated to 40° C. When the reaction was judged complete by TLC (3 h), the epichlorohydrin was removed under high vacuum overnight. (Intermediate 78: LRMS: 257.58.) H$_2$SO$_4$ (9.2 mL, 3.3M) was added, with stirring at room temperature, and the reaction was heated to 150° C. in a preheated oil bath until the reaction was judged complete by TLC (0.5 h). The reaction was removed from heat and cooled by the addition of ice. CH$_2$Cl$_2$ was added, and the organic layer was removed and discarded. EtOAc was added to the acidic aqueous layer, and 10% KOH was added dropwise until the aqueous layer was basic. The organic layer was removed; the aqueous layer was extracted with EtOAc (2×), and the combined organics were dried over sodium sulfate, filtered and concentrated in vacuo to obtain 4-benzyl-2-chloromethyl-1,4-oxazepane (79), which was used without purification in the next step. $^1$H NMR (CD$_3$OD) 7.4–7.2 (5H, m), 3.93–3.75 (3H, m), 3.67 (2H, broad d, J=1.3 Hz), 3.44 (2 H, dd, J=5.9, 4.3 Hz), 2.95 (1H, ddd, J=13.7, 2.5, 1.2 Hz), 2.79 (1H, dddd, J=12.6, 6.8, 4.1, 1.2 Hz), 2.64–2.52 (2H, m), 2.0–1.65 (2H, m) ppm. $^{13}$C NMR (CD$_3$OD) 139.89, 130.33, 129.46, 128.39, 79.26, 68.31, 63.64, 59.59, 55.30, 46.57, 31.35 ppm. $^{13}$C NMR (CDCl$_3$) 139.10, 128.82, 128.32, 127.11, 78.27, 67.43, 62.79, 58.55, 54.26, 45.80, 30.55 ppm. LRMS: 239.54.

EXAMPLE 54

(4-Benzyl-1,4-oxazepan-2-ylmethyl)-phenyl amine 80

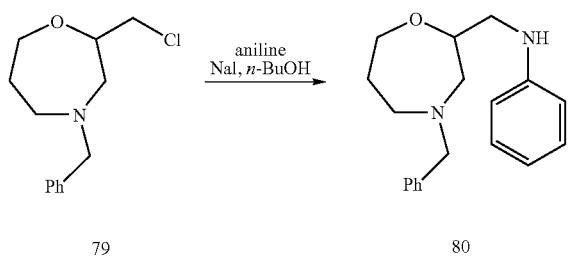

Aniline (2.59 mL, 28.4 mmol) and NaI (4.06 g, 27.1 mmol) were added to a solution of 4-benzyl-2-chloromethyl-1,4-oxazepane (79) (6.49 g, 27.1 mmol) in n-butanol (68 mL, 0.4 M), and the reaction was heated to 110° C. until the reaction was judged complete by TLC (4 h). The reaction was cooled to room temperature, and water and CH$_2$Cl$_2$ were added. The organic layer was removed, and the aqueous layer was extracted with CH$_2$Cl$_2$ (2×). The combined organic extracts were dried over sodium sulfate, filtered and concentrated in vacuo to achieve (4-benzyl-1,4-oxazepan-2-ylmethyl)-phenyl amine 80, which was used without purification in the next reaction. $^1$H NMR (partial, CDCl$_3$) 4.08–3.86 (3H, m), 3.80 (1H, d, J=13.3 Hz), 3.73 (1H, d, J=13.3 Hz), 3.22–3.05 (2H, m), 2.95–2.70 (3H, m), 2.64 (1H, dd, J=13.6, 7.6 Hz), 2.1–1.9 (2H, m) ppm. $^{13}$C NMR (CDCl$_3$) 148.33, 139.38, 129.28, 129.11, 128.46, 127.23, 117.44, 113.13, 76.70, 67.49, 62.92, 59.35, 54.76, 46.93, 30.75 ppm. LRMS: 296.68.

EXAMPLE 55

4-Benzyl-1,4-oxazepan-2-ylmethyl)-N-phenylropionamide 81

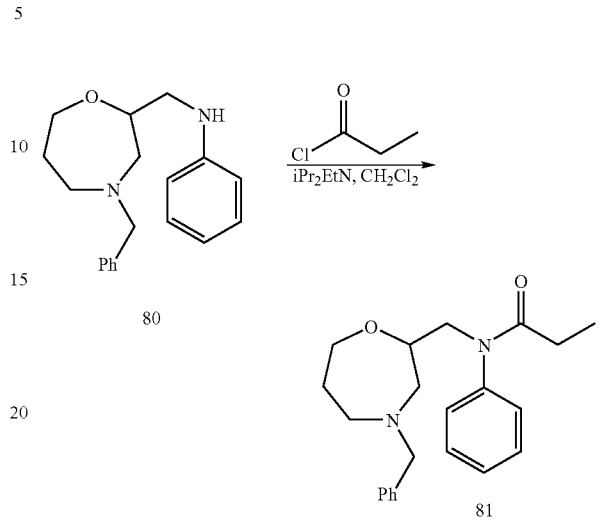

iPr$_2$EtN (4.72 mL, 27.1 mmol) was added to a solution of (4-benzyl-1,4-oxazepan-2-ylmethyl) phenyl amine (80) (27.1 mmol) in CH$_2$Cl$_2$. The solution was cooled to 0° C. in an ice bath, then propionyl chloride (5.17 mL, 59.6 mmol) was added dropwise. The reaction was allowed to warm slowly to room temperature, with stirring, overnight. CH$_2$Cl$_2$ and 10% aqueous NaOH was added. The organic layer was removed and the aqueous layer extracted with CH$_2$Cl$_2$ (2×). The organic extracts were dried with sodium sulfate, filtered and concentrated in vacuo. The resulting oily residue was purified by silica gel chromatography (97:1:2::Hexanes:CH$_2$Cl$_2$:2N NH$_3$ in EtOH) to obtain 4-benzyl-1,4-oxazepan-2-ylmethyl)-N-phenylpropionamide (81) as a pale yellow oil. $^1$H NMR (CDCl$_3$, ppm) 7.36–7.19 (8H, m), 6.94 (2H, broad d, J=6.5 Hz), 3.89–3.38 (5H, m), 3.65 (1H, d, J=13.3 Hz), 3.54 (1H, d, J=13.3 Hz), 2.88–2.75 (2H, m), 2.55 (1H, ddd, J=12.5, 8.9, 4.2 Hz), 2.34 (1H, dd, J=13.5, 8.9 Hz), 1.98–1.68 (4H, m), 0.98 (3H, t, J=7.5 Hz). $^{13}$C NMR (CDCl$_3$) 174.05, 143.19, 139.64, 129.60, 129.15, 128.46, 128.35, 127.79, 127.10, 76.80, 67.25, 62.61, 59.05, 54.43, 51.64, 30.42, 27.91, 9.70 ppm. LRMS: 352.72.

EXAMPLE 56

(4-Phenethyl-1,4-oxazepan-2-ylmethyl)-N-phenyl-propionamide 82

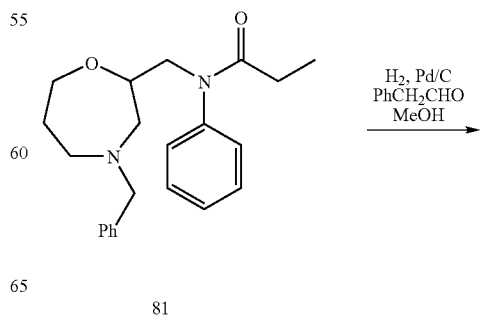

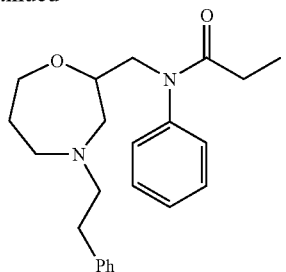

82

Phenylacetaldehyde (0.17 mL, 1.42 mmol) was added to 4-benzyl-1,4-oxazepan-2-ylmethyl)-N-phenylpropionamide (81) (0.115 g, 0.326 mmol) dissolved in MeOH (9.5 mL). 10% Pd/C (0.101 g) was added, and the mixture was shaken under 40 psi $H_2$ until the consumption of $H_2$ ceased and the reaction was judged complete by TLC (4.25 h). The crude reaction mixture was passed through a column of Celite, concentrated in vacuo, and purified by flash column chromatography (50:48:2::Hexanes:$CH_2Cl_2$:2N $NH_3$ in EtOH) to obtain pure (4-phenethyl-1,4-oxazepan-2-ylmethyl)-N-phenylpropionamide (82). $^1$H NMR (CDCl$_3$) 7.50–7.10 (10 H, m), 3.95–3.77 (2H, m), 3.79–3.59 (3H, m), 2.97–2.86 (2H, m), 2.78 (4H, s), 2.68 (1H, ddd, J=12.9, 9.0, 4.0 Hz), 2.51 (1H, dd, J=13.5, 9.1 Hz), 2.08 (2H, q, J=7.5 Hz), 1.98–1.76 (2H, m), 1.07 (3H, t, J=7.5 Hz) ppm. $^{13}$C NMR (CDCl$_3$) 174.17, 143.32, 140.46, 129.64, 128.83, 128.55, 128.45, 127.85, 126.07, 76.28, 67.12, 60.10, 59.63, 53.93, 51.81, 34.23, 30.29, 28.02, 9.78 ppm. LRMS: 366.98.

EXAMPLE 57

(R)- & (S)-(4-Phenethyl-1,4-oxazepan-2-ylmethyl)-N-phenylpropionamide 83 & 84

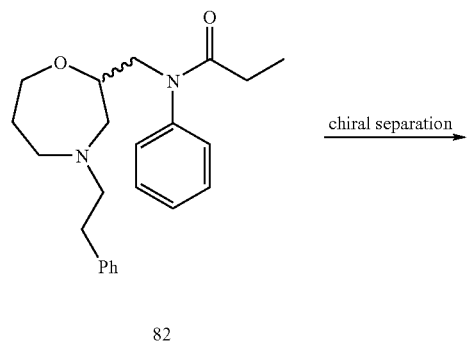

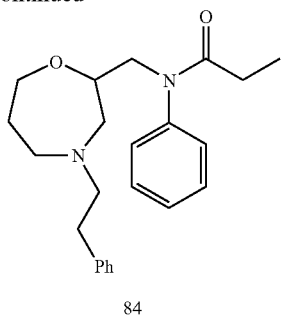

84

The enantiomers of (4-phenethyl-1,4-oxazepan-2-ylmethyl)-N-phenylpropionamide (82) were separated on a chiral column (Chiralpak AD Column number AD00CG-1F001) with (9:1) Hexanes:iPrOH (λ=235 nm; flow rate=5 mL/min). Using an analytical Chiralpak column with 90:10 hexanes:isopropanol (λ=220 nm; flow rate=1 mL/min), the first compound to elute from the column (9.175 min) was randomly assigned 83 (R), and the second compound to elute from the column (13.909 min) was assigned 84 (S). The absolute configurations of 83 and 84 were not established.

EXAMPLE 58

4-Benzyl-1,4-ozazepan-2-ylmethyl)-N-phenylcyclopropanamide 85

85

Pyridine (3.64 mL, 45.0 mmol) was added to a solution of crude amine 80 (30.0 mmol) in $CH_2Cl_2$. The solution was cooled to 0° C. in an ice bath, then cyclopropyl carbonyl chloride (2.99 mL, 33.0 mmol) was added dropwise. The reaction was allowed to warm slowly to room temperature and stirred until the reaction was judged complete by TLC (3.25 h). $CH_2Cl_2$ and saturated $NaHCO_3$ were added. The organic layer was removed and the aqueous layer extracted with $CH_2Cl_2$ (2×). The organic extracts were dried with sodium sulfate, filtered and concentrated in vacuo. The resulting oily residue was purified by alumina gel chromatography (96:2:2::Hexanes:CH₂Cl₂:2N NH₃ in EtOH) to obtain 4-benzyl-1,4-ozazepan-2-ylmethyl)-N-phenylcyclopropanamide (85) as a pale yellow oil. ¹H NMR (CD₃OD) 7.46–7.24 (8H, m), 7.13 (2H, broad d, J=7.2 Hz), 3.90–3.42 (5H, m), 2.92–2.76 (2H, m), 2.62–2.51 (1H, m), 2.30 (1H, dd, 13.7, 8.5Hz), 1.40–1.20 (2H, m), 0.96–0.82 (3H, m), 0.61 (2H, dd, J=7.9, 2.8 Hz) ppm. ¹³C NMR (CD₃OD) 175.84, 144.04, 140.20, 130.82, 130.54, 129.55, 129.08, 128.43, 77.04, 68.00, 63.63, 59.72, 55.83, 52.94, 31.28, 13.76, 9.34,9.07 ppm. LRMS: 364.57.

EXAMPLE 59

4-Phenethyl-1,4-ozazepan-2-ylmethyl)-N-phenylcyclopropanamide 87

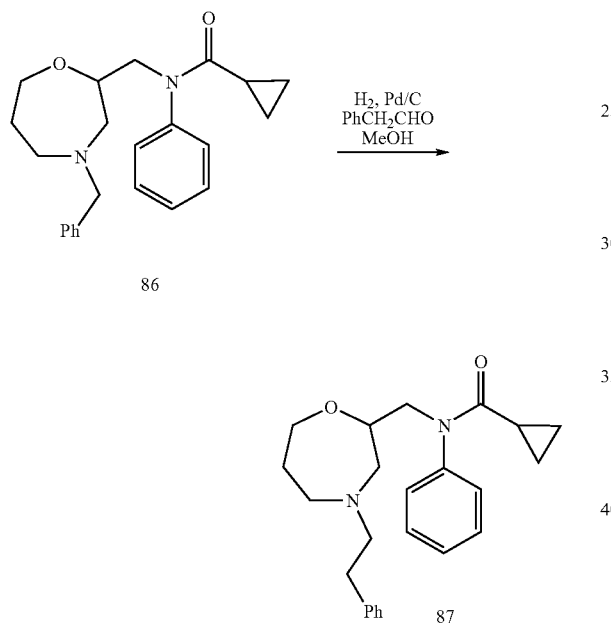

Phenylacetaldehyde (0.091 mL, 0.780 mmol) was added to N-benzylamine 86 (0.055 g, 0.156 mmol) dissolved in MeOH (5.2 mL, 0.03M). 10% Pd/C (0.0557 g) was added, and the mixture was shaken under 40 psi H₂ until the consumption of H₂ ceased and the reaction was judged complete by TLC. The crude reaction mixture was passed through a column of Celite, concentrated in vacuo, and purified by flash column chromatography (50:48:2::Hexanes:CH₂Cl₂:2N NH₃ in EtOH) to obtain pure 4-phenethyl-1,4-ozazepan-2-ylmethyl)-N-phenylcyclopropanamide (87). ¹H NMR (CDCl₃) 7.47 (2H, m), 7.37–7.26 (5H, m), 7.24–7.17 (3H, m), 3.94–3.80 (3H, m), 3.69 (1H, broad dd, J=13.3, 7.8 Hz), 3.62 (1H, ddd, J=11.7, 6.2, 5.3 Hz), 2.96–2.86 (2H, m), 2.77 (4H, s), 2.67 (1H, ddd, J=12.8, 8.9, 4.1 Hz), 2.50 (1H, dd, J=8.9, 6.7 Hz) 2.0–1.74 (2H, m), 1.42–1.28 (1H, m), 1.04 (2H, dtd, J=7.8, 3.4, 1.1 Hz), 0.67–0.60 (2H, m) ppm. ¹³C NMR (CDCl₃) 173.79, 143.39, 140.46, 129.52, 128.82, 128.61, 128.44, 127.53, 126.05, 76.41, 67.15, 60.06, 59.53, 53.90, 52.09, 34.21, 30.28, 12.92, 8.71, 8.50 ppm. LRMS: 378.80.

EXAMPLE 60

(R)- & (S)-4-phenethyl-1,4-ozazepan-2-ylmethyl)-N-phenylcyclopropanamide 88 & 89

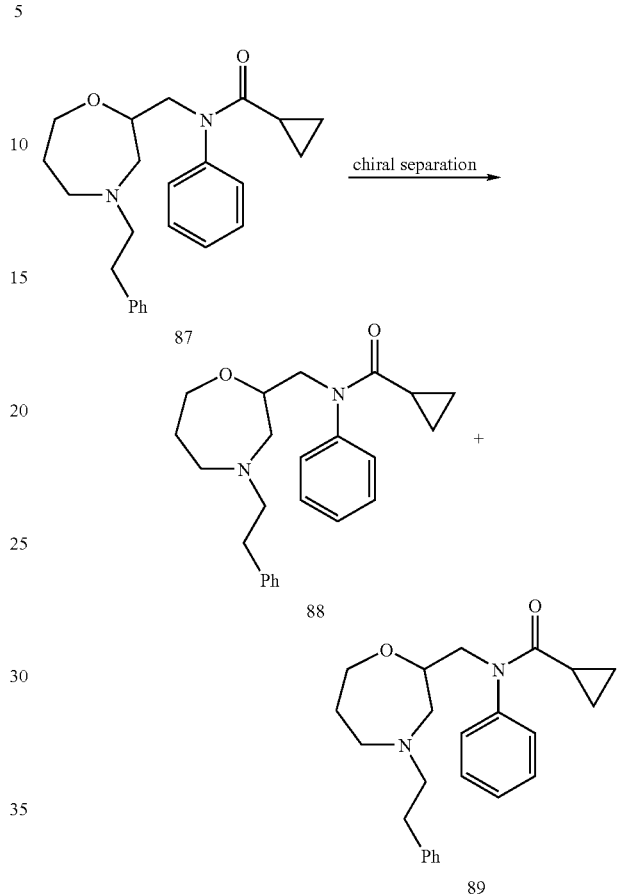

The enantiomers of 4-phenethyl-1,4-ozazepan-2-ylmethyl)-N-phenylcyclopropanamide (87) were separated on a chiral column (Chiralpak AD Column number AD00CG-1F001) with (9:1) Hexanes:iPrOH (λ=235 nm; flow rate=5 mL/min). Using an analytical Chiralpak column with 90:10 hexanes:isopropanol (λ=220 nm; flow rate=1 mL/min), the first compound to elute from the column (9.017 min) was randomly assigned 88 (R), and the second compound to elute from the column (14.275 min) was assigned 89 (S). The the absolute configurations of 88 and 89 have not been established.

EXAMPLE 61

1,4-Dioxa-8-aza-spiro[4.5]-decane-6-carboxylic acid methyl ester 91

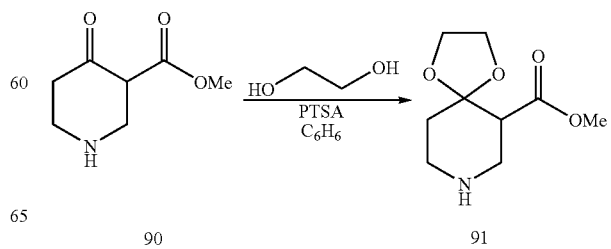

PTSA (24.7, 130 mmol) and ethylene glycol (24.8 mL, 439 mmol) were added to methyl-4-oxo-3-piperidine carboxylate hydrochloride (90) (25.1 g, 130 mmol) in benzene (52 mL, 2.5 M). The solution was stirred and heated to reflux overnight. $H_2O$ was removed using a Dean Stark trap. When the reaction was judged complete by TLC, 5% aqueous $NaHCO_3$ and $CH_2Cl_2$ were added, and the organic layer was removed. The aqueous layer was extracted with $CH_2Cl_2$ (5×), and the combined organics were dried over sodium sulfate, filtered and concentrated in vacuo, and purified by silica gel chromatography with 20:1 $CH_2Cl_2$:2N $NH_3$ in EtOH to provide 91 (16.7 g, 64%). $^1H$ NMR ($CDCl_3$) 3.82–3.70 (4H, m), 3.48 (3H, s), 3.00–2.50 (4H, m), 2.43 (1H, t), 176 (1H, m), 1.30 (1H, m) ppm. $^{13}C$ NMR ($CDCl_3$): 171.83, 106.57, 64.34, 64.17, 51.36, 48.91, 46.54, 43.69, 33.97 ppm.

EXAMPLE 62

8-Benzyloxycarbonyl-1,4-dioxa-8-aza-spiro[4.5] decane-6-carboxylic acid methyl ester 92

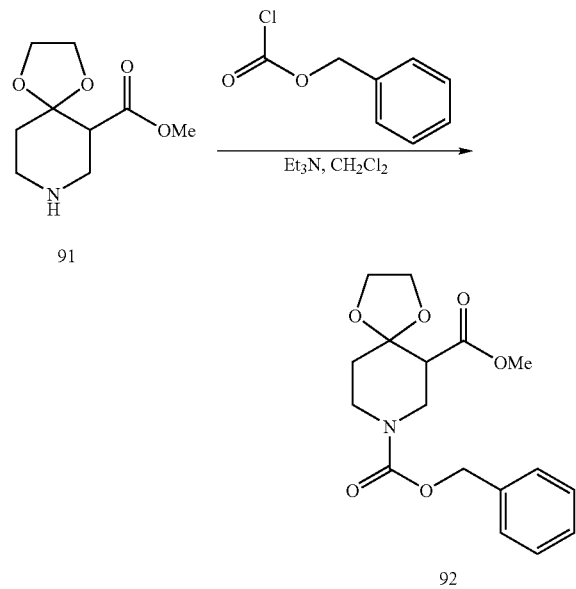

Triethylamine (29.0 mL, 208 mmol) was added to a solution of 1,4-dioxa-8-aza-spiro[4.5]-decane-6-carboxylic acid methyl ester (91) (16.6, 82.5 mmol) in $CH_2Cl_2$ (159 mL, 0.5 M). The solution was cooled to 0° C. in an ice bath, then benzoylchloroformate (12.8 mL, 89.9 mmol) was added dropwise, with stirring, over 40 minutes. When the reaction was judged complete by TLC (0.75 h), the solution was concentrated in vacuo and purified by silica gel chromatography (10:3 Hexanes:EtOAc) to provide pure 8-benzyloxycarbonyl-1,4-dioxa-8-aza-spiro[4.5]-decane-6-carboxylic acid methyl ester (92) (23.43 g, 85%). $^1H$ NMR ($CDCl_3$): 7.41–7.25 (5H, m), 5.10 (2H, broad s), 4.02–3.50 (11 H, m), 2.80–2.62 (1H, broad s), 2.20–2.00 (1H, broad s), 1.70–1.50 (1H, broad s) ppm. $^{13}C$ NMR ($CDCl_3$): 170.26, 154.88, 136.47, 128.32, 127.86, 127.74, 106.78, 67.09, 64.90, 64.59, 51.71, 48.63, 43.94, 41.76, 33.15 ppm.

EXAMPLE 63

8-Benzyloxycarbonyl-1,4-dioxa-8-aza-spiro[4.5] decane-6-carboxylic acid 93

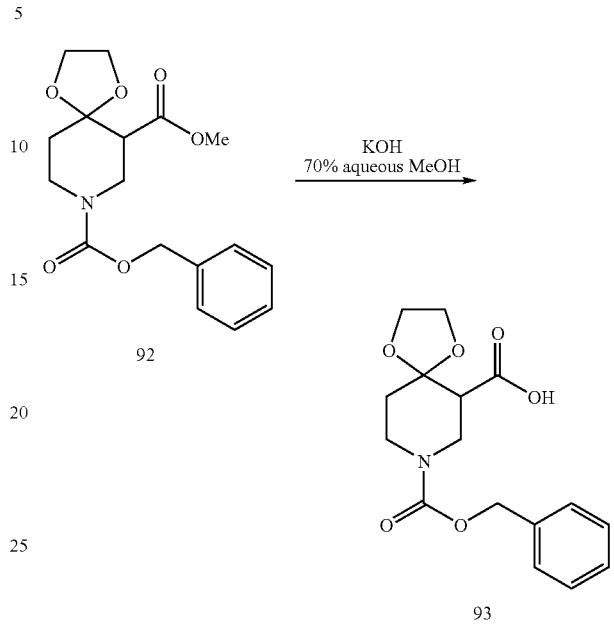

8-Benzyloxycarbonyl-1,4-dioxa-8-aza-spiro[4.5]decane-6-carboxylic acid (92) (15.04 g, 44.8 mmol) was dissolved in 70% aqueous MeOH (136 mL, 0.33M). KOH (3.76 g, 89.7 mmol) was added, and the solution was stirred at room temperature until judged complete by TLC (6.75 h). The reaction was concentrated in vacuo, the $CH_2Cl_2$ and $H_2O$ were added. The organic layer was removed and discarded. The aqueous layer was carefully acidified to pH=6 with saturated $NH_4Cl$. The organic layer was removed and concentrated in vacuo. The crude product 93 was used in the next reaction without further purification (13.3 g, 93% yield). $^1H$ NMR ($CDCl_3$) 9.8–9.2 (1H, broad s), 7.45–7.22 (5H, broad s), 5.18–5.10 (2H, broad s), 4.10–3.94 (4H, m), 3.92–3.78 (2H, m), 3.70–3.54 (2H, m), 2.82–2.70 (1H, broad s), 2.14–2.00 (1H, m), 1.70–1.54 (1H, m) ppm. $^{13}C$ NMR ($CDCl_3$) 174.35, 155.36, 136.58, 128.63, 128.17, 128.02, 107.14, 67.59, 65.17, 64.87, 48.75, 43.93, 41.96, 33.58 ppm. LRMS: 321.3.

EXAMPLE 64

8-Benzyloxycarbonyl-1,4-dioxa-8-aza-spiro[4.5] decane-6-carboxylic acid anilide 94

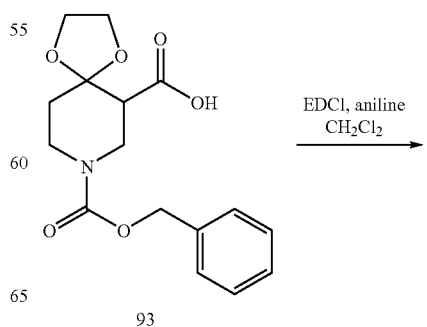

-continued

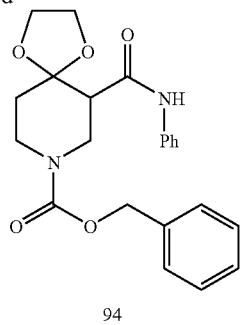

94

1-Ethyl-3-(3-dimethylaminopropyl)carbodiimide hydrochloride (EDCI, 2.13 g, 11.1 mmol) and aniline (1.29 mL, 14.2 mmol) were added to a stirring solution of acid 93 in $CH_2Cl_2$ (66.7 mL, 0.14M). The solution was stirred until judged complete by TLC (3 h). $CH_2Cl_2$ and $H_2O$ were added. The organic was removed, dried over sodium sulfate, filtered and concentrated in vacuo. The crude product was purified with 1:1 Hexanes:EtOAc to obtain pure 8-benzyloxycarbonyl-1,4-dioxa-8-aza-spiro[4.5]-decane-6-carboxylic acid anilide (94) (2.26 g, 61% yield). $^1$H NMR (CDCl$_3$): 8.20–8.00 (1H, broad s), 7.50 (2H, broad dd, J=8.7, 1.1 Hz), 7.39–7.26 (7H, m), 7.09 (1H, tt, J 7.4, 1.0 Hz), 5.17 (1H, d, J=12.5Hz), 5.11 (1H, d, 12.5 Hz), 4.35.(1H, d, J=12.9 Hz), 4.16–3.94 (4H, m), 3.51 (1H, dd, J=13.7, 11.1 Hz), 3.15 (1H, t, J=11.8 Hz), 2.75 (1H, dd, J=10.9, 4.5 Hz), 1.90–1.57 (3H, m) ppm. $^{13}$C NMR (CDCl$_3$): 167.20, 155.24, 138.02, 136.69, 129.23, 128.69, 128.25, 128.16, 124.36, 119.63, 108.22, 67.56, 65.26, 64.91, 50.24, 43.73, 41.87, 34.80 ppm. LRMS: 396.7.

EXAMPLE 65

8-Benzyloxycarbonyl-1,4-dioxa-8-aza-spiro[4.5]-decane-6-ylmethylphenylamine 95

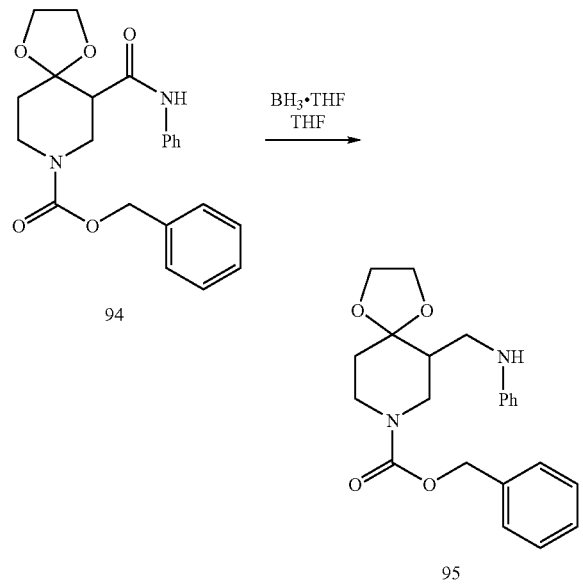

Borane-THF (5.04 mL, 5.04 mmol) was added dropwise to a stirring 0° C. solution of amide 94 (1.03 g, 2.52 mmol) in THF (2.9 mL, 0.86 M). The reaction was allowed to warm to room temperature, and was then heated to reflux until the reaction was judged complete by TLC (2.5 h). The reaction was cooled to room temperature, cooled in an ice bath, and quenched with 5% HCl. $CH_2Cl_2$ was added, and 10% aqueous NaOH was added dropwise until the aqueous layer was basic. The organic layer was removed, and the aqueous layer was extracted with $CH_2Cl_2$ (2×). The organics were dried over sodium sulfate, filtered and purified by silica gel chromatography (8:1:1::Hexanes:EtOAc:$CH_2Cl_2$) to obtain 8-benzyloxycarbonyl-1,4-dioxa-8-aza-spiro[4.5]-decane-6-ylmethylphenylamine (95) (0.72 g, 73%). $^1$H NMR (CDCl$_3$): 7.36 (5H, broad s), 7.16 (2H, t, J=7.1 Hz), 6.72–6.44 (3H, m), 5.22–5.00 (2H, broad s), 4.05–3.95 (4H, m), 3.72 (1H, dd, J=13.6, 3.9 Hz), 3.66–3.30 (4H, m), 2.97 (1H, dd, J=13.3, 8.2 Hz), 2.20–1.98 (1H, broad s), 1.84–1.64 (1H, broad s), 1.64–1.48 (1H, broad s) ppm. $^{13}$C NMR (partial, CDCl$_3$): 155, 148.15, 138, 129.41, 128.75, 128.3, 128.16, 117.28, 112.83, 108.64, 67.50, 65.04, 64.70,44.92, 42.53, 42.19, 41.21, 33.16 ppm. LRMS: 382.88.

EXAMPLE 66

(8-Benzyloxycarbonyl-1,4-dioxa-8-aza-spiro[4.5]decane-6-ylmethyl)-N-phenylpropionamide 96

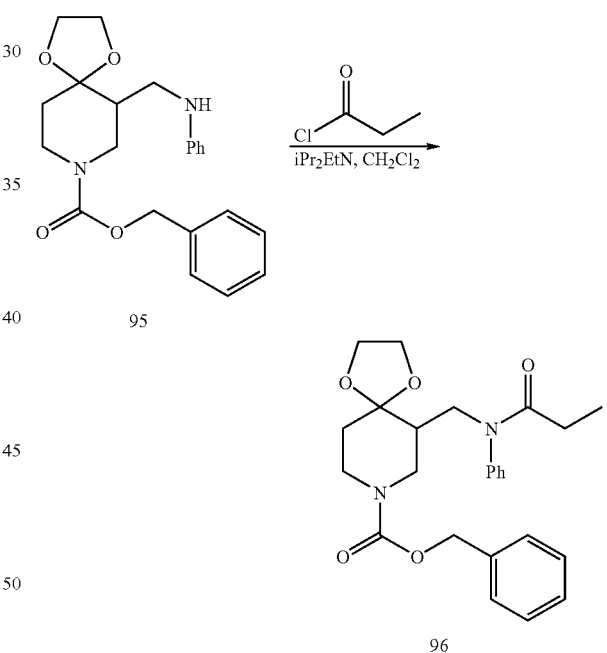

iPr$_2$EtN (0.78 mL, 4.48 mmol) was added to a solution of amine 95 (0.71 g, 1.86 mmol) in $CH_2Cl_2$ (4.6 mL, 0.4M). The solution was cooled to 0° C., then propionyl chloride (0.19 mL, 2.23 mmol) was added dropwise with stirring. The reaction was allowed to slowly warm to room temperature. When the reaction was judged complete by TLC (4.25 h), $CH_2Cl_2$ and $H_2O$ were added. The organic layer was separated and washed with 5% aqueous HCl, then saturated aqueous NaHCO$_3$ and with brine. The organic extracts were dried over Na$_2$SO$_4$, then were purified by silica gel chromatography (6:2:2::Hexanes:EtOAc:$CH_2Cl_2$) to obtain (8-benzyloxycarbonyl-1,4-dioxa-8-aza-spiro[4.5]-decane-6-ylmethyl)-N-phenylpropionamide (96) (0.71 g, 87%). $^1$H NMR (CDCl₃): 7.60–7.08 (8H, m), 7.05–6.88 (2H, broad s), 5.20 (1H, d, J=13 Hz), 5.05 (1H, d, J=13 Hz), 4.30–3.80 (8H, m), 3.60–3.30 (1H, m), 3.20–2.90 (2H, m), 2.20–1.40 (4H, m), 1.18–0.90 (3H, t) ppm. LRMS: 438.84.

EXAMPLE 67

(8-Phenethyl-1,4-dioxa-8-aza-spiro[4.5]decane-6-ylmethyl)-N-phenylpropionamide 97

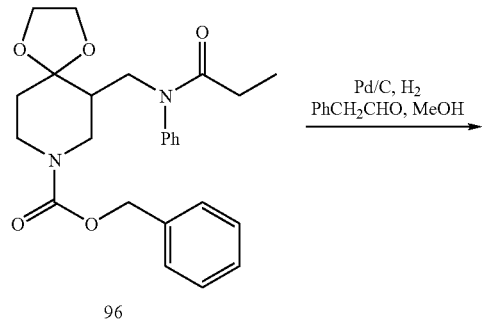

Phenylacetaldehyde (0.87 mL, 7.40 mmol) was added to a solution of (8-benzyloxycarbonyl-1,4-dioxa-8-aza-spiro[4.5]-decane-6-ylmethyl)-N-phenylpropionamide (96) in MeOH (49.4 mL, 0.03M) in a hydrogenation flask. 20% Pd/C (0.53 g) was added, and the mixture was shaken under 40 psi H₂ until the consumption of H₂ ceased and the reaction was judged complete by TLC (3.5 h). The crude reaction mixture was passed through a column of Celite, concentrated in vacuo, and purified by flash column chromatography (60:38:2::Hexanes:CH₂Cl₂:2N NH₃ in EtOH) to obtain pure (8-phenethyl-1,4-dioxa-8-aza-spiro[4.5]-decane-6-ylmethyl)-N-phenylpropionamide (97) (0.59 g, 92%). ¹H NMR (CDCl₃): 7.42–7.12 (10H, m), 4.08 (1H, dd, J=13.4, 9.5 Hz), 3.96–3.77 (4H, m), 3.65 (1H, broad d, J=10.9 Hz), 2.92–2.80 (1H, m), 2.80–2.64 (3H, m), 2.64–2.51 (2H, m), 2.33 (2H, broad t, J=10.3 Hz) 2.20–1.94 (3H, m), 1.72 (1H, dt, J=13.3, 13.2, 3.7 Hz), 1.58 (1H, ddd, J=13.1, 10.9, 4.3 Hz), 1.03 (3H, t, J=7.4 Hz) ppm. LRMS: 408.86.

EXAMPLE 68

1-t-Butoxycarbonylpiperidine-3-ylmethylcarboxylic acid anilide 99

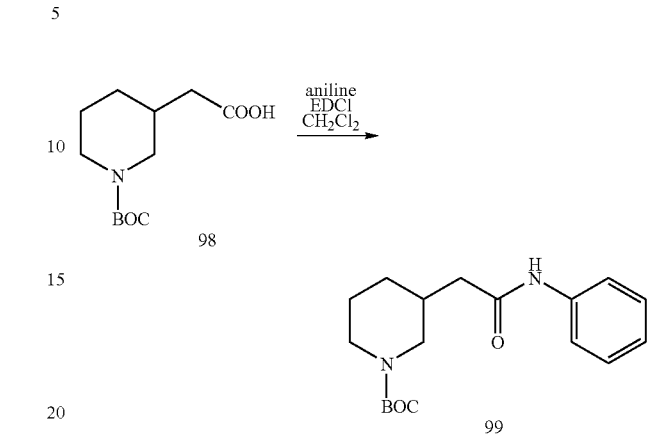

EDCI (4.23 g, 2.20 mmol) and aniline (2.56 mL, 28.1 mmol) were added to a stirring solution of N—BOC-3-piperidine acetic acid (98) (4.5 g, 18.5 mmol) in CH₂Cl₂ (132 mL, 0.14 M). The solution was stirred at room temperature overnight. The reaction was judged complete by TLC. CH₂Cl₂ and H₂O were added. The organic layer was removed and the aqueous layer was extracted with CH₂Cl₂. The combined organics were dried over Sodium sulfate, filtered and concentrated in vacuo. Silica gel purification (90:5:5::Hexanes:EtOAc:CH₂Cl₂) provided pure 1-t-Butoxycarbonylpiperidine-3-ylmethylcarboxylic acid anilide (99) (4.10 g, 70%). ¹H NMR (CDCl₃): 9.03 (1H, broad s), 7.62 (2H, broad s), 7.32 (2H, t, J=8.0 Hz), 7.01 (1H, t, J=7.4 Hz), 3.92–3.3.80 (1H, m), 3.70–3.15 (3H, m), 3.0–2.8 (1H, m), 2.50–2.35 (1H, m), 2.25–2.10 (2H, m), 1.95–1.80 (1H, m), 1.70–1.40 (2H, m), 1.44 (9H, s) ppm. ¹³C NMR (partial, CDCl₃): 129.02, 124.12, 119.95, 40.77, 33.23, 31.06, 28.59 ppm.

EXAMPLE 69

1-t-Butoxycarbonylpiperidine-3-ylethylphenylamine 100

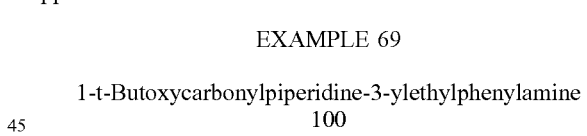

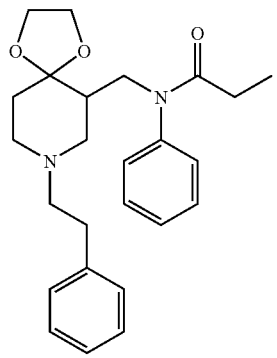

1M Borane-THF (6.28 mL, 6.26 mmol) was added dropwise to a stirring, 0° C. solution of 1-t-Butoxycarbonylpiperidine-3-ylmethylcarboxylic acid anilide (99) (1 g, 3.14 mmol) in THF (3.7 mL). The ice bath was removed, and the reaction was heated to reflux until the reaction was judged complete by TLC (2.5 h). The reaction was cooled to room temperature and quenched with the addition of 5% aqueous HCl. The reaction was diluted with CH₂Cl₂ and 10% aqueous NaOH was added dropwise until the aqueous layer was basic. The organic layer was removed, and the aqueous layer was extracted (2×) with CH₂Cl₂. The combined organics were dried over sodium sulfate, filtered and concentrated in vacuo, and purified by flash column chromatography (90:5:5::Hexanes:EtOAc:CH₂Cl₂) to obtain pure 1-t-Butoxycarbonylpiperidine-3-ylethylphenylamine (100) (0.90 g, 94%). ¹H NMR (CDCl₃): 7.24–7.15 (2H, m), 6.72 (1H, broad t, J=7.3 Hz), 7.66–6.59 (2H, m), 4.0 (1H, broad s), 3.93 (2H, dt, J=13.1, 4.0 Hz), 3.78–3.56 (1H, m), 3.18 (2H, t, J=7.1 Hz), 2.85 (1H, broad t, J=10.8 Hz), 2.58 (1H, broad s), 1.94–1.82 (1H, m), 1.74–1.38 (4H, m), 1.45 (9H, s), 1.24–1.08 (1H, m). ¹³C NMR (CDCl₃): 154.92, 148.36, 129.27, 117.21, 112.71, 79.37, 53.54, 49.27, 41.44, 33.82, 33.36, 30.99, 28.53, 24.87 ppm.

EXAMPLE 70

(1-t-Butoxycarbonylpiperidine-3-ylethyl)-N-phenylpropionamide 101

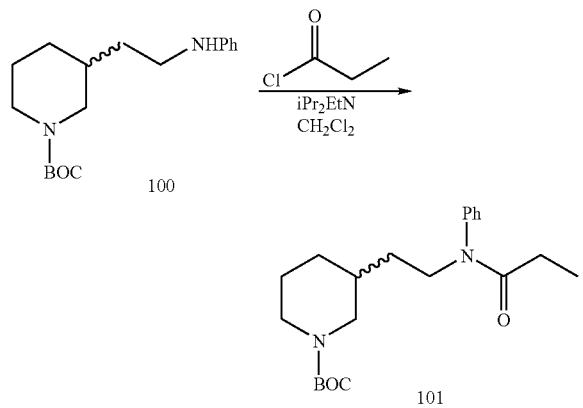

Ipr₂EtN (0.60 mL, 3.47 mmol) was added to a 0° C. solution of 100 (0.88 g, 2.89 mmol) in CH₂Cl₂ (7.22 mL, 0.4M). Propionyl chloride (0.30 mL, 3.47 mmol) was added dropwise, and the solution was allowed to warm to room temperature. When the reaction was judged complete by TLC (5h), the reaction was diluted with CH₂Cl₂. H₂O was added, and the organic layer was separated. The organic layer was washed with 5% aqueous HCl, then saturated NaHCO₃, then brine. The crude product was dried over sodium sulfate, filtered and concentrated in vacuo, and purified by silica gel chromatography (8:1:1::Hexanes:EtOAc:CH₂Cl₂) to obtain pure (1-t-Butoxycarbonylpiperidine-3-ylethyl)-N-phenylpropionamide (101) (0.81 g, 78%). ¹H NMR (CDCl₃): 7.46–7.29 (3H, m), 7.14 (2H, J=7.6 Hz), 3.90–3.60 (4H, m), 2.74 (2H, broad t, J=11.0 Hz), 2.47 (1H, broad s), 2.01 (2H, q, J=7.3 Hz), 1.84 (1H, broad d, J=11.8 Hz), 1.64–1.54 (1H, m), 1.52–1.34 (4H, m), 1.42 (9H, s), 1.02 (3H, t, J=7.4 Hz) ppm. ¹³C NMR (CDCl₃): 173.62, 154.92, 142.73, 129.82, 128.37, 127.98, 79.33, 53.56, 47.19, 44.37, 33.84, 31.47, 30.73, 28.54, 27.94, 24.80, 9.72 ppm. LRMS: 360.44.

EXAMPLE 71

(1-Phenethylpiperidine-3-ylethyl)-N-phenylpropionamide 102

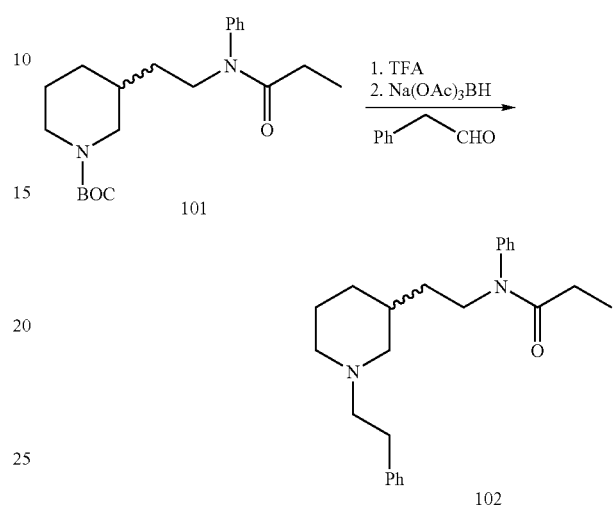

Trifluoroacetic acid (0.38 mL, 4.99 mmol) in CH₂Cl₂ (0.38 mL) was added dropwise to a 0° C. stirring solution of 101 in CH₂Cl₂ (0.40 mL). When the reaction was judged complete by TLC, the solvent and excess trifluoroacetic acid were removed in vacuo. The crude residue was dissolved in DMF (1.54 mL, 0.18M), then phenylacetaldehyde (0.10 mL, 0.832 mmol), acetic acid (0.078 mL), and Na(OAc)₃BH (0.118 g, 0.555 mmol) were added sequentially. When the reaction was judged complete by TLC, saturated aqueous K₂CO₃ was added. The organic layer was removed, and 5% aqueous HCl was added. The organic layer was discarded, and the aqueous layer was basified with saturated aqueous NH₄OH. The organic layer was removed, dried with Na₂SO₄, and concentrated in vacuo. Purification by silica gel chromatography (98:2::CH₂Cl₂:2N NH₃ in EtOH) provided (1-phenethylpiperidine-3-ylethyl)-N-phenylpropionamide (102). ¹³C NMR: 173.64, 142.77, 140.45, 129.82, 128.84, 128.50, 128.45, 127.95, 126.13, 61.08, 60.03, 54.27, 47.06, 33.89, 33.46, 32.57, 30.86, 28.00, 25.31, 9.74 ppm.

EXAMPLE 72

(1-Benzylpiperidine-3-ylethyl)-N-phenylpropionamide 103

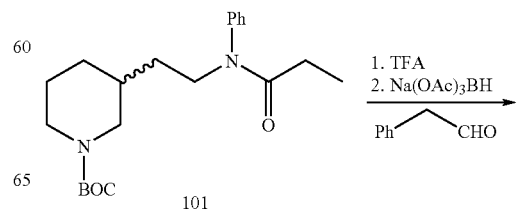

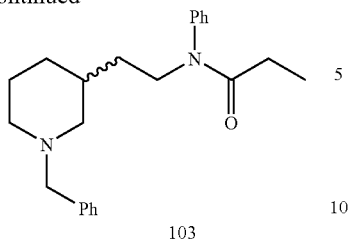

103

Trifluoroacetic acid (0.38 mL, 4.99 mmol) in CH₂Cl₂ (0.38 mL) was added dropwise to a 0° C. stirring solution of 101 (0.115 g, 0.318 mmol) in CH₂Cl₂ (0.40 mL). When the reaction was judged complete by TLC, the solvent and excess trifluoroacetic acid were removed in vacuo. The crude residue was dissolved in DMF (1.54 mL, 0.18M), then phenylacetaldehyde (0.10 mL, 0.832 mmol), acetic acid (0.078 mL), and Na(OAc)₃BH (0.118 g, 0.555 mmol) were added sequentially. When the reaction was judged complete by TLC, saturated aqueous K₂CO₃ was added. The organic layer was removed, and 5% aqueous HCl was added. The organic layer was discarded, and the aqueous layer was basified with saturated aqueous NH₄OH. The organic layer was removed, dried with Na₂SO₄, and concentrated in vacuo. Purification by silica gel chromatography (99:1:: CH₂Cl₂:2N NH₃ in EtOH) provided (1-benzylpiperidine-3-ylethyl)-N-phenylpropionamide (103). ¹H NMR (CDCl₃): 7.46–7.24 (8H, m), 7.15 (2H, broad d, J=7.8 Hz), 3.72 (2H, J=7.8 Hz), 3.52 (1H, J=13.2 Hz), 3.45 (1H, d, J=13.2 Hz), 2.79 (2H, broad d, J=8.2 Hz), 2.03 (2H, q, J=7.3 Hz), 1.91 (1H, td, J=11.0, 3.3 Hz), 1.84–1.30 (7H, m), 1.05 (3H, t, J=7.4 Hz), 0.98–0.84 (1H, m) ppm. ¹³C NMR (CDCl₃): 173.65, 142.93, 138.4, 129.83, 129.35, 128.52, 128.31, 127.95, 127.07 63.68, 60.21, 54.22, 47.34, 34.14, 32.51, 30.84, 28.04, 25.34, 9.78 ppm. LRMS: 350.95.

EXAMPLE 73

5-Benzyl-1-oxa-5-azaspiro[2.5]octane 110

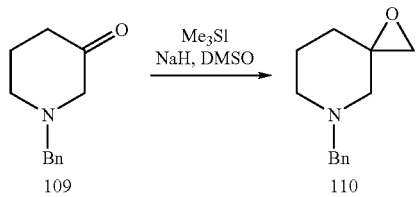

109     110

Trimethylsulfonium iodide (2.13 g, 10.4 mmol) in DMSO (15 mL) was added to NaH (0.4907 g, 20.4 mmol) in DMSO (70 mL). 1-benzyl-3-piperidone hydrochloride hydrate (109) (0.996 g, 4.41 mmol) was taken up in DMSO (15 mL) and was added to the reaction mixture at room temperature. When the reaction was judged complete by TLC (0.5 h), the reaction was poured over ice and the product was extracted with CH₂Cl₂. The organics were washed with H₂O, dried over sodium sulfate, filtered and concentrated in vacuo. Purification with alumina gel chromatography (900:100:3 CH₂Cl₂:Hexanes:2 N NH₃ in EtOH) provided pure 5-benzyl-1-oxa-5-azaspiro[2.5]octane (110). ¹³C NMR (CDCl₃): 137.54, 128.69, 127.83, 126.67, 62.55, 59.28, 53.32, 52.96, 52.48, 30.90, 23.51 ppm.

EXAMPLE 74

1-Benzylpiperidine-3-hydroxy-3-ylmethylphenylamine 111

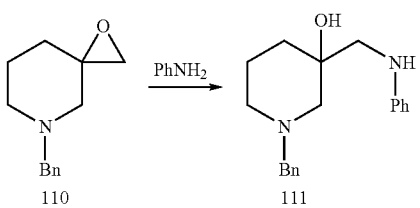

110     111

110 (0.89 g, 4.38 mmol) was dissolved in aniline (2.0 mL, 21.9 mmol) in a sealed tube apparatus, and the reaction was heated to 200° C. When the reaction was judged complete by TLC (2.5 h), H₂O and EtOAc were added. The aqueous layer was brought to pH=8, and the organic layer was removed, dried over sodium sulfate, filtered and concentrated in vacuo. Purification by silica gel chromatography (60:38: 0.2Hexanes:CH₂Cl₂:2N NH₃ in EtOH) provide 0.132 g (10% for two steps) of 1-benzylpiperidine-3-hydroxy-3-ylmethylphenylamine (111). ¹H NMR (CDCl₃):7.42–7.30 (5H, m), 7.28–7.21 (2H, m), 6.81–6.74 (1H, m), 6.73–6.66 (2H, m), 4.15 (1H, broad t), 3.68 (1H, d, J=13.2 Hz), 3.57 (1H, d, J=13.2 Hz), 3.45 (1H, broad s), 3.19 (2H, d, J=5.5 Hz), 2.86 (2H, t, J=11.4 Hz), 2.22–2.04 (2H, m), 1.96–1.74 (2H, m), 1.72–1.60 (1H, m), 1.50–1.32 (1H, m) ppm. ¹³C NMR (CDCl₃): 148.94, 138.09, 129.31, 129.10, 128.44, 127.31, 117.41, 113.17, 70.15, 62.85, 62.11, 53.47, 51.48, 33.88, 21.76 ppm. LRMS: 297.08.

EXAMPLE 75

(1-Benzylpiperidine-3-hydroxy-3-ylethyl-N-phenyl-propionamide 112

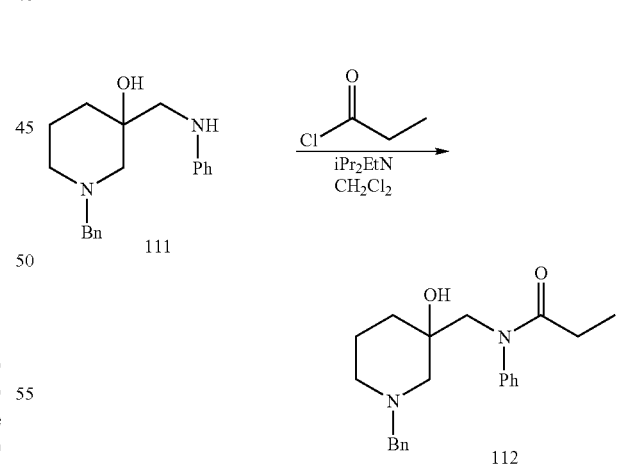

111

112 iPr₂EtN (0.078 mL, 0.45 mmol) was added to a 0° C. solution of amine 111 (0.120 g, 0.405 mmol) in CH₂Cl₂ (1.0 mL, 0.4M). Propionyl chloride (0.039 mL, 0.45 mmol) was added dropwise with stirring. The reaction was allowed to warm to room temperature. When the reaction was judged complete by TLC (overnight), the reaction was diluted with CH₂Cl₂ and quenched with H₂O. The organic layer was removed and the organic layer was extracted with CH₂Cl₂

(2×). The organics were then washed with 5% aqueous HCl, saturated aqueous NaHCO₃, and brine. The crude product was dried over sodium sulfate, filtered and concentrated in vacuo, and purified by silica gel chromatography (96:4:: Hexanes:2N NH₃ in EtOH) to obtain pure (1-benzylpiperidine-3-hydroxy-3-ylethyl)-N-phenylpropionamide (112) (0.117 g, 82%). $^1$H NMR (CDCl₃): 7.44–7.05 (10 H, m), 3.99 (1H, 14.3 Hz), 3.88 (1H, 14.2 Hz), 3.51 (1H, d, J=13.2 Hz), 3.42 (1H, d, J=13.2 Hz), 2.28–2.30 (2H, m), 2.32–2.14 (1H, m), 2.08 (2H, q, J=7.4 Hz), 1.72–1.46 (3H, m), 1.46–1.26 (2H, m), 1.03 (3H, t, J=7.4 Hz) ppm. $^{13}$C NMR (CDCl₃): 144.76, 129.59, 129.16, 128.32, 128.16, 127.71, 127.16, 72.17, 62.78, 61.97, 57.66, 53.34, 34.17, 28.02, 9.76 ppm. LRMS: 352.76.

EXAMPLE 76

(1-Phenethylpiperidine-3-hydroxy-3-ylethyl)-N-phenylpropionamide 113

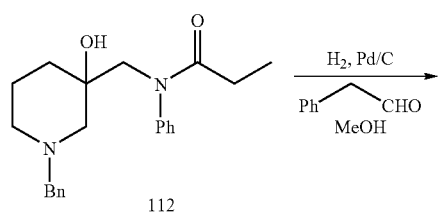

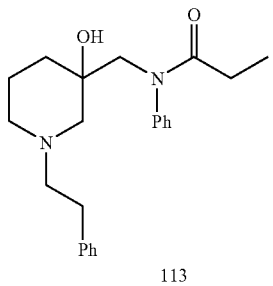

113

Phenylacetaldehyde (0.17 mL, 1.42 mmol) and Pd/C (0.101 g) were added to a solution of 112 (0.0793 g, 0.225 mmol) in MeOH (9.45 mL) in a hydrogenation flask, and the mixture was shaken under 40 psi of H₂ until the consumption of H₂ ceased and the reaction was judged complete by TLC. The crude reaction mixture was passed through a column of Celite, concentrated in vacuo, and purified by silica gel chromatography (80:18:2::Hexanes:CH₂Cl₂:2N NH₃ in EtOH) to provide (1-phenethylpiperidine-3-hydroxy-3-ylethyl)-N-phenylpropionamide (113). $^{13}$C NMR (CDCl₃): 176.66, 144.74, 140.52, 129.63, 128.84, 128.47, 128.18, 127.76, 126.11, 72.04, 62.27, 59.96, 58.11, 53.51, 34.16, 33.58, 28.07, 22.10, 9.85 ppm.

EXAMPLE 77

Synthesis of a Combinatorial Library of Compounds of the Present Invention (See FIG. 1)

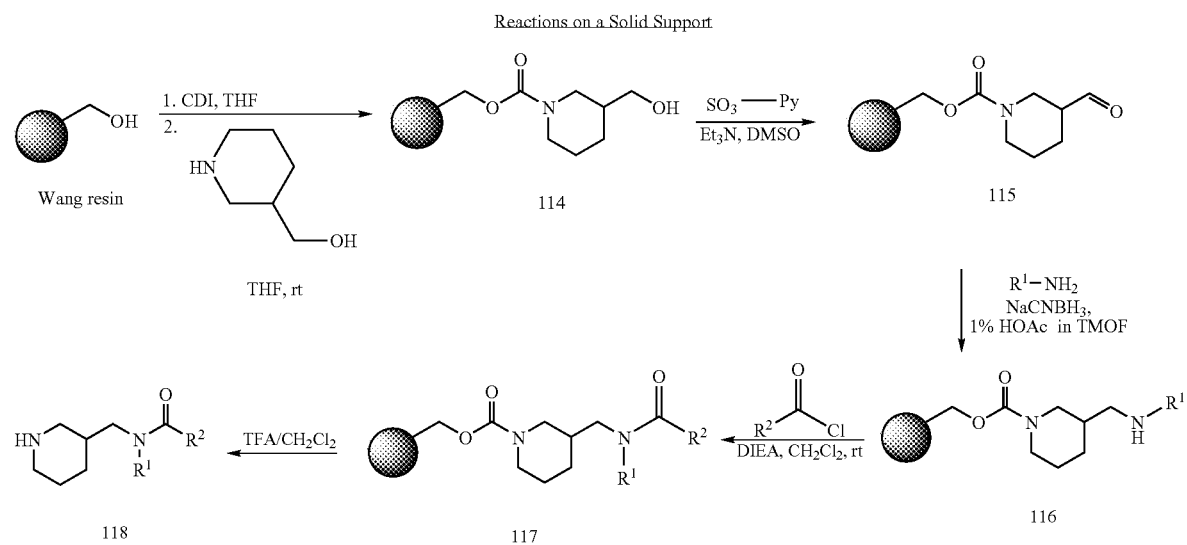

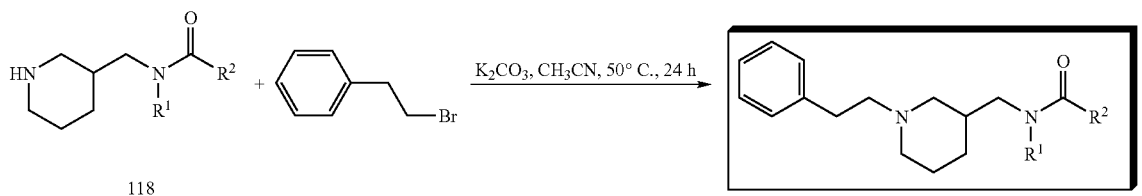

A library of 96 compounds was synthesized from twelve anilines, eight acid chlorides, and (2-bromoethyl)benzene. The reductive amination and acylation reactions were carried out using solid-phase chemistry, while the alkylation of piperidine with (2-bromoethyl)benzene was performed in solution.

A. Preparation of Aldehyde-Functionalized Resin 115.

To the Wang resin (9.6 g, 0.70 mmol/g) in a 250-ml peptide synthesis vessel was added 100 ml of 0.4 N CDI in anhydrous THF, and shaken at room temperature for 17 hours. The resin was thoroughly washed with $CH_2Cl_2$ (3×100 ml) and THF (3×100 ml) to remove the excess CDI and then treated with 100 ml of 0.4 N 3-piperidinemethanol in THF at room temperature for 17 hours. The resulting resin (114) was washed with DMF (3×100 ml), MeOH (4×100 ml), and $CH_2Cl_2$ (4×100 ml) and dried in vacuo. To the alcohol resin 114 was added 100 ml solution of sulfur trioxide pyridine complex (5.35 g, 33.6 mmol) and triethylamine (4.68 ml, 33.6 mmol) in DMSO, and the resulting slurry was shaken at room temperature for 1 hour. The resulting aldehyde-functionalized resin 115 was washed with DMF (3×100 ml), MeOH (4×100 ml), and $CH_2Cl_2$ (4×100 ml) and dried in vacuo. Resin 115 was equally divided into 12 reactors, in which the aldehyde would react with 12 anilines, respectively.

B. Preparation of Resins 116.

To resin 115 (about 0.8 g, 0.56 mmol) was added aniline (5.6 mmol) in 8 ml of trimethyl orthoformate (TMOF) and the mixture shaken at room temperature for 1 hour. $NaCNBH_3$ (700 mg, 11.2 mmol) was added into the mixture followed by 0.08 ml AcOH. After shaking at room temperature for 3 hours, resulting resin 116 was extensively washed with DMF (3×10 ml), MeOH (4×10 ml), and $CH_2Cl_2$ (4×10 ml) and dried in vacuo. Twelve resins 116 were obtained by using twelve anilines in the reductive amination.

C. Preparation of Compounds 118.

Twelve resins 116 were respectively distributed into 96-well reaction block from column 1 to column 12 at 100 mg (0.07 mmol) per well (See FIG. 1). Eight acid chlorides in $CH_2Cl_2$ were respectively dispensed into eight rows, from row A to row H, at 1 ml (containing 0.7 mmol acid chloride) per well; then diisopropylethylamine was dispensed into 96 wells at 0.122 ml (0.7 mmol) per well. The reaction block was shaken at room temperature for 3 hours and the resins were washed with DMF (3×1 ml/well), MeOH (4×1 ml/well), and $CH_2Cl_2$ (4×1 ml/well) and dried in vacuo. The resulting resins 117 were treated with a solution of 50% TFA in $CH_2Cl_2$ at 1 ml per well at room temperature for 30 min to release the polymer-bond piperidines 118 into a 96-deep well plate. After washing the resins with $CH_2Cl_2$ (2×0.5 ml/well), the volatiles were removed under high vacuum to afford the crude compounds.

D. Preparation of Compounds 119.

To piperidines 118 in the 96-deep well plate was added acetonitrile at 0.6 ml per well, dissolving the compounds, and the solutions were transferred into a 96-well reaction block. (2-Bromoethyl)benzene was then dispensed into the 96 wells at 0.010 ml (0.07 mmol) per well followed by $K_2CO_3$ at 50 mg per well. The mixtures were agitated at 50° C. for 24 hours. After the reaction block cooling to room temperature, tris-(2-aminoethyl)-amine polystyrene (2.45 mmol/g) was distributed into 96 wells at 50 mg per well. The mixtures were shaken at 50° C. for another 24 hours. The solutions were filtered into a 96-well format SPE plate with $NH_2$ sorbent, washed the resins with $CH_2Cl_2$ (2×0.6 ml/well), collected the $CH_2Cl_2$ washes into the SPE plate. The compounds were eluted and collected in a 96-deep well plate. The volatiles were removed under high vacuum to afford 96 final compounds 119, which were submitted to HPLC and mass spectra analyses.

EXAMPLE 78

Opiate Receptor Binding of Certain Compounds of the Present Invention ($IC_{50}$ s)

The opioid (μ, κ, δ) receptor-binding capabilities of compounds described herein were determined according to the procedures outlined by Wang et al. (*FEBS Letters* 1994, 338, 217), Maguire et al. (*Eur. J. Pharmacol.* 1992, 213, 219), and Simonin et al. (*Mol. Pharmacol.* 1994, 46, 1015). Certain results from these assays are tabulated below.

| Compound | μ (μM) | κ (μM) | δ (μM) |
|---|---|---|---|
| 6 | <1 | <1 | >10 |
| 30 | <1 | <5 | >10 |
| 32 | <1 | >10 | >10 |
| 39 | <5 | <10 | >10 |
| Racemic 71 | <1 | <1 | >10 |
| 14 | <1 | <5 | >10 |
| 16 | <1 | <5 | >10 |
| 23 | <1 | <10 | >10 |
| 66 | <5 | <5 | >10 |
| 69 | <1 | <5 | >10 |
| 76 | <1 | <5 | >10 |
| 19 | <1 | <10 | >10 |
| 113 | <10 | >10 | >10 |
| 10 | <5 | <10 | >10 |
| 97 | <1 | <5 | >10 |
| 57 | <1 | <1 | >10 |
| 59 | <1 | <1 | >10 |
| 44 | <1 | <5 | >10 |
| 7 | <5 | <5 | >10 |
| 103 | <10 | <5 | >10 |
| 102 | <1 | <5 | >10 |
| 50 | <1 | <5 | >10 |
| 52 | <1 | <5 | >10 |
| 82 | <1 | <5 | >10 |
| 83 | <1 | <5 | >10 |
| 84 | <1 | <1 | >10 |
| 87 | <1 | <1 | <5 |
| 37 | <5 | <5 | >10 |
| 129 | <1 | <1 | <10 |
| 125 | <5 | 10 | >10 |
| 126 | <1 | <1 | >10 |
| 127 | <5 | <10 | >10 |
| 128 | <1 | <5 | >10 |
| 121 | <1 | >10 | >10 |
| 120 | <5 | <5 | >10 |
| 123 | <1 | <5 | >10 |
| 124 | <1 | <10 | >10 |
| 141 | <10 | <5 | >10 |
| 140 | <1 | <5 | >10 |
| 139 | <1 | <1 | >10 |
| 134 | <5 | <10 | <5 |
| 135 | <5 | >10 | <5 |
| 137 | <5 | >10 | >10 |
| 8 | <5 | <5 | >10 |
| 11 | >10 | >10 | <5 |
| 12 | <5 | <5 | >10 |
| 19 | <1 | <10 | >10 |
| 21 | <1 | <10 | <10 |
| 130 | <1 | <5 | >10 |
| 150 | <1 | <10 | >10 |
| 88 | <1 | <5 | >10 |
| 89 | <1 | <1 | >10 |
| 71 | <1 | <1 | >10 |
| 73 | <1 | <5 | >10 |

-continued

| Compound | μ (μM) | κ (μM) | δ (μM) |
|---|---|---|---|
| 163 | <1 | <5 | <5 |
| 170 | <5 | >10 | >10 |
| 171 | <10 | <10 | >10 |
| 176 | <1 | >10 | >10 |
| 177 | <1 | <10 | >10 |
| 178 | <1 | <10 | <5 |
| 179 | <1 | >10 | >10 |
| 180 | <1 | <5 | >10 |
| 182 | <1 | >10 | |
| 185 | <1 | >10 | |
| 186 | <1 | >10 | |
| 195 | <1 | <5 | >10 |
| 196 | <1 | <5 | <5 |
| 197 | <1 | <1 | <10 |
| 198 | <1 | <1 | >10 |
| 199 | <1 | <5 | >10 |
| 204 | <5 | <5 | >10 |

EXAMPLE 79

Analgesia in Mice and Rats (See FIG. 2)

This Example establishes in vivo analgesia in mice and rats for compounds 6, 30, 32, 66, and 69. A "tail-flick" analgesia model known in the art was utilized (D'Amour et al. *J. Pharmacol. Exp. Ther.* 1941, 72, 74). Groups of four male mice (weighing ~22 g) or rats were used, for each dose. Three doses (1, 0.5, and 0.1 mg/kg) of compounds 6, 30, 32, 66, and 69 were dissolved in a vehicle of 50 mM aqueous sodium acetate, and were administered intravenously. The control group received vehicle alone. Before treatment (t=0 minutes), pre-selection was done by using a focused beam of radiant heat applied to the middle dorsal surface of the animal tail to elicit a tail flick response within 6–7.5 seconds. Compounds 6, 30, 32, 66, and 69 were then administered i.v. for 1 minute before stimulation by the focused beam of radiant heat. The time required to elicit the tail-flick response was recorded for each animal and a maximum cut-off of 15 seconds was set. Prolongation by 50% or more of the time required to elicit a tail-flick response relative to control animals indicated analgesic activity.

EXAMPLE 80

N-Phenyl-N-[1-(4-Phenylbutyl)piperidin-3-ylmethyl]propionamide (120)

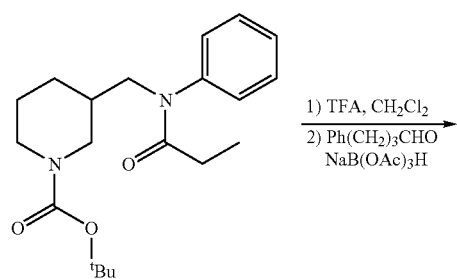

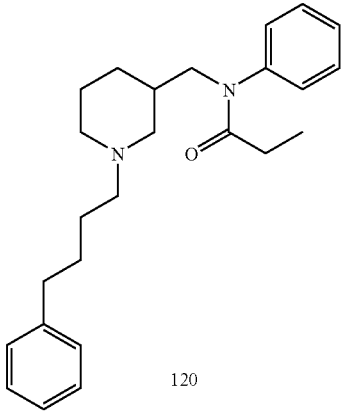

Trifluoroacetic acid (1.0 mL) was added dropwise to a solution of compound N-(1-Boc-piperidin-3-ylmethyl)-N-phenylpropionamide (108 mg, 0.31 mmol) in 1.0 mL of dry $CH_2Cl_2$ at 0° C. (ice-water). The reaction mixture was stirred at room temperature for 30 minutes. TLC showed the reaction was complete. After removal of the solvents, the crude product was used in the next step without purification.

The crude compound from the previous step was dissolved in DMF (0.5 mL) and 4-phenylbutyraldehyde (49 μL, 1.1 equiv) was added. The mixture was stirred at room temperature for 60 min. NaB(OAc)$_3$H (95%, 340 mg, 5 eq.) was introduced in one portion, and the mixture was shaken at room temperature overnight. The mixture was quenched with 5 mL of with NaOH (10%), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography ($CH_2Cl_2$/MeOH, 95:5) to afford N-Phenyl-N-[1-(4-Phenylbutyl) piperidin-3-ylmethyl]propionamide (120) as a colorless oil. LRMS 379(M+H$^+$).

EXAMPLE 81

N-(2-Fluorophenyl)-N-(1-Phenethylpiperidin-3-ylmethyl)propionamide (121)

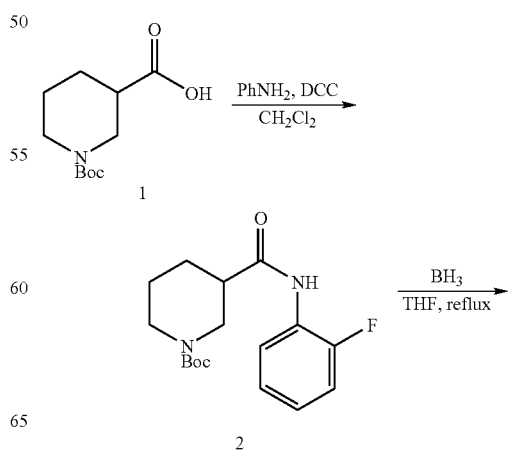

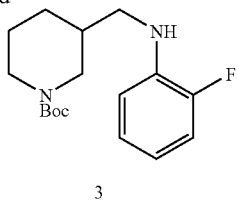

3

To a solution of piperidine-1,3-dicarboxylic acid 1-tert-butyl ester 1 (1.0 g, 4.4 mmol), 2-fluoroaniline (463 µl, 4.8 mmol) in CH₂Cl₂ (25 ml) at 0° C. was added DCC (0.99 g, 4.8 mmol) in several portions. The mixture was stirred at room temperature overnight. The white precipitate was removed by filtration. After removal of solvent, the residue was purified by column chromatography (silica gel, hexane/ethyl acetate, 4:1) to give 3-(2-fluorophenylcarbamoyl)piperidine-1-carboxylic acid tert-butyl ester (2) as a colorless oil (1.13 g, 80%).

To a solution of 3-(2-fluorophenylcarbamoyl)piperidine-1-carboxylic acid tert-butyl ester (2) (1.13 g, 3.5 mmol) in THF (4 ml) at 0° C. was added BH₃-THF solution (1.0 M, 3.5 ml) slowly. The mixture was refluxed for 2 hrs. The reaction was quenched by slow addition of MeOH at 0° C. The solvent was removed by evaporation. The residue was purified by column chromatography (silica gel, hexane/ethyl acetate, 85:15) to give 3-[(2-Fluorophenylamino)methyl]piperidin-1-carboxylic acid tert-butyl ester (3) as a colorless oil (0.97 g, 90%).

washed with aqueous NaHCO₃ (sat., 2×5 mL), dried over Na₂SO₄, filtered and evaporated to give a slightly yellow oil, which was purified by column chromatography (silica gel, hexane/ethyl acetate, 4:1) to give 3-{[(2-fluorophenyl)propionylamino]methyl}piperidine-1-carboxylic acid tert-butyl ester (4) (162 mg, 92%).

To a solution of 3-{[(2-fluorophenyl)propionylamino]methyl}piperidine-1-carboxylic acid tert-butyl ester (4) (162 mg, 0.45 mmol) in CH₂Cl₂ (1 ml) at 0° C. was added TFA (1 ml). After stirring for 30 min., solvent and excess TFA was removed by evaporation. The residue was dissolved in 1.5 ml of CH₃CN (10 ml), to which K₂CO₃ (1245 mg) and (2-bromoethyl) benzene (123 µl, 0.9 mmol) were added. The mixture was stirred at 50° C. overnight. After cooling down to room temperature, 5 mL of 10% NaOH was added. The organic layer was separated. The aqueous layer was extracted with EtOAc (2×10 ml). The combined organic layers were washed with brine and dried with Na₂SO₄, filtered and evaporated. The crude product was purified by flash silica gel chromatography (5% MeOH in CH₂Cl₂) to give colorless N-(2-Fluorophenyl)-N-(1-Phenethylpiperidin-3-ylmethyl)propionamide (121) (141 mg, 85%). LRMS 369 (M+H⁺).

EXAMPLE 82

N-(1-Phenethylpiperidin-3-ylmethyl)-N-phenyl isobutyramide (123)

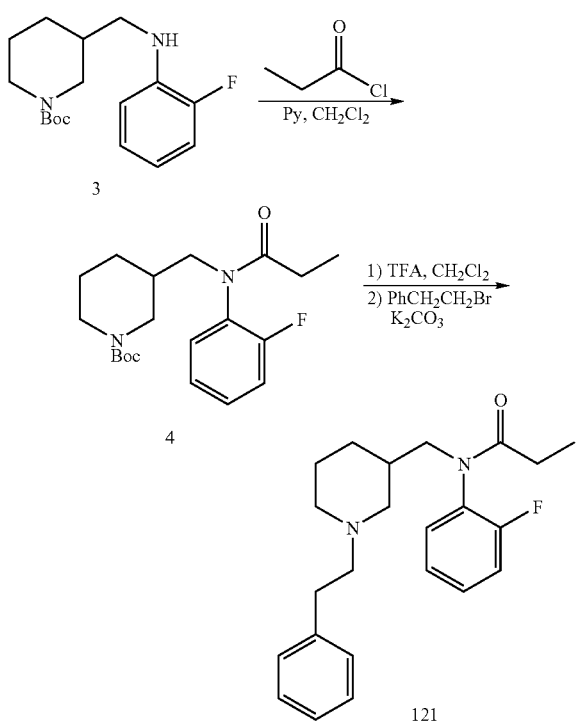

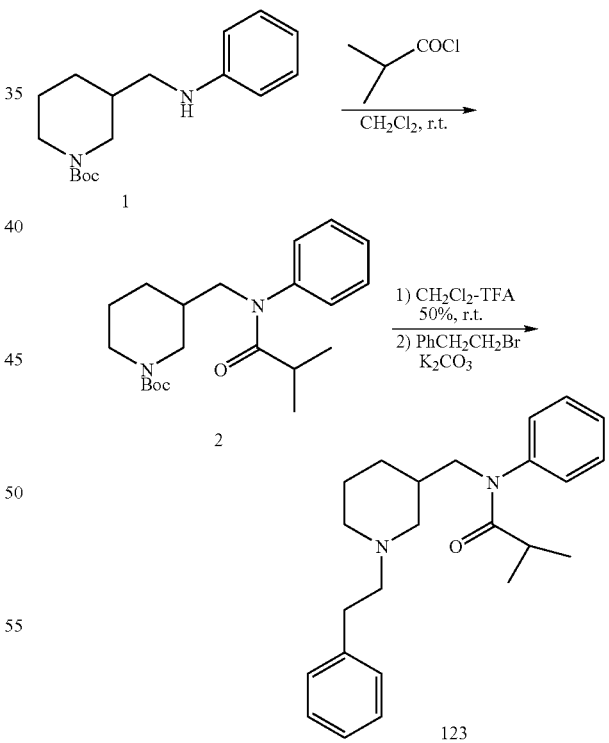

To a solution of 3-[(2-Fluorophenylamino)methyl]piperidin-1-carboxylic acid tert-butyl ester (3) (150 mg, 0.49 mmol), N,N-diisopropylethylamine (435 µl, 2.5 mmol) in CH₂Cl₂ (1 ml) at 0° C. was added propionyl chloride (130 µl, 1.5 mmol). The reaction mixture was shaken overnight. The mixture was poured into 10% NaOH (5 mL), then extracted with ethyl acetate (3×10 mL). The extracts are combined and To a stirred suspension of 3-phenylaminomethylpiperidine-1-carboxylic acid tert-butyl ester (1) (220 mg, 0.76 mmol) and piperidinomethyl polystyrene resin (350 mg) in 2.5 mL of dry CH₂Cl₂ was added isobutyryl chloride (122 µl, 1.5 eq.) at room temperature. After being shaken at room temperature for 3 hours, the reaction mixture was passed through an aminopropyl NH₂ cartridge and washed with CH₂Cl₂. Removal of CH₂Cl₂ afforded 3-[(isobutyrylphenylamino)methylpiperidine-1-carboxylic acid tert-butyl ester (2) (259 mg, 95%).

Trifluoroacetic acid (0.5 mL) was added dropwise to a solution of 3-[(isobutyrylphenylamino)methylpiperidine-1-carboxylic acid tert-butyl ester (2) (106 mg, 0.29 mmol) in 0.5 mL of dry CH₂Cl₂ at 0° C. (ice-water). The reaction mixture was stirred at room temperature for 30 minutes. TLC showed the reaction was complete. After removal of the solvents, the residue was dried under vacuum for 3 hrs. The crude product was used for the next step without purification.

The crude compound from the previous step was dissolved in 1.0 mL of CH₃CN, to which K₂CO₃ (122 mg) and (2-bromoethyl) benzene (82 µl, 2 eq.) were added. The mixture was stirred at 50° C. overnight. After cooling down to room temperature, 5 mL of 10% NaOH was added. The organic layer was separated. The aqueous layer was extracted with EtOAc (2×10 ml). The combined organic layers were dried with Na₂SO₄, filtered and evaporated. The remaining oily residue was purified by preparative thin layer chromatography (EtOAc/MeOH, 9:1) to afford N-(1-Phenethylpiperidin-3-ylmethyl)-N-phenyl isobutyramide (123) as a colorless oil (92 mg, 86%). LRMS 365.

EXAMPLE 83

N-Phenyl-N-[1-(3-Phenylpropylyl)piperidin-3-ylmethyl)]isobutyramide (124)

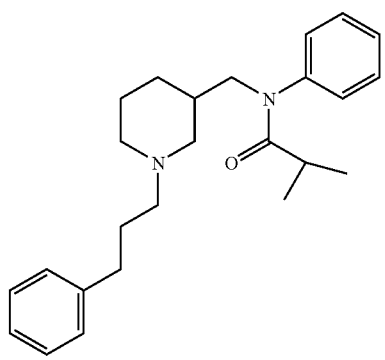

124

N-Phenyl-N-[1-(3-Phenylpropylyl)piperidin-3-ylmethyl)]isobutyramide (124) was synthesized using the procedure outlined in Example 84. LRMS 379.

EXAMPLE 84

N-[1-(1-Methyl-2-Phenethyl)piperidin-3-ylmethyl]-N-phenyl propionamide (125 & 126)

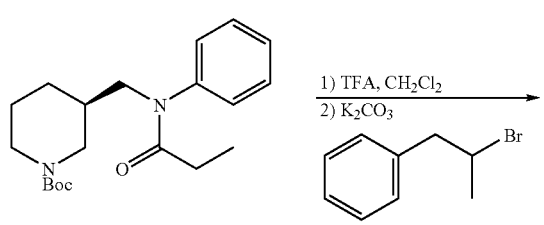

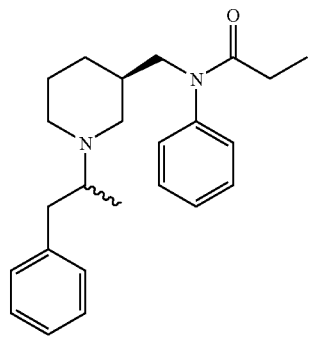

125 & 126

Trifluoroacetic acid (1.0 mL) was added dropwise to a solution of (R)—N-(1-Boc-piperidin-3-ylmethyl)-N-phenylpropionamide (101 mg, 0.29 mmol) in 1.0 mL of dry CH₂Cl₂ at 0° C. (ice-water). The reaction mixture was stirred at room temperature for 30 min. TLC showed the reaction was complete. After removal of the solvents, the crude product was used for the next step without purification.

The crude compound was dissolved in acetonitrile (1.0 mL) and 2-bromo-1-phenyl propane (293 µL), and K₂CO₃ (120 mg) were added. The mixture was stirred at 50° C. overnight. The mixture was quenched with 5 mL of aqueous KOH (10%), then extracted with ethyl acetate (3×10 mL). The extracts were combined and washed with aqueous NaHCO₃ (sat., 2×5 mL), brine (10 mL), and dried over anhydrous sodium sulfate. After the solvent was removed, the remaining oily residue was purified by preparative thin layer chromatography (EtOAc/MeOH, 95:5) to afford N-[1-(1-Methyl-2-Phenethyl)piperidin-3-ylmethyl]-N-phenyl propionamide as a colorless oil (66 mg, 62%) LRMS 365.

The diastereomers of N-[1-(1-Methyl-2-phenethyl)piperidin-3-ylmethyl]-N-phenyl propionamide were separated on a chiral column (Chiralpak AD. Column number AD00CG-1F001) with Hexanes (0.2% of diethylamine):iPrOH (98:2). The first compound to elute from the column was 125, and the second compound to elute from the column was 126.

EXAMPLE 85

N-Phenyl-N-[1-(2-phenylpropyl)piperidin-3-ylmethyl]propionamide (127 & 128)

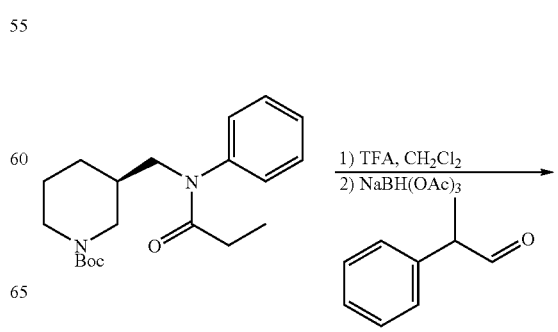

-continued

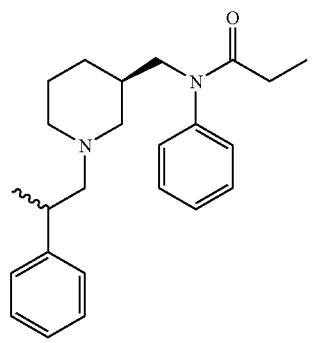

127 & 128

Trifluoroacetic acid (1.0 mL) was added dropwise to a solution of compound (R)—N-(1-Boc-piperidin-3-ylmethyl)-N-phenylpropionamide (158 mg, 0.46 mmol) in 1.0 mL of dry CH$_2$Cl$_2$ at 0° C. (ice-water). The reaction mixture was stirred at room temperature for 30 minutes. TLC showed the reaction was complete. After removal of the solvents, the crude product was used for next step.

The crude compound was dissolved in DMF (1.5 mL) and 2-phenylpropionaldehyde (93 µL, 1.5 equiv) was added. The mixture was stirred at room temperature for 30 min. NaB(OAc)$_3$H (153 mg, 1.5 eq.) was introduced in one portion, and the mixture was shaken at room temperature overnight. The mixture was quenched with 5 mL of NaOH (10%), then extracted with ethyl acetate (3×10 mL). The extracts were combined and washed with aqueous NaHCO$_3$ (sat., 2×5 mL), brine (10 mL), and dried over anhydrous sodium sulfate. After the solvent was removed, the remaining oily residue was purified by preparative thin layer chromatography (EtOAc/MeOH, 95:5) to afford N-Phenyl-N-[1-(2-phenylpropyl) piperidin-3-ylmethyl]propionamide as a colorless oil (19 mg, 71%). LRMS 365.

The diastereomers of N-Phenyl-N-[1-(2-phenylpropyl)piperidin-3-ylmethyl]propionamide were separated on a chiral column (Chiralpak AD. Column number AD00CG-1F001) with Hexanes (0.2% of diethylamine):iPrOH (98:2). The first compound to elute from the column was 127, and the second compound to elute from the column was 128.

EXAMPLE 86

N-[1-(1-phenethylpiperidin-3-yl)ethyl]-N-Phenylpropionamide (129)

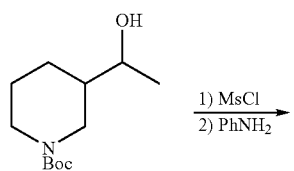

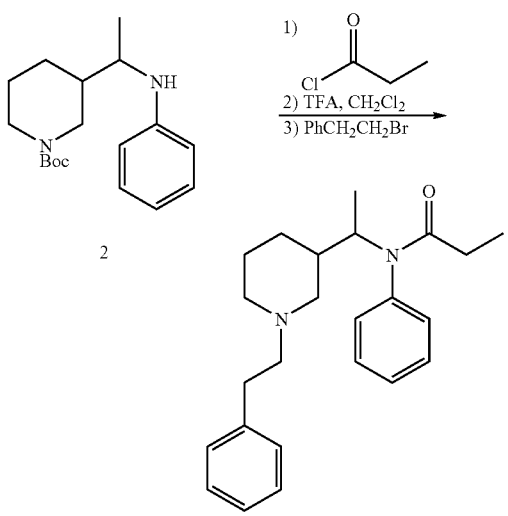

129

To a stirred suspension of 3-(1-hydroxyethyl)piperidine-1-carboxylic acid tert-butyl ester (1) (31 mg, 0.135 mmol) and piperidinomethyl polystyrene resin (60 mg) in 0.5 mL of CH$_2$Cl$_2$ was added methanesulfonyl chloride (15.7 µL, 1.5 eq.). The mixture was stirred at room temperature for 60 min. After removal of solvent, aniline (50 µL) was introduced. The mixture was heated at 95° C. overnight. The crude product was purified by preparative thin layer chromatography (EtOAc/Hexane, 1:2) to afford 3-(1-phenylaminoethyl)piperidine-1-carboxylic acid tert-butyl ester (2) (21 mg, 51%).

Compound 129 was then prepared from 2, using the final steps of the procedure described in Example 81. LRMS 365.

EXAMPLE 87

1-(1-phenethylpiperidin-3-ylmethyl)-3,4-dihydro-1H-quinolin-2-one (130)

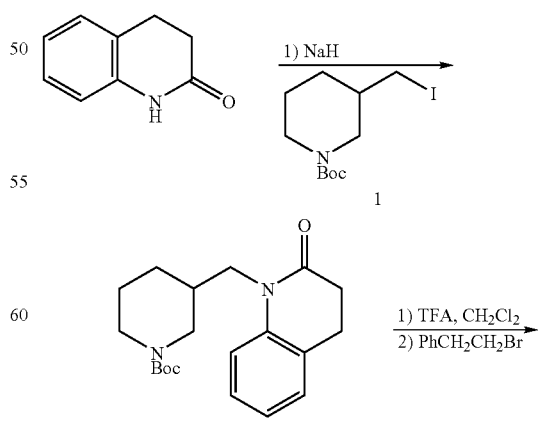

-continued

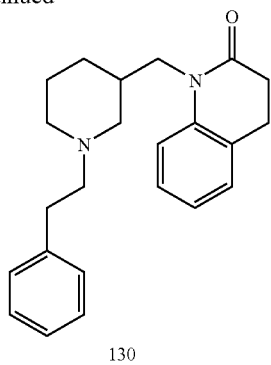

130

To a solution of 3,4-dihydro-1H-quinolin-2-one (96 mg, 0.65 mmol) in 1.5 mL of DMF was added NaH (26 mg, 1 eq.). The mixture was stirred at room temperature for 45 min. 3-Iodomethylpiperidine-1-carboxylic acid tert-butyl ester (200 mg, 0.62 mmol) in 0.5 mL of DMF was introduced slowly to the reaction mixture. The reaction was continued for 1 h. at room temperature. The mixture was diluted with 10 mL of EtOAc and washed with aqueous HCl (5%, 5 mL), NaHCO$_3$ (sat., 5 mL), brine (10 mL), and dried over anhydrous sodium sulfate. After the solvent was removed, the remaining oily residue was purified by preparative thin layer chromatography (EtOAc/Hexane, 3:7) to afford 3-(2-oxo-3,4-dihydro-2H-quinolin-1-ylmethyl)piperidine-1-carboxylic acid tert-butyl ester (2) as a colorless oil (80 mg, 37%).

3-(2-oxo-3,4-dihydro-2H-quinolin-1-ylmethyl)piperidine-1-carboxylic acid tert-butyl ester (2) was converted to 1-(1-phenethylpiperidin-3-ylmethyl)-3,4-dihydro-1H-quinolin-2-one (130) (68 mg, 85%), using the final steps of the procedure described in Example 81. LRMS 349.

EXAMPLE 88

N-4-tert-Butoxycarbonyl-1-Carbobenzyloxy(2-anilinocarboxy)piperazine (131)

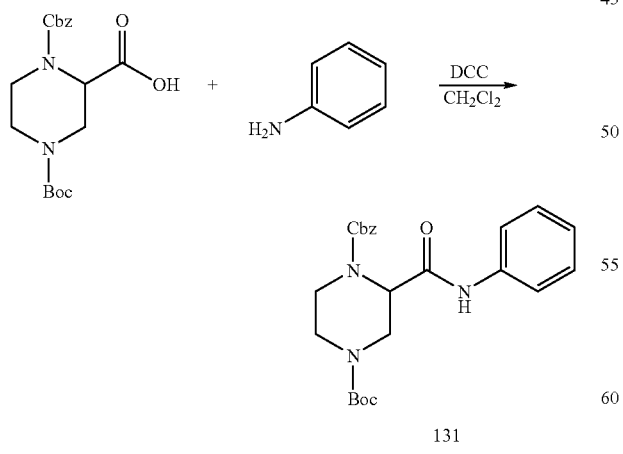

131

A solution of 4-Boc-1-Cbz-piperazine-2-carboxylic acid (2.66 mmol, 0.970 g) and aniline (1.1 equiv, 2.93 mmol, 270 µL) in CH$_2$Cl$_2$ (15 mL) at 0° C. was treated with DCC (2.0 equiv, 5.32 mmol, 1.10 g) under Ar. The reaction mixture was allowed to warm to 25° C. and stirred for 12 h. The reaction mixture was then filtered to remove the urea and the solvents were removed in vacuo. Chromatography (SiO$_2$, 2.5 cm×30.5 cm, 1:1 hexane-EtOAc) of the crude material gave 131 (1.15 g, 1.17 g theoretical, 98%) as a white foam. LRMS m/z 439 (M$^+$, C$_{24}$H$_{29}$N$_3$O$_5$ requires 439).

EXAMPLE 89

N-4-tert-Butoxycarbonyl-1-Carbobenzyloxy(2-anilinomethyl)piperazine (132)

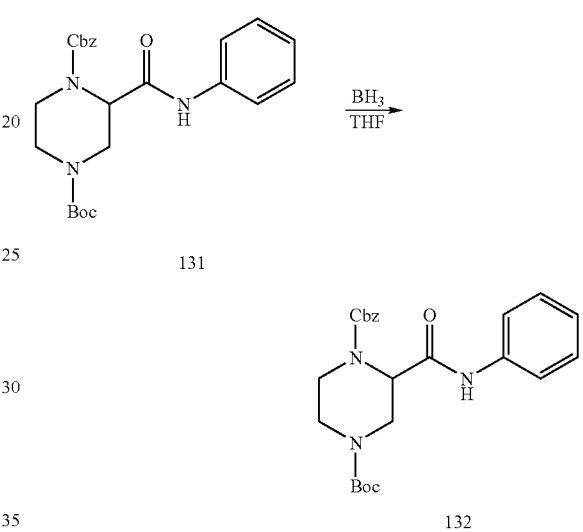

A solution of 131 (0.519 mmol, 228 mg) in THF (1.5 mL) at 0° C. was treated with 1.0 M BH$_3$-THF (2.5 equiv, 1.30 mmol) under Ar. The reaction mixture was then heated to 80° C. and allowed to stir for 12 h. The reaction mixture was then cooled to 0° C. and quenched with 10% aqueous HCl. The pH was adjusted to 10 with 10% aqueous NaOH and the reaction mixture was extracted with EtOAc (3×25 mL). The organics were washed with brine, and dried over MgSO$_4$ to give crude 132.

EXAMPLE 90

N-(4-tert-Butyloxy-1-Carbobenzaloxypiperazin-2-ylmethyl)-N-(anilino)cyclopropionamide (133)

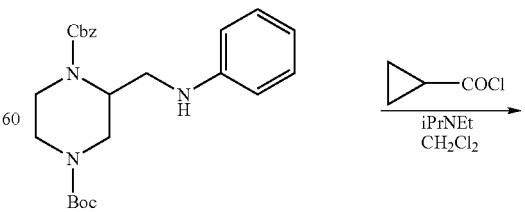

132

-continued

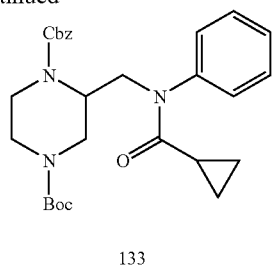

133

A solution of the crude aniline intermediate (132) (0.519 mmol) in $CH_2Cl_2$ at 0° C. was treated with cyclopropanecarbonyl chloride (1.5 equiv, 0.779 mmol, 77 μL) and diisopropylethylamine (2.0 equiv, 1.04 mmol, 181 μL) under Ar. After warming to 25° C. and stirring for 12 h, the reaction mixture was quenched with 10% aqueous $NaHCO_3$. The reaction mixture was then made acidic with 10% aqueous HCl and extracted with EtOAc (3×25 mL). Chromatography (PTLC, $SiO_2$, 20 cm×20 cm, 1 mm, 1:2 EtOAc-Hexane) provided 133 (136 mg, 256 mg theoretical, 53%) as a colorless oil: $R_f$ 0.22 ($SiO_2$, 1:2 EtOAc-Hexane); LRMS m/z 493 ($M^+$, $C_{28}H_{35}N_3O_5$ requires 493).

EXAMPLE 91

N-1-Carbobenzyloxy(4-phenethyl-piperazin-2-ylmethyl)-N-(anilino)cyclopropionamide (134)

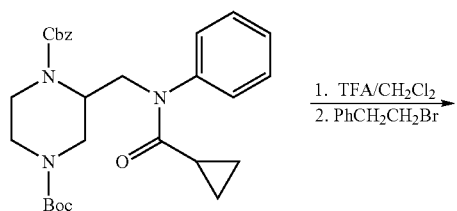

133

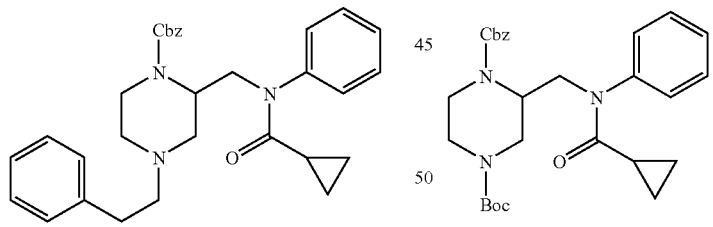

134

A solution of 133 (0.079 mmol, 39 mg) in $CH_2Cl_2$ (1 mL) at 25° C. was treated with 50% TFA in $CH_2Cl_2$ (1 mL). The reaction mixture stirred for 2 h. The solvents were removed in vacuo and the resulting oil was dried under high vacuum for 12 h. The resulting oil was then treated with phenethyl bromide (4.5 equiv, 0.36 mmol, 49 μL) and $K_2CO_3$ (5.0 equiv, 0.39 mmol, 55 mg) in $CH_3CN$ (250 μL). The reaction mixture was stirred for 12 h at 60° C. The reaction mixture was purified directly by chromatography (PTLC, $SiO_2$, 20 cm×20 cm, 1 mm, 1:2 EtOAc-Hexane) which provided 134 (29 mg, 38 mg theoretical, 76%) as a colorless oil: $R_f$ 0.28 ($SiO_2$, 1:2 EtOAc-Hexane); LRMS m/z 497 ($M^+$, $C_{31}H_{35}N_3O_3$ requires 497).

EXAMPLE 92

N-4-Phenethyl-piperazin-2-ylmethyl)-N-(anilino)cyclopropionamide (135)

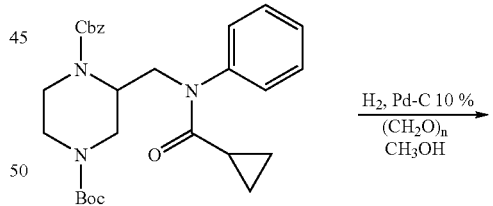

135

A solution of 134 (0.048 mmol, 24 mg) in $CH_3OH$ (1 mL) at 25° C. was treated with 10% Pd—C (20 mg) and then placed under a hydrogen atmosphere. The reaction mixture stirred for 12 h and then was filtered through a pad of Celite. The solvents were removed in vacuo. The reaction mixture was purified directly by chromatography (PTLC, $SiO_2$, 20 cm×20 cm, 1 mm, EtOAc-10% $CH_3OH$) which provided 135 (12 mg, 18 mg theoretical, 67%) as a colorless oil: $R_f$ 0.22 ($SiO_2$, EtOAc-10% $CH_3OH$); LRMS m/z 363 ($M^+$, $C_{23}H_{29}N_3O$ requires 363).

EXAMPLE 93

N-1-Methyl(4-tert-Butyloxypiperazin-2-ylmethyl)-N-(anilino)cyclopropionamide (136)

133

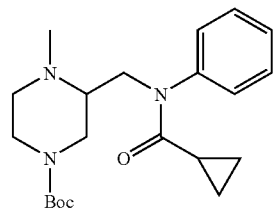

136

A solution of 133 (0.18 mmol, 90 mg) in $CH_3OH$ (1.5 mL) at 25° C. was treated with 10% Pd—C (20 mg) and paraformaldehyde (11 mg) and then placed under a hydrogen atmosphere. The reaction mixture stirred for 12 h and then was filtered through a pad of celite. The solvents were removed in vacuo and the resulting oil was purified by chromatography (PTLC, SiO$_2$, 20 cm×20 cm, 1 mm, EtOAc-10% CH$_3$OH) which provided 136 (38 mg, 68 mg theoretical, 56%) as a colorless oil: R$_f$ 0.40 (SiO$_2$, EtOAc-10% CH$_3$OH); LRMS m/z 373 (M$^+$, C$_{21}$H$_{31}$N$_3$O$_3$ requires 373).

EXAMPLE 94

N-1-Methyl(4-phenethyl-piperazin-2-ylmethyl)-N-(anilino)cyclopropionamide (137)

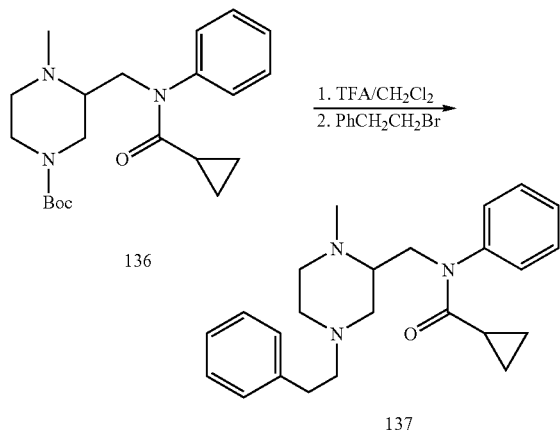

Compound 136 (0.091 mmol, 34 mg) was treated with 50% TFA in CH$_2$Cl$_2$ (1 mL) at 25° C. The reaction mixture stirred for 2 h. The solvents were removed in vacuo and the resulting oil was dried under high vacuum for 12 h. The resulting oil was then treated with phenethyl bromide (2.0 equiv, 0.18 mmol, 25 µL) and K$_2$CO$_3$ (2.0 equiv, 0.18 mmol, 25 mg) in CH$_3$CN (300 µL). The reaction mixture stirred for 12 h at 60° C. The reaction mixture was purified directly by chromatography (PTLC, SiO$_2$, 20 cm×20 cm, 1 mm, EtOAc-10% CH$_3$OH) which provided 137 (34 mg, 34 mg theoretical, 99%) as a colorless oil: R$_f$ 0.33 (SiO$_2$, EtOAc-10% CH$_3$OH); LRMS m/z 377 (M$^+$, C$_{24}$H$_{31}$N$_3$O requires 377).

EXAMPLE 95

N-(1-Cyclohexylethyl-piperidin-3-R-ylmethyl)-N-(anilino-3-yl)propionamide (139)

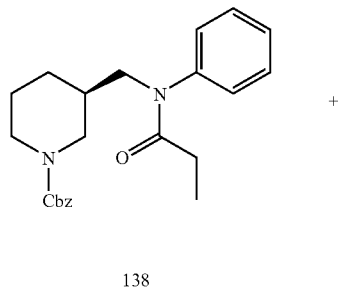

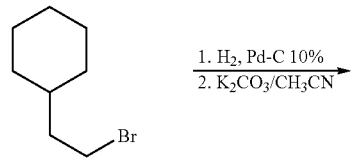

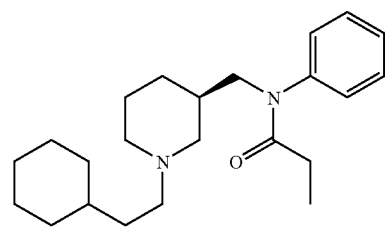

A solution of 138 (0.471 mmol, 116 mg) in CH$_3$OH (1 mL) at 25° C. was treated with 10% Pd—C (20 mg) and then placed under a hydrogen atmosphere. The reaction mixture stirred for 12 h and then was filtered through a pad of Celite. The solvents were removed in vacuo and the resulting oil was then treated with 1-bromo-2-cyclohexylethane (1.5 equiv, 0.707 mmol, 111 µL) and K$_2$CO$_3$ (1.5 equiv, 0.707 mmol, 98 mg) in CH$_3$CN (1 mL). The reaction mixture stirred for 12 h at 60° C. The reaction mixture was then purified directly by chromatography (PTLC, SiO$_2$, 20 cm×20 cm, 1 mm, EtOAc-10% CH$_3$OH) which provided 139 (137 mg, 168 mg theoretical, 82%) as yellow oil: R$_f$ 0.29 (SiO$_2$, EtOAc-10% CH$_3$OH); LRMS m/z 356 (M$^+$, C$_{23}$H$_{36}$N$_2$O requires 356).

EXAMPLE 96

N-(1-(3-ethylindole)piperidin-3-R-ylmethyl)-N-(anilino-3-yl)propionamide (140)

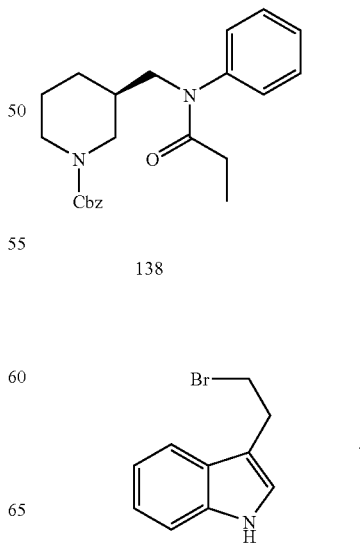

-continued

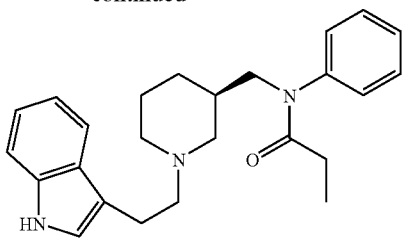

140

A solution of 138 (0.451 mmol, 172 mg) in CH$_3$OH (1 mL) at 25° C. was treated with 10% Pd—C (20 mg) and then placed under a hydrogen atmosphere. The reaction mixture was stirred for 12 h and then was filtered through a pad of Celite. The solvents were removed in vacuo and the resulting oil was then treated with 3-(2-bromoethyl)indole (1.5 equiv, 0.677 mmol, 152 mg) and K$_2$CO$_3$ (1.5 equiv, 0.677 mmol, 94 mg) in CH$_3$CN (1 mL). The reaction mixture stirred for 12 h at 60° C. The reaction mixture was then purified directly by chromatography (PTLC, SiO$_2$, 20 cm×20 cm, 1 mm, EtOAc-10% CH$_3$OH) which provided 140 (176 mg, 88 mg theoretical, 50%) as yellow oil: R$_f$ 0.22 (SiO$_2$, EtOAc-10% CH$_3$OH); LRMS m/z 389 (M$^+$, C$_{25}$H$_{31}$N$_3$O requires 389).

EXAMPLE 97

N-(1-(1,1-difluoroethylbenzene)piperidin-3-R-ylm-ethyl)-N-(anilino-3-yl)propionamide (141)

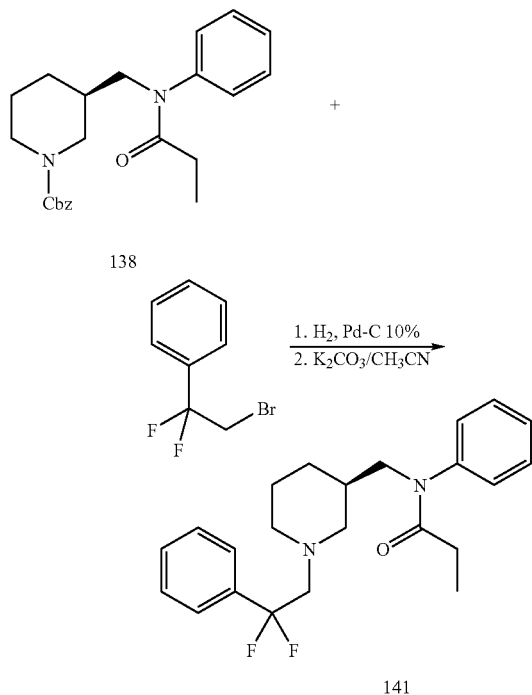

141

A solution of 138 (0.487 mmol, 185 mg) in CH$_3$OH (1 mL) at 25° C. was treated with 10% Pd—C (20 mg) and then placed under a hydrogen atmosphere. The reaction mixture stirred for 12 h and then was filtered through a pad of celite. The solvents were removed in vacuo and the resulting oil was then treated with (2-bromo-1,1-difluoroethyl)benzene (1.5 equiv, 0.731 mmol, 162 mg) and K$_2$CO$_3$ (1.5 equiv, 0.731 mmol, 101 mg) in CH$_3$CN (1 mL). The reaction mixture stirred for 12 h at 60° C. The reaction mixture was then purified directly by chromatography (PTLC, SiO$_2$, 20 cm×20 cm, 1 mm, 2:1 Hexane-EtOAc) which provided 141 (20 mg, 188 mg theoretical, 11%) as yellow oil: R$_f$ 0.52 (SiO$_2$, 2:1 Hexane-EtOAc); LRMS m/z 386 (M$^+$, C$_{23}$H$_{28}$F$_2$N$_2$O requires 386).

EXAMPLE 98

1-Benzyl-azepan-2-one (142)

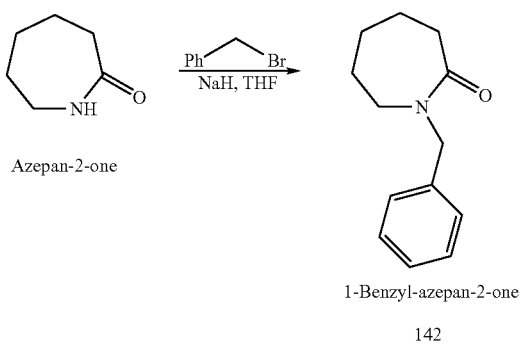

To a stirring 0° C. suspension of NaH (18.3 g, 763 mmol) in THF (195 mL) was added by addition funnel azepan-2-one (75.0 g, 667 mmol) in THF. An additional 2 L of solvent was added as the reaction progressed in order to maintain agitation of the very viscous reaction suspension. Following addition, the reaction was allowed to warm to room temperature, and when the evolution of H$_2$ ceased after stirring overnight, benzyl bromide was added dropwise by addition funnel and the reaction was stirred overnight. The crude product was filtered through Celite and concentrated in vacuo. Recrystallization from hexanes and ethyl acetate provided pure 1-benzyl-azepan-2-one (142) as a white fluffy solid. $^1$H NMR (CDCl$_3$) 7.38–7.24 (5H, m), 4.61 (2H, s), 3.33–3.29 (2H, m), 2.65–2.61 (2H, m), 1.77–1.66 (4H, m), 1.56–1.46 (2H, m) ppm. $^{13}$C NMR (CDCl$_3$, 75 MHz) 176.13, 138.06, 128.67, 128.31, 127.43, 51.20, 49.04, 37.33, 30.12, 28.26, 23.58 ppm.

EXAMPLE 99

1-Benzyl-2-oxo-azepane-3-carboxylic acid methyl ester (143)

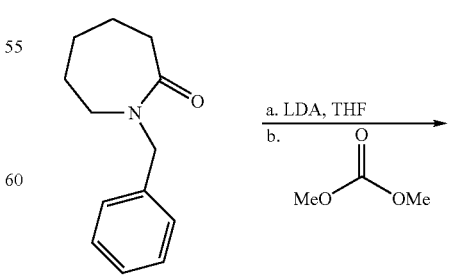

1-Benzyl-azepan-2-one
142

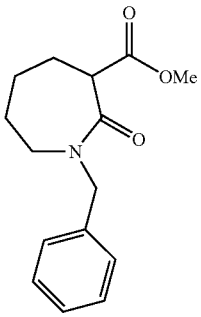

1-Benzyl-2-oxo-azepane-3-carboxylic acid methyl ester
143

LDA was prepared as follows: Diisopropyl amine (15.2 mL, 110 mmol) freshly distilled under $N_2$ and over $CaH_2$ was added to 110 mL of anhydrous THF in a dry flask, and the solution was cooled to 0° C. in an ice bath. nBuLi (73.3 mL, 111 mmol) was added dropwise, and the reaction was stirred at 0° C. for 1 hour. The freshly prepared LDA was added dropwise to a −70° C. solution of 1-Benzyl-azepan-2-one (142) (10.98 g, 544.0 mmol) dissolved in anhydrous $Et_2O$ (70 mL). The reaction was stirred at −70° C. for 1 hour, then dimethyl carbonate (4.55 mL, 544 mmol) was added dropwise. The reaction was allowed to warm to room temperature overnight. The reaction was judged complete by HPLC, and was slowly poured into 5N HCl stirring in an ice bath. The organic layer was extracted. The aqueous layer was washed with $CH_2Cl_2$ two times, and the combined organics were dried with sodium sulfate, filtered and concentrated in vacuo. Crude material was purified on an automated flash column with 80:20 Hexanes:EtOAc to obtain 10.85g, (77%) of 1-benzyl-2-oxo-azepane-3-carboxylic acid methyl ester (143) as a pale yellow oil. $^1$H NMR ($CDCl_3$) 7.42–7.10 (5H, broad s), 4.61 (1H, d, J=14.7 Hz), 4.50 (1H, d, J=14.7 Hz), 3.74 (3H, s), 3.7–3.64 (1H, m), 3.40–3.13 (2H, m), 2.12–1.98 (1H, m), 1.92–1.73 (2H, m), 1.66–1.42 (2H, m), 1.32–1.16 (1H, m) ppm. $^{13}$C NMR ($CDCl_3$, 75 MHz) 171.94, 171.04, 137.28, 128.55, 128.24, 127.43, 52.15 (2), 51.27, 48.31, 27.87, 27.41, 25.91 ppm. LRMS: 261.73.

EXAMPLE 100

(1-Benzyl-azepan-3-yl)-methanol (144)

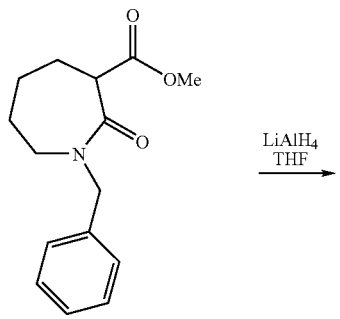

1-Benzyl-2-oxo-azepane-3-
carboxylic acid methyl ester
143

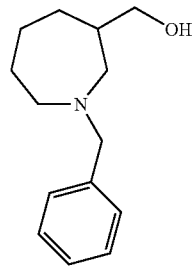

(1-Benzyl-azepan-3-yl)-methanol
144

1-Benzyl-2-oxo-azepan-2-carboxylic acid methyl ester (143) (0.2154 g, 0.8243 mmol) dissolved in anhydrous THF (2.9 mL) was added to a stirring suspension of $LiAlH_4$ in THF (1.5 mL) over approx. 1.5 hours. The reaction mixture was stirred overnight. The reaction was judged complete by TLC and was quenched by the sequential addition of $H_2O$ (0.4 mL), then 2N NaOH (1.0 mL) and $H_2O$ (0.4 mL). The mixture was stirred at room temperature for 30 minutes, then was filtered, dried with $Na_2SO_4$, and concentrated in vacuo. Crude material was purified by automated silica gel chromatography with 15:85:5 $CH_2Cl_2$:Hexanes:2N $NH_3$ in EtOH to obtain 0.1062 g (59%) of pure (1-benzyl-azepan-3-yl)-methanol (144). $^1$H NMR ($CDCl_3$) 7.40–7.23 (5H, m), 3.65 (2H, s), 3.54 (1H, dd, J=10.4, 3.5 Hz), 3.43 (1H, dd, J=10.4, 5.4 Hz), 2.82 (1H, J=13.3, 3.1Hz), 2.77 (2H, m), 2.44 (1H, ddd, J=12.2, 8.6, 3.3 Hz), 1.90–1.45 (6H, m) ppm. $^{13}$C NMR ($CDCl_3$, 75 MHz) 139.14, 128.97, 128.14, 126.91, 67.20, 63.85, 58.49, 56.87, 39.59, 29.68, 29.43, 25.23 ppm. LRMS: 219.64.

EXAMPLE 101

Azepan-3-yl-methanol (145)

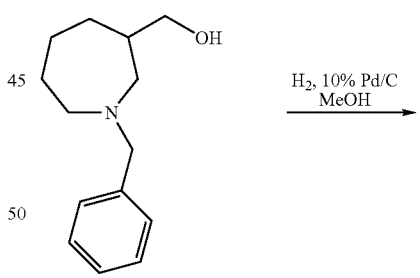

(1-Benzyl-azepan-
3-yl)-methanol
144

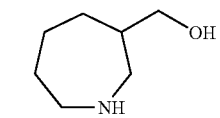

Azepan-3-yl-methanol
145

(1-Benzyl-azepan-3-yl)-methanol (144) (0.0922 g, 0.4192 mmol) dissolved in MeOH (1 mL) was added to a stirring suspension of 10% Pd/C (14.4 mg) in 5 mL MeOH. The reaction was purged with $H_2$, and the reaction was stirred at room temperature overnight. The reaction was judged complete by $^1$H-NMR analysis of an aliquot from the reaction. The reaction was filtered through a pad of Celite wet with MeOH and was rinsed with MeOH, and concentrated in vacuo to obtain pure azepan-3-yl-methanol (145) in 60% yield (0.0323 g). Compound 145 was used in the next Example without further purification. $^1$ H NMR (CDCl$_3$, partial) 3.14–2.70 (4H, m), 1.92–1.73 (4H, m), 1.68–1.42 (3H, m) ppm. $^{13}$C NMR (CDCl$_3$, 75 MHz) 67.32, 52.01, 50.33, 41.31, 31.05, 29.76, 25.44 ppm.

EXAMPLE 102

3-Hydroxymethyl-azepan-1-carboxylic acid benzyl ester (146)

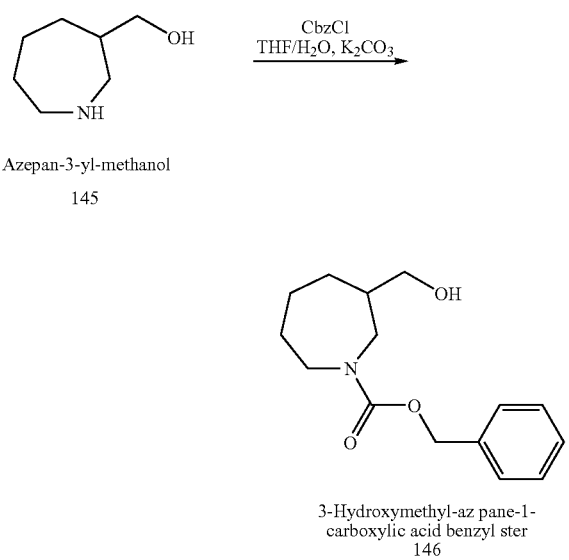

3-Hydroxymethyl-az pane-1-carboxylic acid benzyl ster
146

Potassium carbonate was added to a mixture of azepan-3-yl-methanol (145) (0.032 g, 0.2485 mmol) in THF/H$_2$O (2:1, 0.31 mL). The suspension was cooled to 0° C., and (benzyloxy)carbonyl chloride (0.071 mL, 0.497 mmol) was added dropwise. The reaction was allowed to warm to room temperature overnight, and was then concentrated in vacuo. CH$_2$Cl$_2$ and H$_2$O were added. The organics were extracted, washed with brine, dried over sodium sulfate, filtered and concentrated in vacuo. The crude material was purified by automated silica gel chromatography with 75:25 Hexanes:EtOAc to obtain 3-Hydroxymethyl-azepan-1-carboxylic acid benzyl ester (146) in approximately 94% yield.

Because 146 bears a Cbz group, many of the peaks in the $^1$ H and $^{13}$C NMR spectra appear as two sets of peaks. When provided, the value in parentheses is for the smaller of the two sets of peaks that corresponds to the same proton or carbon. $^1$H NMR (CDCl$_3$) 7.38–7.26 (5H, m), 5.13 (2H, s), (3.77) 3.73 (2H, q, J=5.4 Hz), 3.53–3.42 (2H, m), 3.36 (3.31) 1H, d, J=4.3 Hz), 3.23–3.12 (1H, m), 2.10–1.20 (7H, m) ppm. $^{13}$C NMR (CDCl$_3$, 75 MHz) 157.02 (156.06), (136.89) 136.74, 128.42, 127.91, 127.66, 67.16 (66.87), (65.27) 64.69, (48.12) 47.89, (42.13) 41.23, (30.05) 29.78, 28.78 (28.11), (24.87) 24.61, 14.13 ppm.

EXAMPLE 103

3-Formyl-azepane-1-carboxylic acid benzyl ester (147)

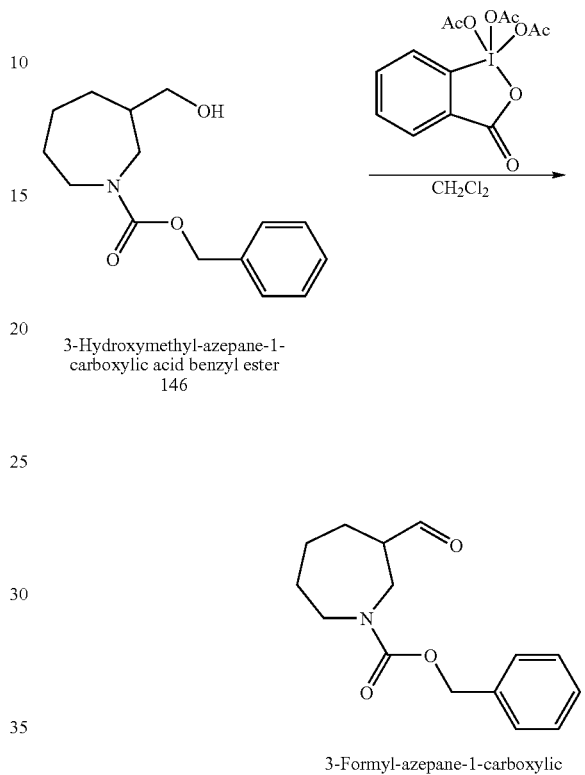

Dess-Martin periodinane (2.78 g, 6.56 mmol) was slowly added to a stirring 0° C. solution of 3-hydroxymethyl-azepane-1-carboxylic acid benzyl ester (146) (1.2516 g, 5.02 mmol) in CH$_2$Cl$_2$ (18.2 mL). The reaction was stirred for 1 hour until the reaction was judged complete by HPLC. The reaction was concentrated in vacuo, and a minimal amount of CH$_2$Cl$_2$ was added. Et$_2$O was added to precipitate the periodinane by-product, and the reaction was filtered, concentrated, and immediately purified through an automated silica gel column with 1:1 Hexanes:EtOAc to obtain pure 3-formyl-azepane-1-carboxylic acid benzyl ester (147) (0.3086 g) in 62% yield.

Because 147 bears a Cbz group, many of the peaks in the $^1$H and $^{13}$C NMR spectra appear as two sets of peaks. When provided, the value in parentheses is for the smaller of the two sets of peaks that correspond to the same proton or carbon. $^1$H NMR (CDCl$_3$) 9.67 (9.56) (1H, s), 7.32–7.22 (5H, m), (5.09, 2H, s) 5.12 (1H, d, J=12.6 Hz) 5.02 (1H, d) J=12.3 Hz), (3.80) 3.75 (1H, t, J=6.3 Hz), 3.60–3.28 (3H, m), 2.70–2.53 (1H, m), 190–1.40 (6H, m) ppm. $^{13}$C NMR (CDCl$_3$, 75 MHz) 202.52 (202.35), 155.98 (155.55), (136.59) 136.44, 128.31, 127.81, 127.61, 66.97, (51.57) 51.20, (48.68) 48.20, 46.02 (45.43), 28.67 (28.23), (26.27) 26.09, (24.37) 24.30 ppm.

EXAMPLE 104

3-Phenylaminomethyl-azepane-1-carboxylic acid benzyl ester (148)

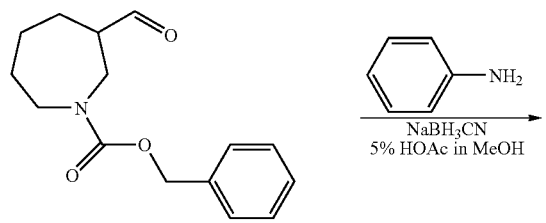

3-Formyl-azepan-1-carboxylic acid benzyl ester
147

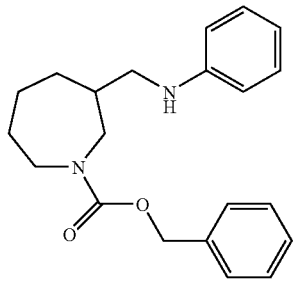

3-Phenylaminomethyl-azepane-1-carboxylic acid benzyl ster
148

Aniline (0.126 mL, 1.38 mmol) was added to a solution of 3-formyl-azepane-1-carboxylic acid benzyl ester (147) (0.300 g, 1.15 mmol) in 5% HOAc in MeOH (11.5 mL). The reaction was stirred for approx. 20 minutes, then NaBH$_3$CN (0.2164 g, 3.44 mmol) was slowly added and the reaction was stirred at room temperature overnight. The reaction was then concentrated in vacuo and EtOAc and a few drops of 10% NaOH were added. The organic was washed with saturated NaCl (aq), dried with Na$_2$SO$_4$, concentrated in vacuo, to give crude 3-phenylaminomethyl-azepane-1-carboxylic acid benzyl ester (148). Compound 148 was used in the next step without further purification.

EXAMPLE 105

3-[(Phenyl-propionyl-amino)-methyl]-azepane-1-carboxylic acid benzyl ester (149)

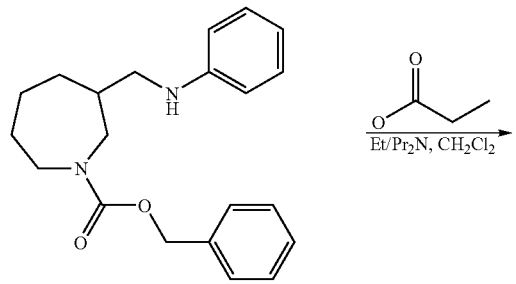

3-Phenylaminomethyl-azepane-1-carboxylic acid benzyl ester
148

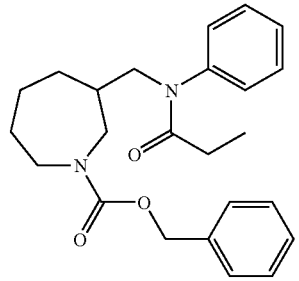

3-[(Phenyl-propionyl-amino)-methyl]-azepane-1-carboxylic acid benzyl ester
149

Et(iPr)$_2$N (0.24 mL, 1.38 mmol) was added to a stirring solution of crude 3-phenylaminomethyl-azepane-1-carboxylic acid benzyl ester (148) in CH$_2$Cl$_2$ (2.3 mL) under N$_2$. The reaction was cooled to 0° C. in an ice bath, then propionyl chloride (0.22 mL, 2.53 mmol) was added dropwise. The reaction was allowed to warm to room temperature overnight. The reaction was then judged complete by TLC. It was concentrated in vacuo and EtOAc and 10% NaOH (aq) were added. The organic layer was dried over sodium sulfate, filtered and concentrated in vacuo, and purified by automated silica gel chromatography with 96:2:2 Hexanes:CH$_2$Cl$_2$:2N NH$_3$ in EtOH to obtain 3-[(phenyl-propionyl-amino)-methyl]-azepane-1-carboxylic acid benzyl ester (149) (0.3266 g) in 72% yield for two steps.

Because 149 bears a Cbz group, many of the peaks in the $^1$H and $^{13}$C NMR spectra appear as two sets of peaks. When provided, the value in parentheses is for the smaller of the two sets of peaks that corresponds to the same proton or carbon. $^1$H NMR (CDCl$_3$) 7.55–7.20 (9H, m), 7.15–6.90 (1H, m), 5.24–5.05 (2H, m), 4.20–4.05 (1H, m), 400–3.05 (5H, m), 2.95–2.75 (1H, m), 2.07–2.00 (2H, m), 2.00–0.85 (9H, m) ppm. $^{13}$C NMR (CDCl$_3$, 75 MHz) (174.1) 1743.98, 156.15 (156.03), 142.71, (137.11) 136.97, 129.78 (129.67), (128.69) 128.55, 128.47, 128.26, 128.06, 127.84, 127.61, 67.14 (66.90), 52.33 (51.87), 49.67 (49.46), 47.64 (47.12), (38.83) 38.30, 32.01 (31.58), (27.87) 27.73, 24.75 (24.47), 9.63 ppm. LRMS: 394.37.

EXAMPLE 106

N-(1-Phenethylaminomethyl-azepane-3-ylmethyl)-N-phenylpropionamide (150)

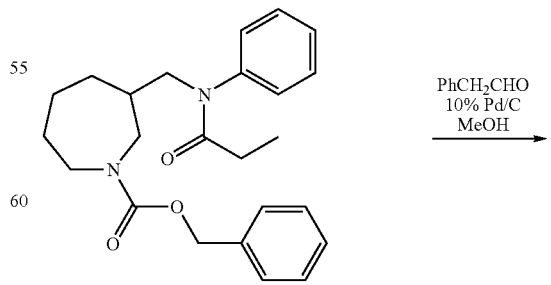

3-[(Phenyl-propionyl-amino)-methyl]-azepane-1-carboxylic acid benzyl ester
149

-continued

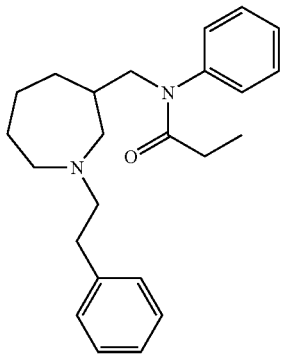

N-(1-Phenethyl-azepan-3-ylmethyl)-
N-phenyl-propionamide
150

3-[(phenyl-propionyl-amino)-methyl]-azepane-1-carboxylic acid benzyl ester (149) and phenylacetaldehyde (0.148 mL, 1.27 mmol) in 1.5 mL MeOH were added to a suspension of 10% Pd/C (0.0553 g) in 7.0 mL MeOH. The reaction mixture was shaken under 40 psi $H_2$ until the consumption of $H_2$ ceased and the reaction was judged complete by TLC. The crude reaction mixture was passed through a column of Celite wet with MeOH, concentrated in vacuo, and purified by flash column chromatography 80:18:2 Hexanes:$CH_2Cl_2$:2N $NH_3$ in EtOH to obtain N-(1-Phenethylaminomethyl-azepane-3-ylmethyl)-N-phenylpropionamide (150) (0.0404 g) in 43% yield. $^1$H NMR (CDCl$_3$) 7.47–7.15 (10 H, m), 3.64 (2H, broad dd, J=7.5, 1.8 Hz), 2.82–2.59 (4H, m), 2.74 (4H, broad s), 2.45 (1H, dd, J=13.3, 8.6 Hz), 2.07 (2H, q, J=7.4 Hz), 1.96–1.82 (1H, m), 1.76–1.76–1.26 (5H, m), 1.07 (3H, t, J=7.4 Hz) ppm. $^{13}$C NMR (CDCl$_3$, 75 MHz) 174.23, 143.08, 140.88, 129.85, 128.93, 128.46 (2), 127.91, 126.01, 61.22, 58.35, 56.34, 53.02, 37.84, 34.21, 31.14, 28.80, 28.11, 25.00, 9.92 ppm. LRMS: 364.30.

EXAMPLE 107

Synthesis of Diazepine 154

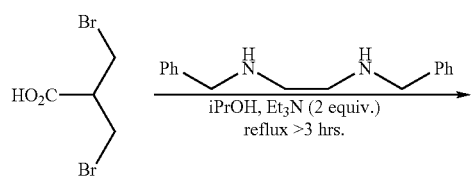

153

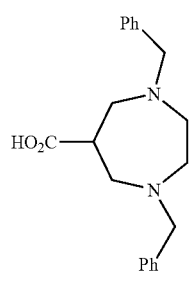

154

Dibromide 153 (30.0 g, 122 mmol) in 500 mL of isopropanol was cooled to 0° C. A solution of dibenzylethylenediamine (122 mmol, 28.8 mL) and triethylamine (TEA) (269 mmol, 2.2 equiv., 37.5 mL) in 125 mL of isopropanol was added dropwise to the well-stirred solution over 1 hr. (a white precipitate, TEA-HBr, is formed). After complete addition and rinsing of the addition funnel with isopropanol (3×10 mL), the cooling bath was removed and the solution was heated to a gentle reflux for 3 hours. The solution was placed in a −20° C. freezer overnight. The precipitated TEA-HBr was removed by filtration and the filter cake was washed with cold isopropanol. The filtrate was concentrated on a rotary evaporator and the residue was dissolved in 300 mL of THF. This solution was cooled to −20° C. and then filtered to remove additional TEA-HBr. The filtrate was concentrated on a rotary evaporator and placed under 1 mm Hg vacuum overnight to give acid 154, a sticky brown foam (33 g) which was not purified further.

EXAMPLE 108

Synthesis of Diazepine 155

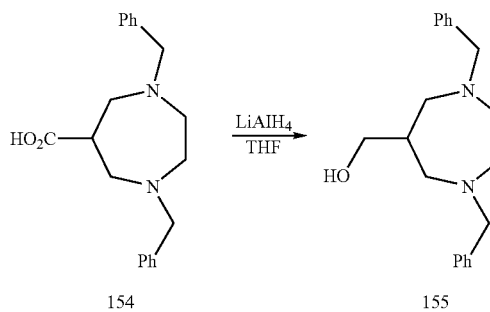

154                                     155

Crude acid 154 (33 g) in 400 mL of THF was cooled to 0° C. 250 mL of a 1 M solution of LAH in THF was added dropwise over 45 minutes. The cooling bath was removed and the solution was heated to a gentle reflux for 45 minutes and cooled to 0° C. The vigorously stirred cold solution was quenched by dropwise addition of 10 mL water, 10 mL 1M NaOH, and 30 mL of water. The suspension was stirred for 30 minutes, filtered and the filter cake was washed with THF and methylene chloride. The filtrate was concentrated on a rotary evaporator. The residue was dissolved in methylene chloride, filtered, and the filtrate was concentrated on a rotary evaporator and then placed under 1 mm Hg vacuum overnight to give a yellow viscous oil (155) (28 g, 74% crude yield for two steps). The product can be purified by silica gel chromatography to obtain a colorless oil using EtOAc with 0.5% ammonium hydroxide as eluent, but crude material was normally not purified.

EXAMPLE 109

Synthesis of Diazepine 156

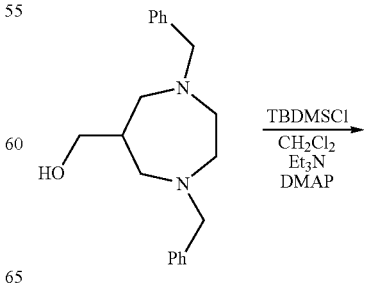

155

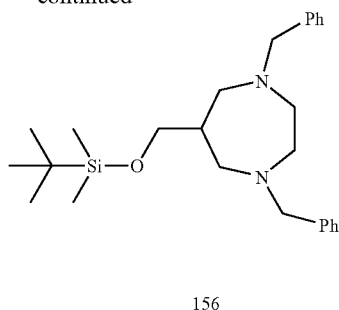

156

Crude alcohol 155 (28 g, 90.3 mmol) in 100 mL of methylene chloride was stirred at 25° C. TEA (1.1 equiv., 99.3 mmol, 13.8 mL) was added followed by TBDMSCl (1.05 equiv., 94.8 mmol, 14.3 g) and DMAP (0.02 equiv., 1.8 mmol, 220 mg) in 50 mL of methylene chloride. The solution became clouded and the resulting suspension was stirred overnight and then filtered. The filtrate was concentrated on a rotary evaporator. The residue was dissolved in 150 mL of chloroform and the solution was washed in a separatory funnel with water, with brine, then dried over sodium sulfate and filtered. The filtrate was concentrated on a rotary evaporator and then placed under 1 mm Hg vacuum overnight to give a yellow-brown viscous oil that was purified on silica gel using 80:20 hexane:EtOAc containing ca. 0.5% ammonium hydroxide. Colorless oil 156 (32 g, 83%) was obtained.

EXAMPLE 110

Synthesis of Diazepine 157

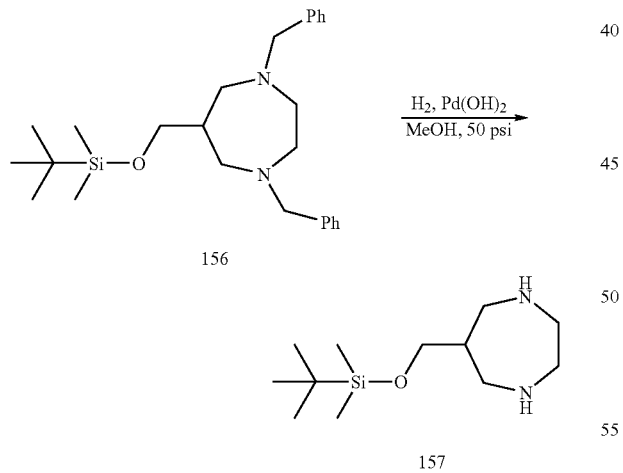

Crude diamine 156 (16 g, 37.7 mmol) in 50 mL of methanol was placed in a dry Parr bottle and 20% palladium hydroxide catalyst (ca. 3 g) was added. After vacuum purging, the suspension was hydrogenated on a Parr shaker at 50 psi hydrogen pressure overnight. The suspension was filtered and the filter cake was washed with methylene chloride. The filtrate was concentrated on a rotary evaporator to give colorless oil 157, which partly solidified upon standing (9.1 g, 99%).

EXAMPLE 111

Synthesis of Diazepine 158

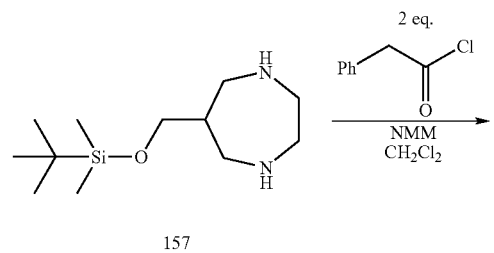

157

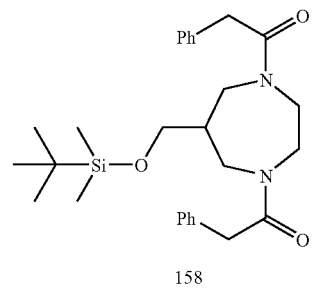

158

Diamine 157 (2.1 g, 8.6 mmol) was converted at 0° C. by standard procedures to bis-amide 158 using methylene chloride as solvent (80 mL) and 2.2 equivalents (18.9 mmol) of both N-methylmorpholine and phenylacetyl chloride, aqueous workup, and silica gel chromatography. Bis-amide 158 was isolated as a colorless foam (3.9 g, 94%).

EXAMPLE 112

Synthesis of Diazepine 159

158

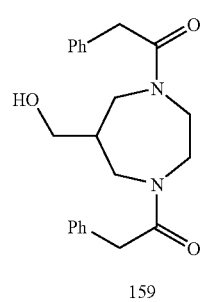

159

Silyl ether 158 (3.9 g, 8.1 mmol) was converted at 25° C. by standard procedures to alcohol 159 using THF as solvent (80 mL) and 1.1 equivalents (8.9 mmol) of a commercial 1

M solution of tetra-butylammonium fluoride in THF, aqueous workup, and silica gel chromatography. Alcohol 159 was isolated as a colorless foam (2.2 g, 73%).

EXAMPLE 113

Synthesis of Diazepine 160

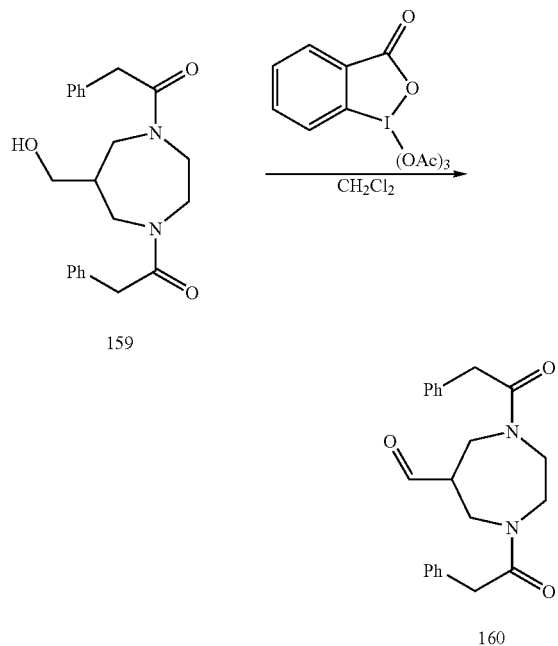

Alcohol 159 (2.16 g, 5.9 mmol) was converted at 25° C. by standard procedures to aldehyde 160 using methylene chloride as solvent (50 mL) and 1.2 equivalents (8.9 mmol) of commercial Dess-Martin periodinane reagent, treatment with 50 mL 1 N NaOH, aqueous workup, and silica gel chromatography. Aldehyde 160 was isolated as a colorless solid (1.8 g, 85%).

EXAMPLE 114

Synthesis of Diazepine 161

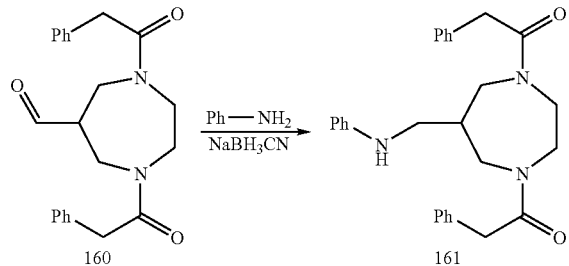

Aldehyde 160 (1.08 g, 3.0 mmol) was converted at 25° C. by standard procedures to amine 161, using 99:1 trimethylorthoformate:acetic acid as solvent (20 mL), 1.1 equivalents of aniline (3.3 mmol), and after 1 hour adding 1.5 equivalents (8.9 mmol) of commercial 1M sodium cyanoborohydride THF solution. Aqueous workup and silica gel chromatography (eluent: 90:10:1 ethyl acetate:hexane:ammonium hydroxide) gave amine 161 as a colorless foam (0.93 g, 70%).

EXAMPLE 115

Synthesis of Diazepine 162

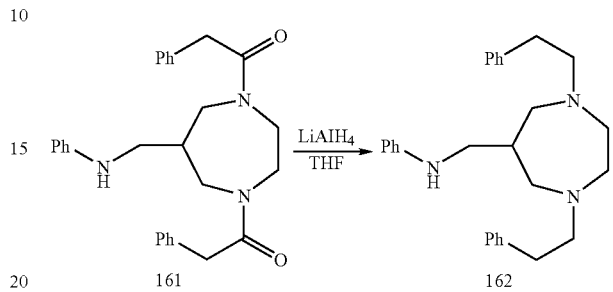

Amine 161 (0.90 g, 2.0 mmol) was converted by standard procedures to amine 162, using THF as solvent (15 mL), and adding 6 equivalents (12 mmol) of commercial 1M lithium aluminum hydride in THF solution at 0° C. followed by 1 hr. at reflux. Dropwise water/1N NaOH/water quench, dilution with methylene chloride (50 mL), filtration of the slurry, and silica gel chromatography (eluent: 100:1 ethyl acetate:ammonium hydroxide) gave amine 162 as a colorless oil (0.58 g, 69%). Physical data for compound 162: $^1$H NMR (CDCl$_3$, free base): δ 7.1–7.4 (m, 12H), 6.68 (t, J=7.3 Hz, 1H), 6.56 (dd, J=7.5 Hz, 1.0 Hz, 2H), 2.99 (d, J =6.9 Hz, 2H), 2.61–2.98 (m, 16H), 2.22 (m, 1H). MS (M+1): 414.3.

EXAMPLE 116

Synthesis of Diazepine 163

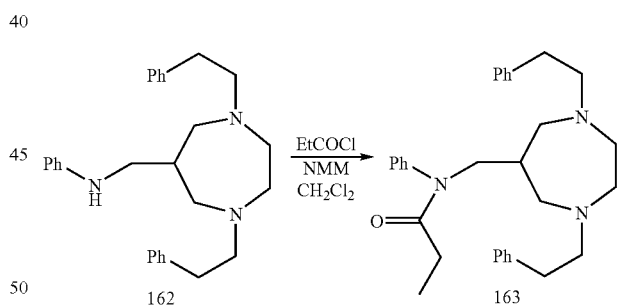

Amine 162 (0.55 g, 1.3 mmol) was converted at 0° C. by standard procedures to amide 163 using methylene chloride as solvent (5 mL) and 1.1 equivalents (1.5 mmol) of both N-methylmorpholine and propionyl chloride, aqueous workup, and silica gel chromatography. Amide 163 was isolated as a colorless foam (0.56 g, 90%). The HCl salt was prepared by dissolution of 163 in methanol (1.5 mL), addition of 1.5 mL of commercial 4N HCl in dioxane, and concentration in vacuo. Physical data for compound 163: $^{13}$C NMR (CDCl$_3$, free base): δ 174.3, 143.1, 140.8, 130.0, 129.0, 128.55, 128.53, 128.0, 126.1, 61.2, 57.8, 56.5, 51.5, 38.1, 34.2, 28.2, 10.0. $^1$H NMR (CDCl$_3$, free base): δ 7.1–7.4 (m, 15H), 3.62 (d, J=7.2 Hz, 2H), 2.49–2.78 (m, 16H), 2.05 (m, 1H), 2.04 (q, J=7.5 Hz, 2H), 1.04 (t, J=7.5 Hz, 3H). MS (M+1): 470.3.

EXAMPLE 117

Synthesis of (1-Benzyl-piperidin-3-yl)-phenyl-amine (164)

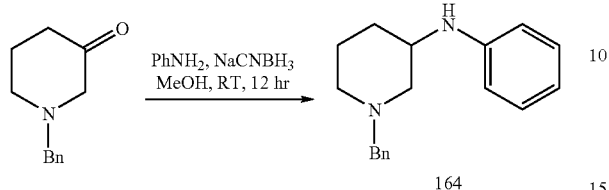

To a solution of 1-benzyl-piperidin-3-one hydrochloride salt (2.02 g, 8.95 mmol), aniline (1.67 ml, 17.89 mmol) in MeOH (20 ml) at room temperature was added NaCNBH$_3$ (1.8 g, 28.64 mmol) in several portions. The mixture was stirred over night. The mixture was taken up in 50 ml of water, the pH was increased to 12 with 2N KOH and extracted with CH$_2$Cl$_2$ (3×50 ml). Standard work-up of the organic solution provided 164 as a dried residue which was used in the next step without further purification. LRMS (calculated for C$_{18}$H$_{22}$N$_2$) 266. found 266.

EXAMPLE 118

Synthesis of N-(1-Benzyl-piperidin-3-yl)-N-phenyl-propionamide (165)

To the crude (1-benzyl-piperidin-3-yl)-phenyl-amine (164) (1.11 g) in CH$_2$Cl$_2$ (5 ml) at 0° C. was added i-Pr$_2$NEt (1.45 ml) and propionyl chloride (0.54 ml). The mixture was stirred for 2 hr. The mixture was diluted with CH$_2$Cl$_2$ (20 ml), washed with sat. NaHCO$_3$ (2×10 ml), brine (10 ml) and water (10 ml) and dried with Na$_2$SO$_4$. After filtration, the filtrate was concentrated under vacuum. The residue was purified by silica gel chromatography (0.5% to 2% MeOH in CH$_2$Cl$_2$) to give 165 as a colorless oil. LRMS (calculated for C$_{21}$H$_{26}$N$_2$O) 322. found 322; IR (film) 3059, 2937, 2863, 2797, 1657, 1594, 1499, 1390, 1264, 1101, 1074, 739, 703 cm$^{-1}$.

EXAMPLE 119

Synthesis of N-phenyl-N-piperidin-3-yl-propionamide (166)

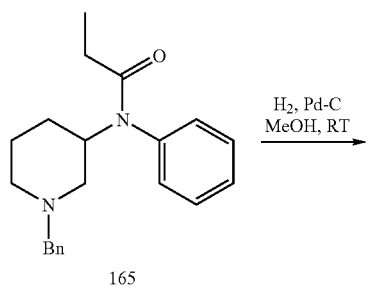

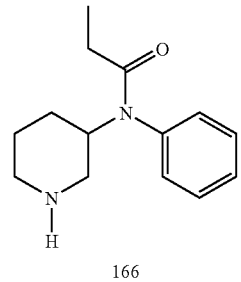

A mixture of N-(1-benzyl-piperidin-3-yl)-N-phenyl-propionamide (165) (150 mg) and Pd—C(10%, 50 mg) and MeOH (50 ml) was stirred under H$_2$ (1 atm) for 24 hr. The catalyst was removed by filtration through Celite to give 166 as a colorless oil (105 mg, 97%). $^1$H-NMR (300 MHz, CDCl$_3$) δ 7.41 (m, 3H), 7.10 (m, 2H), 3.20 (m 1H), 2.90 (m, 1H), 2.40–2.20 (m, 2H), 1.90 (m, 2H), 1.60 (m, 4H), 1.20 (m, 1H), 1.00 (t, 3H) ppm; LRMS (calculated for C$_{14}$H$_{21}$N$_2$O) (M+1)$^+$ 233. found 233.

EXAMPLE 120

Synthesis of 3-(Phenyl-propionyl-amino)-piperidine-1-carboxylic acid tert-butyl ester (167)

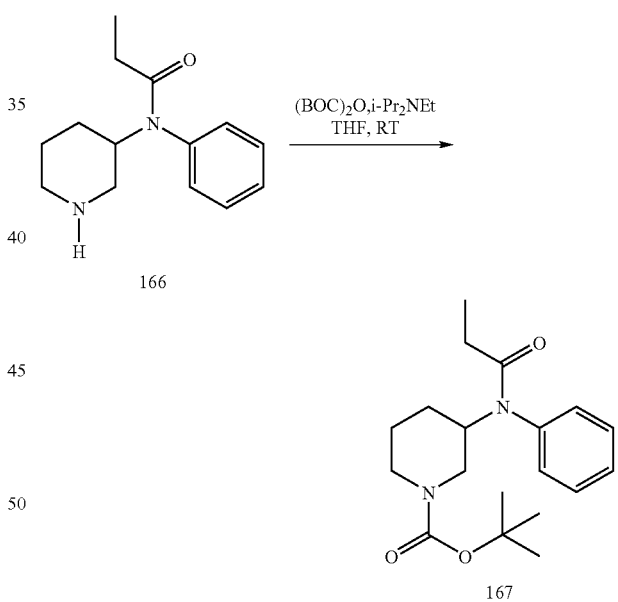

To a solution of N-phenyl-N-piperidin-3-yl-propionamide (166) (105 mg, 0.45 mmol) and i-Pr$_2$NEt (0.26 ml, 1.5 mmol) in THF (2 ml) was added di-tert-butyl dicarbonate (1.0 in THF, 1.0 ml, 1.0 mmol). The mixture was stirred overnight. After removal the solvent, the residue was dissolved in CH$_2$Cl$_2$ (10 ml), washed with sat. NaHCO$_3$, brine and water and dried over Na$_2$SO$_4$. After filtration, the filtrate was concentrated under vacuum. The residue was filtered through a short silica gel pad to give 167 as a light yellow oil. $^1$H-NMR (300 MHz, CDCl$_3$) δ 7.40 (m, 3H), 7.10 (m, 2H), 4.80 (m, 1H), 0.20 (m, 1H), 4.00 (m, 1H), 2.40 (m, 2H), 1.95 (m, 3H), 1.61 (m, 1H), 1.51 (m, 1H), 1.50 (s, 9H), 1.30

(m, 1H), 1.00 (t, 3H) ppm; LRMS (calculated for $CH_{28}N_2O_3$-BOC)$^+$ 232. found 232; IR (film) 2978, 2937, 2860, 1693, 1662, 1698, 1494, 1422, 1363, 1264, 1151, 1386, 1182cm$^{-1}$.

EXAMPLE 121

HPLC Separation of 3-(S)-(Phenyl-propionyl-amino)-piperidine-1-carboxylic acid tert-butyl ester (168) and 3-(R)-(Phenyl-propionyl-amino)-piperidine-1-carboxylic acid tert-butyl ester (169)

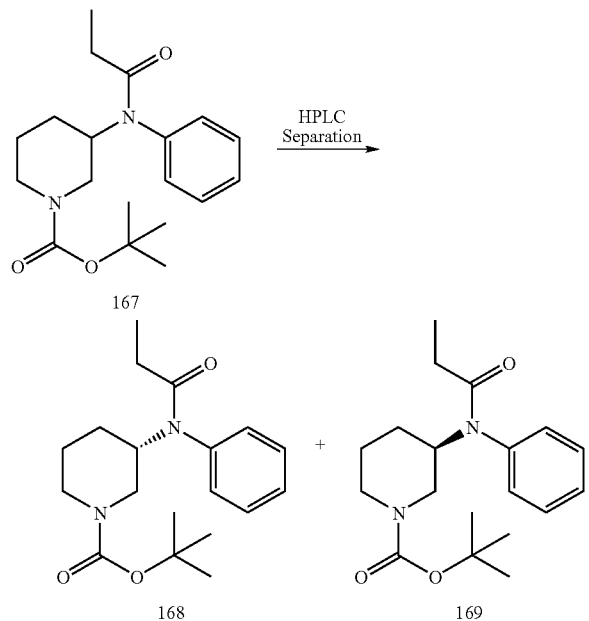

The enantiomers of 167 were separated on a chiral column (Chiralpak AD Column; μ=5 m/min; λ=254 nm) with (9:1) Hexanes:iPrOH. The first compound to elute from the column (retention time=4.956 minutes) was randomly assigned structure 168 (S); and the second compound to elute from the column (retention time=5.540 minutes) was assigned structure 169 (R).

EXAMPLE 122

Synthesis of (R)—N-(1-phenethyl-piperidin-3-yl)-N-phenyl-propioamide (170)

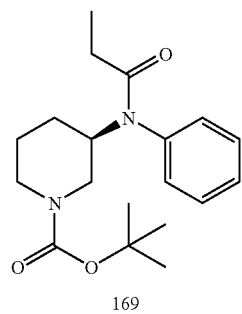

1. 20% TFA/CH$_2$Cl$_2$, 1 hr
2. PhCH$_2$CH$_2$Br, CH$_3$CN—H$_2$O
   K$_2$CO$_3$, 70° C., 12 hr

-continued

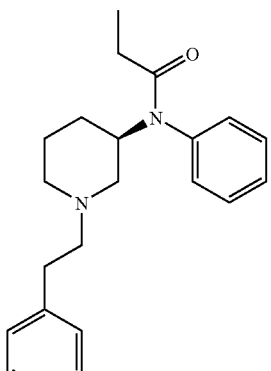

170

3(R)-(Phenyl-propionyl-amino)-piperidine-1-carboxylic acid tert-butyl ester (169) (100 mg) was dissolved in a mixture of TFA-CH$_2$Cl$_2$ (1 ml, 20%) and stirred for 1 hr. After removal of solvent, the residue was dried under vacuum for 30 min and dissolved in 5 ml of CH$_2$Cl$_2$, washed with sat. K$_2$CO$_3$, dried (Na$_2$SO$_4$), filtered. After evaporation of the solvent, the residue was dissolved in CH$_3$CN (1 ml). Then K$_2$CO$_3$ (125 mg, 3 eq), water (1 ml) and (2-bromoethyl)benzene (0.05 ml, 1.2 eq) was added. The mixture was heated at 70° C. for 12 hr. After cooling to room temperature, the mixture was diluted with sat. NaHCO$_3$ (5 ml), extracted with CH$_2$Cl$_2$ (2×10 ml). The combined organic layers were dried (Na$_2$SO$_4$), filtered and evaporated. The residue was purified by silica gel chromatography (100% CH$_2$Cl$_2$, 2%–4% MeOH in CH$_2$Cl$_2$) to give 170 as a colorless oil.

$^1$H-NMR (300 MHz, CDCl$_3$) δ 7.40 (m, 3H), 7.10 (m, 2H), 4.80 (m, 1H), 0.20 (m, 1H), 4.00 (m, 1H), 2.40 (m, 2H), 1.95 (m, 3H), 1.61 (m, 1H), 1.51 (m, 1H), 1.50 (s, 9H), 1.30 (m, 1H), 1.00 (t, 3H) ppm; LRMS (calculated for $C_{22}H_{28}N_2O_2$)$^+$ 336. found 336; IR (film) 2978, 2937, 2860, 1693, 1662, 1698, 1494, 1422, 1363, 1264, 1151, 1386, 1182 cm$^-$.

EXAMPLE 123

Synthesis of (S)—N-(1-phenethyl-piperidin-3-yl)-N-phenyl-propioamide (171)

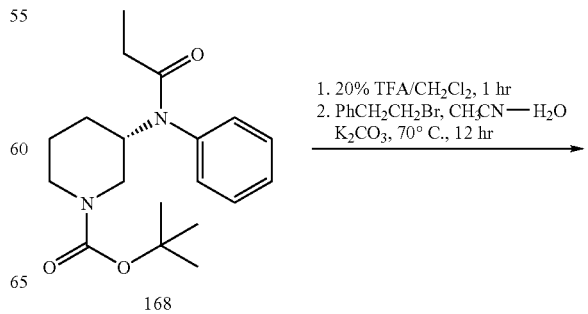

1. 20% TFA/CH$_2$Cl$_2$, 1 hr
2. PhCH$_2$CH$_2$Br, CH$_3$CN—H$_2$O
   K$_2$CO$_3$, 70° C., 12 hr

-continued

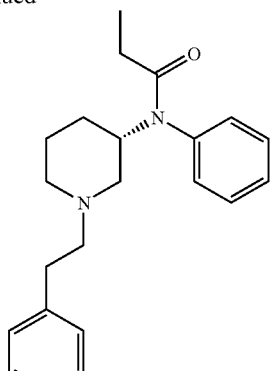

171

3(S)-(Phenyl-propionyl-amino)-piperidine-1-carboxylic acid tert-butyl ester (168) (100 mg) was dissolved in a mixture of TFA-CH$_2$Cl$_2$ (1 ml, 20%) and stirred for 1 hr. After removal of solvent, the residue was dried under vacuum for 30 min and dissolved in 5 ml of CH$_2$Cl$_2$, washed with sat. K$_2$CO$_3$, dried (Na$_2$SO$_4$), filtered. After evaporation of the solvent, the residue was dissolved in CH$_3$CN (1 ml). Then K$_2$CO$_3$ (125 mg, 3 eq), water (1 ml) and (2-bromoethyl)benzene (0.05 ml, 1.2 eq) was added. The mixture was heated at 70° C. for 12 hr. After cool to room temperature, the mixture was diluted with sat. NaHCO$_3$ (5 ml), extracted with CH$_2$Cl$_2$ (2×10 ml). The combined organic layers were dried (Na$_2$SO$_4$), filtered and evaporated. The residue was purified by silica gel chromatography (100% CH$_2$Cl$_2$, 2%–4% MeOH in CH$_2$Cl$_2$) to give 171 as a colorless oil.

$^1$H-NMR (300 MHz, CDCl$_3$) δ 7.40 (m, 3H), 7.10 (m, 2H), 4.80 (m, 1H), 0.20 (m, 1H), 4.00 (m, 1H), 2.40 (m, 2H), 1.95 (m, 3H), 1.61 (m, 1H), 1.51 (m, 1H), 1.50 (s, 9H), 1.30 (m, 1H), 1.00 (t, 3H) ppm; LRMS (calculated for C$_{22}$H$_{28}$N$_2$O$_2$)$^+$ 336. found 336; IR (film) 2978, 2937, 2860, 1693, 1662, 1698, 1494, 1422, 1363, 1264, 1151, 1386, 1182 cm$^{-1}$.

EXAMPLE 124

Synthesis of (1-Benzyl-1,2,5,6,tetrahydro-pyridin-3-yl)methanol (172)

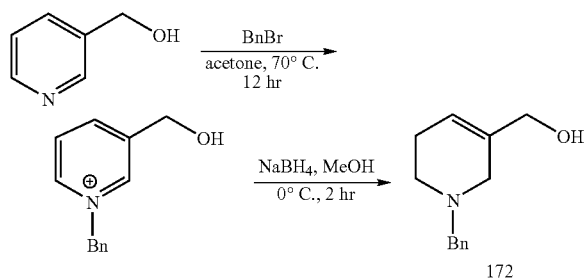

To a solution of 3-hydroxymethylpyrridine (5.0 g, 45.9 mmol) in acetone (50 ml) was added benzyl bromide (7.0 ml). The mixture was refluxed for 24 hr. The mixture was cooled to room temperature. The solvent was removed. The residue was dissolved in MeOH (100 ml), cooled by an ice-water bath. NaBH$_4$ (1.5 eq.) was added slowly. After addition, the mixture was stirred for 2 hr at 0° C. After removal of MeOH, aq. NaHCO$_3$ (100 ml) was added. The mixture was extracted with EtOAc (3×100 ml). The combined organic solution was dried (Na$_2$SO$_4$), filtered. The filtrate was concentrated under vacuum. Silica gel chromatography (2%–10% MeOH in CH$_2$Cl$_2$) provided 172 as a light yellow oil (8.2 g, 88%). $^1$H-NMR (300 MHz, CDCl$_3$) δ 7.40–7.20 (m, 5H), 5.70 (broad s, 1H), 4.00 (s, 2H), 3.65 (s, 2H), 3.00 (s, 2H), 2.55 (t, 2H), 2.20 (broad s, 2H) ppm; LRMS (calculated for C$_{13}$H$_{17}$NO) 203. found 203.

EXAMPLE 125

Synthesis of (3-Benzyl-3-aza-bicyclo[4.1.0]hept-1-yl)-methanol (173)

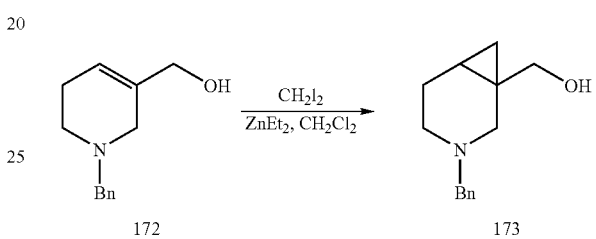

To a solution of ZnEt$_2$ (17.3 ml, 1.0 M) in CH$_2$Cl$_2$ (20 ml) at 0° C. was added CH$_2$I$_2$ (1.4 ml) (CAUTION: exothermic!). After stirring for 15 min, a solution of 172 (352 mg, 1.73 mmol) in CH$_2$Cl$_2$ (2 ml) was added. The mixture was stirred from 0° C. to room temperature overnight. 5% HCl was added to bring the mixture to a homogeneous solution. (white solid dissolved). The two layers were separated. Aqueous layer was neutralized with 2N KOH to pH=10–12, extracted with CH$_2$Cl$_2$ (twice). The combined organic solution was dried (K$_2$CO$_3$/Na$_2$SO$_4$), filtered and concentrated. The LRMS of the crude mixture showed that the ratio of 173 to 172 was about 1:1. The product was not isolated from the starting material due to their similar polarities. LRMS (calculated for C$_{14}$H$_{19}$NO) 217. found 217.

EXAMPLE 126

Synthesis of 3-Benzyl-3-aza-bicyclo[4.1.0]heptane-1-carbaldehyde (174)

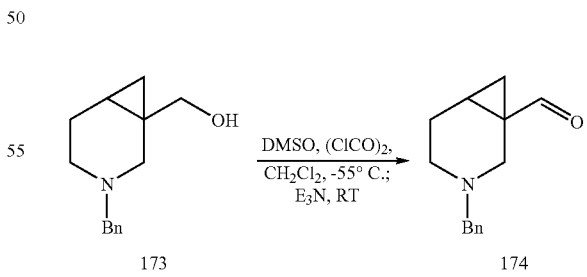

To a solution of oxalyl chloride (0.22 ml, 2.54 mmol) in CH$_2$Cl$_2$ (2 ml) at −55° C. was added a solution of DMSO (0.30 ml, 4.24 mmol) in CH$_2$Cl$_2$ (1 ml). The mixture was stirred for 2 min. Then, a solution of 173 (230 mg, 1.06 mmol) in CH$_2$Cl$_2$ (1 ml) was added dropwise. After stirring for 15 min at −55° C., Et$_3$N (1.4 ml) was added slowly. The mixture was stirred for 5 min and then warmed to room temperature. Aqueous NaHCO$_3$ (5 ml) was added. The two layers were separated; and the aqueous layer was extracted with CH$_2$Cl$_2$ (2×5 ml). The combined organics were dried (Na$_2$SO$_4$), filtered and evaporated to give the crude product. Chromatography (1% MeOH in CH$_2$Cl$_2$) gave 174 as a light red liquid. $^1$H-NMR (300 MHz, CDCl$_3$) (partial) δ 9.42 (s, 1H), 7.30 (m, 5H); LRMS (calculated for C$_{14}$H$_{17}$NO) 215. found 215.

EXAMPLE 127

Synthesis of (3-Benzyl-3-aza-bicyclo[4.1.0]hept-1-ylmethyl)-phenyl-amine (175)

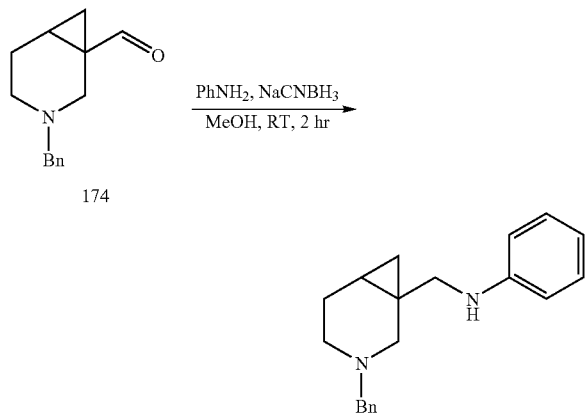

To a solution of 3-Benzyl-3-aza-bicyclo[4.1.0]heptane-1-carbaldehyde (174) (300 mg, 1.39 mmol) in 5% HOAc in MeOH (2 ml) was added aniline (0.38 ml, 4.18 mmol) and NaCNBH$_3$ (250 mg, 3.97 mmol). The mixture was stirred at room temperature 2 hrs. MeOH was removed by evaporation. Water (5 mL) was added to the residue. The mixture was neutralized with 2N KOH to pH=10. Extraction with CH$_2$Cl$_2$ (2×10 ml) followed by standard work-up provided crude 175 which was purified by silica gel chromatography (1% MeOH in CH$_2$Cl$_2$). LRMS (calculated for C$_{20}$H$_{25}$N$_2$, M+1) 293. found 293.

EXAMPLE 128

Synthesis of N-(3-Benzyl-3-aza-bicyclo4.1.0]hept-1-ylmethyl)-N-phenyl-propionamide (176)

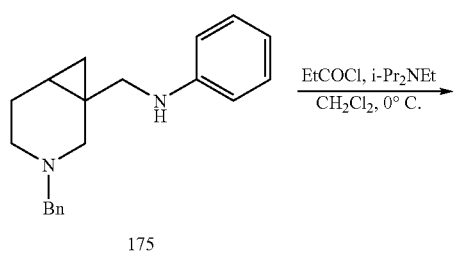

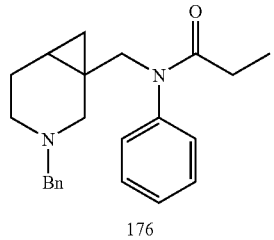

To the a solution of 3-Benzyl-3-aza-bicyclo[4.1.0]hept-1-ylmethyl)-phenyl-amine (175) (250 mg, 0.86 mmol) in CH$_2$Cl$_2$ (2 ml) at 0° C. was added i-Pr$_2$NEt (0.30 ml, 1.72 mmol)) and propionyl chloride (0.11 ml, 1.29 mmol). The mixture was stirred for 2 hrs. The mixture was diluted with CH$_2$Cl$_2$ (5 ml), washed with sat. NaHCO$_3$ (2×5 ml), brine (5 ml) and water (5 ml) and dried with Na$_2$SO$_4$. After filtration, the filtrate was concentrated under vacuum. The residue was purified by silica gel chromatography (0.5% to 2% MeOH in CH$_2$Cl$_2$) to give 176 as a colorless oil. $^1$H-NMR (300 MHz, CDCl$_3$) δ 7.41–7.20 (m, 10H), 4.20 (d, 1H), 3.42 (AB, 2H), 3.21 (d, 1H), 2.65 (q, 2H), 2.20–2.00 (m, 4H), 1.80–1.60 (m, 2H), 1.30 (m, 1H), 1.05 (t, 3H), 0.80–0.20 (m, 2H) ppm; LRMS (calculated for C$_{23}$H$_{28}$N$_2$O) 348. found 348; IR (film) 3308, 3105, 3064, 2978, 2937, 2874, 2811, 1689 m 1666, 1598, 1540, 1499, 1445, 1314, 1246, 1196, 1074, 757 cm$^-$.

EXAMPLE 129

Solid-phase Synthesis of N-[1-(4-Fluorophenethyl)-piperidine-3-ylmethyl]-N-phenyl-propionamide (177)

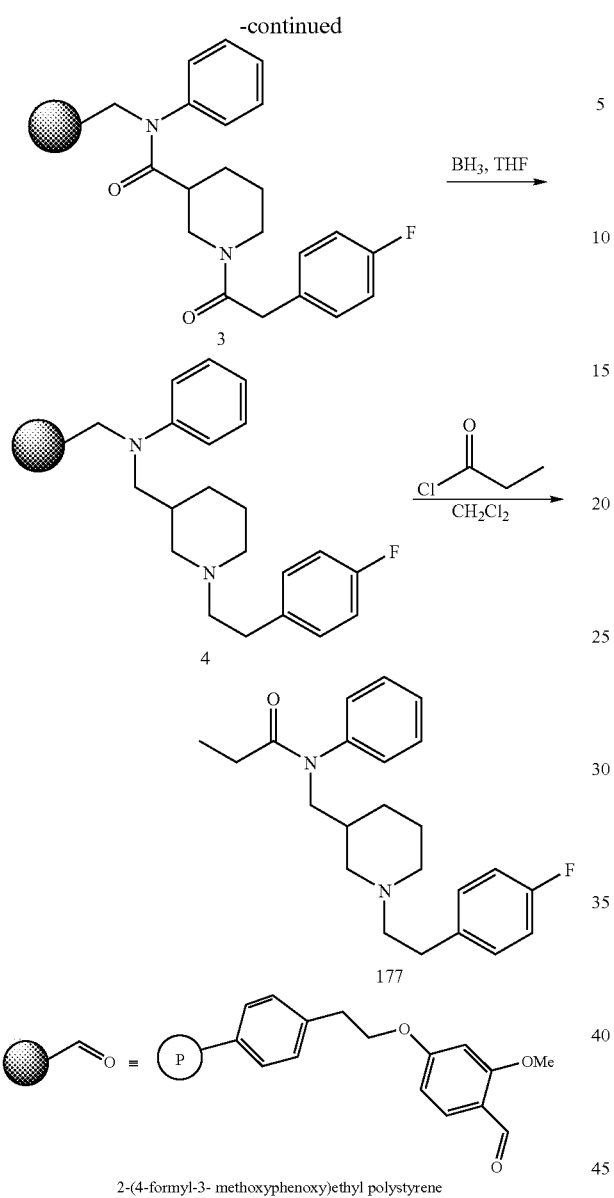

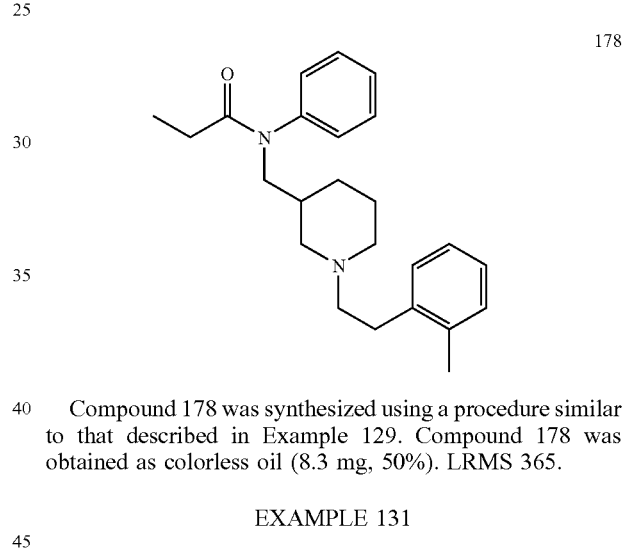

To 2-(4-formyl-3-methoxyphenoxy)ethyl polystyrene (100 mg, 0.46 mmol/g) was added 1 ml DMF followed by 91 μl aniline (0.46 mmol). After shaking at room temperature for 30 min, 195 mg of Na(OAc)$_3$BH (0.92 mmol) and 50 μl HOAc were added, then the reaction mixture was agitated at room temperature overnight. The resulting resin (1) was thoroughly washed with DMF (3×1 ml), MeOH (4×1 ml), and CH$_2$Cl$_2$ (4×1 ml), then dried in vacuo. To 1 was added N-Fmoc-nipecotic acid (81 mg, 0.23 mmol) and PyBroP (107 mg, 0.23 mmol) in 1 ml DMF followed by 40 μl N,N-diisopropylethylamine (0.23 mmol), and the resulting slurry was shaken at room temperature for 2 hours. The resulting resin 2 was washed with DMF (3×1 ml), MeOH (4×1 ml), and CH$_2$Cl$_2$ (4×1 ml) and dried in vacuo.

Resin 2 was treated with 1 ml 25% piperidine in DMF at room temperature for 30 min, then washed with DMF (3×1 ml), MeOH (4×1 ml), and CH$_2$Cl$_2$ (4×1 ml) and dried in vacuo. To the resulting resin was added 4-fluorophenylacetic acid (36 mg, 0.23 mmol) and PyBOP (120 mg, 0.23 mmol) in 1 ml DMF followed by 26 μl N-methylmorpholine (0.23 mmol). After shaking at room temperature for 3 hours, the resulting resin (3) was washed extensively with DMF (3×1 ml), MeOH (4×1 ml), and CH$_2$Cl$_2$ (4×1 ml) and dried in vacuo. Resin 3 was treated with 1 ml of 1 M BH$_3$-THF solution at room temperature for 20 hours. After washing with THF (3×1 ml) and MeOH (3×1 ml), the resin suspended in 1 ml MeOH was heated at 60° C. for 6 hours. The resulting resin (4) was washed with MeOH (4×1 ml) and CH$_2$Cl$_2$ (4×1 ml) and dried in vacuo.

Propionyl chloride (28 μl, 0.322 mmol) was added to the Resin 4 suspended in 1.5 ml CH$_2$Cl$_2$, and the mixture was agitated at room temperature for 24 hours. The mixture was filtered and washed with CH$_2$Cl$_2$ (2×1 ml). Removal of the volatiles under a stream of nitrogen followed by lyophilizing with 50% CH$_3$CN in water afforded the compound 177 as colorless oil (9.0 mg, 53%). LRMS 369.

EXAMPLE 130

Solid-phase synthesis of N-[1-(2-Methylphenethyl)-piperidine-3-ylmethyl]-N-phenyl-propionamide (178)

Compound 178 was synthesized using a procedure similar to that described in Example 129. Compound 178 was obtained as colorless oil (8.3 mg, 50%). LRMS 365.

EXAMPLE 131

Chromatographic Separation of (R)- & (S)—N-(1-Phenethyl-azepan-3-ylmethyl)-N-phenethylpropionamide (179 & 180)

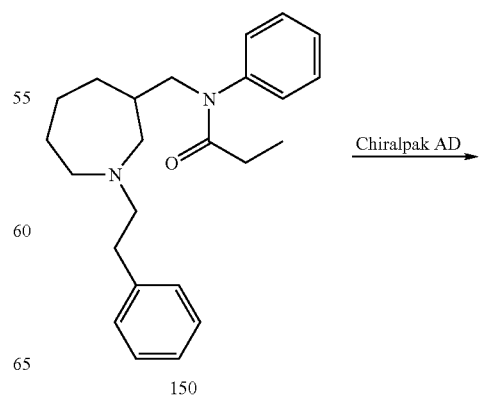

-continued

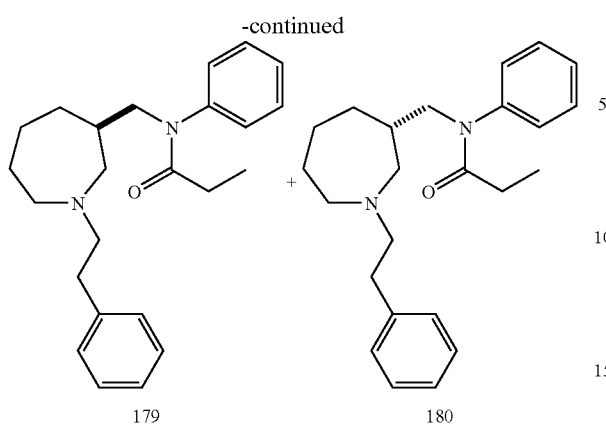

179  180

The enantiomers of N-(1-Phenethyl-azepan-3-ylmethyl)-N-phenethylpropionamide (150) were separated on a 2 cm ID Chiralpak AD column (Column number ADOOCJ-AB009), using 92:8:0.1Hexanes:EtOH:Et$_2$NH ($\lambda$=235 nm; flow rate=6 mL/min). On an analytical Chiralpak AD column (using 95:5:0.1 Hexanes:EtOH:Et$_2$NH; flow=1 mL/min; $\lambda$=230 nm, run time=30 minutes), the first compound to elute from the column (9.871 min) was assigned 180 (S), and the second compound to elute from the column (22.826 min) was assigned 179 (R). The absolute configuration has not been determined conclusively.

EXAMPLE 132

(R)—N-(1-tert-Butyloxypiperidin-3-ylmethyl)-N-anilinotrifluoroacetamide (181)

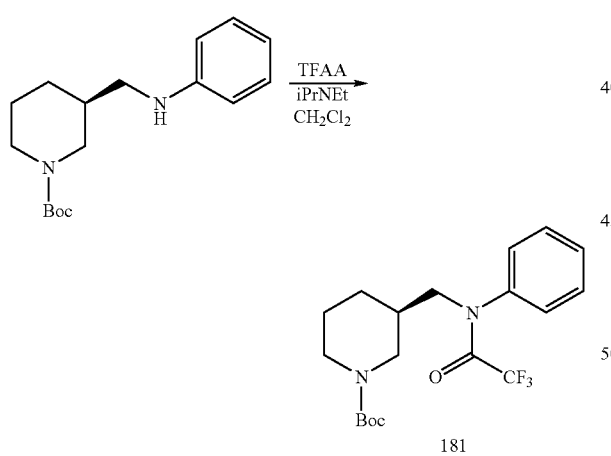

181

A solution of the aniline intermediate (1.72 mmol, 500 mg) in CH$_2$Cl$_2$ (5 mL) at 0° C. was treated with trifluoroacetic anhydride (TFAA) (1.2 equiv, 2.06 mmol, 292 µL) and diisopropylethylamine (1.5 equiv, 2.58 mmol, 450 µL) under Ar. After warming to 25° C. and stirring for 12 h, the reaction mixture was quenched with 10% aqueous NaHCO$_3$. The reaction mixture was then made acidic with 10% aqueous HCl and extracted with 3×EtOAc (25 mL). Chromatography (PTLC, SiO$_2$, 20 cm×20 cm, 1 mm, 1:4 EtOAc-Hexane) provided 181 (655 mg, 665 mg theoretical, 98%) as a colorless oil: R$_f$ 0.22 (SiO$_2$, 1:4 EtOAc-Hexane); LRMS m/z 386 (M$^+$, C$_{19}$H$_{25}$F$_3$N$_2$O$_3$, requires 386).

EXAMPLE 133

(R)—N-1-(phenethylpiperidin-3-ylmethyl)-N-anilinotrifluoroacetamide (182)

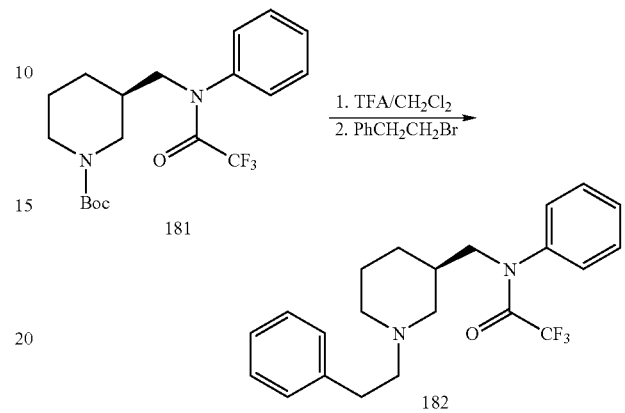

182

A solution of 181 (0.285 mmol, 110 mg) in CH$_2$Cl$_2$ (1 mL) at 25° C. was treated with 50% TFA in CH$_2$Cl$_2$ (1 mL). The reaction mixture stirred for 2 h. The solvents were removed in vacuo and the resulting oil was dried under high vacuum for 12 h. The resulting oil was then treated with phenethyl bromide (2.0 equiv, 0.57 mmol, 78 µL) and K$_2$CO$_3$ (2.5 equiv, 0.71 mmol, 98 mg) in CH$_3$CN (1 mL). The reaction mixture stirred for 12 h at 60° C. The reaction mixture was purified directly by chromatography (PTLC, SiO$_2$, 20 cm×20 cm, 1 mm, 9:1 EtOAc-CH$_3$OH) which provided 182 (107 mg, 111 mg theoretical, 96%) as a colorless oil: R$_f$ 0.30 (SiO$_2$, 9:1 EtOAc-CH$_3$OH); LRMS m/z 390 (M$^+$, C$_{22}$H$_{25}$F$_3$N$_2$O, requires 390).

EXAMPLE 134

N-1-acetophenone-3-anilinocarboxypiperidine (183)

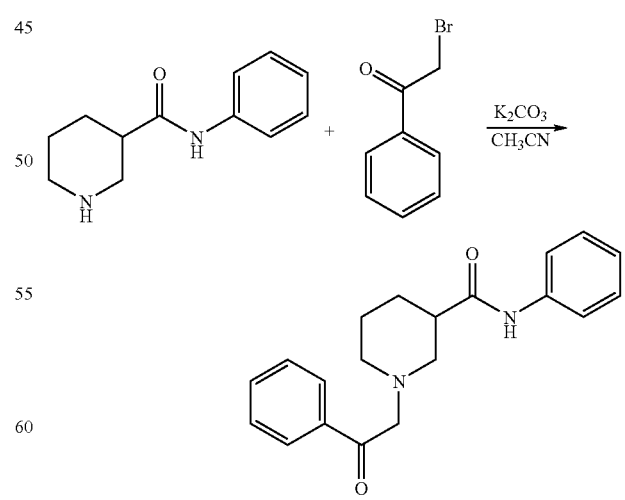

183

A solution of the aminoamide (5.91 mmol) in CH$_3$CN (20 mL) was treated with bromoacetophenone (1.1 equiv, 8.87 mmol, 1.23 g) and K$_2$CO$_3$ (1.5 equiv, 8.87 mmol, 1.23 g) under Ar. After warming to 60° C. and stirring for 12 h, the reaction mixture was quenched with 10% aqueous NaHCO$_3$ and extracted with EtOAc (3×25 mL). Chromatography (SiO$_2$, 2.5 cm×30.5 cm, 1:1 hexane-EtOAc then 9:1 EtOAc-CH$_3$OH) provided 183 (1.08 g, 2.10 g theoretical, 51%) as a yellow foam: R$_f$ 0.45 (SiO$_2$, 9:1 EtOAc-CH$_3$OH); LRMS m/z 322 (M$^+$, C$_{20}$H$_{22}$N$_2$O$_2$, requires 322).

EXAMPLE 135

N-1-(2'-oxo-phenethylpiperidin-3-ylmethyl)-N-aniline (184)

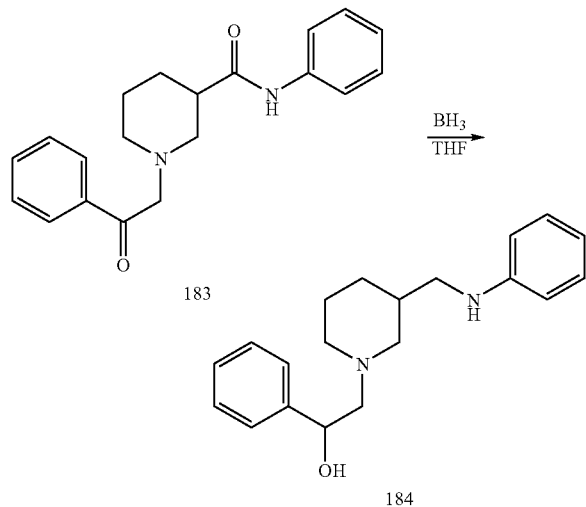

A solution of 183 (0.775 mmol, 250 mg) in THF (3 mL) at 0° C. was treated with 1.0 M BH$_3$-THF (2.0 equiv, 1.55 mmol) under Ar. The reaction mixture was then heated to 75° C. and allowed to stir for 12 h. The reaction mixture was then cooled to 0° C. and quenched with 10% aqueous HCl. The pH was adjusted to 10 with 10% aqueous NaOH and the reaction mixture was extracted with EtOAc (3×25 mL). The organics were dried with NaCl$_{(sat)}$ and MgSO$_{4(s)}$. The reaction mixture was purified directly by chromatography (PTLC, SiO$_2$, 20 cm×20 cm, 1 mm, 9:1 EtOAc-CH$_3$OH) which provided 184 (184 mg, 241 mg theoretical, 76%) as a colorless oil: R$_f$ 0.40 (SiO$_2$, 9:1 EtOAc-CH$_3$OH); LRMS m/z 310 (M$^+$, C$_{20}$H$_{26}$N$_2$O, requires 310).

EXAMPLE 136

N-1-(2'-acetoxy-phenethylpiperidin-3-ylmethyl-N-anilinopropionamide (185)

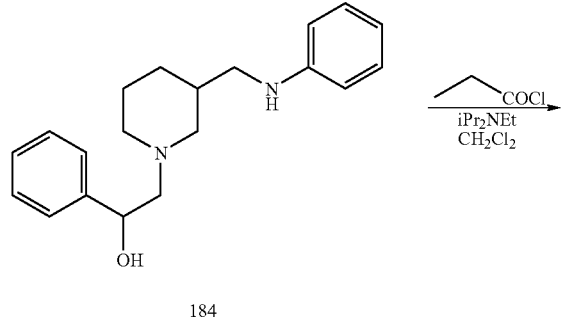

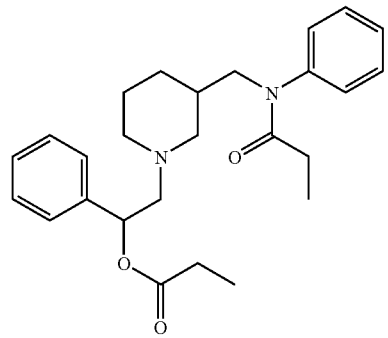

A solution of 184 (0.58 mmol, 181 mg) in CH$_2$Cl$_2$ (2 mL) at 0° C. was treated with propionyl chloride (2.5 equiv, 1.45 mmol, 126 µL) and diisopropylethylamine (2.5 equiv, 1.45 mmol, 253 µL) under Ar. After warming to 25° C. and stirring for 12 h, the reaction mixture was purified directly by chromatography (PTLC, SiO$_2$, 20 cm×20 cm, 1 mm, 1:1 EtOAc-Hexane) which provided 185 (193 mg, 245 mg theoretical, 70%) as a colorless oil: R$_f$ 0.36 (SiO$_2$, 1:1 EtOAc-Hexane); LRMS m/z 422 (M+, C$_{26}$H$_{34}$N$_2$O$_3$, requires 422).

EXAMPLE 137

N-1-(2'-oxo-phenethylpiperidin-3-ylmethyl)-N-anilinopropionamide (186)

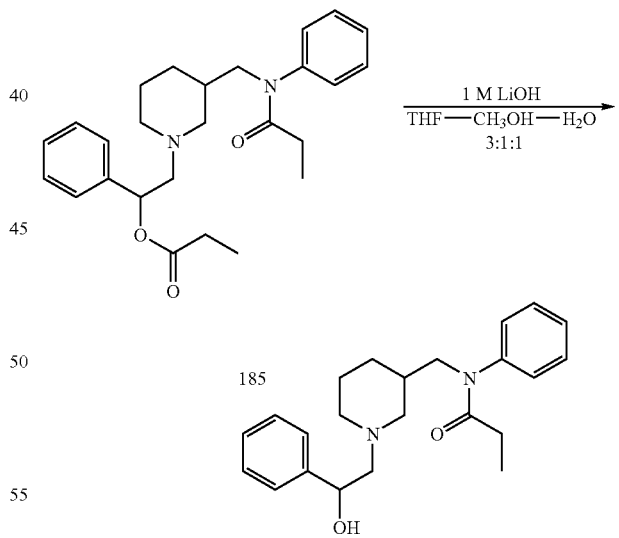

A solution of 185 (0.457 mmol, 193 mg) in THF—CH$_3$OH—H$_2$O 3:1:1(1 mL) at 0°C. was treated with 1 M LiOH (2.0 equiv, 0.914 mmol, 914 µL). After warming to 25° C. and stirring for 3 h, the reaction mixture was quenched with pH 7 buffer and then extracted with EtOAc (3×10 mL). The organics were dried with NaCl$_{(sat)}$ and MgSO$_{4(s)}$. The resulting oil was purified by chromatography (PTLC, SiO$_2$, 20 cm×20 cm, 1 mm, 9:1 EtOAc-CH$_3$OH) to give 186 as a colorless oil (114 mg, 167 mg theoretical, 68%): R$_f$ 0.28 (SiO$_2$, 9:1 EtOAc —CH$_3$OH); LRMS m/z 366 (M$^+$, C$_{23}$H$_{30}$N$_2$O$_2$, requires 366).

EXAMPLE 138

Synthesis and Purification of the Four Diastereomers of N-[1-(1-phenethylpiperidin-3-yl)ethyl]-N-Phenylpropionamide (195, 196, 197, 198)

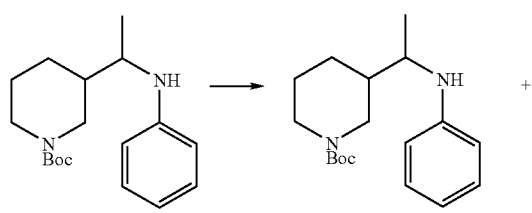

See Example 86 for synthesis 187
fast-eluting diastereomer 188
slow-eluting diasteromer The starting mono-Boc-diamine (see Example 86) was separated into diastereomers 187 and 188 using HPLC with a semi-prep silica gel column (Hexane:$^i$PrOH, 90:10). Diastereomer 187 was the first compound to elute from the column (7.72 min) (LRMS 305, 249, 205); while 188 was the second compound to elute from the column (8.43 min) (LRMS 305, 249, 205).

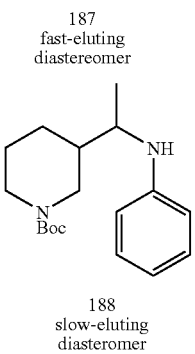

187

189

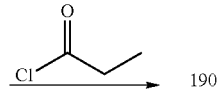

188 → 190

Following standard procedures described elsewhere in the Exemplification, diastereomers 187 and 188 were converted to the diastereomeric amides 189 and 190, respectively.

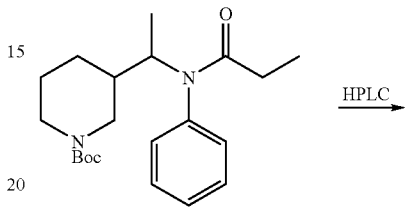

189
single diastereomer

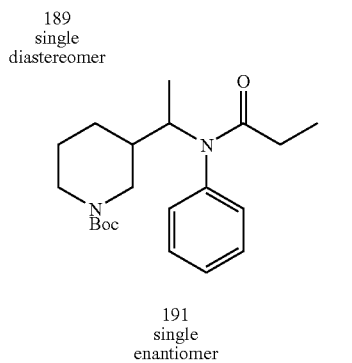

191
single enantiomer 192
single enantiomer

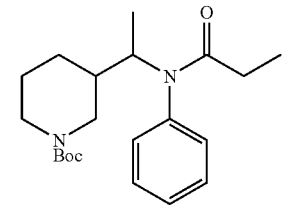

190          193              194
single   HPLC  single    +   single
diastereomer  enantiomer    enantiomer Using chiral chromatography, diastereomer 189 was then separated into its two constituent enantiomers, 191 and 192. Specifically, HPLC with a semi-prep Chiralpak AD column (Hexane:$^i$PrOH, 95:5) was used to provide 191 (the first compound to elute from the column) and 192 (the second compound to elute from the column). Using an analytical Chiralpak AD column (Hexane:$^i$PrOH, 95:5), the retention time for 191 was 8.35 min (LRMS 261, M-100); while the retention time for 192 was 9.46 min (LRMS 261, M-100).

Likewise, diastereomer 190 was separated into its two constituent enantiomers, 193 and 194. Specifically, HPLC with a semi-prep Chiralpak AD column (Hexane:$^i$PrOH, 95:5) was used to provide 193 (the first compound to elute from the column) and 194 (the second compound to elute from the column). On an analytical Chiralpak AD column (Hexane:$^i$PrOH, 95:5), the retention time for 193 was 7.78 min (LRMS 261, M-100); while the retention time for 194 was 11.90 min (LRMS 261, M-100).

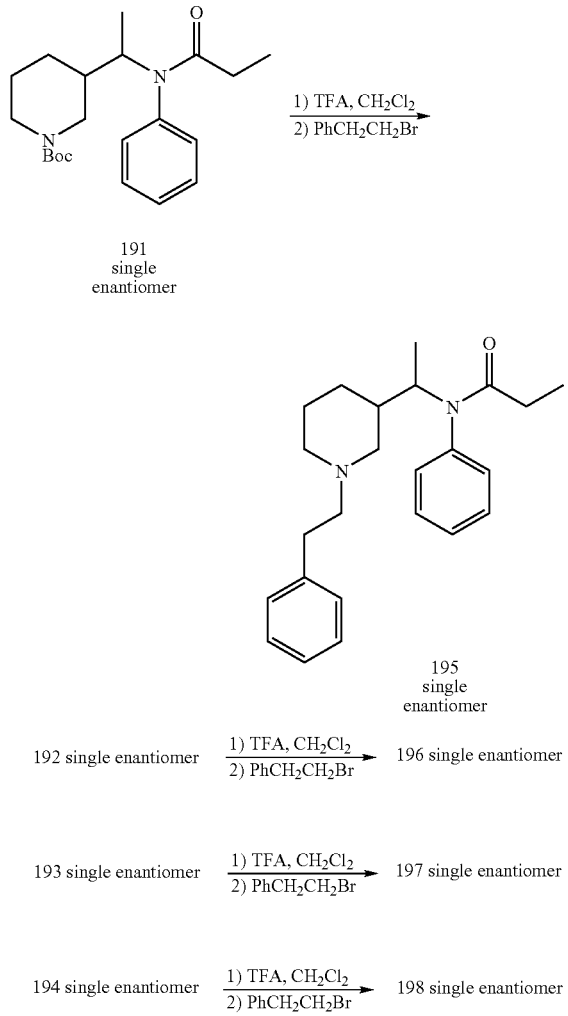

191
single enantiomer 195
single enantiomer 192 single enantiomer → 196 single enantiomer
  1) TFA, CH$_2$Cl$_2$
  2) PhCH$_2$CH$_2$Br 193 single enantiomer → 197 single enantiomer
  1) TFA, CH$_2$Cl$_2$
  2) PhCH$_2$CH$_2$Br 194 single enantiomer → 198 single enantiomer
  1) TFA, CH$_2$Cl$_2$
  2) PhCH$_2$CH$_2$Br Finally, following standard procedures described elsewhere in the Exemplification, single enantiomers 191, 192, 193 and 194 were converted to enantiomerically pure tertiary amine-amides 195 (LRMS 365), 196 (LRMS 365), 197 (LRMS 365), and 198 (LRMS 365), respectively.

EXAMPLE 139

N-(1-Indan-2-yl-piperidin-3-ylmethyl)-N-phenylpropionamide (199)

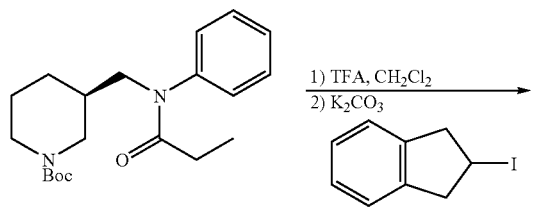

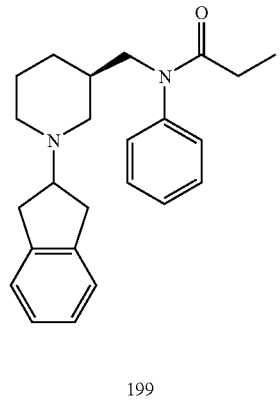

199

Trifluoroacetic acid (1.0 mL) was added dropwise to a solution of compound (R)—N-(1-Boc-piperidin-3-ylmethyl)-N-phenylpropionamide (200 mg, 0.58 mmol) in 1.0 mL of dry CH$_2$Cl$_2$ at 0° C. (ice-water). The reaction mixture was stirred at room temperature for 30 minutes. TLC showed the reaction was complete. After removal of the solvents, the crude product was used for next step without purification.

The crude compound from the previous step was dissolved in CH$_3$CN (1.3 mL) and K$_2$CO$_3$ (240 mg) and 2-iodoindan (283 mg, 1.16 mmol) were added. The mixture was heated at 50° C. overnight. The reaction mixture was poured into 10 mL of H$_2$O, then extracted with ethyl acetate (3×10 mL). The extracts were combined and washed with aqueous NaOH (10%, 2×5 mL), HCl (5%, 2×5 mL), brine (10 mL), dried over anhydrous sodium sulfate, and filtered. The crude product was purified by a preparative thin layer chromatography (CH$_2$Cl$_2$/MeOH, 95:5) to afford N-(1-Indan-2-yl-piperidin-3-ylmethyl)-N-phenylpropionamide as a colorless oil. LRMS 363.

EXAMPLE 140

1-[1-(4-Chloro-phenyl)-cylobutanecarbonyl]-piperidine-3-carboxylic acid phenylamide (202)

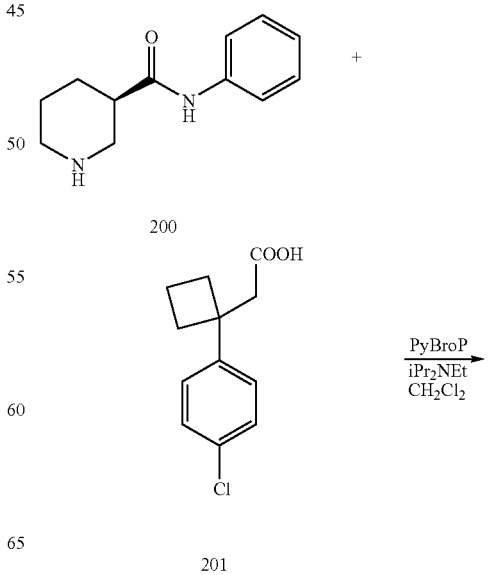

-continued

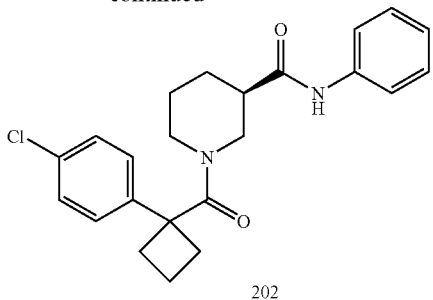

202

A solution of 200 (2.95 mmol, 603 mg), 1-(4-Chlorophenyl)-1-cyclobutane carboxylic acid (201) (1.5 equiv, 4.43 mmol, 932 mg) and iPr$_2$NEt (3.0 equiv, 8.85 mmol, 1.5 mL) in CH$_2$Cl$_2$ (10 mL) was treated with PyBroP (1.5 equiv, 4.43 mmol, 2.07 g) under Ar at 0° C. After warming to 25° C. and stirring for 12 h, the reaction mixture was quenched with 10% aqueous HCl and extracted with EtOAc (3×25 mL). The organic layer was then washed with NaHCO$_3$ (sat) and dried with NaCl$_{(sat)}$ and MgSO$_{4(s)}$. Chromatography (SiO$_2$, 2.5 cm×30.5 cm, 2:1 hexane-EtOAc) provided 202 (0.851 g, 1.17 g theoretical, 73%) as a white foam: R$_f$ 0.17 (SiO$_2$, 2:1 hexane-EtOAc); LRMS m/z 396 (M$^+$, C$_{23}$H$_{25}$ClN$_2$O$_2$, requires 396).

EXAMPLE 141

{1-[1-(4-Chloro-phenyl)-cyclobutylmethyl]-piperidin-3-ylmethyl}-phenyl-amine (203)

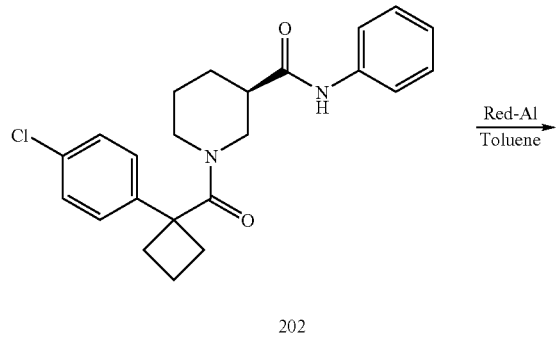

202

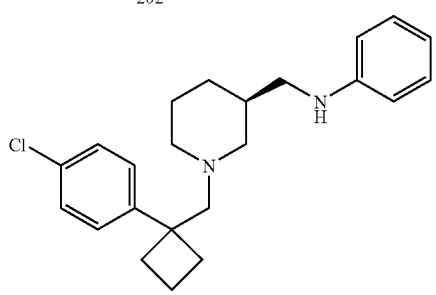

203

A solution of 202 (0.504 mmol, 200 mg) in Toluene (2 mL) at 0° C. was treated with 3.0 M Red-Al (3.5 equiv, 1.76 mmol) under Ar. The reaction mixture stirred for 12 h and returned to 25° C. The reaction mixture was then cooled to 0° C., quenched with 10% aqueous NaOH and extracted with EtOAc (3×25 mL). The organics were dried with NaCl$_{(sat)}$ and Na$_2$SO$_{4(s)}$. The reaction mixture was purified by chromatography (PTLC, SiO$_2$, 20 cm×20 cm, 1 mm, 2:1 hexane-EtOAc) which provided 203 (170 mg, 186 mg theoretical, 91%) as a colorless oil: R$_f$ 0.61 (SiO$_2$, 2:1 hexane-EtOAc); LRMS m/z 368 (M$^+$, C$_{23}$H$_{29}$ClN$_2$, requires 368).

EXAMPLE 142

Cyclobutanecarboxylic acid {1-[1-(4-chloro-phenyl-cyclobutylmethyl]-piperidin-3-ylmethyl}-phenyl-amide (204)

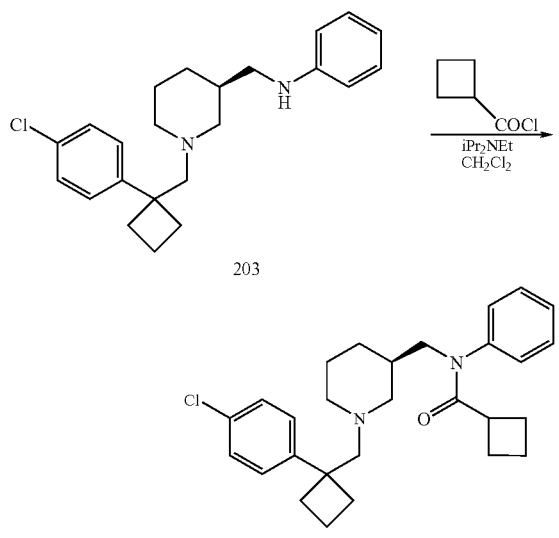

204

A solution of 203 (0.276 mmol, 102 mg) in CH$_2$Cl$_2$ (2 mL) at 0° C. was treated with cyclobutanecarbonyl chloride (1.5 equiv, 0.414 mmol, 50 µL) and diisopropylethylamine (1.5 equiv, 0.414 mmol, 72 µL) under Ar. After warming to 25° C. and stirring for 12 h, the reaction mixture was purified directly by chromatography (PTLC, SiO$_2$, 20 cm×20 cm, 1 mm, 8:1 hexane-acetone) which provided 204 (100 mg, 124 mg theoretical, 81%) as a yellow oil: R$_f$ 0.27 (SiO$_2$, 8:1 hexane-acetone); LRMS m/z 451 (M$^+$, C$_{28}$H$_{25}$ClN$_2$O, requires 451).

EXAMPLE 143

N-[1-(3-methylbutane)piperidin-3-R-ylmethyl]-N-(anilino-3-yl)propionamide (205)

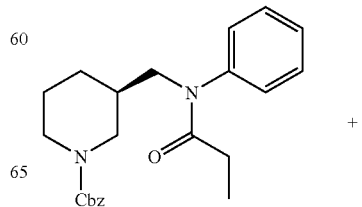

+

-continued

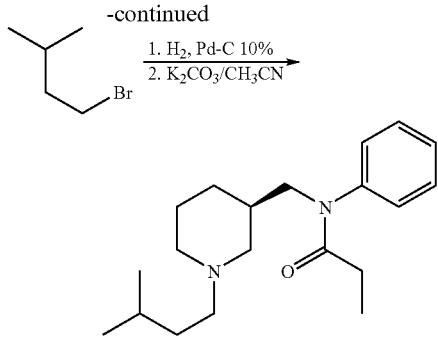

A solution of 138 (0.170 mmol, 65 mg) in CH₃OH (1 mL) at 25° C. was treated with 10% Pd—C (20 mg) and then placed under a hydrogen atmosphere. The reaction mixture stirred for 12 h and then was filtered through a pad of Celite. The solvents were removed in vacuo and the resulting oil was then treated with 1-bromo-3-methylbutane (1.5 equiv, 0.255 mmol, 31 µL) and K₂CO₃ (1.5 equiv, 0.255 mmol, 35 mg) in CH₃CN (0.5 mL). The reaction mixture stirred for 12 h at 65° C. The reaction mixture was then purified directly by chromatography (PTLC, SiO₂, 20 cm×20 cm, 1 mm, EtOAc10% CH₃OH) which provided 205 (36 mg, 54 mg theoretical, 67%) as colorless oil: $R_f$ 0.60 (SiO₂, EtOAc-10% CH₃OH); LRMS m/z 316 (M⁺, $C_{20}H_{32}N_2O$, requires 316).

EXAMPLE 144

N-4-tert-Butoxycarbonyl-1-carbobenzyloxy[2-(2'-fluoroanilinocarboxy)]piperazine (206)

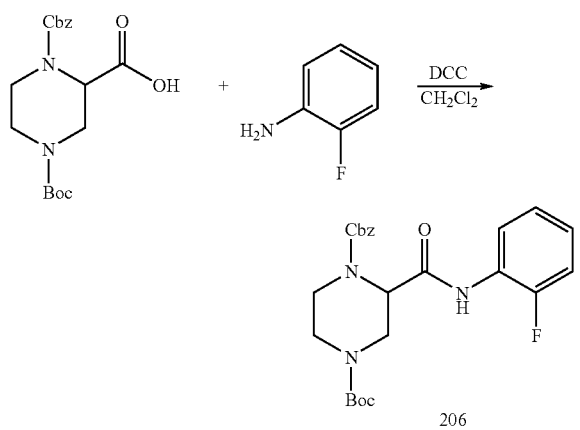

A solution of 4-Boc-1-Cbz-piperazine-2-carboxylic acid (5.49 mmol, 2.00 g) and 2-fluoroaniline (1.5 equiv, 8.24 mmol, 796 µL) in CH₂Cl₂ (10 mL) at 0° C. was treated with DCC (1.5 equiv, 8.24 mmol, 1.70 g) under Ar. The reaction mixture was allowed to warm to 25° C. and stirred for 12 h. The reaction mixture was then filtered to remove the urea and the solvents were removed in vacuo. Chromatography (SiO₂, 2.5 cm×30.5 cm, 3:1 hexane-EtOAc) to give 206 (1.83 g, 2.51 g theoretical, 73%) as a white foam: $R_f$ 0.11 (SiO₂, 3:1 hexane-EtOAc); LRMS m/z 457 (M⁺, $C_{24}H_{28}FN_3O_5$, requires 457).

EXAMPLE 145

N-4-tert-Butoxycarbonyl-1-Carbobenzyloxy[2-(2'-fluoroanilinomethyl)]piperazine (207)

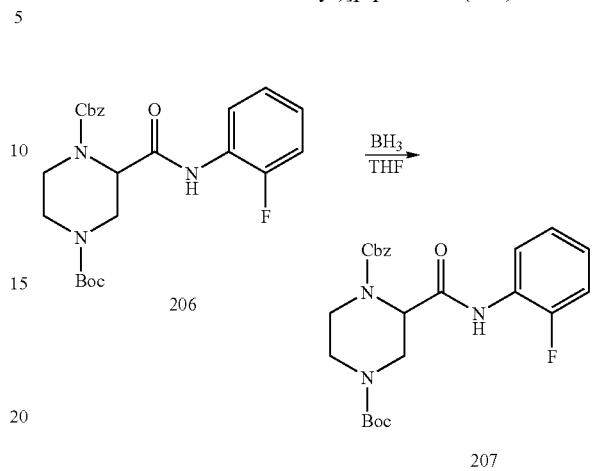

A solution of 206 (2.19 mmol, 1.00 g) in THF (8.0 mL) at 0° C. was treated with 1.0 M BH₃-THF (3.0 equiv, 6.57 mmol) under Ar. The reaction mixture was then heated to 75° C. and allowed to stir for 12 h. The reaction mixture was then cooled to 0° C. and quenched with 10% aqueous HCl. The pH was adjusted to 10 with 10% aqueous NaOH and the reaction mixture was extracted with EtOAc (3×25 mL). The organics were dried with NaCl$_{(sat)}$ and MgSO$_{4(s)}$. Chromatography (SiO₂, 2.5 cm×30.5 cm, 3:1 hexane-EtOAc) to give 207 (0.744 g, 0.971 g theoretical, 77%) as a colorless oil: $R_f$ 0.35 (SiO₂, 3:1 hexane-EtOAc); LRMS m/z 443 (M⁺, $C_{24}H_{30}FN_3O_4$, requires 443).

EXAMPLE 146

N-(4-tert-Butyloxy-1-Carbobenzyloxypiperazin-2-ylmethyl)-N-(2'-fluoroanilino)-cyclobutylcarboxamide (208)

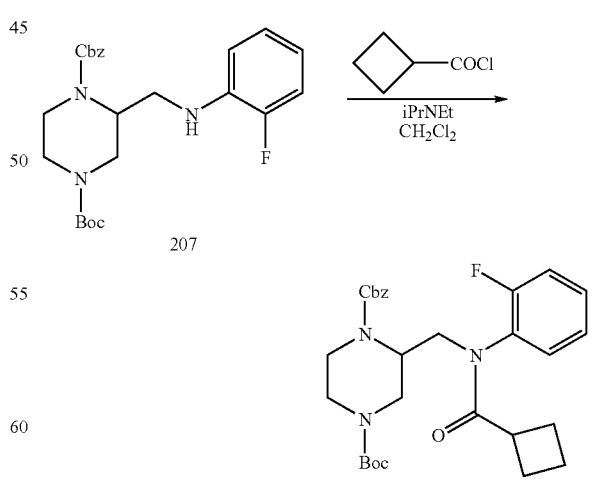

A solution of 207 (0.248 mmol, 110 mg) in CH₂Cl₂ (1 mL) at 0° C. was treated with cyclobutanecarbonyl chloride (1.5 equiv, 0.779 mmol, 77 µL) and diisopropylethylamine (2.0 equiv, 1.04 mmol, 181 µL) under Ar. After warming to 25° C. and stirring for 12 h, the reaction mixture was purified directly by chromatography (PTLC, SiO$_2$, 20 cm×20 cm, 1 mm, 1:1 hexane-EtOAc) which provided 208 (130 mg, 130 mg theoretical, 99%) as a colorless oil: R$_f$ 0.45 (SiO$_2$, 1:1 hexane-EtOAc); LRMS m/z 525 (M$^+$, C$_{29}$H$_{36}$FN$_3$O$_5$, requires 525).

EXAMPLE 147

N-1-Methyl(4-tert-Butyloxypiperazin-2-ylmethyl)-N-(2'-fluoroanilino)-cyclobutylcarboxamide (209)

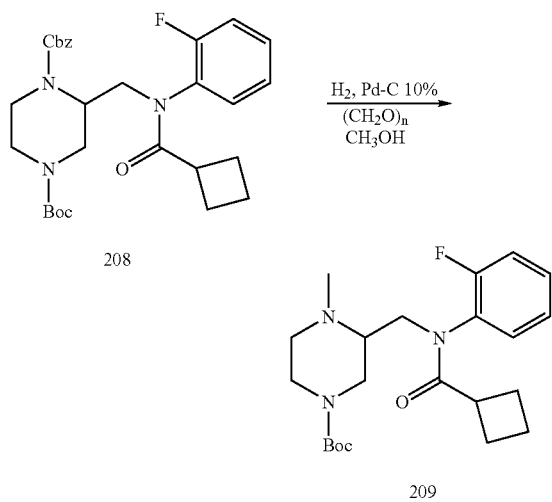

A solution of 208 (0.247 mmol, 130 mg) in CH$_3$OH (2.0 mL) at 25° C. was treated with 30% Pd—C (20 mg) and paraformaldehyde (74 mg) and then placed under a hydrogen atmosphere. The reaction mixture stirred for 12 h and then was filtered through a pad of celite. The solvents were removed in vacuo and the resulting oil was purified by chromatography (PTLC, SiO$_2$, 20 cm×20 cm, 1 mm, EtOAc-20% CH$_3$OH) which provided 209 (74 mg, 100 mg theoretical, 74%) as colorless oil: R$_f$ 0.58 (SiO$_2$, EtOAc-20% CH$_3$OH); LRMS m/z 405 (M$^+$, C$_{22}$H$_{32}$FN$_3$O$_3$, requires 405).

EXAMPLE 148

N-1-Methyl(4-phenethyl-piperazin-2-ylmethyl)-N-(2'-fluoroanilino)-cyclobutylcarboxamide (210)

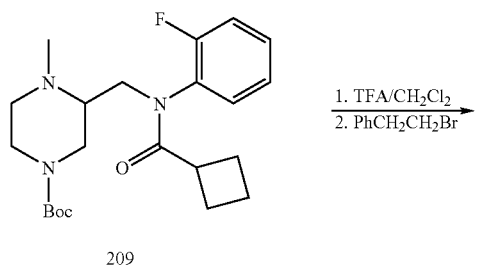

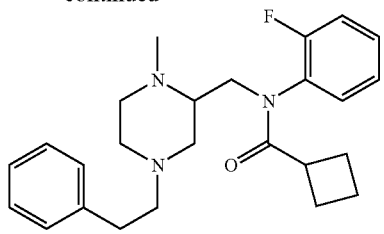

Compound 209 (0.182 mmol, 74 mg) was treated with 50% TFA in CH$_2$Cl$_2$ (1 mL) at 25° C. The reaction mixture stirred for 2 h. The solvents were removed in vacuo and the resulting oil was dried under high vacuum for 5 h. The resulting oil was then treated with phenethyl bromide (2.0 equiv, 0.364 mmol, 50 µL) and K$_2$CO$_3$ (4.0 equiv, 0.728 mmol, 100 mg) in CH$_3$CN (1.0 mL). The reaction mixture stirred for 12 h at 60° C. The reaction mixture was purified directly by chromatography (PTLC, SiO$_2$, 20 cm×20 cm, 1 mm, EtOAc-10% CH$_3$OH) which provided 210 (64 mg, 75 mg theoretical, 85%) as colorless oil: R$_f$ 0.46 (SiO$_2$, EtOAc-10% CH$_3$OH); LRMS m/z 409 (M$^+$, C$_{25}$H$_{32}$FN$_3$O, requires 409).

EXAMPLE 149

N-1-carbobenzyloxy[3-(2'-methylanilino)carboxy]piperazine (211)

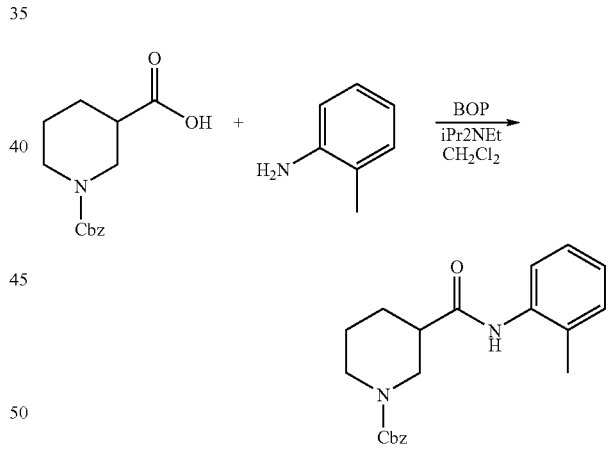

A solution of Cbz-nipecotic acid (3.80 mmol, 1.00 g), o-toluidine (2.0 equiv, 7.60 mmol, 811 µL) and diisopropylethylamine (2.0 equiv, 7.60 mmol, 1.3 mL) in CH$_2$Cl$_2$ (10 mL) at 0° C. was treated with BOP (2.0 equiv, 7.60 mmol, 3.36 g) under Ar. The reaction mixture was allowed to warm to 25° C. and stirred for 12 h. The reaction mixture was quenched with 10% aqueous HCl and extracted with EtOAc (3×25 mL). The organic layer was then washed with NaHCO$_3$ (sat) and dried with NaCl $_{(sat)}$ and MgSO$_{4\ (s)}$. Chromatography (SiO$_2$, 2.5 cm×30.5 cm, 2:1 hexane-EtOAc) provided 211 (1.16 g, 1.34 g theoretical, 87%) as a white foam: R$_f$ 0.34 (SiO$_2$, 2:1 hexane-EtOAc); LRMS m/z 352 (M$^+$, C$_{21}$H$_{24}$N$_2$O$_3$, requires 352).

EXAMPLE 150

N-1-carbobenzyloxy[3-(2'-methylanilino)methyl]piperazine (212)

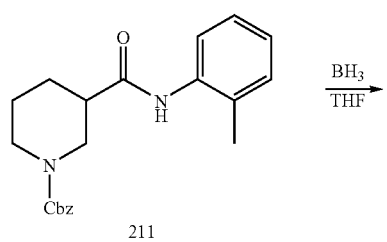

A solution of 211 (0.567 mmol, 0.200 g) in THF (1.0 mL) at 0° C. was treated with 1.0 M BH$_3$-THF (2.0 equiv, 1.13 mmol) under Ar. The reaction mixture was then heated to 80° C. and allowed to stir for 12 h. The reaction mixture was then cooled to 0° C. and quenched with 10% aqueous HCl. The pH was adjusted to 10 with 10% aqueous NaOH and the reaction mixture was extracted with 3× EtOAc (25 mL). The organics were dried with NaCl $_{(sat)}$ and MgSO$_4$ $_{(s)}$. The reaction mixture was purified by chromatography (PTLC, SiO$_2$, 20 cm×20 cm, 1 mm, 3:1 hexane-EtOAc) which provided 212 (102 mg, 192 mg theoretical, 53%) as a colorless oil: R$_f$ 0.54 (SiO$_2$, 3:1 hexane-EtOAc); LRMS m/z 338 (M$^+$, C$_{21}$H$_{26}$N$_2$O$_2$, requires 338).

EXAMPLE 151

N-(Carbobenzyloxypiperazin-3-ylmethyl)-N-(2'-methylanilino)cyclobutylcarboxamide (213)

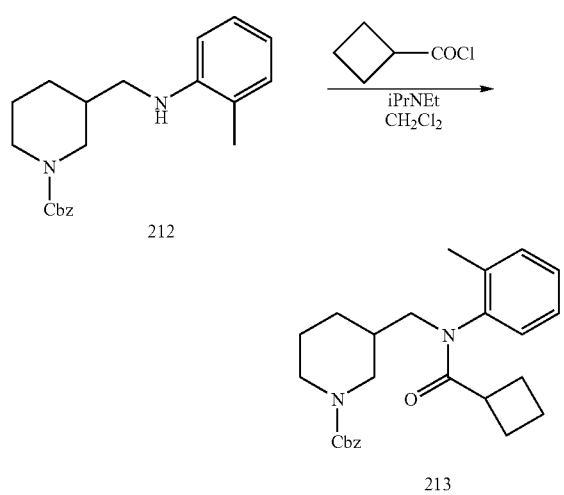

A solution of 212 (0.301 mmol, 102 mg) in CH$_2$Cl$_2$ (1 mL) at 0° C. was treated with cyclobutanecarbonyl chloride (1.5 equiv, 0.452 mmol, 52 µL) and diisopropylethylamine (1.5 equiv, 0.452 mmol, 79 µL) under Ar. After warming to 25° C. and stirring for 12 h, the reaction mixture was purified directly by chromatography (PTLC, SiO$_2$, 20 cm×20 cm, 1 mm, 2:1 hexane-EtOAc) which provided 213 (127 mg, 127 mg theoretical, 99%) as a colorless oil: R$_f$ 0.16 (SiO$_2$, 2:1 hexane-EtOAc); LRMS m/z 420 (M$^+$, C$_{21}$H$_{32}$N$_2$O$_3$, requires 420).

EXAMPLE 152

N-(Phenethyl-piperazin-3-ylmethyl)-N-(2'-methylanilino)cyclobutylcarboxamide (214)

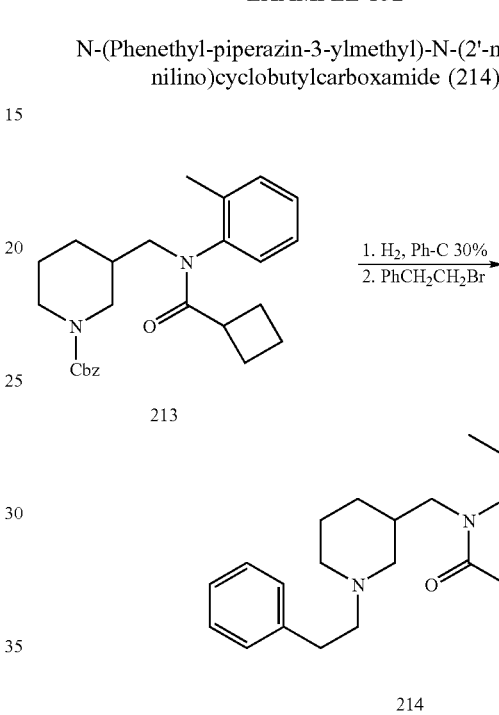

A solution of 213 (0.302 mmol, 127 mg) in CH$_3$OH (1 mL) at 25° C. was treated with 30% Pd—C (25 mg) and then placed under a hydrogen atmosphere. The reaction mixture stirred for 12 h and then was filtered through a pad of celite. The solvents were removed in vacuo and the resulting oil was then treated with phenethyl bromide (1.5 equiv, 0.453 mmol, 62 µL) and K$_2$CO$_3$ (2.0 equiv, 0.604 mmol, 83 mg) in CH$_3$CN (1.0 mL). The reaction mixture stirred for 12 h at 65° C. The reaction mixture was then purified directly by chromatography (PTLC, SiO$_2$, 20 cm×20 cm, 1 mm, EtOAc-10% CH$_3$OH) which provided 214 (51 mg, 118 mg theoretical, 43%) as colorless oil: R$_f$ 0.45 (SiO$_2$, EtOAc-10% CH$_3$OH); LRMS m/z 390 (M$^+$, C$_{26}$H$_{34}$N$_2$O, requires 390).

Incorporation By Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A compound represented by A:

$$\text{(CH}_2)_n-X-\overset{R_3}{\underset{R_6}{C}}-(\overset{R_5}{\underset{}{C}})_y-\overset{}{\underset{R_1}{N}}-\overset{O}{\underset{}{C}}-R_2$$

with N—(CR$_5$R$_6$)$_m$—R$_4$ wherein
m is 1,2,3 or 4;
n is 1;
y is 1 or 2;
R$_1$ represents alkyl, aryl, heteroaryl, or cycloalkyl;
R$_2$ represents independently for each occurrence H, alkyl, fluoroalkyl, heteroaryl, or cycloalkyl;
R$_1$ and R$_2$ may be connected through a covalent bond;
R$_3$ represents independently for each occurrence H, alkyl, aryl, OR$_2$, OC(O)R$_2$, CH$_2$OR$_2$, or CO$_2$R$_2$;
R$_4$ represents independently for each occurrence H, alkyl, aryl, heteroaryl, alkenyl, or cycloalkyl;
R$_5$ represents independently for each occurrence H, alkyl, CH$_2$Y, aryl, heteroaryl, F, OR$_2$, or OC(O)R$_2$;
R$_6$ represents independently for each occurrence H, alkyl, CH$_2$Y, aryl, heteroaryl, F, OR$_2$, or OC(O)R$_2$;
Y represents independently for each occurrence OR$_2$, N(R$_2$)$_2$, SR$_2$, S(O)R$_2$, S(O)$_2$R$_2$, or P(O)(OR$_2$)$_2$;
any two geminal or vicinal instances of R$_5$ and R$_6$ may be connected through a covalent bond;
X represents C(R$_3$)$_2$, or C=O; and
the stereochemical configuration at any stereocenter of a compound represented by A is R, S, or a mixture of these configurations.

2. The compound of claim 1, wherein X is C(R$_3$)$_2$.

3. The compound of claim 1, wherein m is 2 or 3.

4. The compound of claim 1, wherein y is 1.

5. The compound of claim 1, wherein R$_1$ represents aryl or heteroaryl.

6. The compound of claim 1, wherein R$_2$ represents independently for each occurrence alkyl.

7. The compound of claim 1, wherein R$_3$ represents independently for each occurrence H or alkyl.

8. The compound of claim 1, wherein R$_4$ represents cycloalkyl, aryl, or heteroaryl.

9. The compound of claim 1, wherein R$_5$ represents independently for each occurrence H, alkyl, aryl, heteroaryl, or F.

10. The compound of claim 1, wherein R$_6$ represents independently for each occurrence H, alkyl, aryl, heteroaryl, or F.

11. The compound of claim 1, wherein X is C(R$_3$)$_2$; and y is 1.

12. The compound of claim 1, wherein X is C(R$_3$)$_2$, or C=O; and R$_1$ represents aryl or heteroaryl.

13. The compound of claim 1, wherein X is C(R$_3$)$_2$; and R$_1$ represents aryl or heteroaryl.

14. The compound of claim 1, wherein X is C(R$_3$)$_2$; and R$_2$ represents independently for each occurrence alkyl.

15. The compound of claim 1, wherein X is C(R$_3$)$_2$; and R$_1$ represents aryl or heteroaryl.

16. The compound of claim 1, wherein X is C(R$_3$)$_2$; R$_1$ represents aryl or heteroaryl; and R$_2$ represents independently for each occurrence alkyl.

17. The compound of claim 1, wherein X is C(R$_3$)$_2$; R$_1$ represents aryl or heteroaryl; R$_2$ represents independently for each occurrence alkyl; and R$_3$ represents independently for each occurrence H or alkyl.

18. The compound of claim 1, wherein X is C(R$_3$)$_2$; R$_1$ represents aryl or heteroaryl; R$_2$ represents independently for each occurrence alkyl; R$_3$ represents independently for each occurrence H or alkyl; and R$_4$ represents cycloalkyl, aryl, or heteroaryl.

19. The compound of claim 1, wherein X is C(R$_3$)$_2$; R$_1$ represents aryl or heteroaryl; R$_2$ represents independently for each occurrence alkyl; R$_3$ represents independently for each occurrence H or alkyl; R$_4$ represents cycloalkyl, aryl, or heteroaryl; and R$_5$ represents independently for each occurrence H, alkyl, aryl, heteroaryl, or F.

20. The compound of claim 1, wherein said compound is a single stereoisomer.

21. A composition, comprising a compound of claim 1; and a pharmaceutically acceptable excipient.

22. A method of treating pain, drug addiction, or tinnitus in a mammal, comprising the step of:
administering to a mammal with pain, drug addiction, or tinnitus an effective amount of a formulation of claim 21.

23. The method of claim 22, wherein said mammal is a primate, equine, canine or feline.

24. The method claim 22, wherein said mammal is a human.

25. The method of claim 22, wherein said composition is administered orally.

26. The method of claim 22, wherein said composition is administered intravenously.

27. The method of claim 22, wherein said composition is administered sublingually.

28. The method of claim 22, wherein said composition is administered ocularly.

* * * * *